US012173009B2

(12) United States Patent
Arnaiz et al.

(10) Patent No.: US 12,173,009 B2
(45) Date of Patent: Dec. 24, 2024

(54) DIAMINE DERIVATIVES AS INHIBITORS OF LEUKOTRIENE A₄ HYDROLASE

(71) Applicant: CELLTAXIS, LLC, Atlanta, GA (US)

(72) Inventors: Damian O. Arnaiz, El Sobrante, CA (US); Greg Brown, Oakland, CA (US); Emmanuel Claret, Besancon (FR); Arwed Cleve, Berlin (DE); David Davey, Landing, NJ (US); William Guilford, Belmont, CA (US); Seock-Kyu Khim, Orinda, CA (US); Thomas Kirkland, Atascadero, CA (US); Monica J. Kochanny, Benicia, CA (US); Amy Liang, Vallejo, CA (US); David Light, San Mateo, CA (US); John Parkinson, Martinez, CA (US); Guo Ping Wei, San Ramon, CA (US); Bin Ye, Moraga, CA (US)

(73) Assignee: Celltaxis, LLC, Atlanta, GA (US)

( * ) Notice: Subject to any disclaimer, the term of this patent is extended or adjusted under 35 U.S.C. 154(b) by 0 days.

(21) Appl. No.: 17/944,782

(22) Filed: Sep. 14, 2022

(65) Prior Publication Data
US 2023/0250104 A1 Aug. 10, 2023

Related U.S. Application Data

(60) Division of application No. 17/666,149, filed on Feb. 7, 2022, now abandoned, which is a division of
(Continued)

(51) Int. Cl.
C07D 487/08 (2006.01)
C07C 217/58 (2006.01)
(Continued)

(52) U.S. Cl.
CPC .......... C07D 487/08 (2013.01); C07C 217/58 (2013.01); C07C 229/08 (2013.01); C07C 229/38 (2013.01); C07C 233/78 (2013.01); C07C 255/57 (2013.01); C07C 271/20 (2013.01); C07D 207/04 (2013.01); C07D 207/09 (2013.01); C07D 207/16 (2013.01); C07D 211/26 (2013.01); C07D 211/34 (2013.01); C07D 211/58 (2013.01); C07D 243/08 (2013.01); C07D 263/14 (2013.01); C07D 263/32 (2013.01); C07D 277/22 (2013.01); C07D 277/68 (2013.01); C07D 295/04 (2013.01); C07D 295/096 (2013.01); C07D 295/16 (2013.01); C07D 401/10 (2013.01); C07D 401/12 (2013.01); C07D 403/12 (2013.01); C07D 405/12 (2013.01); C07D 409/12 (2013.01);
(Continued)

(58) Field of Classification Search
CPC ........................... C07D 487/08; C07C 217/58
See application file for complete search history.

(56) References Cited

U.S. PATENT DOCUMENTS 3,929,765 A 12/1975 Suzuki
4,576,943 A 3/1986 Tomcufcik et al.
(Continued)

FOREIGN PATENT DOCUMENTS

CN 102030700 A 4/2011
CN 103159742 A 6/2013
(Continued)

OTHER PUBLICATIONS

CAS registry No. 1300708-42-2; STN entry date: May 25, 2011; Chemical name: Benzamide, N-[[6-(4-methoxyphenoxy)-3-pyridinyl]methyl]-4-(3-pyridinyloxy).
CAS registry No. 1317623-53-2; STN entry date: Aug. 14, 2011; Chemical name: Benzamide, 4-[4-(aminocarbonyl)phenoxy]-N-[[6-(1-piperidinyl)-3-pyridinyl]methyl].
CAS registry No. 1390429-79-4; STN entry date: Aug. 13, 2012; Chemical name: Benzamide, N-[1-(4-phenoxyphenyl)ethyl]-3-(1H-tetrazol-1-yl).
CAS registry No. 1394435-93-8; STN entry date: Sep. 18, 2012; Chemical name: Benzamide, Nmethyl-3-(2-oxo-1-pyrrolidinyl)-N-[[3-(1H-pyrazol-1-yl)phenyl]methyl].
CAS registry No. 1411077-00-3; STN entry date: Dec. 4, 2012; Chemical name: Benzenemethanamine, N-[(1S)-1-phenylethyl]-4-(trifluoromethoxy).
Database Registry [online], [retrieved on Jan. 7, 2019], Dec. 23, 2004, Retrieved from STN, <URL:https://stnweb-japan.cas.org/>, RN: 802038-23-9.
Database Registry [online], [retrieved on Jan. 7, 2019], Jun. 13, 2008, Retrieved from STN, <URL:https://stnweb-japan.cas.org/>, RN: 1027957-31-8.
(Continued)

Primary Examiner — Golam M Shameem
(74) Attorney, Agent, or Firm — Elmore Patent Law Group, P.C.; Mahreen Chaudhry Hoda; Carolyn S. Elmore

(57) ABSTRACT

This invention is directed to compounds of formula (I):

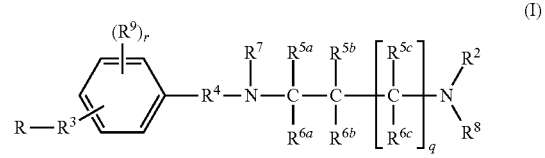

where r, q, R, $R^2$, $R^3$, $R^4$, $R^{5a}$, $R^{5b}$, $R^{5c}$, $R^{6a}$, $R^{6b}$, $R^{6c}$, $R^7$, $R^8$, and $R^9$ are described herein, as single stereoisomers or as mixtures of stereoisomers, or pharmaceutically acceptable salts, solvates, clathrates, polymorphs, ammonium ions, N-oxides or prodrugs thereof; which are leukotriene $A_4$ hydrolase inhibitors and therefore useful in treating inflammatory disorders. Pharmaceutical compositions comprising the compounds of the invention and methods of preparing the compounds of the invention are also disclosed.

23 Claims, No Drawings

Related U.S. Application Data application No. 16/738,190, filed on Jan. 9, 2020, now Pat. No. 11,267,819, which is a division of application No. 15/891,585, filed on Feb. 8, 2018, now abandoned, which is a division of application No. 15/069,484, filed on Mar. 14, 2016, now abandoned, which is a continuation of application No. 14/313,672, filed on Jun. 24, 2014, now Pat. No. 9,315,509, which is a division of application No. 13/654,669, filed on Oct. 18, 2012, now abandoned, which is a continuation of application No. 12/771,659, filed on Apr. 30, 2010, now Pat. No. 8,569,303, which is a continuation of application No. 11/644,244, filed on Dec. 22, 2006, now Pat. No. 7,737,145.

(60) Provisional application No. 60/755,421, filed on Dec. 29, 2005, provisional application No. 60/835,819, filed on Aug. 4, 2006.

(51) Int. Cl.

| | |
|---|---|
| *C07C 229/08* | (2006.01) |
| *C07C 229/38* | (2006.01) |
| *C07C 233/78* | (2006.01) |
| *C07C 255/57* | (2006.01) |
| *C07C 271/20* | (2006.01) |
| *C07D 207/04* | (2006.01) |
| *C07D 207/09* | (2006.01) |
| *C07D 207/16* | (2006.01) |
| *C07D 211/26* | (2006.01) |
| *C07D 211/34* | (2006.01) |
| *C07D 211/58* | (2006.01) |
| *C07D 243/08* | (2006.01) |
| *C07D 263/14* | (2006.01) |
| *C07D 263/32* | (2006.01) |
| *C07D 277/22* | (2006.01) |
| *C07D 277/68* | (2006.01) |
| *C07D 295/04* | (2006.01) |
| *C07D 295/096* | (2006.01) |
| *C07D 295/16* | (2006.01) |
| *C07D 401/10* | (2006.01) |
| *C07D 401/12* | (2006.01) |
| *C07D 403/12* | (2006.01) |
| *C07D 405/12* | (2006.01) |
| *C07D 409/12* | (2006.01) |
| *C07D 413/12* | (2006.01) |
| *C07D 451/02* | (2006.01) |
| *C07D 451/04* | (2006.01) |

(52) U.S. Cl.
CPC ......... *C07D 413/12* (2013.01); *C07D 451/02* (2013.01); *C07D 451/04* (2013.01); C07B 2200/07 (2013.01); C07C 2601/14 (2017.05)

(56) References Cited

U.S. PATENT DOCUMENTS

| | | | |
|---|---|---|---|
| 4,582,833 A | 4/1986 | Tomcufcik et al. |
| 5,308,852 A | 5/1994 | Girard et al. |
| 5,631,401 A | 5/1997 | Stein et al. |
| 5,719,306 A | 2/1998 | Chandrakumar et al. |
| 5,723,492 A | 3/1998 | Chandrakumar et al. |
| 5,952,349 A | 9/1999 | Asberom et al. |
| 6,054,590 A | 4/2000 | Poindexter et al. |
| 6,265,433 B1 | 7/2001 | Chen et al. |
| 6,309,561 B1 | 10/2001 | Hasegawa et al. |
| 6,348,487 B1 | 2/2002 | Connor et al. |
| 6,372,736 B1 | 4/2002 | Kemp et al. |
| 6,380,203 B1 | 4/2002 | Bilodeau et al. |
| 6,407,140 B1 | 6/2002 | Gregory et al. |
| 6,451,798 B2 | 9/2002 | Varkhedkar et al. |
| 6,492,368 B1 | 12/2002 | Dorsch et al. |
| 6,534,521 B2 | 3/2003 | Connor et al. |
| 6,552,023 B2 | 4/2003 | Zablocki et al. |
| 6,635,644 B2 | 10/2003 | Salituro et al. |
| 6,699,873 B1 | 3/2004 | Maguire et al. |
| 6,734,184 B1 | 5/2004 | Barlaam et al. |
| 6,846,812 B2 | 1/2005 | Dalko et al. |
| 6,869,975 B2 | 3/2005 | Abe et al. |
| 6,875,483 B2 | 4/2005 | Matsuoka et al. |
| 6,924,313 B1 | 8/2005 | Sikorski et al. |
| 7,169,779 B2 | 1/2007 | Salituro et al. |
| 7,402,684 B2 | 7/2008 | Sandanayaka et al. |
| 7,488,741 B2 | 2/2009 | Lamberty et al. |
| 7,597,897 B2 | 10/2009 | Capecchi et al. |
| 7,645,779 B2 | 1/2010 | Abe et al. |
| 7,674,899 B2 | 3/2010 | Peters et al. |
| 7,708,650 B2 | 5/2010 | Lloyd |
| 7,718,669 B2 | 5/2010 | Petry et al. |
| 7,737,145 B2 | 6/2010 | Arnaiz et al. |
| 7,816,365 B2 | 10/2010 | Schiemann et al. |
| 7,820,675 B2 | 10/2010 | Johansson et al. |
| 7,820,821 B2 | 10/2010 | Gopalaswamy et al. |
| 7,893,257 B2 | 2/2011 | Grimm et al. |
| 7,902,181 B2 | 3/2011 | Furber et al. |
| 7,915,298 B2 | 3/2011 | Gosselin et al. |
| 7,932,272 B2 | 4/2011 | Nakamoto et al. |
| 7,935,707 B2 | 5/2011 | Aebi et al. |
| 8,008,305 B2 | 8/2011 | Galley et al. |
| 8,246,935 B2 | 8/2012 | Mueller-Walz et al. |
| 8,357,684 B2 | 1/2013 | Bacani et al. |
| 8,569,303 B2 | 10/2013 | Ye et al. |
| 8,609,669 B2 | 12/2013 | Xu et al. |
| 8,846,655 B2 | 9/2014 | Decorte et al. |
| 9,006,235 B2 | 4/2015 | Naidu et al. |
| 9,133,146 B2 | 9/2015 | Abeywardane et al. |
| 9,315,509 B2 | 4/2016 | Arnaiz et al. |
| 9,642,888 B2 | 5/2017 | Lander et al. |
| 9,820,974 B2 | 11/2017 | Springman et al. |
| 9,856,249 B2 | 1/2018 | Guilford |
| 9,861,601 B2 | 1/2018 | Nicolls et al. |
| 10,350,197 B2 | 7/2019 | Springman et al. |
| 11,267,819 B2 * | 3/2022 | Arnaiz ............... C07D 277/22 |
| 2004/0006114 A1 | 1/2004 | Coleman et al. |
| 2004/0198777 A1 | 10/2004 | Ghosh et al. |
| 2005/0043378 A1 | 2/2005 | Axe et al. |
| 2005/0043379 A1 | 2/2005 | Axe et al. |
| 2005/0113408 A1 | 5/2005 | Helgadottir et al. |
| 2006/0063784 A1 | 3/2006 | Wang et al. |
| 2006/0211729 A1 | 9/2006 | Fyrnys et al. |
| 2006/0223792 A1 | 10/2006 | Butler et al. |
| 2007/0112006 A1 | 5/2007 | Schiemann et al. |
| 2007/0155727 A1 | 7/2007 | Chen et al. |
| 2008/0096906 A1 | 4/2008 | Galley et al. |
| 2008/0267885 A1 | 10/2008 | Capecchi et al. |
| 2008/0269275 A1 | 10/2008 | Brown et al. |
| 2009/0233922 A1 | 9/2009 | Zhuo et al. |
| 2010/0029619 A1 | 2/2010 | Uchikawa et al. |
| 2010/0029657 A1 | 2/2010 | Levin et al. |
| 2010/0069417 A1 | 3/2010 | Bouaboula et al. |
| 2010/0093668 A1 | 4/2010 | Babin et al. |
| 2010/0099694 A1 | 4/2010 | Babin et al. |
| 2010/0210630 A1 | 8/2010 | Arnaiz et al. |
| 2010/0260859 A1 | 10/2010 | Ruddy et al. |
| 2011/0009429 A1 | 1/2011 | Oakley et al. |
| 2011/0009454 A1 | 1/2011 | Matsuzaki et al. |
| 2011/0105475 A1 | 5/2011 | Roche et al. |
| 2012/0028954 A1 | 2/2012 | Goff et al. |
| 2012/0302541 A1 | 11/2012 | Coats et al. |
| 2012/0302610 A1 | 11/2012 | Chakravarty et al. |
| 2013/0116323 A1 | 5/2013 | Tirouvanziam et al. |
| 2013/0123243 A1 | 5/2013 | Arnaiz et al. |
| 2013/0237499 A1 | 9/2013 | Zheng et al. |
| 2013/0251787 A1 | 9/2013 | Nicolls et al. |
| 2016/0067226 A1 | 3/2016 | Grosswald et al. |
| 2016/0068522 A1 | 3/2016 | Davey et al. |
| 2016/0068524 A1 | 3/2016 | Guilford |
| 2016/0068534 A1 | 3/2016 | Guilford |

(56) References Cited

U.S. PATENT DOCUMENTS

| | | |
|---|---|---|
| 2016/0272649 A1 | 9/2016 | Kochanny et al. |
| 2018/0117014 A1 | 5/2018 | Springman et al. |
| 2018/0230159 A1 | 8/2018 | Arnaiz et al. |
| 2020/0138791 A1 | 5/2020 | Springman et al. |

FOREIGN PATENT DOCUMENTS

| | | |
|---|---|---|
| EP | 1611902 A1 | 1/2006 |
| EP | 1878730 A1 | 1/2008 |
| GB | 1221006 A | 2/1971 |
| JP | 2001354657 A | 12/2001 |
| JP | 2005008581 A | 1/2005 |
| JP | 2008137997 A | 6/2008 |
| WO | 9610559 A1 | 4/1996 |
| WO | 0069810 A1 | 11/2000 |
| WO | 02064211 A1 | 8/2002 |
| WO | 02069901 A2 | 9/2002 |
| WO | 02072621 A2 | 9/2002 |
| WO | 03010158 A1 | 2/2003 |
| WO | 02072621 A3 | 5/2003 |
| WO | 03037271 A2 | 5/2003 |
| WO | 02069901 A3 | 10/2003 |
| WO | 03093297 A2 | 11/2003 |
| WO | 2004026305 A1 | 4/2004 |
| WO | 2004035746 A2 | 4/2004 |
| WO | 2004089410 A1 | 10/2004 |
| WO | 2004099164 A1 | 11/2004 |
| WO | 2005027886 A2 | 3/2005 |
| WO | 2005027886 A3 | 6/2005 |
| WO | 2006117669 A1 | 11/2006 |
| WO | 2007007069 A1 | 1/2007 |
| WO | 2007079003 A2 | 7/2007 |
| WO | 2010011912 A1 | 1/2010 |
| WO | 2010015818 A1 | 2/2010 |
| WO | 2011071758 A1 | 6/2011 |
| WO | 2011078370 A1 | 6/2011 |
| WO | 2012125832 A2 | 9/2012 |
| WO | 2015175773 A1 | 11/2015 |

OTHER PUBLICATIONS

Database Registry [online], [retrieved on Jan. 7, 2019], May 12, 2011, Retrieved from STN, <URL:https://stnweb-japan.cas.org/>, RN: 1293490-03-5.

Database Registry [online], [retrieved on Jan. 7, 2019], May 18, 2011, Retrieved from STN, <URL:https://stnweb-japan.cas.org/>, RN: 1296842-44-8.

Database Registry [online], [retrieved on Jan. 7, 2019], Dec. 4, 2011, Retrieved from STN, <URL:https://stnweb-japan.can.org/>, RN: 1348056-14-3.

Database Registry [online], [retrieved on Jan. 7, 2019], Aug. 8, 2012, Retrieved from SN, <URL:https://stnweb-japan.cas.org/>, RN: 1387895-19-3.

International Search Report dated Jun. 18, 2007, cited in Application No. PCT/US2006/049273.

Online "http://web.archive.org/web/20120317091129/, http://www.fchgroup.net/" dated Mar. 1, 2012, accessed Oct. 12, 2016.

Online "http://web.archive.org/web/20130122020518/http://www.chembridge.com/screening_libraries/" 2011, accessed Oct. 10, 2015.

Online: "http://web.archive.org/web/20070630171813/http://www.enamine.net/index.php?option=com_content&task=view&id=22&menuid=51&PHPSESSID=64a4f248f69d671a413f487bb62c4d90" dated Jun. 30, 2007, accessed Apr. 1, 2015.

Online: "http://web.archive.org/web/20120301075525/http://www.fchgroup.net/products.php" dated Mar. 1, 2012 accessed Oct. 12, 2016.

STN-Chemical database Registry RN 1322312-60-6 for N-[(3-Phenoxyphenyl)methyl]-6-(1-piperidinyl)-3-Pyridinemethanamine, Entered STN: Aug. 24, 2011.

Inflammation, Wikipedia, 2017.

"Pharmaceutical Acceptable Excipients" FDA guidelines, 2005, 1-12.

"Practical Fragments: Fragments in the Clinic: DG-051", Online "http://practicalfragments.blogspot.com/2010/01/fragments-in-clinic-dg-051.html" accessed Feb. 17, 2016.

Adam, O. R, et al., "Symptomatic Treatment of Huntington Disease", Neurotherapeutics: The Journal of the American Society for Experimental Neuro Therapeutics, vol. 5, Apr. 2008, 181-197.

Anonymous, "Celtaxsys Announces Successful Completion of Phase 1 Clinical Trial for Development of CTX-4430—FirstWord Pharma", Retrieved from the Internet: URL:http://www.firstwordpharma.com/node/1139589?tsid=17#axzz4M7ubNn38 [retrieved on Oct. 4, 2016], Sep. 16, 2013.

Argollo, M., et al., "Novel therapeutic targets for inflammatory bowel disease", Journal of Autoimmunity, 85, 103-116 (2017).

Arnaiz, D., et al., "Diamine derivatives as inhibitors of leukotriene A4 hydrolase and their preparation, pharmaceutical compositions and use in the treatment of inflammatory disorders", CA147:166353.

Banker, G. S, et al., "Prodrugs", Modern Pharmaceutics, 3rd., Marcel Dekker, Inc., NY, 1996, 2 pgs.

Beaumont, K., et al., "Design of Ester Prodrugs to Enhance Oral Absorption of Poorly Permeable Compounds: Challenges to the Discovery Scientist", Current Drug Metabolism, 4, 461-485 (2003).

Belikov, V. G., et al., "Pharmaceutical Chemistry", 4th Ed., Moscow, MEDpress-inform, 2007, 27-29.

Bhatt, et al., Seminars in Immunology, 33, 2017, 65-73.

Binder, B. F, "Inhibition of development in Caenorhabditis elegans (Nematoda) by a reduced aromatic Schiff base and related compounds", Journal of Agricultural and Food Chemistry, 40(9), 1475-1477, 1992.

Boniface, M. M, et al., "Multidisciplinary management for esophageal and gastric cancer", Cancer Management and Research, 8, 2016, 39-44.

Breitenstein, W., et al., "Preparation of substituted pyrrolidines as renin inhibitors", CA145: 103533, 2006.

Bridger, G. J, et al., "Preparation of piperidines as chemokine receptor, particularly CCR5, modulators for treatment of inflammatory and autoimmune diseases", CA143: 97274, 2005.

Brodin, P., et al., "Benzamides, pyridopyrimidines and related compounds as antiinfective compounds and their preparation and use in the treatment of tuberculosis", CA152: 168983, 2010.

Campochiaro, P. A, "The Complexity of Animal Model Generation for Complex Diseases", JAMA, vol. 303, No. 7, Feb. 17, 2010, 657-658.

Celli, B. R, et al., "Bronchodilator responsiveness and onset of effect with budesonide/formoterol pMDI in COPD", Respiratory Medicine, vol. 105, 2011, 1176-1188.

Celtaxsys, et al., "Results from Celtaxsys' Acebilustat Phase 2 Trial in Cystic", Oct. 22, 2018, Retrieved from the Internethttps://www.globenewswire.com/news-release/2018/10/22/1624627/0/en/Results-fromCeltaxsys-Acebilustat-Phase-2-Trial-in-Cystic-Fibrosis-Patients-Showing-Clinically-Meaningful-Improvement-in-Pulmonary-Exacerbations-Presented-at-the-North-American-Cy.html.

Chiba, T., "Emerging Therapeutic Strategies in Alzheimer's Disease", Intech, Chap 9, 181-226 (2013).

Coats, S. J, et al., "4-Substituted 2-phenoxyphenylamines as delta opioid receptor modulators and their preparation and use in the treatment of diseases", CA154: 540153, 2011.

Connors, K. A, "The Stability of Cyclodextrin Complexes in Solution", Chem. Rev., 97, 1997, 1325-1357.

Costigan, M., et al., "Neuropathic Pain: A Maladaptive Response of the Nervous System to Damage", Annu. Rev. Neurosci., 32, 1-32 (2009).

Damia, G., et al., "Contemporary pre-clinical development of anticancer agents—What are the optimal preclinical models?", European Journal of Cancer, 45, 2768-2781 (2009).

De Boeck, et al., "Progress in Therapies for Cystic Fibrosis", The lancet Respiratory Medicine, 4(8), Aug. 1, 2016, 662-674.

Deweerdt, S., "Parkinson's disease 4 Big Questions", vol. 538, S17 (2016).

D'Onofrio, G., et al., "Advances in the identification of g-secretase inhibitors for the treatment of Alzheimer's disease", Expert Opinion on Drug Discovery, 7(1), 19-37 (2012).

(56) References Cited

OTHER PUBLICATIONS

Dyson, G., et al., "Chemistry of Synthetic Drugs (in Russian), translated from English. Moscow: Mir", 1964, 12-19.

Edwards, A. O, et al., "Molecular genetics of AMD and current animal models", Angiogenesis, 10, 2007, 119-132.

Elborn, J. S, "Cystic fibrosis", The Lancet, Published online Apr. 29, 2016 Online "http://dx.doi.org/10.1016/S0140-6736(16)00576-6", 1-13 (2016).

Elborn, J. S, et al., "Empire-CF study: A phase 2 clinical trial of leukotriene A4 hydrolase inhibitor acebilustat in adult subjects with cystic fibrosis", J. Cyst. Fibros., 20(6): 1026-1034 (2021) doi: 10.1016/j.jcf.2021.08.007.

Elborn, J. S, et al., "Phase I Studies of Acebilustat: Biomarker Response and Safety in Patients with Cystic Fibrosis", Clin. Transl. Sci., 10(1): 28-34 (2017) https://doi.org/10.1111/cts.12428.

Elborn, J. S, et al., "Phase I Studies of Acebilustat: Pharmacokinetics, Pharmacodynamics, Food Effect, and CYP3A Induction", Clin. Transl Sci., 10(1): 20-27 (2017) https://doi.org/10.1111/cts.12426.

Elborn, S. J, et al., "Empire-CF: A phase II randomized placebo-controlled trial of once-daily, oral acebilustat in adult patients with cystic fibrosis—Study design and patient demographics", Contemp. Clin. Trials, 72: 86-94 (2018) DOI:10.1016/j.cct.2018.07.01.

Estey, E., et al., "New drug approvals in acute myeloid leukemia: what's the best end point?" Leukemia, 30, 521-525 (2016).

Fieser, L., et al., "Reagents for Organic Synthesis," vol. 1, Wiley: NY, 1974, 723-730.

Freundlich, J. S, et al., "Synthesis, biological activity, and X-ray crystal structural analysis of diaryl ether inhibitors of malarial enoyl acyl carrier protein reductase. Part 1:4'-Substituted triclosan derivatives", Bioorganic & Medicinal Chemistry Letters, 15(23), 2005, 5247-5252.

Garrido, A. G, et al., "Experimental models of sepsis and septic shock: an overview", Acta Cirurgica Brasileira, vol. 19(2), 2004, 82-88.

Garson, K., et al., "Models of ovarian cancer—Are we there yet?", Molecular and Cellular Endocrinology, 239, 15-26 (2005).

Gerratana, L., et al., "Do platinum salts fit all triple negative breast cancers?", Cancer Treatment Reviews, 48, 34-41 (2016).

Greene, T. W, et al., "Protective Groups in Organic Synthesis," John Wiley & Sons: NY, 1982, 218-220, 224, 251.

Grice, C. A, et al., "Identification of a Potent, Selective, and Orally Active Leukotriene A4 Hydrolase Inhibitor with Anti-inflammatory Activity", J. Med. Chem., 51, 2008, 4150-4169.

Hauptmann, et al., Chem. Rev., 62, 1962, 347-404.

Hook, V. Y.H, "Neuroproteases in Peptide Neurotransmission and Neurodegenerative Diseases Applications to Drug Discovery Research", Biodrugs, 20, 2006, 105-119.

Howington, J. A, et al., "Treatment of Stage I and II Non-small Cell Lung Cancer Diagnosis and Management of Lung Cancer, 3rd ed: American College of Chest Physicians Evidence-Based Clinical Practice Guidelines", Chest, 143(5)(Suppl): e278S-e313S, 2013.

Hutchins, T. O, "Selective Reductive Displacement of Alkyl Halides and Sulfonate Esters with Cyanoborohydride Reagents in Hexamethylphosphoramide", J. Org. Chem., 42(1), 1977, 82-91.

Jackson-Lewis, V., et al., "Animal models of Parkinson's disease", Parkinsonism and Related Disorders, 18S1: S183-S185 (2012).

Jantzen, et al., Modern Pharmaceutics, 1996, 596.

Jett, J. B, et al., "Treatment of Small Cell Lung Cancer Diagnosis and Management of Lung Cancer, 3rd ed: American College of Chest Physicians Evidence-Based Clinical Practice Guidelines", Chest, 143(5)(Suppl), 2013, e400S-e419S.

Jhee, S., et al., "B-amyloid therapies in Alzheimer's disease", Expert Opinion on Investigational Drugs, 10(4), 593-605 (2001).

Johnson, J. I, et al., "Relationships between drug activity in NCI preclinical in vitro and in vivo models and early clinical trials", British Journal of Cancer, 84, 2001, 1424-1431.

Julien, J-P., et al., "Transgenic mouse models of amyotrophic lateral sclerosis", Biochimica et Biophysica Acta, 1762: 1013-1024 (2006).

Kalia, L., et al., "Parkinson's disease", Lancet; 386, 896-912 (2015).

Khim, S. K, et al., "Discovery of novel and potent aryl diamines as leukotriene A4 hydrolase inhibitors", Bioorg. Med. Chem. Lett., 18(14), Jul. 15, 2008, 3895-3898.

King, F. D, et al., "Bioisosteres, Conformational Restriction, and Pro-drugs—Case History: An Example of a Conformational Restriction Approach", Ch. 14 in Med. Chem: Principle & Practice, Jan. 1, 1994, 206-2335.

Konstan, M. W, et al., "A randomized double blind, placebo controlled phase 2 trial of Blil 284 BS (an LTB4 receptor antagonist) for the treatment of lung disease in children and adults with cystic fibrosis", Journal of Cystic Fibrosis, 13, 2014, 148-155.

Krishnan, S. R, et al., "Multiple myeloma and persistence of drug resistance in the age of novel drugs (Review)", International Journal of Oncology, 49, 2016, 33-50.

Kurimura, M., et al., "Preparation of N,N-substituted 3-aminopyrrolidine compounds useful as monoamines reuptake inhibitors", CA149: 53863, 2008.

Labaudiniere, R., et al., "w-[(w-Arylalkyl)aryl]alkanoic Acids: A New Class of Specific LTA4 Hydrolase Inhibitors", J. Med. Chem., 35, 3156-3169 (1992).

Le Bars, D., et al., "Animal Models of Nociception", Pharmacological Reviews, 53(4), 597-652 (2001).

Ledford, H., "US cancer institute overhauls cell lines", Nature, vol. 530, 391 (2016).

Liu, M., et al., "The role of leukotrienes in allergic diseases", Allergology International, 64, 17-26 (2015).

Low, Caroline M., et al., "The development of novel LTA4H modulators to selectively target LTB4 generation", Nature Scientific Reports 7:44449, 2017, 1-13.

Marshall, J. C, "Why have clinical trials in sepsis failed?", Trends in Molecular Medicine, vol. 20, No. 4, Apr. 2014, 195-203.

Martin, Y. C, et al., "Do Structurally Similar Molecules Have Similar Biological Activity?", J. Med. Chem., 45, 2002, 4350-4358.

Miller, D. T, et al., "Atherosclerosis", Journal of the American College of Cardiology, vol. 49, No. 15, 2007, 1589-99.

Mitchell, R. H, et al., "The Neutral Deoxygenation (Reduction) of Aryl Carbonyl Compounds With Raney-Nickel. An Alternative to the Clemmenson, Wolf-Kishner or Mozingo (Thioketal) Reductions", Tetrahedron Letters, 21, 1980.

Ocana, A., et al., "Preclinical development of molecular targeted agents for cancer", Nat. Rev. Clin. Oncol., 8, 200-209 (2011).

Penning, T. D, et al., "Structure-Activity Relationship Studies on 1-[2-(4-Phenylphenoxy)ethyl]pyrrolidine (SC-22716), a Potent Inhibitor of Leukotriene A4 (LTA4) Hydrolase", J. Med. Chem., 43(4), 2000, 721-735.

Pilz, G., et al., "Modern multiple sclerosis treatment—what is approved, what is on the horizon", Drug Discovery Today, vol. 13, Nos. 23/24, 1013-1025 (2008).

Pitt, W. R, et al., "Heteroaromatic Rings of the Future", J. Med. Chem., 52, 2009, 2952-2963.

Poli-De-Figueiredo, L. F, et al., "Experimental Models of Sepsis and Their Clinical Relevance", Shock, vol. 30, Supplement 1, 2008, 53-59.

Pozharskii, et al., Heterocycles in Life and Society Wiley, 1997, 1-6.

Pui, C-H., "Treatment of Acute Lymphoblastic Leukemia", New England Journal of Medicine, 354, 166-78 (2006).

Rafeeq, M. M, et al., "Cystic fibrosis: current therapeutic targets and future approaches", J. Transl. Med., 15(84)DOI: 10.1186/s12967-017-1193-9, Apr. 1, 2017, 1-9.

Rautio, J., et al., Nat. Rev. Drug Disc., 7, 2008, 255-270.

Sale, S., et al., "Models of ovarian cancer metastasis: Murine models", Drug Discovery Today: Disease Models, 3, 149-154 (2006).

Sanders, W. J, et al., "Discovery of Potent Inhibitors of Dihydronepterin Aldolase Using CrystaLead High-Throughput X-ray Crystallograpic Screening and Structure-Directed Lead Optimization", J. Med. Chem., 47, 2004, 1709-1718.

Sanz-Garcia, E., et al., "Current and advancing treatments for metastatic colorectal cancer", Expert Opinion on Biological Therapy, 16(1), 93-110 (2016).

(56) References Cited

OTHER PUBLICATIONS

Satoh, T., et al., "Comparison of the Inhibitory Action of Synthetic Capsaicin Ananlogues with Various NADH-ubiquinone Oxidoreductases", Biochemica et Biophysica Acta, Bioenergetics, vol. 1273, No. 1, 21-30 (1996).

Schober, M., et al., "New Advances in the Treatment of Metastatic Pancreatic Cancer", Digestion, 92, 175-184 (2015).

Sharma, S. V, et al., "Cell line-based platforms to evaluate the therapeutic efficacy of candidate anticancer agents", Nature Reviews Cancer, vol. 10, Apr. 2010, 241-253.

Shen, H. C, et al., "A strategy of employing aminoheterocycles as amide mimics to identify novel, potent and bioavailable soluble epoxide hydrolase inhibitors", Bioorganic & Medicinal Chemistry Letters, 19, 2009, 5716-5721.

Shim, Y. M, et al., "Leukotriene A4 Hydrolase—an Evoloving Therapeutic Target", Inflammatory Diseases-Immunopathology, Clinical and Pharmacological Bases, Dr Mahin Khatami (Ed.), InTech, 2012, 253-278.

Simone, J. V, Oncology: Introduction, Cecil Textbook of Medicine, 20th Edition, vol. 1, 1996, 1004-1010.

Skerlj, R., et al., "Design and synthesis of pyridin-2-ylmethylaminopiperidin-1-ylbutyl amide CCR5 antagonists that are potent inhibitors of M-tropic (RS) HIV-1 replication", CA156: 10919, 2011.

Skrupy, L. P, et al., "Advances in the Management of Sepsis and in the Understanding of Key Immunologic Defects of the Disorder", Anesthesiology, 115(6), Dec. 2011, 1349-1362.

Socinski, M. A, et al., "Treatment of Stage IV Non-small Cell Lung Cancer Diagnosis and Management of Lung Cancer, 3rd ed: American College of Chest Physicians Evidence-Based Clinical Practice Guideline", Chest, 143(5)(Suppl):e341S-e368S, 2013.

Springman, E. B, et al., "A phase 1 study of human safety, pharmacokinetics and pharmacodynamics of CTX-4430", Peditatric Pulmonology, 48, Abstract 269, Oct. 1, 2013, 302.

Stewart, A. K, "Novel therapeutics in multiple myeloma", Hematology, 17(S1), 2012, S105-S108.

Szczesniak, R., et al., "Use of FEV1 in cystic fibrosis epidemiologic studies and clinical trials: A statistical perspective for the clinical researcher", J. Cystic Fibrosis, 16(3), 318-326 (2017).

Tanaka, A., et al., "Inhibitors of Acyl-CoA:Cholesterol O-Acyltransferase. 3. Discovery of a NOvel Series of N-Alkyl-N-[(fluorophenoxy)benzyl]-N-arylureas with Weak Toxicological Effects on Adrenal Glands", J. Med. Chem., 41, 4408-4420 (1998).

Van Der Laan, S. W, et al., "Variants in ALOX5, ALOX5AP and LTA4H are not associated with atherosclerotic plaque phenotypes: The Athero-Express Genomics Study", Atherosclerosis, 239, 2015, 528-538.

Vardiman, J. W, et al., "The World Health Organization (WHO) classification of the myeloid neoplasms", Blood, 100(7), 2002, 2292-2302.

Vippagunta, S. R, et al., "Crystalline Solids", Advanced Drug Delivery Reviews, 48, 2001, 3-26.

Vyaznikovtseva, O. V, et al., "Hydrogenation of 3-phenocybenzonitrile and benzonitrile on Raney nickel catalysts", Izvestiya Akademii Nauk Kasakhskoi SSR, Seriya Khimecheskaya, No. 5, 1990, 18-22.

Wolff, M. E, Burger's Medicinal Chemistry and Drug Discovery, Fifth Edition, vol. 5(1): "Principles and Practice" published by John Wiley and Sons, 1994, 975-977.

Wu, K.-M., et al., "Regulatory perspectives of Type II prodrug development and time-dependent toxicity management: Nonclinical Pharm/Tox analysis and the role of comparative toxicology," Toxicology, 236: 1-6 (2007).

Yoo, S., et al., "New drugs in prostate cancer", Prostate Int., 4, 37-42 (2016).

\* cited by examiner

DIAMINE DERIVATIVES AS INHIBITORS OF LEUKOTRIENE $A_4$ HYDROLASE

RELATED APPLICATIONS

This application is a divisional of U.S. application Ser. No. 17/666,149, filed Feb. 7, 2022, which is a divisional of U.S. application Ser. No. 16/738,190, filed Jan. 9, 2020 (now U.S. Pat. No. 11,267,819), which is a divisional of U.S. application Ser. No. 15/891,585, filed on Feb. 8, 2018, which is a divisional of U.S. application Ser. No. 15/069,484, filed Mar. 14, 2016, which is a continuation of U.S. application Ser. No. 14/313,672, filed Jun. 24, 2014, now U.S. Pat. No. 9,315,509, which is a divisional of U.S. application Ser. No. 13/654,669, filed Oct. 18, 2012, which is a continuation of U.S. application Ser. No. 12/771,659, filed Apr. 30, 2010, now U.S. Pat. No. 8,569,303, which is a continuation of U.S. patent application Ser. No. 11/644,244, filed Dec. 22, 2006, now U.S. Pat. No. 7,737,145, which claims the benefit of U.S. Provisional Patent Application No. 60/755,421, filed Dec. 29, 2005, and of U.S. Provisional Patent Application No. 60/835,819, filed Aug. 4, 2006. The entire teachings of the above applications are incorporated herein by reference.

BACKGROUND

Inflammation is normally an acute response by the immune system to invasion by microbial pathogens, chemicals or physical injury. In some cases, however, the inflammatory response can progress to a chronic state and be the cause of inflammatory disease. Therapeutic control of this chronic inflammation in diverse diseases is a major medical need.

Leukotriene $B_4$ ($LTB_4$) is a potent pro-inflammatory activator of inflammatory cells, including neutrophils (J. Palmblad, *J. Rheumatol.* 1984, 13(2):163-172), eosinophils (A. M. Tager, et al., J. Exp. Med. 2000, 192(3):439-446), monocytes (N. Dugas et al., *Immmunol.* 1996, 88(3):384-388), macrophages (L. Gagnon et al., Agents Actions 1989, 34(1-2):172-174), T cells (H. Morita et al., *Biochem. Biophys. Res. Commun.* 1999, 264(2):321-326) and B cells (B. Dugas et al., *J. Immunol.* 1990, 145(10):3405-3411). Immune cell priming and activation by $LTB_4$ can promote chemotaxis, adhesion, free radical release, degranulation and cytokine release. $LTB_4$ stimulates T-cell proliferation and cytokine release in response to IL-2, concanavalin-A and CD3 ligation (H. Morita et al., *Biochem. Biophys. Res. Commun.* 1999, 264(2):321-326). $LTB_4$ is a chemoattractant for T-cells creating a functional link between early innate and late adaptive immune responses to inflammation (K. Goodarzi, et al., *Nat, Immunol.* 2003, 4:965-973; V. L. Ott, et al., *Nat. Immunol.* 2003, 4:974-981; A. M. Tager, et al., *Nat. Immunol.* 2003, 4:982-990). There is substantial evidence that $LTB_4$ plays a significant role in the amplification of many inflammatory disease states (R. A. Lewis et al., *N. Engl. J. Med.* 1990, 323:645; W. R. Henderson, Ann. Intern. Med. 1994, 121:684) including asthma (D. A. Munafo et al., *J. Clin. Invest.* 1994, 93(3):1042-1050), inflammatory bowel disease (IBD) (P. Sharon and W. F. Stenson, Gastroenterology 1984, 86(3):453-460), chronic obstructive pulmonary disease (COPD) (P. J. Barnes, Respiration 2001, 68(5):441-448), arthritis (R. J. Griffiths et al., *Proc. Natl. Acad. Sci. U.S.A.* 1995, 92(2):517-521; F. Tsuji et al., *Life Sci.* 1998 64(3): L51-L56), psoriasis (K. Ikal, J. Dermatol. Sci. 1999, 21(3):135-146; Y. I. Zhu and M. J. Stiller, *Skin Pharmacol. Appl. Skin Physiol.* 2000, 13(5):235-245), and atherosclerosis (E. B. Friedrich, et al., *Arterioscler. Thromb. Vasc. Biol.* 2003, 23:1761-1767; K. Subbarao, et al., *Arterioscler. Thromb. Vasc. Biol.* 2004, 24:369-375; A. Helgadottir, et al., *Nat. Genet.* 2004, 36:233-239; V. R. Jala, et al., *Trends in Immun.* 2004, 25:315-322). $LTB_4$ also simulates the production of various cytokines and may play a role in immunoregulation (A. W. Ford-Hutchinson, *Immunology* 1990, 10:1). Furthermore, it has recently been shown that $LTB_4$ levels are elevated in brochoalveolar lavage fluid from patients with scleroderma lung disease (see Kowal-Bielecka, O. et al., *Arthritis Rheum.* (Nov. 30, 2005), Vol. 52, No. 12, pp. 3783-3791). Therefore, a therapeutic agent that inhibits the biosynthesis of LTB4 or the response of cells to $LTB_4$ may be useful for the treatment of these inflammatory conditions.

The biosynthesis of $LTB_4$ from arachidonic acid (AA) involves the action of three enzymes: phospholipase $A_2$ ($PLA_2$), to release AA from the membrane lipids; 5-lipoxygenase (5-LO), to form the unstable epoxide Leukotriene $A_4$ ($LTA_4$); and leukotriene $A_4$ hydrolase ($LTA_4$-h), to form $LTB_4$ (A. W. Ford-Hutchinson, et al., Annu. Rev. Biochem. 1994, 63:383-347). The cysteinyl leukotrienes are formed by the addition of glutathione to $LTA_4$ by the action of $LTC_4$ synthase (Aharony, D., *Am. J. Respir. Crit. Care Med.* 1998, 157 (6, Pt 2), S214-S218) into the pro-inflammatory cysteinyl leukotrienes $LTC_4$, $LTD_4$ and $LTE_4$. An alternative path for $LTA_4$ is conversion via transcellular biosynthesis and the action of lipoxygenases into lipoxin $A_4$ ($LXA_4$) and lipoxin $B_4$ ($LXB_4$) (C. N. Serhan, *Prostaglandins* 1997, 53:107-137).

$LTA_4$-h is a monomeric, soluble 69 kD zinc metalloenzyme. A high resolution crystal structure of recombinant $LTA_4$-h with bound inhibitors has been obtained (M. M. Thunissen et al., *Nat Struct. Biol.* 2001, 8(2): 131-135). $LTA_4$-h is a bifunctional zinc-dependent metalloenzyme of the M1 class of metallohydrolases. It catalyses two reactions: the stereospecific epoxide hydrolase reaction to convert $LTA_4$ to $LTB_4$ and a peptidase cleavage of chromogenic substrates. The Zn center is critical to both activities. $LTA_4$-h is related to aminopeptidases M and B, which have no $LTA_4$-hydrolase activity. $LTA_4$-h has high substrate specificity, accepting only a 5,6-trans-epoxide with a free carboxylic acid at C-1 of the fatty acid. The double-bond geometry of the substrate is essential for catalysis. $LTA_3$ and $LTA_5$ are the only other weak substrates known to date. In contrast, $LTA_4$-h peptidase activity appears to be promiscuous, cleaving nitroanilide and 2-naphthylamide derivatives of various amino acids, e.g. in particular alanine and arginine. Arg-Gly-Asp, Arg-Gly-Gly, and Arg-His-Phe tripeptides are hydrolyzed with specificity constants ($k_{cat}/K_m$) similar to the epoxide hydrolase reaction. There is no known physiological peptide substrate for $LTA_4$-h.

$LTA_4$-h is widely expressed as a soluble intracellular enzyme in intestine, spleen, lung and kidney. High activity levels are found in neutrophils, monocytes, lymphocytes and erythrocytes. Tissue macrophages can have high $LTA_4$-h levels. An interesting feature is that the cellular distribution of $LTA_4$-h and 5-LO are distinct, requiring close apposition of cells such as neutrophils and epithelial cells for efficient transcellular $LTB_4$ synthesis. Many studies support this concept, including recent data from bone marrow chimeras derived from $LTA_4$-h$^{-/-}$ and 5-LO$^{-/-}$ mice (J. E. Fabre et al., *J. Clin. Invest.* 2002, 109(10):1373-1380).

These important functions of $LTB_4$ in inflammation and potentially in autoimmunity prompted an aggressive search at numerous pharmaceutical companies to discover potent $LTB_4$ receptor antagonists. These efforts were initiated long before the molecular identity of $LTB_4$ receptors was known.

Drug discovery efforts focused on competition binding of small molecule antagonists or agonists at [$^3$H]-LTB$_4$ binding sites and functional responses, e.g. chemotaxis in human neutrophils. Despite the presence of a stereospecific, high affinity [$^3$H]-LTB$_4$ receptor ($K_d$<1 nM) on human neutrophils, it was apparent from early studies that additional lower affinity LTB$_4$ receptors ($K_d$>60 nM) were also present on neutrophils (D. W. Goldman and E. J. Goetzl, *J. Exp. Med.* 1984 159(4):1027-1041). This LTB$_4$ receptor heterogeneity was subsequently confirmed in HL-60 leukemia cells (C. W. Benjamin et al., *J. Biol. Chem.* 1985, 260(26): 14208-14213), alveolar macrophages (A. J. de Brum et al., *Prostaglandins* 1990, 40(5):515-527), peritoneal eosinophils (R. Sehmi et al., *Immunol.* 1992, 77(1):129-135) and other cell types.

The seminal work of Takao Shimizu and colleagues in cloning human LTB$_4$ receptors has recently defined two pharmacologically distinct receptors (T. Shimizu et al., *Ernst Schering Res. Found. Workshop* 2000, (31):125-141). Human BLT1 and its mouse, rat and guinea pig orthologues represent the high affinity LTB$_4$ receptor ($K_d$ 0.1-0.7 nM). BLT1 has a restricted expression in inflammatory cells, e.g. neutrophils, monocytes, thymus and spleen. Human and mouse BLT2 have a wider tissue expression profile than BLT1, with evidence for mRNA transcripts predominantly in spleen, liver, ovary and leukocytes and lower transcript levels in many other tissues (T. Yokomizo et al., *J. Exp. Med.* 2000, 192(3):421-432; T. Yokomizo et al., *J. Biol. Chem.* 2001, 276(15):12454-12459). Human BLT2 had 20-fold lower affinity for LTB$_4$ ($K_d$=23 nM) than BLT1 and much weaker, but measurable affinity for other eicosanoids. The distinct pharmacology of BLT1 and BLT2 receptors was shown by [$^3$H]-LTB$_4$ competition binding studies with industry-standard LTB$_4$ receptor antagonists. Most known LTB$_4$ receptor antagonists were able to compete for binding to BLT1 but not to BLT2.

These findings suggest that local concentrations of LTB$_4$ generated at sites of inflammation will provide graded responses to different cell types based on either unique or regulated co-expression of BLT1 and BLT2 receptors. This was confirmed by co-expression of BLT1 and BLT2 in CHO cells, which exhibited a broader dose response range to LTB$_4$-stimulated chemotaxis than either receptor alone (T. Yokomizo et al., *Life Sci.* 2001, 68(19-20):2207-2212). The data also suggest that the failure or success of a given LTB$_4$ receptor antagonist in pre-clinical efficacy models of inflammatory or autoimmune disease and in human clinical trials needs to be re-examined in light of pharmacological effects at these distinct BLT1 and BLT2 receptors.

Further analysis of LTB$_4$ receptor subtype expression in immune cells has been performed by semi-quantitative PCR analysis (T. Yokomizo et al., *Life Sci.* 2001, 68(19-20):2207-2212). Data suggest BLT1 mRNA expression is highest in CD14+ monocytes, while BLT2 mRNA expression is high in CD8+ cytotoxic T-, CD4+ helper T-, and CD19+ B-cells. These findings have not been corroborated with clear evidence for differential BLT1 and BLT2 expression at the protein level. Although a BLT1-specific antibody has been reported (A. Pettersson et al., *Biochem. Biophys. Res. Commun.* 2000, 279(2):520-525), anti-BLT2 antibody are not yet available. Nevertheless, the known responses of some of these cell types to LTB$_4$ (see above) suggest a role for BLT2 in modulating T- and B-lymphocyte-dependent immune biology. While an LTB$_4$ receptor antagonist may differ in its affinity for BLT1 vs BLT2, blocking the production of LTB$_4$ using LTA$_4$-h inhibitors would be expected to inhibit the downstream events mediated through both BLT1 and BLT2.

Studies have shown that introduction of exogenous LTB$_4$ into normal tissues can induce inflammatory symptoms (R. D. R. Camp et al., *Br. J. Pharmacol.* 1983, 80(3):497-502; R. Camp et al., *J. Invest. Dermatol.* 1984, 82(2):202-204). Elevated levels of LTB$_4$ have been observed in a number of inflammatory diseases including inflammatory bowel disease (IBD), chronic obstructed pulmonary disease (COPD), psoriasis, rheumatoid arthritis (RA), cystic fibrosis, multiple sclerosis (MS), and asthma (S. W. Crooks and R. S. Stockley, *Int. J. Biochem. Cell Biol.* 1998, 30(2):173-178). Therefore, reduction of LTB$_4$ production by an inhibitor of LTA$_4$-h activity would be predicted to have therapeutic potential in a wide range of diseases.

This idea is supported by a study of LTA$_4$-h-deficient mice that, while otherwise healthy, exhibited markedly decreased neutrophil influx in arachidonic acid-induced ear inflammation and zymosan-induced peritonitis models (R. S. Byrum et al., *J. Immunol.* 1999, 163(12):6810-68129). LTA$_4$-h inhibitors have been shown to be effective anti-inflammatory agents in preclinical studies. For example, oral administration of LTA$_4$-h inhibitor SC57461 caused inhibition of ionophore-induced LTB4 production in mouse blood ex vivo, and in rat peritoneum in vivo (J. K. Kachur et al., *J. Pharm. Exp. Thr.* 2002, 300(2): 583-587). Eight weeks of treatment with the same inhibitor significantly improved colitis symptoms in cotton top tamarins (T. D. Penning, *Curr. Pharm. Des.* 2001, 7(3):163-179). The spontaneous colitis that develops in these animals is very similar to human IBD. The results therefore indicate that LTA$_4$-h inhibitors would have therapeutic utility in this and other human inflammatory diseases.

Inflammation may be observed in any one of a plurality of conditions, such as asthma, COPD, atherosclerosis, rheumatoid arthritis, multiple sclerosis, inflammatory bowel diseases (IBD, including Crohn's disease and ulcerative colitis), or psoriasis, which are each characterized by excessive or prolonged inflammation at some stage of the disease. The connection between inflammatory diseases and cancer has been strengthened by the strong link established between a mutation of the oncogene ras and a de-novo expression of the BLT2 receptor as well as activation of LTB$_4$ synthesis in tumor cells (M.-H. Yoo et al. 2004, Oncogene, 23, 9259). Previously it was shown in various cell models that oncogenic ras induces cytosolic phospolipase A (cPLA$_2$) thus increasing the release of arachidonic acid (L. E. Heasley et al. 1997, *J. Biol. Chem.*, 272, 14501) and the synthesis of LTB$_4$. Inhibition of this pathway through an LTA$_4$-h inhibitor would have a therapeutic utility in the treatment of cancers.

Events that elicit the inflammatory response include the formation of the pro-inflammatory mediator LTB$_4$, which can be blocked with an LTA$_4$-h inhibitor, thus providing the ability to prevent and/or treat leukotriene-mediated conditions, such as inflammation. The inflammatory response is characterized by pain, increased temperature, redness, swelling, or reduced function, or by a combination of two or more of these symptoms. Regarding the onset and evolution of inflammation, inflammatory diseases or inflammation-mediated diseases or conditions include, but are not limited to, acute inflammation, allergic inflammation, and chronic inflammation.

Background and review material on inflammation and conditions related with inflammation can be found in articles such as the following: C. Nathan, Points of control in inflammation, *Nature* 2002, 420:846-852; K. J. Tracey, The inflammatory reflex, *Nature* 2002, 420:853-859; L. M. Coussens and Z. Werb, Inflammation and cancer, *Nature*

2002, 420:860-867; P. Libby, Inflammation in atherosclerosis, *Nature* 2002, 420:868-874; C. Benoist and D. Mathis, Mast cells in autoimmune disease, *Nature* 2002, 420:875-878; H. L. Weiner and D. J. Selkoe, Inflammation and therapeutic vaccination in CNS diseases, *Nature* 2002, 420: 879-884; J. Cohen, The immunopathogenesis of sepsis, *Nature* 2002, 420:885-891; D. Steinberg, Atherogenesis in perspective: Hypercholesterolemia and inflammation as partners in crime, *Nature Medicine* 2002, 8(11):1211-1217. Cited references are incorporated herein by reference.

The connection between members of the leukotriene pathway, particularly $LTA_4$-h and $LTB_4$, and myocardial infarction and acute coronary syndrome has recently been disclosed in PCT Published Patent Application WO 2004/035741, PCT Published Patent Application WO 2004/035746, PCT Published Patent Application WO 2005/027886, PCT Published Patent Application WO 2005/075022, and U.S. Published Patent Application US 2005/0113408, the pertinent disclosures of which are incorporated by reference in their entireties, and in *Nature Genetics*, Advanced Online Communication, Nov. 10, 2005.

Accordingly, there exists a need for inhibitors of the $LTA_4$-h enzyme, particularly inhibitors that are useful in the inhibition of pro-inflammatory mediators, such as the $LTB_4$ mediator. Such inhibitors would be useful in the treatment of diseases and conditions as set forth herein.

SUMMARY

This invention is directed to compounds, as single stereoisomers or as mixtures of stereoisomers, or pharmaceutically acceptable salts, solvates, polymorphs, clathrates, ammonium ions, N-oxides or prodrugs thereof, that inhibit the activity of $LTA_4$-h and are therefore useful as pharmaceutical agents for the treatment of diseases and disorders which are ameliorated by the inhibition of $LTA_4$-h activity.

Accordingly, in one aspect, the invention provides compounds of Formula (I):

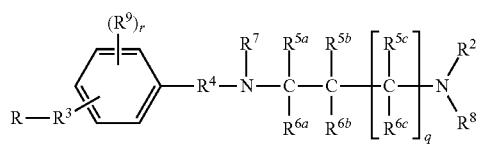

wherein:
R is i) the group

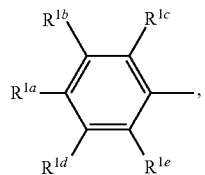

ii) the group

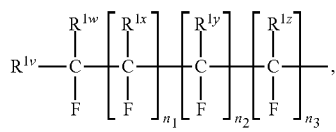

or iii) an optionally substituted heteroaryl;

$n_1$, $n_2$, and $n_3$ are each independently 0 to 2;

r is 0 to 4;

q is 0 to 2;

$R^{1a}$, $R^{1b}$, $R^{1c}$, $R^{1d}$ and $R^{1e}$ are each independently hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, or optionally substituted heterocyclylalkyl;

$R^{1v}$, $R^{1w}$, $R^{1x}$, $R^{1y}$ and $R^{1z}$ are each independently hydrogen or fluoro;

$R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, or optionally substituted heterocyclylalkyl;

or $R^2$ and $R^7$, together with the nitrogens to which they are attached, form an optionally substituted 5- to 7-membered N-heterocyclyl;

or $R^2$ and $R^7$, together with the nitrogens to which they are attached and one of $R^{5a}$, $R^{5b}$ and $R^{5c}$, form an optionally substituted 6- to 10-membered bridged N-heterocyclyl;

or $R^2$ and $R^{5a}$, together with the nitrogen and carbon to which they are attached, form an optionally substituted 5- to 7-membered N-heterocyclyl or an optionally substituted 6- to 10-membered bridged N-heterocyclyl;

or $R^2$ and $R^{5b}$, together with the nitrogen and carbon to which they are attached, form an optionally substituted 5- to 7-membered N-heterocyclyl;

or $R^2$ and $R^8$, together with the nitrogen to which they are attached, form an optionally substituted N-heterocyclyl or an optionally substituted N-heteroaryl;

$R^3$ is a direct bond, $-O-$, $-R^{12}-O-$, $-O-R^{12}-$, $-O-R^{12}-O-$, an optionally substituted straight or branched alkylene chain, an optionally substituted straight or branched alkenylene chain, or an optionally substituted straight or branched alkynylene chain;

$R^4$ is a direct bond, $-O-R^{12a}-$, an optionally substituted straight or branched alkylene chain, an optionally substituted straight or branched alkenylene chain, or an optionally substituted straight or branched alkynylene chain;

each $R^{5a}$, $R^{5b}$, $R^{5c}$, $R^{6a}$, $R^{6b}$ and $R^{6c}$ are each independently hydrogen, alkyl, haloalkyl or hydroxyalkyl;

or any one of $R^{5a}$ and $R^{6a}$ together, $R^{5b}$ and $R^{6b}$ together, and $R^{5c}$ and $R^{6c}$ together can be an oxo group;

or $R^{5a}$ and $R^{5b}$, together with the carbons to which they are attached, form an optionally substituted 3- to 7-membered cycloalkyl;

or $R^{5a}$ and $R^{5c}$, together with the carbons to which they are attached, form an optionally substituted 4- to 7-membered cycloalkyl;

or $R^{5b}$ and $R^{6b}$, together with the carbon to which they are attached, form an optionally substituted 3- to 7-membered cycloalkyl;

$R^7$ is hydrogen, $-R^{13}-OR^{10}$, $-R^{13}-C(=O)R^{10}$, $-R^{13}-C(=O)OR^{10}$, $-R^{13}-C(=O)-R^{13}-N(R^{10})R^{11}$, $-R^{13}-N(R^{10})C(=O)N(R^{10})R^{11}$, alkyl, haloalkyl, optionally substituted cycloalkyl, optionally substituted cycloalkylalkyl, optionally substituted aryl, optionally substituted aralkyl, optionally substituted heteroarylalkyl, or optionally substituted heterocyclylalkyl;

or $R^7$ and $R^{5a}$, together with the nitrogen and carbon to which they are attached, form an optionally substituted 5- to 7-membered N-heterocyclyl;

or $R^7$ and $R^{5a}$, together with the nitrogen and carbon to which they are attached, form an optionally substituted 5- to 7-membered N-heterocyclyl and $R^2$ and $R^{5c}$, together with the nitrogen and carbon to which are they are attached, form an optionally substituted 5- to 7-membered N-heterocyclyl;

or $R^7$ and $R^{5b}$, together with the nitrogen and carbon to which they are attached, form an optionally substituted 5- to 7-membered N-heterocyclyl;

or $R^7$ and $R^{5c}$, together with the nitrogen and carbon to which they are attached, form an optionally substituted 5- to 7-membered N-heterocyclyl or an optionally substituted 6- to 10-membered bridged N-heterocyclyl;

$R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2);

or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$;

each $R^9$ is independently —O—$R^{10}$, alkyl, hydroxyalkyl, halo, haloalkyl, aryl or aralkyl;

each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl;

or $R^{10}$ and $R^{11}$, together with the nitrogen to which they are attached, form an optionally substituted N-heterocyclyl or an optionally substituted N-heteroaryl;

$R^{12}$ is an optionally substituted straight or branched alkylene chain, an optionally substituted straight or branched alkenylene chain, or an optionally substituted straight or branched alkynylene chain;

$R^{12a}$ is an optionally substituted straight or branched alkylene chain, an optionally substituted straight or branched alkenylene chain, or an optionally substituted straight or branched alkynylene chain;

each $R^{13}$ is independently a direct bond, an optionally substituted straight or branched alkylene chain, an optionally substituted straight or branched alkenylene chain, or an optionally substituted straight or branched alkynylene chain; and each $R^{14}$ is independently an optionally substituted straight or branched alkylene chain, an optionally substituted straight or branched alkenylene chain, or an optionally substituted straight or branched alkynylene chain;

as a single stereoisomer or as a mixture of stereoisomers;

or a pharmaceutically acceptable salt, solvate, polymorph, clathrate, ammonium ion, N-oxide or prodrug thereof.

In another aspect, this invention provides pharmaceutical compositions, which composition comprises a therapeutically effective amount of a compound of formula (I) as described above, and a pharmaceutically acceptable excipient.

In another aspect, this invention provides a method of treating a disease or disorder ameliorated by the inhibition of LTA$_4$-h activity in a mammal, which method comprises administering to a mammal in need thereof a therapeutically effective amount of a compound of formula (I) as described above.

DESCRIPTION OF REPRESENTATIVE EMBODIMENTS

Definitions

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

Furthermore, as used in the specification and appended claims, unless specified to the contrary, the following terms have the meaning indicated:

"Amino" refers to the —NH$_2$ radical.
"Cyano" refers to the —CN radical.
"Hydroxy" refers to the —OH radical.
"Nitro" refers to the —NO$_2$ radical.
"Oxo" refers to the =O radical.
"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group may be optionally substituted by one of the following substituents: halo, cyano, nitro, oxo, trimethylsilyl, —$OR^{15}$, —OC(=O)—$R^{15}$, —N($R^{15}$)$_2$, —C(=O)$R^{15}$, —C(=O)$OR^{15}$, —C(=O)N($R^{15}$)$_2$, —N($R^{15}$)C(=O)$OR^{15}$, —N($R^{15}$)C(=O)$R^{15}$, —N($R^{15}$)S(=O)$_t$$R^{15}$ (where t is 1 or 2), —S(=O)$_t$$OR^{15}$ (where t is 1 or 2), —S(=O)$_p$$R^{15}$ (where p is 0, 1 or 2), and —S(=O)$_t$N($R^{15}$)$_2$ (where t is 1 or 2) where each $R^{15}$ is independently hydrogen, alkyl, haloalkyl, cycloalkyl, cycloalkylalkyl, aryl (optionally substituted with one or more halo or alkyl groups), aralkyl, heterocyclyl, heterocyclylalkyl, heteroaryl or heteroarylalkyl, and where each of the above substituents is unsubstituted unless otherwise indicated unless specifically defined otherwise.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, for example, ethenyl, prop-1-enyl, but-1-enyl, pent-1-enyl, penta-1,4-dienyl, and the like. Unless stated otherwise specifically in the specification, an alkenyl group may be optionally substituted by one of the following substituents: cyano, nitro, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated unless specifically defined otherwise.

"Alkynyl" refers to a straight or branched hydrocarbon chain radical group consisting solely of carbon and hydrogen atoms, containing at least one triple bond, optionally containing at least one double bond, having from two to twelve carbon atoms, preferably two to eight carbon atoms and which is attached to the rest of the molecule by a single bond, for example, ethynyl, propynyl, butynyl, pentynyl, hexynyl, and the like. Unless stated otherwise specifically in the specification, an alkynyl group may be optionally substituted by one of the following substituents: cyano, nitro, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless specifically defined otherwise.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain may be optionally substituted by one of the following substituents: halo, cyano, nitro, aryl, cycloalkyl, heterocyclyl, heteroaryl, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following substituents: halo, cyano, nitro, aryl, cycloalkyl, heterocyclyl, heteroaryl, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{10}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, for example, propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following substituents: alkyl, alkenyl, halo, haloalkenyl, cyano, nitro, aryl, cycloalkyl, heterocyclyl, heteroaryl, oxo, trimethylsilyl, $-OR^{15}$, $-OC(=O)-R^{15}$, $-N(R^{15})_2$, $-C(=O)R^{15}$, $-C(=O)OR^{15}$, $-C(=O)N(R^{15})_2$, $-N(R^{15})C(=O)OR^{15}$, $-N(R^{15})C(=O)R^{15}$, $-N(R^{15})S(=O)_tR^{15}$ (where t is 1 or 2), $-S(=O)_tOR^{15}$ (where t is 1 or 2), $-S(=O)_pR^{15}$ (where p is 0, 1 or 2), and $-S(=O)_tN(R^{15})_2$ (where t is 1 or 2) where each $R^{15}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl, and where each of the above substituents is unsubstituted unless otherwise indicated.

"Alkoxy" refers to a radical of the formula $-OR_a$ where $R_a$ is an alkyl radical as defined above containing one to twelve carbon atoms. The alkyl part of the alkoxy radical may be optionally substituted as defined above for an alkyl radical.

"Alkoxyalkyl" refers to a radical of the formula $-R_a-O-R_a$ where each $R_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})C(=O)N(R^{15})_2$, $-R^{16}-N(R^{15})S(=O)_tR^{15}$ (where t is 1 or 2), $-R^{16}-S(=O)_tOR^{15}$ (where t is 1 or 2), $-R^{16}-S(=O)_pR^{15}$ (where p is 0, 1 or 2), and $-R^{16}-S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"Aralkyl" refers to a radical of the formula $-R_aR_b$ where $R_a$ is an alkyl radical as defined above and $R_b$ is one or more aryl radicals as defined above, for example, benzyl, diphenylmethyl and the like. The aryl radical(s) may be optionally substituted as described above.

"Aralkenyl" refers to a radical of the formula $-R_cR_b$ where $R_c$ is an alkenyl radical as defined above and $R_b$ is one or more aryl radicals as defined above. The aryl part of the aralkenyl radical may be optionally substituted as described above for an aryl group. The alkenyl part of the aralkenyl radical may be optionally substituted as defined above for an alkenyl group.

"Aralkynyl" refers to a radical of the formula $-R_dR_b$ where $R_d$ is an alkynyl radical as defined above and $R_b$ is one or more aryl radicals as defined above. The aryl part of the aralkynyl radical may be optionally substituted as described above for an aryl group. The alkynyl part of the aralkynyl radical may be optionally substituted as defined above for an alkynyl group.

"Aryloxy" refers to a radical of the formula $-OR_b$ where $R_b$ is an aryl group as defined above. The aryl part of the aryloxy radical may be optionally substituted as defined above.

"Aralkyloxy" refers to a radical of the formula $-OR_b$ where $R_b$ is an aralkyl group as defined above. The aralkyl part of the aralkyloxy radical may be optionally substituted as defined above.

"Ammonium ion" refers to a nitrogen within a compound of the invention containing a positive charge due to the additional substitution of the nitrogen with an optionally substituted alkyl group as defined above.

"Clathrates" as used herein refers to substances which fix gases, liquids or compounds as inclusion complexes so that the complex may be handled in solid form and the included constituent (or "guest" molecule) is subsequently released by the action of a solvent or by melting. The term "clathrate" is used interchangeably herein with the phrase "inclusion molecule" or with the phrase "inclusion complex". Clathrates used in the instant invention are prepared from cyclodextrins. Cyclodextrins are widely known as having the ability to form clathrates (i.e., inclusion compounds) with a variety of molecules. See, for example, *Inclusion Compounds*, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2-44; Weber, E. et al., "Functional Group Assisted Clathrate Formation—Scissor-Like and Roof-Shaped Host Molecules", *Topics in Current Chemistry* (1988), Vol. 149, pp. 45-135; and MacNicol, D. D. et al., "Clathrates and Molecular Inclusion Phenomena", *Chemical Society Reviews* (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344-362; U.S. Pat. No. 4,886,788 (Schering AG); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cyclodextrin" refers to cyclic oligosaccharides consisting of at least six glucopyranose units which are joined together by α(1-4) linkages. The oligosaccharide ring forms a torus with the primary hydroxyl groups of the glucose residues lying on the narrow end of the torus. The secondary glucopyranose hydroxyl groups are located on the wider end. Cyclodextrins have been shown to form inclusion complexes with hydrophobic molecules in aqueous solutions by binding the molecules into their cavities. The formation of such complexes protects the "guest" molecule from loss of evaporation, from attack by oxygen, visible and ultraviolet light and from intra- and intermolecular reactions. Such complexes also serve to "fix" a volatile material until the complex encounters a warm moist environment, at which point the complex will dissolve and dissociate into the guest molecule and the cyclodextrin. For purposes of this invention, the six-glucose unit containing cyclodextrin is specified as α-cyclodextrin, while the cyclodextrins with seven and eight glucose residues are designated as β-cyclodextrin and γ-cyclodextrin, respectively. The most common alternative to the cyclodextrin nomenclature is the naming of these compounds as cycloamyloses.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantine, norbornane, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N$ ($R^{15}$)C(=O)N($R^{15}$)$_2$, —$R^{16}$—N($R^{15}$)S(=O)$_t$$R^{15}$ (where t is 1 or 2), —$R^{16}$—S(=O)$_t$OR$^{15}$ (where t is 1 or 2), —$R^{16}$—S(=O), $R^{15}$ (where p is 0, 1 or 2), and —$R^{16}$—S(=O)$_t$N($R^{15}$)$_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"Cycloalkylalkyl" refers to a radical of the formula —$R_a R_e$ where $R_a$ is an alkyl radical as defined above and $R_e$ is a cycloalkyl radical as defined above. The alkyl radical and the cycloalkyl radical may be optionally substituted as defined above.

"Cycloalkylalkenyl" refers to a radical of the formula —$R_c R_e$ where $R_c$ is an alkenyl radical as defined above and $R_e$ is a cycloalkyl radical as defined above. The alkenyl radical and the cycloalkyl radical may be optionally substituted as defined above.

"Cycloalkylalkynyl" refers to a radical of the formula —$R_d R_e$ where $R_d$ is an alkynyl radical as defined above and $R_e$ is a cycloalkyl radical as defined above. The alkynyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Haloalkenyl" refers to an alkenyl radical, as defined above, that is substituted by one or more halo radicals, as defined above. The alkenyl part of the haloalkyl radical may be optionally substituted as defined above for an alkenyl group.

"Haloalkynyl" refers to an alkynyl radical, as defined above, that is substituted by one or more halo radicals, as defined above. The alkynyl part of the haloalkyl radical may be optionally substituted as defined above for an alkynyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azepinyl, 2,5-diazabicyclo[2.2.1]heptan-2-yl, hexahydro-1H-1,4-diazepinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxiranyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{16}$—OR$^{15}$, —$R^{16}$—OC(=O)—$R^{15}$, —$R^{16}$—N($R^{15}$)$_2$, —$R^{16}$—C(=O)R$^{15}$, —$R^{16}$—C(=O)OR$^1$b, —$R^{16}$—C(=O)N($R^{15}$)$_2$, —$R^{16}$—N($R^{15}$)C(=O)OR$^{15}$, —$R^{16}$—N($R^{15}$)C(=O)R$^{15}$, —$R^{16}$—N($R^{15}$)C(=O)N($R^{15}$)$_2$, —$R^{16}$—N($R^{15}$)S(=O), $R^{15}$ (where t is 1 or 2), —$R^{16}$—S(=O)$_t$OR$^{15}$ (where t is 1 or 2), —$R^{16}$—S(=O), $R^{15}$ (where p is 0, 1 or 2), and —$R^{16}$—S(=O)$_t$N($R^{15}$)$_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical may be optionally substituted as described above for heterocyclyl radicals.

"Heterocyclylalkyl" refers to a radical of the formula —$R_a R_f$ where $R_a$ is an alkyl radical as defined above and $R_f$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heterocyclylalkenyl" refers to a radical of the formula —$R_c R_f$ where $R_c$ is an alkenyl radical as defined above and $R_f$ is a heterocyclyl radical as defined above, and if the heterocyclyl is a nitrogen-containing heterocyclyl, the heterocyclyl may be attached to the alkenyl radical at the nitrogen atom. The alkenyl part of the heterocyclylalkenyl radical may be optionally substituted as defined above for an alkenyl group. The heterocyclyl part of the heterocyclylalkenyl radical may be optionally substituted as defined above for a heterocyclyl group.

"Heterocyclylalkynyl" refers to a radical of the formula —$R_d R_f$ where $R_d$ is an alkynyl radical as defined above and $R_f$ is a heterocyclyl radical as defined above, and if the heterocyclyl is a nitrogen-containing heterocyclyl, the heterocyclyl may be attached to the alkynyl radical at the nitrogen atom. The alkynyl part of the heterocyclylalkynyl radical may be optionally substituted as defined above for an alkynyl group. The heterocyclyl part of the heterocyclylalkynyl radical may be optionally substituted as defined above for a heterocyclyl group.

"Heteroaryl" refers to a 3- to 18-membered fully or partially aromatic ring radical which consists of one to thirteen carbon atoms and from one to six heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; the nitrogen, carbon or sulfur atoms in the heteroaryl radical may be optionally oxidized; and the nitrogen atom may be optionally quaternized. Examples include, but are not limited to, acridinyl, benzimidazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrazolyl, pyridinyl, pyrazinyl, pyrimidinyl, pyridazinyl, pyrrolyl, quinazolinyl, quinoxalinyl, quinolinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, oxo, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{19})_2$, $-R^{16}-N(R^{15})C(=O)OR^{15}$, $-R^{16}-N(R^{15})C(=O)R^{15}$, $-R^{16}-N(R^{15})C(=O)N(R^{15})_2$, $-R^{16}-N(R^{15})S(=O)_tR^{15}$ (where t is 1 or 2), $-R^{16}-S(=O)_tOR^{15}$ (where t is 1 or 2), $-R^{16}-S(=O)_pR^{15}$ (where p is 0, 1 or 2), and $-R^{16}-S(=O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical may be optionally substituted as described above for heteroaryl radicals.

"Heteroarylalkyl" refers to a radical of the formula $-R_aR_g$ where $R_a$ is an alkyl radical as defined above and $R_g$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula $-R_cR_g$ where $R_c$ is an alkenyl radical as defined above and $R_g$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Heteroarylalkynyl" refers to a radical of the formula $-R_dR_g$ where $R_d$ is an alkynyl radical as defined above and $R_g$ is a heteroaryl radical as defined above. The heteroaryl part of the heteroarylalkynyl radical may be optionally substituted as defined above for a heteroaryl group. The alkynyl part of the heteroarylalkynyl radical may be optionally substituted as defined above for an alkynyl group.

"Hydroxyalkyl" refers to an alkyl radical, as defined above, substituted by one or more hydroxy (—OH) groups. If the hydroxyalkyl radical is attached to a hetero atom (e.g., oxygen or nitrogen), a hydroxy group can not be attached to a carbon in the alkyl group which is directly attached to the hetero atom.

"Hydroxyiminoalkyl" refers to an alkyl radical, as defined above, substituted by a hydroxyimino (=NOH) group.

"Polymorph" refers to a polymorphic form of compound of the invention. Solids exist in either amorphous or crystalline forms. In the case of crystalline forms, molecules are positioned in 3-dimensional lattice sites. When a compound recrystallizes from a solution or slurry, it may crystallize with different spatial lattice arrangements, a property referred to as "polymorphism," with the different crystal forms individually being referred to as a "polymorph". Different polymorphic forms of a given substance may differ from each other with respect to one or more physical properties, such as solubility and dissociation, true density, crystal shape, compaction behavior, flow properties, and/or solid state stability. In the case of a chemical substance that exists in two (or more) polymorphic forms, the unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability. However, the metastable form may exhibit sufficient chemical and physical stability under normal storage conditions to permit its use in a commercial form. In this case, the metastable form, although less stable, may exhibit properties desirable over those of the stable form, such as enhanced solubility or better oral bioavailability.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients.

"Solvate" refers to an aggregate that comprises one or more molecules of a compound of the invention with one or more molecules of solvent. The solvent may be water, in which case the solvate may be a hydrate. Alternatively, the solvent may be an organic solvent.

Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

"Therapeutically effective amount" refers to that amount of a compound of the invention that, when administered to a mammal, preferably a human, is sufficient to effect treatment, as defined below, of a disease or condition of interest in the mammal, preferably a human. The amount of a compound of the invention which constitutes a "therapeutically effective amount" will vary depending on, e.g., the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy, but it can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as for example, but not limited to, HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The chemical naming protocol and structure diagrams used herein employ and rely on the Chemical Abstracts Service (CAS) rules. For complex chemical names employed herein, a substituent group is named before the group to which it attaches. For example, 2-cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

For example, a compound of formula (I) wherein r is 0; q is 1; $R^{1a}$ is 2-oxazolyl; $R^{1b}$, $R^{1c}$, $R^{1d}$ and $R^{1e}$ are each hydrogen; $R^2$ is methyl; $R^3$ is —O—; $R^4$ is methylene; $R^{5a}$, $R^{5b}$, $R^{5c}$, $R^{6a}$, $R^{6b}$, and $R^{6c}$ are each hydrogen; $R^7$ is methyl; and $R^8$ is 4-carboxybenzyl; i.e., a compound of the following formula:

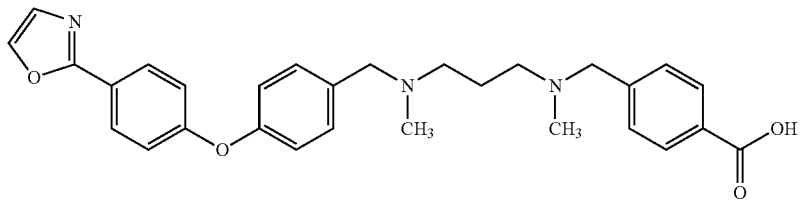 [SMILES: CN(CCCN(C)Cc1ccc(C(=O)O)cc1)Cc1ccc(Oc2ccc(-c3ncco3)cc2)cc1]

is named herein as 4-[[methyl[3-[methyl[[4-[4-(2-oxazolyl)phenoxy]phenyl]methyl]amino]propyl]amino]methyl]benzoic acid.

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors and can be determined routinely by one of ordinary skill in the art. Generally, a therapeutically effective daily dose is (for a 70 kg mammal) from about 0.001 mg/kg (i.e., 0.7 mg) to about 100 mg/kg (i.e., 7.0 gm); preferably a therapeutically effective dose is (for a 70 kg mammal) from about 0.01 mg/kg (i.e., 7 mg) to about 50 mg/kg (i.e., 3.5 gm); more preferably a therapeutically effective dose is (for a 70 kg mammal) from about 1 mg/kg (i.e., 70 mg) to about 25 mg/kg (i.e., 1.75 gm).

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent can be administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Utility of the Compounds of the Invention

The compounds of the invention are inhibitors of $LTA_4$-h activity and are therefore useful in treating diseases and disorders which are ameliorated by the inhibition of $LTA_4$-h activity. Such diseases and conditions include inflammatory and autoimmune disorders and pulmonary and respiratory tract inflammation.

Accordingly, the compounds are useful in the treatment of the following diseases or disorders in mammals, particularly humans: acute or chronic inflammation, anaphylactic reactions, allergic reactions, allergic contact dermatitis, allergic rhinitis, chemical and non-specific irritant contact dermatitis, urticaria, atopic dermatitis, psoriasis, fistulas associated with Crohn's disease, pouchitis, septic or endotoxic shock, hemorrhagic shock, shock-like syndromes, capillary leak syndromes induced by immunotherapy of cancer, acute respiratory distress syndrome, traumatic shock, immune- and pathogen-induced pneumonias, immune complex-mediated pulmonary injury and chronic obstructive pulmonary disease, inflammatory bowel diseases (including ulcerative colitis, Crohn's disease and post-surgical trauma), gastrointestinal ulcers, diseases associated with ischemia-reperfusion injury (including acute myocardial ischemia and infarction, acute renal failure, ischemic bowel disease and acute hemorrhagic or ischemic stroke), immune-complex-mediated glomerulonephritis, autoimmune diseases (including insulin-dependent diabetes mellitus, multiple sclerosis, rheumatoid arthritis, osteoarthritis and systemic lupus erythematosus), acute and chronic organ transplant rejection, transplant arteriosclerosis and fibrosis, cardiovascular disorders (including hypertension, atherosclerosis, aneurysm, critical leg ischemia, peripheral arterial occlusive disease and Reynaud's syndrome), complications of diabetes (including diabetic nephropathy, neuropathy and retinopathy), ocular disorders (including macular degeneration and glaucoma), neurodegenerative disorders (including delayed neurodegeneration in stroke, Alzheimer's disease, Parkinson's disease, encephalitis and HIV dementia), inflammatory and neuropathic pain including arthritic pain, periodontal disease including gingivitis, ear infections, migraine, benign prostatic hyperplasia, and cancers (including, but not limited to, leukemias and lymphomas, prostate cancer, breast cancer, lung cancer, malignant melanoma, renal carcinoma, head and neck tumors and colorectal cancer).

The compounds are also useful in treating folliculitis induced by inhibitors of epidermal growth factor (EGF) or epidermal growth factor receptor (EGFR) kinase used in the treatment of solid tumors. Clinical trials have revealed folliculitis (inflammation of the hair follicle manifested by severe acne-like skin rash on the face, chest and upper back) as a major dose-limiting side effect of such treatments. Such folliculitis is associated with an infiltration of neutrophils suggesting products secreted by activated neutrophils to be the cause of the inflammation. The compounds of the invention inhibit neutrophil or eosinophil-mediated inflammation, and are therefore useful in treating such folliculitis, thereby improving the quality of life of the treated cancer patients but also allowing for the increase of the dosage of the EGF inhibitor or EGFR kinase inhibitor or the extension of the duration of the treatment, resulting in improved efficacy of the desired inhibitor.

The compounds are also useful in the treatment of pulmonary and respiratory inflammation disorders in mammals, particularly humans, including, but not limited to, asthma, chronic bronchitis, bronchiolitis, bronchiolitis obliterans (including such with organizing pneumonia), allergic inflammation of the respiratory tract (including rhinitis and sinusitis), eosinophilic granuloma, pneumonias, pulmonary fibroses, pulmonary manifestations of connective tissue diseases, acute or chronic lung injury, chronic obstructive pulmonary diseases, adult respiratory distress syndrome, and other non-infectious inflammatory disorders of the lung characterized by eosinophil infiltration.

For example, the compounds of the invention are useful in the inhibition of: eosinophil-mediated inflammation of the lung or tissues; neutrophil-mediated inflammation of the lung; lymphocyte-mediated inflammation of the lung; airway hyper-responsiveness; and airway and vascular inflammation.

The compounds are also useful in the treatment of myocardial infarction or susceptibility to myocardial infarction in mammals, particularly humans, transient ischemic attack, transient monocular blindness, stroke or susceptibility of stroke, claudication, peripheral arterial occlusive disease or susceptibility to peripheral arterial occlusive disease, and acute coronary syndrome (such as unstable angina, non-ST-elevation myocardial infarction or ST-elevation myocardial infarction). The compounds are also useful in the methods for reducing the risk of myocardial infarction, stroke or peripheral arterial occlusive disease in mammals and reducing the risk of a second myocardial infarction or stroke.

The compounds are also useful in the treatment of atherosclerosis in mammals, particularly humans who require treatment (such as angioplasty, stents, coronary artery bypass graft) in order to restore blood flow in the arteries (such as in the coronary arteries).

The compounds are also useful in inhibiting the synthesis of leukotriene $B_4$ in both in vitro and in vivo assays.

Testing of the Compounds of the Invention

The compounds of the invention were tested for their ability to inhibit $LTA_4$-h by various known assays and by assays described herein. For example, the compounds were tested for their ability to inhibit $LTA_4$-h activity by assaying the compounds in the hydrolase-homogeneous time resolved fluorescence assay. This assay, which is a two-step assay, measures the hydrolysis of $LTA_4$ to $LTB_4$ by analyzing the amount of $LTB_4$ produced. The first step involves the enzymatic conversion of $LTA_4$ to $LTB_4$ and the second step involves the quantification of the $LTB_4$ formed with a homogeneous time resolved fluorescence assay.

Since $LTA_4$ hydrolase is grouped with the M1 family of zinc metalloproteases (see, Rudberg, P. C. et al., *J. Biol. Chem.* 2002, Vol. 277, page 1398-1404), the compounds of the invention can be tested in the standard hydrolase and peptidase assay to determine the compounds' kinetic constants for binding to $LTA_4$ hydrolase and for inhibiting $LTB_4$ synthesis (see Askonas, L. J., et al., *The Journal of Pharmacology and Experimental Therapeutics* 2002, 300(2): 577-582; Penning, T. D., *J. Med. Chem.* 2000, 43(4): 721-735; Kull, F. et al., *The Journal of Biological Chemistry* 1999, 274 (49): 34683-34690).

Compounds of the invention can also be tested for their ability as inhibitors of $LTA_4$ hydrolase in the whole blood assay using human, mouse, rat or dog whole blood (see Penning, T. D. et al., *J. Med. Chem.* (2000), 43(4): 721-735 for a description of a human whole blood assay and a mouse whole blood assay).

A hallmark of inflammation is the adhesion and transmigration across endothelium of neutrophils, eosinophils and other inflammatory cells. A similar process is observed for the migration of cells across polarized epithelial cells that occur in the lung, gastrointestinal tract and other organs. Cell culture models of these processes are available and can be used to show the ability of the compounds of the invention to inhibit the transmigration of human neutrophils across human endothelial cells and epithelial cells, including the human intestinal epithelial cell line $T_{84}$. Accordingly, one of ordinary skill in the art can test the compounds of the invention for their ability to inhibit the transmigration of human neutrophils and eosinophils across human endothelial cells and epithelial cells by performing assays similar to those described in Colgan, S. P., et al., *J. Clin. Invest.* 1993, Vol. 92, No. 1, pp. 75-82, and Serhan, C. N., et al., *Biochemistry* 1995, Vol. 34, No. 44, pp. 14609-14615.

The air pouch model and/or the mouse zymosan-induced peritonitis model may be used to evaluate the in vivo efficacy of the compounds of the invention in treating an inflammatory response. These are acute experimental models of inflammation characterized by infiltration of inflammatory cells into a localized area. See, e.g., the in vivo assays described in Ajuebor, M. N., et al., *Immunology* 1998, Vol. 95, pp. 625-630; Gronert, K., et al., *Am. J. Pathol.* 2001, Vol. 158, pp. 3-9; Pouliot, M., et al., *Biochemistry* 2000, Vol. 39. pp. 4761-4768; Clish, C. B., et al., *Proc. Natl. Acad. Sci. U.S.A.* 1999, Vol. 96, pp. 8247-8252; Hachicha, M., et al., *J. Exp. Med.* 1999, Vol. 189, pp. 1923-30.

Animal models (i.e., in vivo assays) may also be utilized to determine the efficacy of the compounds of the invention in treating asthma and related disorders of the pulmonary and respiratory tract, including, but not limited to, asthma. See, e.g., the assays described in De Sanctis, G. T. et al., *Journal of Clinical Investigation* 1999, Vol. 103, pp. 507-515, and Campbell, E. M., et al., *J. Immunol.* 1998, Vol. 161, No. 12, pp. 7047-7053.

EXEMPLARY EMBODIMENTS OF THE INVENTION

A. One aspect of the invention are the compounds of Formula (I), as single stereoisomers or as mixtures of stereoisomers, and the pharmaceutically acceptable salts, solvates, polymorphs, clathrates, ammonium ions, N-oxides or prodrugs thereof, as set forth above in the Summary.

Another aspect of the invention are the compounds of Formula (I-1)), as single stereoisomers or as mixtures of stereoisomers, and the pharmaceutically acceptable salts, solvates, polymorphs, clathrates, ammonium ions, N-oxides or prodrugs thereof, as set forth above in the Summary:

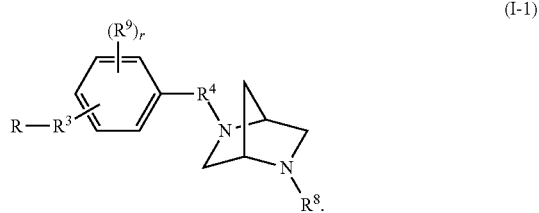

(I-1)

Another aspect of the invention are the compounds of Formula (I-2), as single stereoisomers or as mixtures of stereoisomers, and the pharmaceutically acceptable salts, solvates, polymorphs, clathrates, ammonium ions, N-oxides or prodrugs thereof, as set forth above in the Summary:

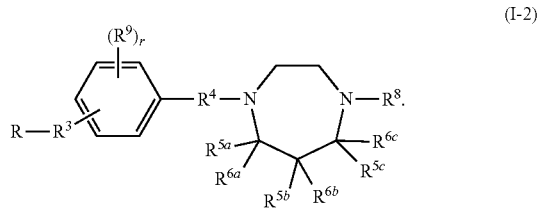

(I-2)

Another aspect of the invention are the compounds of Formula (I-3), as single stereoisomers or as mixtures of stereoisomers, and the pharmaceutically acceptable salts, solvates, polymorphs, clathrates, ammonium ions, N-oxides or prodrugs thereof, as set forth above in the Summary:

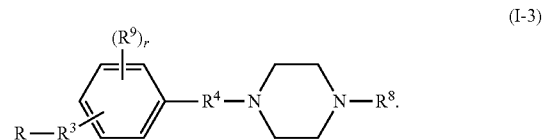

(I-3)

Another aspect of the invention are the compounds of Formula (I-4), as single stereoisomers or as mixtures of stereoisomers, and the pharmaceutically acceptable salts, solvates, polymorphs, clathrates, ammonium ions, N-oxides or prodrugs thereof, as set forth above in the Summary:

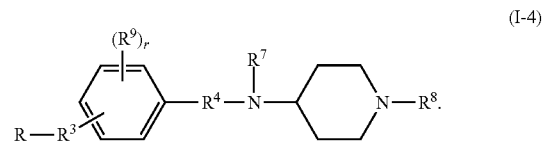

(I-4)

Another aspect of the invention are the compounds of Formula (I-5), as single stereoisomers or as mixtures of stereoisomers, and the pharmaceutically acceptable salts, solvates, polymorphs, clathrates, ammonium ions, N-oxides or prodrugs thereof, as set forth above in the Summary:

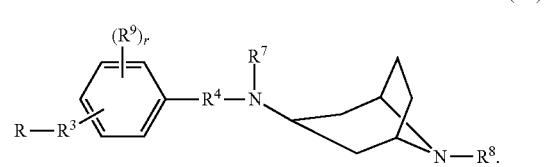

(I-5)

B. Another aspect of the invention are the compounds of Formula (I) where R is an optionally substituted phenyl and having Formula (I-B):

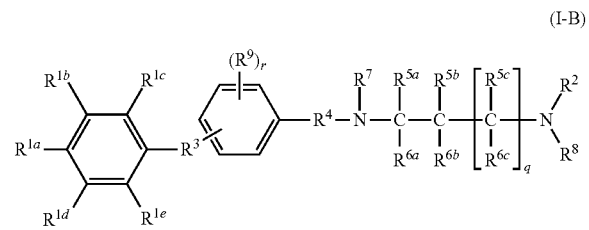

(I-B)

wherein the substituents are as described above in the Summary.

Accordingly, one embodiment of the compounds of Formula (I-B) are those wherein r is 0 to 4; q is 0 to 2; $R^{1a}$, $R^{1b}$, $R^{1c}$, $R^{1d}$ and $R^{1e}$ are each independently selected from the group consisting of hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^2$ and $R^7$, together with the nitrogens to which they are attached and one of $R^{5a}$, $R^{5b}$ and $R^{5c}$, form an optionally substituted 6- to 10-membered bridged N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(O)$_t$N($R^{10}$)$R^{11}$, —$R^{13}$—N($R^{10}$)C(=O)—$R^{13}$—N($R^{10}$)C(=O)$OR^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$, and —$R^{13}$—O—$R^{14}$—C(=O)$OR^{10}$, where t is 1 or 2; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-B) having the following formula (I-B-1):

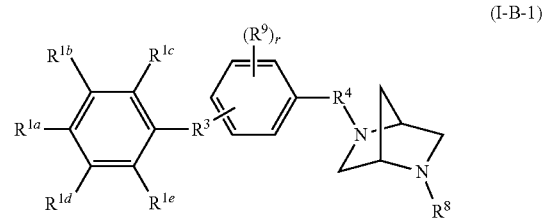

(I-B-1)

wherein r is 0 to 4; $R^{1a}$, $R^{1b}$, $R^{1c}$, $R^{1d}$ and $R^{1e}$ are each independently selected from the group consisting of hydrogen, —$R^{13}$—$OR^{10}$, —$R^{13}$—C(=O)$OR^{10}$, —$R^{13}$—C(=O)$R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$, —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$, —$R^{13}$—N($R^{10}$)C(=O)—$R^{13}$—N($R^{10}$)C(=O)$OR^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$, and —$R^{13}$—O—$R^{14}$—C(=O)$OR^{10}$, where t is 1 or 2; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-B-1) wherein r is 0 to 4; $R^{1a}$ is hydrogen, —$R^{13}$—C(=O)O$R^{10}$, —$R^{13}$—C(=O)$R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{1b}$, $R^{1c}$, $R^{1d}$ and $R^{1e}$ are each independently hydrogen or halo; $R^3$ is a direct bond, —O—, —$R^{12}$—O—, —O—$R^{12}$—O—, or an optionally substituted straight or branched alkylene chain; $R^4$ is a direct bond, —O—$R^{12}$, or an optionally substituted straight or branched alkylene chain; $R^8$ is aralkyl optionally substituted with —$R^{13}$—C(=O)O$R^{10}$ or —$R^{13}$—C(=O)N($R^{10}$)$R^{11}$; each $R^9$ is independently alkyl, halo or —O—$R^{10}$; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; and each $R^{13}$ is a direct bond or an optionally substituted straight or branched alkylene chain.

Another embodiment are those compounds of formula (I-B-1) wherein r is 0 to 4; $R^{1a}$ is hydrogen, —$R^{13}$—C(=O)O$R^{10}$, —$R^{13}$—C(=O)$R^{10}$, alkyl, halo, haloalkyl, optionally substituted phenyl, furanyl, thienyl, thiazolyl, or optionally substituted oxazolyl; $R^{1b}$, $R^{1c}$, $R^{1d}$ and $R^{1e}$ are each hydrogen; $R^3$ is a direct bond, —O—, —$R^{12}$—O—, —O—$R^{12}$—O— or methylene; $R^4$ is a direct bond, —O—$R^{12a}$— or an optionally substituted straight or branched alkylene chain; each $R^{5a}$, $R^{5b}$, $R^{6a}$ and $R^{6b}$ are hydrogen; $R^8$ is benzyl substituted with —$R^{13}$—C(=O)O$R^{10}$; each $R^9$ is independently —O—$R^{10}$, or halo; $R^{10}$ is hydrogen, alkyl or optionally substituted aryl; each $R^{12}$ is methylene or ethylene; $R^{12a}$ is methylene or ethylene; and each $R^{13}$ is a direct bond or an optionally substituted straight or branched alkylene chain.

Specific embodiments of the compounds of formula (I-B-1) include the following compounds:

4-[[(1S,4S)-5-[2-[4-(phenylmethyl)phenoxy]ethyl]-2,5-diazabicyclo[2.2.1]hept-2-yl]methyl]benzoic acid;

4-[[(1S,4S)-5-[(4-phenoxyphenyl)methyl]-2,5-diazabicyclo[2.2.1]hept-2-yl]methyl]benzoic acid;

4-[[(1S,4S)-5-[[4-(4-fluorophenoxy)phenyl]methyl]-2,5-diazabicyclo[2.2.1]hept-2-yl]methyl]benzoic acid;

4-[[(1S,4S)-5-[[4-(2-phenylethoxy)phenyl]methyl]-2,5-diazabicyclo[2.2.1]hept-2-yl]methyl]benzoic acid;

4-[[(1S,4S)-5-[3-(4-phenoxyphenyl)propyl]-2,5-diazabicyclo[2.2.1]hept-2-yl]methyl]benzoic acid;

4-[[(1S,4S)-5-[[4-(4-chlorophenoxy)phenyl]methyl]-2,5-diazabicyclo[2.2.1]hept-2-yl]methyl]benzoic acid;

4-[[(1S,4S)-5-[2-(4-phenoxyphenyl)ethyl]-2,5-diazabicyclo[2.2.1]hept-2-yl]methyl]benzoic acid;

4-[[(1S,4S)-5-[[4-(2-phenoxyethoxy)phenyl]methyl]-2,5-diazabicyclo[2.2.1]hept-2-yl]methyl]benzoic acid;

4-[[(1S,4S)-5-[[4-(4-bromophenoxy)phenyl]methyl]-2,5-diazabicyclo[2.2.1]hept-2-yl]methyl]benzoic acid;

4-[[(1S,4S)-5-[2-[4-[(4-chlorophenyl)methyl]phenoxy]ethyl]-2,5-diazabicyclo[2.2.1]hept-2-yl]methyl]benzoic acid;

4-[[(1S,4S)-5-[2-[4-[(4-fluorophenyl)methyl]phenoxy]ethyl]-2,5-diazabicyclo[2.2.1]hept-2-yl]methyl]benzoic acid;

4-[[(1S,4S)-5-[[4-[(2'-fluoro[1,1'-biphenyl]-4-yl)oxy]phenyl]methyl]-2,5-diazabicyclo[2.2.1]hept-2-yl]methyl]benzoic acid;

4-[[(1S,4S)-5-[[4-[4-(3-furanyl)phenoxy]phenyl]methyl]-2,5-diazabicyclo[2.2.1]hept-2-yl]methyl]benzoic acid;

4-[[(1S,4S)-5-[[4-[4-(trifluoromethyl)phenoxy]phenyl]methyl]-2,5-diazabicyclo[2.2.1]hept-2-yl]methyl]benzoic acid;

4-[[(1S,4S)-5-[[4-(4-acetylphenoxy)phenyl]methyl]-2,5-diazabicyclo[2.2.1]hept-2-yl]methyl]benzoic acid;

4-[[(1S,4S)-5-[[4-[4-(3-thienyl)phenoxy]phenyl]methyl]-2,5-diazabicyclo[2.2.1]hept-2-yl]methyl]benzoic acid;

4-[[(1S,4S)-5-[[4-[4-(3,5-dimethyl-4-isoxazolyl)phenoxy]phenyl]methyl]-2,5-diazabicyclo[2.2.1]hept-2-yl]methyl]benzoic acid;

4-[[(1S,4S)-5-[(3-fluoro-4-phenoxyphenyl)methyl]-2,5-diazabicyclo[2.2.1]hept-2-yl]methyl]benzoic acid;

4-[[(1S,4S)-5-[[3-(2-phenylethoxy)phenyl]methyl]-2,5-diazabicyclo[2.2.1]hept-2-yl]methyl]benzoic acid;

4-[[(1S,4S)-5-[[4-[4-(2-oxazolyl)phenoxy]phenyl]methyl]-2,5-diazabicyclo[2.2.1]hept-2-yl]methyl]benzoic acid;

4-[[(1S,4S)-5-[(4-fluoro-2-phenoxyphenyl)methyl]-2,5-diazabicyclo[2.2.1]hept-2-yl]methyl]benzoic acid;

4-[[(1S,4S)-5-[(3-phenoxyphenyl)methyl]-2,5-diazabicyclo[2.2.1]hept-2-yl]methyl]benzoic acid;

4-[[(1S,4S)-5-[(2-fluoro-4-phenoxyphenyl)methyl]-2,5-diazabicyclo[2.2.1]hept-2-yl]methyl]benzoic acid;

4-[[(1S,4S)-5-[(2,4-diphenoxyphenyl)methyl]-2,5-diazabicyclo[2.2.1]hept-2-yl]methyl]benzoic acid;

4-[[(1S,4S)-5-([1,1'-biphenyl]-4-ylmethyl)-2,5-diazabicyclo[2.2.1]hept-2-yl]methyl]benzoic acid;

4-[[(1S,4S)-5-[(4-phenoxyphenyl)methyl]-2,5-diazabicyclo[2.2.1]hept-2-yl]methyl]benzeneacetic acid;

4-[[(1S,4S)-5-[[4-(2-phenoxyethoxy)phenyl]methyl]-2,5-diazabicyclo[2.2.1]hept-2-yl]methyl]benzeneacetic acid;

4-[[(1S,4S)-5-[[4-(2-phenylethoxy)phenyl]methyl]-2,5-diazabicyclo[2.2.1]hept-2-yl]methyl]benzeneacetic acid;

methyl 4-[[(1S,4S)-5-[[4-[4-(2-oxazolyl)phenoxy]phenyl]methyl]-2,5-diazabicyclo[2.2.1]hept-2-yl]methyl]benzoate;

4-[[(1S,4S)-5-[[4-[4-(2-thiazolyl)phenoxy]phenyl]methyl]-2,5-diazabicyclo[2.2.1]hept-2-yl]methyl]benzoic acid; and methyl 4-[[(1S,4S)-5-[[4-[4-(2-thiazolyl)phenoxy]phenyl]methyl]-2,5-diazabicyclo[2.2.1]hept-2-yl]methyl]benzoate.

Another embodiment of the compounds of formula (I-B) are those wherein r is 0 to 4; q is 0 to 2; $R^{1a}$, $R^{1b}$, $R^{1c}$, $R^{1d}$ and $R^{1e}$ are each independently selected from the group consisting of hydrogen, —$R^{13}$—O$R^{10}$, —$R^{13}$—C(=O)O$R^{10}$, —$R^{13}$—C(=O)$R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^2$ and $R^7$, together with the nitrogens to which they are attached, form an optionally substituted 5- to 7-membered N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; each Rea, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$, —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$, and —$R^{13}$—O—$R^{14}$—C(=O)$OR^{10}$, where t is 1 or 2; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I) having the following formula (I-B-2):

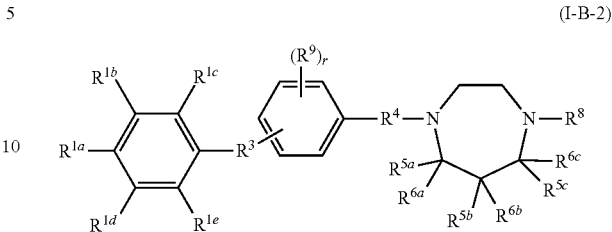

(I-B-2)

wherein r is 0 to 4; $R^{1a}$, $R^{1b}$, $R^{1c}$, $R^{1d}$ and $R^{1e}$ are each independently selected from the group consisting of hydrogen, —$R^{13}$—$OR^{10}$, —$R^{13}$—C(=O)$OR^{10}$, —$R^{13}$—C(=O)$R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$, —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^4$—N($R^{10}$)$R^{11}$, —$R^{13}$—N($R^{10}$)S(=O)$_t$N($R^{10}$)$R^{11}$, and —$R^{13}$—O—$R^{14}$—C(=O)$OR^{10}$, where t is 1 or 2; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{44}$ is an optionally substituted straight or branched alkylene chain, an optionally substituted straight or branched alkenylene chain, or an optionally substituted straight or branched alkynylene chain.

Another embodiment are those compounds of formula (I-B-2) wherein $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more substituents selected from the group consisting of halo), optionally substituted aralkyl, heteroaryl (optionally substituted with one or more substituents selected from the group consisting of alkyl), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^3$ is a direct bond, $-O-$, $-R^{12}-O-$, $-O-R^{12}-$, $-O-R^{12}-O-$, or an optionally substituted straight or branched alkylene chain; $R^4$ is a direct bond, $-O-R^{12}-$, or an optionally substituted straight or branched alkylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{14}-C(=O)OR^{10}$, $-R^{13}-C(=O)R^{10}$, $-R^{13}-C(=O)OR^{10}$, $-R^{13}-C(=O)-R^{14}-C(=O)OR^{10}$, $-R^{13}-C(=O)-R^{13}-N(R^{10})R^{11}$, $-R^{13}-C(=O)-R^{14}-S(=O)_tN(R^{10})R^{11}$ (where t is 1 or 2), or $-R^{14}-S(=O)_pR^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{11}$, $-R^{13}-C(=O)OR^{10}$, $-R^{13}-C(=O)-R^{13}-N(R^{10})R^{11}$, $-R-C(=O)N(R^{10})-R^{14}-N(R^{10})R^{11}$, $-R^{13}-S(=O)_tN(R^{10})R^{11}$, $-R^{13}-N(R^{10})R^{11}$, $-R^{13}-N(R^{10})C(=O)R^{11}$, $-R^{13}-N(R^{10})C(=O)-R^{13}-N(R^{10})R^{11}$, $-R^{13}-N(R^{10})-R^{14}-C(=O)OR^{10}$, $-R^{13}-N(R^{10})C(=O)-R^{14}-S(=O)_tN(R^{10})R^{11}$, $-R^{13}-N(R^{10})C(=O)-R^{13}-N(R^{10})C(=O)R^{10}$, $-R^{13}-N(R^{10})C(=O)-R^{13}-N(R^{10})-R^{14}-N(R^{10})R^{11}$, $-R^{13}-N(R^{10})S(=O)_tN(R^{10})R^{11}$, and $-R^{13}-O-R^{14}-C(=O)OR^{10}$, where t is 1 or 2; each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-B-2) wherein r is 0 to 4; $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^3$ is a direct bond, $-O-$, $-R^{12}-O-$, $-O-R^{12}-$, $-O-R^{12a}-$, or an optionally substituted straight or branched alkylene chain; $R^4$ is a direct bond, $-O-R^{12a}-$, or an optionally substituted straight or branched alkylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{14}-C(=O)OR^{10}$, $-R^{13}-C(=O)R^{10}$, $-R^{13}-C(=O)OR^{10}$, $-R^{13}-C(=O)-R^{14}-C(=O)OR^{10}$, $-R^{13}-C(=O)-R^{13}-N(R^{10})R^{11}$, $-R^{13}-C(=O)-R^{14}-S(=O)_tN(R^{10})R^{11}$ (where t is 1 or 2), or $-R^{14}-S(=O)_pR^{10}$ (where p is 0, 1 or 2); each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Specific compounds of this embodiment include the following:

hexahydro-1-[[4-(phenylmethoxy)phenyl]methyl]-1H-1,4-diazepine;

methyl hexahydro-4-[[4-(phenylmethoxy)phenyl]methyl]-1H-1,4-diazepine-1-acetate;

ethyl hexahydro-4-[[4-(phenylmethoxy)phenyl]methyl]-1H-1,4-diazepin-1-butanoate;

methyl hexahydro-4-[[4-(phenylmethoxy)phenyl]methyl]-1H-1,4-diazepine-1-propanoate;
hexahydro-S-oxo-4-[[4-(phenylmethoxy)phenyl]methyl]-1H-1,4-diazepine-1-butanesulfonamide;
hexahydro-4-[[4-(phenylmethoxy)phenyl]methyl]-1H-1,4-diazepine-1-propanoic acid; hexahydro-4-[[4-(phenylmethoxy)phenyl]methyl]-1H-1,4-diazepine-1-butanoic acid; and
hexahydro-1-[[4-(phenylmethoxy)phenyl]methyl]-4-[2-(phenylsulfonyl)ethyl]-1H-1,4-diazepine.

Another embodiment of the compounds of formula (I-B-2) include those compounds wherein r is 0 to 4; $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^3$ is a direct bond, $-O-$, $-R^{12}-O-$, $-O-R^{12}-$, $-O-R^{1}-O-$, or an optionally substituted straight or branched alkylene chain; $R^4$ is a direct bond, $-O-R^{12a}-$, or an optionally substituted straight or branched alkylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is aralkyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{11}$, $-R^{13}-C(=O)OR^{10}$, $-R^{13}-C(=O)-R^{13}-N(R^{10})R^{11}$, $-R^{13}-C(=O)N(R^{10})-R^{14}-N(R^{10})R^{11}$, $-R^{13}-S(=O)_tN(R^{10})R^{11}$, $-R^{13}-N(R^{10})R^{11}$, $-R^{13}-N(R^{10})C(=O)R^{10}$, $-R^{13}-N(R^{10})C(=O)-R^{13}-N(R^{10})R^{11}$, $-R^{13}-N(R^{10})-R^{14}-C(=O)OR^{10}$, $-R^{13}-N(R^{10})C(=O)-R^{14}-S(=O)_tN(R^{10})R^{11}$, $-R^{13}-N(R^{10})C(=O)-R^{13}-N(R^{10})C(=O)R^{10}$, $-R^{13}-N(R^{10})C(=O)-R^{13}-N(R^{10})-R^{14}-N(R^{10})R^{11}$, $-R^{13}-N(R^{10})S(=O)_tN(R^{10})R^{11}$, and $-R^{13}-O-R^{14}-C(=O)OR^{10}$, where t is 1 or 2; each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-B-2) are those compounds wherein r is 0 to 4; $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^3$ is a direct bond, $-O-$, $-R^{12}-O-$, $-O-R^{12}-$, $-O-R^{12}-O-$, or an optionally substituted straight or branched alkylene chain; $R^4$ is a direct bond, $-O-R^{12a}-$, or an optionally substituted straight or branched alkylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is benzyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{10}$, $-R^{13}-C(=O)OR^{10}$, $-R^{13}-C(=O)-R^{13}-N(R^{10})R^{11}$, $-R^{13}-C(=O)N(R^{10})-R^{14}-N(R^{10})R^{11}$, $-R^{13}-S(=O)_tN(R^{10})R^{11}$, $-R^{13}-N(R^{10})R^{11}$, $-R^{13}-N(R^{10})C(=O)R^{10}$, $-R^{13}-N(R^{10})C(=O)-R^{13}-N(R^{10})R^{11}$, $-R^{13}-N(R^{10})-R^{14}-C(=O)OR^{10}$, $-R^{13}-N(R^{10})C(=O)-R^{14}-S(=O)_tN(R^{10})R^{11}$, $-R^{13}-N(R^{10})C(=O)-R^{13}-N(R^{10})C(=O)R^{10}$, $-R^{13}-N(R^{10})C(=O)-R^{13}-N(R^{10})-R^{14}-N(R^{10})R^{11}$, $-R^{13}-N(R^{10})S(=O)_tN(R^{10})R^{11}$, and $-R^{13}-O-R^{14}-C(=O)OR^{10}$, where t is 1 or 2; each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; each $R^{12}$ is an optionally substituted straight or branched alkylene chain; $R^{12}$, is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-B-2) are those compounds wherein r is 0; $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^3$ is a direct bond, $-O-$, $-R^{12}-O-$, $-O-R^{12}-$, $-O-R^{12}-O-$, or an optionally substituted straight or branched methylene or ethylene chain; $R^4$ is a direct bond, $-O-R^{12a}-$, or an optionally substituted straight or branched methylene, ethylene or propylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is benzyl substituted with $-R^{13}-C(=O)OR^{10}$; each $R^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; each $R^{12}$ is a methylene, ethylene or propylene chain (each optionally substituted with one or more substituents selected from the group consisting of $-OR^{10}$); $R^{12a}$ is a methylene, ethylene or propylene chain (each optionally substituted with one or more substituents selected from the group consisting of $-OR^{10}$); and each $R^{13}$ is a direct bond or an optionally substituted straight or branched alkylene chain.

Specific compounds of this embodiment include the following:
4-[[hexahydro-4-[[4-(phenylmethoxy)phenyl]methyl]-1H-1,4-diazepin-1-yl]methyl]benzoic acid;
4-[[hexahydro-4-[(4-phenoxyphenyl)methyl]-1H-1,4-diazepin-1-yl]methyl]benzoic acid;
4-[[hexahydro-4-[3-[4-(phenylmethyl)phenoxy]propyl]-1H-1,4-diazepin-1-yl]methyl]benzoic acid;
4-[[hexahydro-4-[2-[4-(phenylmethyl)phenoxy]ethyl]-1H-1,4-diazepin-1-yl]methyl]benzoic acid;

4-[[4-[[4-(4-fluorophenoxy)phenyl]methyl]hexahydro-1H-1,4-diazepin-1-yl]methyl]benzoic acid;
4-[[hexahydro-4-[[4-[4-(1H-pyrrol-1-yl)phenoxy]phenyl]methyl]-1H-1,4-diazepin-1-yl]methyl]benzoic acid;
4-[[hexahydro-4-[[4-[(RS)-2-hydroxy-2-phenylethoxy]phenyl]methyl]-1H-1,4-diazepin-1-yl]methyl]benzoic acid;
4-[[hexahydro-4-[[4-(2-phenylethyl)phenyl]methyl]-1H-1,4-diazepin-1-yl]methyl]benzoic acid;
4-[[hexahydro-4-[[4-(2-phenylethoxy)phenyl]methyl]-1H-1,4-diazepin-1-yl]methyl]benzoic acid;
4-[[hexahydro-4-[[4-(2-phenoxyethoxy)phenyl]methyl]-1H-1,4-diazepin-1-yl]methyl]benzoic acid;
4-[[hexahydro-4-[3-(4-phenoxyphenyl)propyl]-1H-1,4-diazepin-1-yl]methyl]benzoic acid;
4-[[hexahydro-4-[2-(4-phenoxyphenyl)ethyl]-1H-1,4-diazepin-1-yl]methyl]benzoic acid;
4-[[4-[[4-(4-bromophenoxy)phenyl]methyl]hexahydro-1H-1,4-diazepin-1-yl]methyl]benzoic acid;
4-[[hexahydro-4-[[4-[(4'-methoxy[1,1'-biphenyl]-4-yl)oxy]phenyl]methyl]-1H-1,4-diazepin-1-yl]methyl]benzoic acid;
4-[[4-[[4-[(4'-fluoro[1,1'-biphenyl]-4-yl)oxy]phenyl]methyl]-hexahydro-1H-1,4-diazepin-1-yl]methyl]benzoic acid;
4-[[4-[[4-[(2'-fluoro[1,1'-biphenyl]-4-yl)oxy]phenyl]methyl]-hexahydro-1H-1,4-diazepin-1-yl]methyl]benzoic acid;
4-[[4-[[4-[4-(3-furanyl)phenoxy]phenyl]methyl]-hexahydro-1H-1,4-diazepin-1-yl]methyl]benzoic acid;
4-[[hexahydro-4-[[4-[4-(3-thienyl)phenoxy]phenyl]methyl]-1H-1,4-diazepin-1-yl]methyl]benzoic acid;
4-[[4-[[4-[(4'-cyano[1,1'-biphenyl]-4-yl)oxy]phenyl]methyl]-hexahydro-1H-1,4-diazepin-1-yl]methyl]benzoic acid;
4-[[4-[[4-[4-(1,1-dimethylethyl)phenoxy]phenyl]methyl]hexahydro-1H-1,4-diazepin-1-yl]methyl]benzoic acid;
4-[[4-[[4-[(1,3-benzodioxol-5-yl)oxy]phenyl]methyl]-hexahydro-1H-1,4-diazepin-1-yl]methyl]benzoic acid;
4-[[[[4-[2,3-dihydro-2,2,3,3-tetrafluoro-1,4-benzodioxin-6-yl)oxy]phenyl]methyl]hexahydro-1H-1,4-diazepin-1-yl]methyl]benzoic acid;
4-[[hexahydro-4-[[4-[4-(trifluoromethyl)phenoxy]phenyl]methyl]-1H-1,4-diazepin-1-yl]methyl]benzoic acid;
4-[[4-[[4-(2,4-difluorophenoxy)phenyl]methyl]-hexahydro-1H-1,4-diazepin-1-yl]methyl]benzoic acid;
4-[[4-[[4-(3,4-difluorophenoxy)phenyl]methyl]-hexahydro-1H-1,4-diazepin-1-yl]methyl]benzoic acid;
4-[[hexahydro-4-[[4-(3,4,5-trifluorophenoxy)phenyl]methyl]-1H-1,4-diazepin-1-yl]methyl]benzoic acid;
4-[[4-[[4-(4-chlorophenoxy)phenyl]methyl]hexahydro-1H-1,4-diazepin-1-yl]methyl]benzoic acid;
4-[[4-[[4-([1,1'-biphenyl]-4-yloxy)phenyl]methyl]hexahydro-1H-1,4-diazepin-1-yl]methyl]benzoic acid;
4-[[hexahydro-4-[[4-(2,3,4-trifluorophenoxy)phenyl]methyl]-1H-1,4-diazepin-1-yl]methyl]benzoic acid;
4-[[4-[[4-(4-acetylphenoxy)phenyl]methyl]hexahydro-1H-1,4-diazepin-1-yl]methyl]benzoic acid;
4-[[4-[[4-[4-(2-oxazolyl)phenoxy]phenyl]methyl]-hexahydro-1H-1,4-diazepin-1-yl]methyl]benzoic acid;
4-[[4-[[4-[2-(4-fluorophenyl)ethoxy]phenyl]methyl]hexahydro-1H-1,4-diazepin-1-yl]methyl]benzoic acid;
4-[[hexahydro-4-[2-(4-phenoxyphenoxy)ethyl]-1H-1,4-diazepin-1-yl]methyl]benzoic acid;
4-[[hexahydro-4-[3-[4-[4-(trifluoromethyl)phenoxy]phenoxy]propyl]-1H-1,4-diazepin-1-yl]methyl]benzoic acid;
4-[[hexahydro-4-[[4-(phenylmethoxy)phenyl]methyl]-1H-1,4-diazepin-1-yl]methyl]benzoic acid;
4-[[hexahydro-7-oxo-4-[(4-phenoxyphenyl)methyl]-1H-1,4-diazepin-1-yl]methyl]benzoic acid;
4-[[hexahydro-5-oxo-4-[(4-phenoxyphenyl)methyl]-1H-1,4-diazepin-1-yl]methyl]benzoic acid;
3-[[hexahydro-4-[(4-phenoxyphenyl)methyl]-1H-1,4-diazepin-1-yl]methyl]benzoic acid; and
3-[[hexahydro-4-[[4-(phenylmethoxy)phenyl]methyl]-1H-1,4-diazepin-1-yl]methyl]benzoic acid.

Another embodiment of the compounds of formula (I-B-2) are those wherein r is 0; $R^{10}$ is hydrogen, $—R^{13}—OR^{10}$, $—R^{13}—C(=O)OR^{10}$, $—R^{13}—C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^2$ and $R^7$, together with the nitrogens to which they are attached, form hexahydro-1H-diazepinyl (optionally substituted with oxo); $R^3$ is a direct bond, $—O—$; $—R^{12}—O—$, $—O—R^{12}—$, $—O—R^{12}—O—$, or an optionally substituted straight or branched methylene or ethylene chain; $R^4$ is a direct bond, $—O—R^{12a}—$, or an optionally substituted straight or branched methylene, ethylene or propylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is benzyl substituted with optionally substituted with one or more substituents selected from the group consisting of halo, nitro, cyano, optionally substituted heteroaryl, hydroxyiminoalkyl, $—R^{13}—OR^{10}$, $—R^{13}—C(=O)R^{10}$, $—R^{13}—C(=O)—R^{13}—N(R^{10})R^{11}$, $—R^{13}—C(=O)N(R^{10})—R^{14}—N(R^{10})R^{11}$, $—R^{13}—S(=O)_tN(R^{10})R^{11}$, $—R^{13}—N(R^{10})R^{11}$, $—R^{13}—N(R^{10})C(=O)R^{10}$, $—R^{13}—N(R^{10})C(=O)—R^{13}—N(R^{10})R^{11}$, $—R^{13}—N(R^{10})—R^{14}—C(=O)OR^{10}$, $—R^{13}—N(R^{10})C(=O)—R^{14}—S(=O)_tN(R^{10})R^{11}$, $—R^{13}—N(R^{10})C(=O)—R^{13}—N(R^{10})C(=O)R^{10}$, $—R^{13}—N(R^{10})C(=O)—R^{13}—N(R^{10})—R^{14}—N(R^{10})R^{11}$, $—R^{13}—N(R^{10})S(=O)_tN(R^{10})R^{11}$, and $—R^{13}—O—R^{14}—C(=O)OR^{10}$, where t is 1 or 2; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; each $R^{12}$ is a methylene, ethylene or propylene chain (each optionally substituted with one or more substituents selected from the group consisting of $—OR^{10}$); $R^{12}_a$ is a methylene, ethylene or propylene chain (each optionally substituted with one or more substituents selected from the group consisting of $—OR^{10}$); each $R^{13}$ is a direct bond or an optionally substituted straight or branched alkylene chain; and each $R^{14}$ is an optionally substituted straight or branched alkylene chain.

Specific compounds of this embodiment include the following:
[4-[[hexahydro-4-[(4-phenoxyphenyl)methyl]-1H-1,4-diazepin-1-yl]methyl]phenyl]methanol;
4-[[hexahydro-4-[(4-phenoxyphenyl)methyl]-1H-1,4-diazepin-1-yl]methyl]-α,α-dimethylbenzenemethanol;
4-[[hexahydro-4-[(4-phenoxyphenyl)methyl]-1H-1,4-diazepin-1-yl]methyl]benzonitrile;
(E)-4-[[hexahydro-4-[(4-phenoxyphenyl)methyl]-1H-1,4-diazepin-1-yl]methyl]benzaldehyde oxime;
1-[4-[[hexahydro-4-[(4-phenoxyphenyl)methyl]-1H-1,4-diazepin-1-yl]methyl]phenyl]ethanone;
N-[2-[[hexahydro-4-[[4-(phenylmethoxy)phenyl]methyl]-1H-1,4-diazepin-1-yl]methyl]phenyl]acetamide;

N-[4-[[hexahydro-4-[[4-(phenylmethoxy)phenyl]methyl]-1H-1,4-diazepin-1-yl]methyl]phenyl]acetamide;
2-amino-N-[3-[[hexahydro-4-[[4-(phenylmethoxy)phenyl]methyl]-1H-1,4-diazepin-1-yl]methyl]phenyl]acetamide;
2-amino-N-[2-[[hexahydro-4-[[4-(phenylmethoxy)phenyl]methyl]-1H-1,4-diazepin-1-yl]methyl]phenyl]acetamide;
2-(acetylamino)-N-[2-[[hexahydro-4-[[4-(phenylmethoxy)phenyl]methyl]-1H-1,4-diazepin-1-yl]methyl]phenyl]acetamide;
N-[2-[[hexahydro-4-[[4-(phenylmethoxy)phenyl]methyl]-1H-1,4-diazepin-1-yl]methyl]phenyl]-5-methyl-2-thiophenecarboxamide;
N-[4-[[hexahydro-4-[[4-(phenylmethoxy)phenyl]methyl]-1H-1,4-diazepin-1-yl]methyl]phenyl]-2-methyl-3-pyridinecarboxamide;
N-[3-[[hexahydro-4-[[4-(phenylmethoxy)phenyl]methyl]-1H-1,4-diazepin-1-yl]methyl]phenyl]-N'-(2-hydroxyethyl)urea;
N-[3-[[hexahydro-4-[[4-(phenylmethoxy)phenyl]methyl]-1H-1,4-diazepin-1-yl]methyl]phenyl]-N'-(3-hydroxypropyl)urea;
N-[3-[[hexahydro-4-[[4-(phenylmethoxy)phenyl]methyl]-1H-1,4-diazepin-1-yl]methyl]phenyl]-N-[3-(1H-imidazol-1-yl)propyl]urea;
N-[3-[[hexahydro-4-[[4-(phenylmethoxy)phenyl]methyl]-1H-1,4-diazepin-1-yl]methyl]phenyl]-N'-[2-(1H-imidazol-4-yl)ethyl]urea;
N-[3-[[hexahydro-4-[[4-(phenylmethoxy)phenyl]methyl]-1H-1,4-diazepin-1-yl]methyl]phenyl]-N'-[3-(4-morpholinyl)propyl]urea;
N-[4-[[hexahydro-4-[[4-(phenylmethoxy)phenyl]methyl]-1H-1,4-diazepin-1-yl]methyl]phenyl]-N'-(2-hydroxyethyl)urea;
N-[4-[[hexahydro-4-[[4-(phenylmethoxy)phenyl]methyl]-1H-1,4-diazepin-1-yl]methyl]phenyl]-N'-(3-hydroxypropyl)urea;
N-[4-[[hexahydro-4-[[4-(phenylmethoxy)phenyl]methyl]-1H-1,4-diazepin-1-yl]methyl]phenyl]-N'-[3-(1H-imidazol-1-yl)propyl]urea;
N-[4-[[hexahydro-4-[[4-(phenylmethoxy)phenyl]methyl]-1H-1,4-diazepin-1-yl]methyl]phenyl]-N'-[2-(1H-imidazol-4-yl)ethyl]urea;
N-[2-[[hexahydro-4-[[4-(phenylmethoxy)phenyl]methyl]-1H-1,4-diazepin-1-yl]methyl]phenyl]-N'-[3-(1H-imidazol-1-yl)propyl]urea;
N-[2-[[hexahydro-4-[[4-(phenylmethoxy)phenyl]methyl]-1H-1,4-diazepin-1-yl]methyl]phenyl]-N'-[3-(4-morpholinyl)propyl]urea;
3-amino-N-[2-[[hexahydro-4-[[4-(phenylmethoxy)phenyl]methyl]-1H-1,4-diazepin-1-yl]methyl]phenyl]propanamide;
N-[2-[[hexahydro-4-[[4-(phenylmethoxy)phenyl]methyl]-1H-1,4-diazepin-1-yl]methyl]phenyl]-N'-(2-hydroxyethyl)urea;
2-amino-N-[2-[[hexahydro-4-[[4-(phenylmethoxy)phenyl]methyl]-1H-1,4-diazepin-1-yl]methyl]phenyl]-2-methylpropanamide;
2-amino-N-[4-[[hexahydro-4-[[4-(phenylmethoxy)phenyl]methyl]-1H-1,4-diazepin-1-yl]methyl]phenyl]acetamide;
(S)-α-amino-N-[4-[[hexahydro-4-[[4-(phenylmethoxy)phenyl]methyl]-1H-1,4-diazepin-1-yl]methyl]phenyl]benzenepropanamide;
2-(acetylamino)-N-[4-[[hexahydro-4-[[4-(phenylmethoxy)phenyl]methyl]-1H-1,4-diazepin-1-yl]methyl]phenyl]acetamide;
2-(dimethylamino)-N-[4-[[hexahydro-4-[[4-(phenylmethoxy)phenyl]methyl]-1H-1,4-diazepin-1-yl]methyl]phenyl]acetamide;
N-(2-aminoethyl)-N'-[2-[[hexahydro-4-[[4-(phenylmethoxy)phenyl]methyl]-1H-1,4-diazepin-1-yl]methyl]phenyl]urea;
(S)-2-amino-5-oxo-5-[[4-[[hexahydro-4-[[4-(phenylmethoxy)phenyl]methyl]-1H-1,4-diazepin-1-yl]methyl]phenyl]amino]pentanoic acid;
4-(aminosulfonyl)-N-[2-[[hexahydro-4-[[4-(phenylmethoxy)phenyl]methyl]-1H-1,4-diazepin-1-yl]methyl]phenyl]butanamide;
3-amino-N-[4-[[hexahydro-4-[[4-(phenylmethoxy)phenyl]methyl]-1H-1,4-diazepin-1-yl]methyl]phenyl]propanamide;
(S)—N-[4-[[hexahydro-4-[[4-(phenylmethoxy)phenyl]methyl]-1H-1,4-diazepin-1-yl]methyl]phenyl]pyrrolidine-2-carboxamide;
2-[[3-[[hexahydro-4-[[4-(phenylmethoxy)phenyl]methyl]-1H-1,4-diazepin-1-yl]methyl]phenyl]amino]acetic acid;
2-[[4-[[hexahydro-4-[[4-(phenylmethoxy)phenyl]methyl]-1H-1,4-diazepin-1-yl]methyl]phenyl]amino]acetic acid;
4-[[hexahydro-4-[[4-(phenylmethoxy)phenyl]methyl]-1H-1,4-diazepin-1-yl]methyl]benzenemethanol;
N-[3-[[hexahydro-4-[[4-(phenylmethoxy)phenyl]methyl]-1H-1,4-diazepin-1-yl]methyl]phenyl]sulfamide;
2-[4-[[hexahydro-4-[[4-(phenylmethoxy)phenyl]methyl]-1H-1,4-diazepin-1-yl]methyl]phenoxy]acetic acid; and
2-[3-[[hexahydro-4-[[4-(phenylmethoxy)phenyl]methyl]-1H-1,4-diazepin-1-yl]methyl]phenoxy]acetic acid.

Another embodiment of the compounds of formula (I-B) are those wherein r is 0 to 4; q is 0 to 2; $R^{1a}$, $R^{1b}$, $R^{1c}$, $R^{1d}$ and $R^{1e}$ are each independently selected from the group consisting of hydrogen, —$R^{13}$—$OR^{10}$, —$R^{13}$—C(=O)$OR^{10}$, —$R^{13}$—C(=O)$R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; or $R^{5a}$ and $R^{5b}$, together with the carbons to which they are attached, form an optionally substituted 3- to 7-membered cycloalkyl; or $R^{5a}$ and $R^{5c}$, together with the carbons to which they are attached, form an optionally substituted 4- to 7-membered cycloalkyl; or $R^{5b}$ and $R^{6b}$, together with the carbon to which they are attached, form an optionally substituted 3- to 7-membered cycloalkyl; $R^1$ is selected from the group consisting of hydrogen, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, or optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$, and —$R^{13}$—O—$R^{14}$—C(=O)$OR^{10}$ (where t is 1 or 2); each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-B) are those compounds of formula (I) wherein r is 0 to 4; q is 0 to 2; $R^{1a}$ is hydrogen, —$R^{13}$—$OR^{10}$, —$R^{13}$—C(=O)$OR^{10}$, —$R^{13}$—C(=O)$R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^2$ is hydrogen, alkyl, haloalkyl, hydroxyalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; or $R^{5a}$ and $R^{5b}$, together with the carbons to which they are attached, form an optionally substituted 3- to 7-membered cycloalkyl; or $R^{5a}$ and $R^{5c}$, together with the carbons to which they are attached, form an optionally substituted 4- to 7-membered cycloalkyl; or $R^{5b}$ and $R^{6b}$, together with the carbon to which they are attached, form an optionally substituted 3- to 7-membered cycloalkyl; $R^7$ is selected from the group consisting of hydrogen, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, or optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$, —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$, and —$R^{13}$—O—$R^{14}$—C(=O)$OR^{10}$, where t is 1 or 2; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-B) are those wherein r is 0 to 4; q is 0 to 2; $R^{1a}$ is hydrogen, alkyl, halo, haloalkyl, cyano, or heteroaryl (optionally substituted with one or more alkyl groups); $R^{1b}$, $R^{1c}$, $R^{1d}$ and $R^{1e}$ are each independently hydrogen or halo; $R^2$ is hydrogen, alkyl, haloalkyl, hydroxyalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or $R^{5a}$ and $R^{5b}$, together with the carbons to which they are attached, form an optionally substituted 3- to 7-membered cycloalkyl; or $R^{5a}$ and $R^{5c}$, together with the carbons to which they are attached, form an optionally substituted 4- to 7-membered cycloalkyl; or $R^{5b}$ and $R^{6b}$, together with the carbon to which they are attached, form an optionally substituted 3- to 7-membered cycloalkyl; $R^1$ is selected from the group consisting of hydrogen, —$R^{13}$—C(=O)O$R^{10}$, alkyl, haloalkyl, and optionally substituted aralkyl; $R^8$ is selected from the group consisting of hydrogen, alkyl, or —$R^{13}$—C(=O)$R^{10}$; or $R^8$ is aralkyl optionally substituted with —$R^{13}$—C(=O)O$R^{10}$; each $R^9$ is independently —O—$R^{10}$, alkyl, hydroxyalkyl, halo, haloalkyl, aryl or aralkyl; each $R^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; each $R^{12}$ is an optionally substituted straight or branched alkylene chain; $R^{12a}$ is an optionally substituted straight or branched alkylene chain; and each $R^{13}$ is a direct bond or an optionally substituted straight or branched alkylene chain.

Specific compounds of this embodiment include the following compounds:
4-[[methyl[2-[methyl[[4-(phenylmethoxy)phenyl]methyl]amino]ethyl]amino]methyl]benzoic acid;
4-[[methyl[3-[methyl[[4-(phenylmethoxy)phenyl]methyl]amino]propyl]amino]methyl]benzoic acid;
4-[[methyl[3-[methyl[[4-(2-phenoxyethoxy)phenyl]methyl]amino]propyl]amino]methyl]benzoic acid;
4-[[methyl[2-[methyl[[4-(2-phenylethoxy)phenyl]methyl]amino]ethyl]amino]methyl]benzoic acid;
4-[[methyl[3-[methyl[[4-(2-phenylethoxy)phenyl]methyl]amino]propyl]amino]methyl]benzoic acid;
4-[[methyl[2-[methyl[[4-(2-phenoxyethoxy)phenyl]methyl]amino]ethyl]amino]methyl]benzoic acid;
4-[[methyl[2-[methyl[[4-[4-(2-oxazolyl)phenoxy]phenyl]methyl]amino]ethyl]amino]methyl]benzoic acid;
4-[[methyl[3-[methyl[[4-[4-(2-oxazolyl)phenoxy]phenyl]methyl]amino]propyl]amino]methyl]benzoic acid;
4-[[[4-[[(4-phenoxyphenyl)methyl]amino]cyclohexyl]amino]methyl]benzoic acid;
4-[[methyl[2,2-dimethyl-3-[[[4-[4-(2-oxazolyl)phenoxy]phenyl]methyl]amino]propyl]amino]methyl]benzoic acid;
4-[[methyl[2,2-dimethyl-3-[methyl[[4-(2-phenoxyethoxy)phenyl]methyl]amino]propyl]amino]methyl]benzoic acid;
4-[[methyl[2,2-dimethyl-3-[methyl[[4-[4-(2-oxazolyl)phenoxy]phenyl]methyl]amino]propyl]amino]methyl]benzoic acid;
4-[[methyl[2,2-dimethyl-3-[methyl[[4-(2-phenylethoxy)phenyl]methyl]amino]propyl]amino]methyl]benzoic acid;
N-[2-[[[4-(phenylmethoxy)phenyl]methyl]amino]ethyl]-4-(1H-imidazol-1-yl)benzamide;
4-[[[[4-(4-bromophenoxy)phenyl]methyl][2-(1-pyrrolidinyl)ethyl]amino]methyl]benzoic acid;
1,1-dimethylethyl (2-aminoethyl)[(4-phenoxyphenyl)methyl]carbamate;
N-[(4-phenoxyphenyl)methyl]-1,2-ethanediamine;
N-[5-[(4-phenoxyphenyl)methyl]pentyl]-4-(2H-tetrazol-5-yl)benzamide;
N-[3-[(4-phenoxyphenyl)methyl]propyl]-4-(2H-tetrazol-5-yl)benzamide;
methyl 4-[[[2-(4-morpholinyl)ethyl][(4-phenoxyphenyl)methyl]amino]methyl]benzoate;
4-[[[2-(4-morpholinyl)ethyl][(4-phenoxyphenyl)methyl]amino]methyl]benzoic acid;
N-[[4-(phenylmethoxy)phenyl]methyl]-1,2-ethanediamine;
N-[[4-[(4-methylphenyl)methoxy]phenyl]methyl]-1,2-ethanediamine;
N-[[4-[(2-naphthalenylmethoxy)phenyl]methyl]-1,2-ethanediamine;
(S)-4-methyl-N-[[4-(phenylmethoxy)phenyl]methyl]-1,2-pentanediamine;
N-methyl-N'-[[4-(phenylmethoxy)phenyl]methyl]-1,2-ethanediamine;
3-[[methyl[2-[methyl[[4-(phenylmethoxy)phenyl]methyl]amino]ethyl]amino]methyl]benzoic acid;
4-(1H-imidazol-1-yl)-N-[2-[[(4-phenoxyphenyl)methyl]amino]ethyl]benzamide;
4-fluoro-N-[2-[[(4-phenoxyphenyl)methyl]amino]ethyl]benzamide;
4-cyano-N-[2-[[(4-phenoxyphenyl)methyl]amino]ethyl]benzamide;
4-[[[2-[[(4-phenoxyphenyl)methyl]amino]ethyl]amino]carbonyl]benzoic acid;
4-(4-methyl-1H-imidazol-1-yl)-N-[2-[[(4-phenoxyphenyl)methyl]amino]ethyl]benzamide;
4-(2-methyl-1H-imidazol-1-yl)-N-[2-[[(4-phenoxyphenyl)methyl]amino]ethyl]benzamide;
4-[[[2-(4-morpholinyl)ethyl][2-[4-[[4-(2-oxazolyl)phenyl]methyl]phenoxy]ethyl]amino]methyl]benzoic acid;
N-[2-[[(4-phenoxyphenyl)methyl]amino]ethyl]-4-(2H-tetrazol-5-yl)benzamide; and
N-[2-[[(4-phenoxyphenyl)methyl]amino]ethyl]-3-(2H-tetrazol-5-yl)benzamide.

Another embodiment of this aspect of the invention are compounds of formula (I-B) having the following formula (I-B-3):

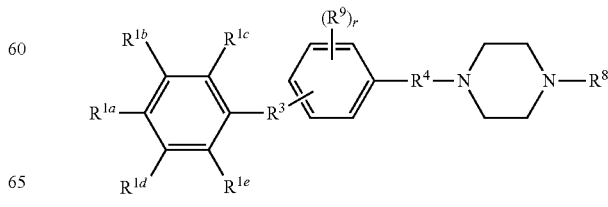

(I-B-3)

wherein r is 0 to 4; $R^{1a}$, $R^{1b}$, $R^{1c}$, $R^{1d}$ and $R^{1e}$ are each independently selected from the group consisting of hydrogen, —$R^{13}$—$OR^{10}$, —$R^{13}$—C(=O)$OR^{10}$, —$R^{13}$—C(=O)$R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(O)$_t$N($R^{10}$)$R^{11}$, and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-B-3) are those wherein r is 0 to 4; $R^{1a}$ is hydrogen, halo, or heteroaryl (optionally substituted with one or more alkyl groups); $R^{1b}$, $R^{1c}$, $R^{1d}$ and R are each independently hydrogen or halo; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; $R^B$ is selected from the group consisting of —$R^{13}$—C(=O)—$R^{14}$—C(=O)$OR^{10}$ or —$R^{13}$—C(=O)—$R^{14}$—S(O)$_1$N($R^{10}$)$R^{11}$; or $R^a$ is aralkyl optionally substituted with one or more substituents selected from the group consisting of —$R^{13}$—C(=O)$OR^{10}$, —$R^{13}$—C(=O)—$R^{13}$—N($R^{10}$)$R^{11}$, —$R^{13}$—N($R^{10}$)C(=O)$R^{10}$, and —$R^{13}$—N($R^{10}$)C(=O)—$R^{13}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Specific embodiments of these compounds include the following:

4-[[4-[[4-(phenylmethoxy)phenyl]methyl]-1-piperazinyl]methyl]benzoic acid;
4-[[4-[[4-(2-phenoxyethoxy)phenyl]methyl]-1-piperazinyl]methyl]benzoic acid;
4-[[4-[[4-(2-phenylethoxy)phenyl]methyl]-1-piperazinyl]methyl]benzoic acid;
4-[[4-[[4-[4-(2-oxazolyl)phenoxy]phenyl]methyl]-1-piperazinyl]methyl]benzoic acid;
N-[2-[[4-[[4-(phenylmethoxy)phenyl]methyl]-1-piperazinyl]methyl]phenyl]-2-thiophenecarboxamide;
N-(2-hydroxyethyl)-N'-[2-[[4-[[4-(phenylmethoxy)phenyl]methyl]-1-piperazinyl]methyl]phenyl]urea;
(S)-2-amino-N-[3-[[4-[[4-(phenylmethoxy)phenyl]methyl]-1-piperazinyl]methyl]phenyl]propanamide;
3-amino-N-[3-[[4-[[4-(phenylmethoxy)phenyl]methyl]-1-piperazinyl]methyl]phenyl]propanamide;
(S)-4-amino-5-oxo-5-[4-[[4-(phenylmethoxy)phenyl]methyl]-1-piperazinyl]pentanoic acid;
δ-oxo-4-[[4-(phenylmethoxy)phenyl]methyl]-1-piperazinebutanesulfonamide; and
3-[[4-[[4-(phenylmethoxy)phenyl]methyl]-1-piperazinyl]methyl]benzoic acid.

Another embodiment of the compounds of formula (I-B) are those wherein r is 0 to 4; q is 0 to 2; $R^{1a}$, $R^{1b}$, $R^{1c}$, $R^{1d}$ and $R^{1e}$ are each independently selected from the group consisting of hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^2$ and $R^{5a}$, together with the nitrogen and carbon to which they are attached, form an optionally substituted 5- to 7-membered N-heterocyclyl or an optionally substituted 6- to 10-membered bridged N-heterocyclyl; or $R^2$ and $R^{5b}$, together with the nitrogen and carbon to which they are attached, form an optionally substituted 5- to 7-membered N-heterocyclyl; $R^3$ is a direct bond, $-O-$, $-R^{12}-O-$, $-O-R^{12}-$, $-O-R^{12}-O-$, an optionally substituted straight or branched alkylene chain, an optionally substituted straight or branched alkenylene chain, or an optionally substituted straight or branched alkynylene chain; $R^4$ is a direct bond, $-O-R^{12}-$, an optionally substituted straight or branched alkylene chain, an optionally substituted straight or branched alkenylene chain, or an optionally substituted straight or branched alkynylene chain; each $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5b}$ and $R^{6b}$ together, and $R^{5c}$ and $R^{6c}$ together can be an oxo group; or $R^{5b}$ and $R^{6b}$, together with the carbon to which they are attached, form an optionally substituted 3- to 7-membered cycloalkyl; $R^1$ is selected from the group consisting of hydrogen, $-R^{13}-OR^{10}$, $-R^{13}-C(=O)R^{10}$, $-R^{13}-C(=O)OR^{10}$, $-R^{13}-C(=O)-R^{13}-N(R^{10})R^{11}$, $-R^{13}-N(R^{10})C(=O)N(R^{10})R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{14}-C(=O)OR^{10}$, $-R^{13}-C(=O)R^{10}$, $-R^{13}-C(=O)OR^{10}$, $-R^{13}-C(=O)-R^{14}-C(=O)OR^{10}$, $-R^{13}-C(=O)-R^{13}-N(R^{10})R^{11}$, $-R^{13}-C(=O)-R^{14}-S(=O)_tN(R^{10})R^{11}$ (where t is 1 or 2), or $-R^{14}-S(=O)_pR^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{10}$, $-R^{13}-C(=O)OR^{10}$, $-R^1-C(=O)-R^{13}-N(R^{10})R^{11}$, $-R^{13}-C(=O)N(R^{10})-R^{14}-N(R^{10})R^{11}$, $-R^{13}-S(O)_tN(R^{10})R^{11}$ (where t is 1 or 2), $-R^{13}-N(R^{10})R^{11}$, $-R^{13}-N(R^{10})C(=O)R^{10}$, $-R^{13}-N(R^{10})C(=O)-R^{13}-N(R^{10})R^{11}$, $-R^{13}-N(R^{10})-R^{13}-N(R^{10})C(=O)OR^{10}$, $-R^{13}-N(R^{10})C(=O)-R^{14}-S(O)_tN(R^{10})R^{11}$, $-R^{13}-N(R^{10})C(=O)-R^{13}-N(R^{10})C(=O)R^{10}$, $-R^{13}-N(R^{10})C(=O)-R^{13}-N(R^{10})-R^{14}-N(R^{10})R^{11}$, $-R^{13}-N(R^{10})S(O)_tN(R^{10})R^{11}$, and $-R^{13}-O-R^{14}-C(=O)OR^{10}$; each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-B) are those wherein r is 0 to 4; q is 0 to 2; $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^2$ and $R^{5a}$, together with the nitrogen and carbon to which they are attached, form an optionally substituted 5- to 7-membered N-heterocyclyl or an optionally substituted 6- to 10-membered bridged N-heterocyclyl; or $R^2$ and $R^{5b}$, together with the nitrogen and carbon to which they are attached, form an optionally substituted 5- to 7-membered N-heterocyclyl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12}$—, or an optionally substituted straight or branched alkylene chain; each $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5b}$ and $R^{6b}$ together, and $R^{5c}$ and $R^{6c}$ together can be an oxo group; or $R^{5b}$ and $R^{6b}$, together with the carbon to which they are attached, form an optionally substituted 3- to 7-membered cycloalkyl; $R^1$ is selected from the group consisting of hydrogen, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^a$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(O)$_t$N($R^{10}$)$R^{11}$, and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-B) are those wherein r is 0 to 4; q is 0 to 2; $R^{1a}$ is hydrogen, halo, or heteroaryl (optionally substituted with one or more alkyl groups); $R^{1b}$, $R^{1c}$, $R^{1d}$ and $R^{1e}$ are each independently hydrogen or halo; $R^2$ and $R^{5a}$, together with the nitrogen and carbon to which they are attached, form an optionally substituted piperidinyl, an optionally substituted pyrrolidinyl, or an optionally substituted 6- to 10-membered bridged N-heterocyclyl; or $R^2$ and $R^{5b}$, together with the nitrogen and carbon to which they are attached, form an optionally substituted pyrrolidinyl or an optionally substituted piperidinyl; $R^3$ is a direct bond, —O—$R^{12}$—, or an optionally substituted straight or branched alkylene chain; $R^4$ is a direct bond, —O—$R^{12a}$, or an optionally substituted straight or branched alkylene chain; each $R^{5b}$, $R^{5c}$, $R^{6a}$, $R^{6b}$ and $R^{6c}$ are each independently selected from hydrogen, alkyl, haloalkyl or hydroxyalkyl; $R^1$ is selected from the group consisting of hydrogen, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen or aralkyl optionally substituted with one or more substituents selected from the group consisting of —$R^{13}$—C(=O)$OR^{10}$, —$R^{13}$—C(=O)—$R^{13}$—N($R^{10}$)$R^{11}$, or —$R^{13}$—C(=O)N($R^{14}$)—$R^{14}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Specific embodiments of these compounds include the following:

4-[[4-[methyl[(4-phenoxyphenyl)methyl]amino]-1-piperidinyl]methyl]benzoic acid;

4-[[4-[methyl[2-[4-(phenylmethyl)phenoxy]ethyl]amino]-1-piperidinyl]methyl]benzoic acid;

4-[[4-[methyl[2-(4-phenoxyphenyl)ethyl]amino]-1-piperidinyl]methyl]benzoic acid;

4-[[4-[[[4-(4-bromophenoxy)phenyl]methyl]amino]-1-piperidinyl]methyl]benzoic acid;

4-[[4-[[[4-(4-bromophenoxy)phenyl]methyl]methylamino]-1-piperidinyl]methyl]benzoic acid;

4-[[(RS)-2-[[[[4-(4-bromophenoxy)phenyl]methyl]methylamino]methyl]-1-piperidinyl]methyl]benzoic acid;

4-[[4-[[[4-(4-bromophenoxy)phenyl]methyl][(methylamino)carbonyl]amino]-1-piperidinyl]methyl]benzoic acid;

4-[[4-[(4-phenoxyphenyl)amino]-1-piperidinyl]methyl]benzoic acid;

4-[[4-[methyl(4-phenoxyphenyl)amino]-1-piperidinyl]methyl]benzoic acid;

4-[[4-[[4-(4-chlorophenoxy)phenyl]amino]-1-piperidinyl]methyl]benzoic acid;

4-[[4-[[4-(2-phenylethoxy)phenyl]amino]-1-piperidinyl]methyl]benzoic acid;

4-[[4-[[(4-phenoxyphenyl)methyl]amino]-1-piperidinyl]methyl]benzoic acid;

4-[[(S)-3-[[methyl[(4-phenoxyphenyl)methyl]amino]methyl]-1-pyrrolidinyl]methyl]benzoic acid;

4-[[(R)-3-[[methyl[(4-phenoxyphenyl)methyl]amino]methyl]-1-pyrrolidinyl]methyl]benzoic acid;

4-[[(3-exo)-3-[[[4-(4-bromophenoxy)phenyl]methyl]methylamino]-8-azabicyclo[3.2.1]oct-8-yl]methyl]benzoic acid;

4-[[4-[[(methylamino)carbonyl][2-(4-phenoxyphenyl)ethyl]amino]-1-piperidinyl]methyl]benzoic acid;
4-[[4-[acetyl[2-[4-(4-bromophenoxy)phenyl]ethyl]amino]-1-piperidinyl]methyl]benzoic acid;
4-[[(R)-2-[[[[4-(4-bromophenoxy)phenyl]methyl]methylamino]methyl]-1-pyrrolidinyl]methyl]benzoic acid;
4-[[(3-exo)-3-[[(4-phenoxyphenyl)methyl]amino]-8-azabicyclo[3.2.1]oct-8-yl]methyl]benzoic acid;
4-[[(RS)-3-[methyl[2-(4-phenoxyphenyl)ethyl]amino]-1-pyrrolidinyl]methyl]benzoic acid;
methyl 4-[[4-[[4-(4-chlorophenoxy)phenyl]amino]-1-piperidinyl]methyl]benzoate;
4-[[4-[[4-(4-chlorophenoxy)phenyl]amino]-1-piperidinyl]methyl]-N-(2-hydroxyethyl)benzamide;
N-[4-(4-chlorophenoxy)phenyl]-4-piperidinamine;
4-[[4-[[4-(4-chlorophenoxy)phenyl]amino]-1-piperidinyl]methyl]-N-[2-(dimethylamino)ethyl]benzamide;
4-[2-[4-[[4-(4-chlorophenoxy)phenyl]amino]-1-piperidinyl]ethyl]benzoic acid;
4-[3-[4-[[4-(4-chlorophenoxy)phenyl]amino]-1-piperidinyl]propyl]benzoic acid;
4-[[(3-exo)-3-[[4-(4-chlorophenoxy)phenyl]amino]-8-azabicyclo[3.2.1]oct-8-yl]methyl]benzoic acid; and
4-[2-[4-[[4-[4-(2-oxazolyl)phenoxy]phenyl]amino]-1-piperidinyl]ethyl]benzoic acid.

Another embodiment of the compounds of formula (I-B) are those wherein r is 0 to 4; q is 0 to 2; $R^{1a}$, $R^{1b}$, $R^{1c}$, $R^{1d}$ and $R^{1e}$ are each independently selected from the group consisting of hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl, and optionally substituted heterocyclylalkyl; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, $-R^{12}-O-$, $-O-R^{12}-$, $-O-R^{12}-O-$, an optionally substituted straight or branched alkylene chain, an optionally substituted straight or branched alkenylene chain, or an optionally substituted straight or branched alkynylene chain; $R^4$ is a direct bond, $-O-R^{12a}-$, an optionally substituted straight or branched alkylene chain, an optionally substituted straight or branched alkenylene chain, or an optionally substituted straight or branched alkynylene chain; each $R^{6a}$, $R^{6b}$ and $R^{6c}$ are each independently selected from hydrogen, alkyl, haloalkyl or hydroxyalkyl; $R^7$ and $R^{5a}$, together with the nitrogen and carbon to which they are attached, form an optionally substituted 5- to 7-membered N-heterocyclyl; or $R^7$ and $R^{5a}$, together with the nitrogen and carbon to which they are attached, form an optionally substituted 5- to 7-membered N-heterocyclyl and $R^2$ and $R^{5c}$, together with the nitrogen and carbon to which are they are attached, form an optionally substituted 5- to 7-membered N-heterocyclyl; or $R^7$ and $R^{5b}$, together with the nitrogen and carbon to which they are attached, form an optionally substituted 5- to 7-membered N-heterocyclyl; or $R^7$ and $R^{5c}$, together with the nitrogen and carbon to which are they are attached, form an optionally substituted 5- to 7-membered N-heterocyclyl or an optionally substituted 6- to 10-membered bridged N-heterocyclyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{14}-C(=O)OR^{10}$, $-R^{13}-C(=O)R^{10}$, $-R^{13}-C(=O)OR^{10}$, $-R^{13}-C(=O)-R^{14}-C(=O)OR^{10}$, $-R^{13}-C(=O)-R^{13}-N(R^{10})R^{11}$, $-R^{13}-C(=O)-R^{14}-S(=O)_tN(R^{10})R^{11}$ (where t is 1 or 2), or $-R^{14}-S(=O)_pR^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{10}$, $-R^{-13}C(=O)OR^{10}$, $-R^{13}-C(=O)-R^{13}-N(R^{10})R^{11}$, $-R^{13}-C(=O)N(R^{10})-R^{14}-N(R^{10})R^{11}$, $-R^{13}-S(O)_tN(R^{10})R^{11}$ (where t is 1 or 2), $-R^{13}-N(R^{10})R^{11}$, $-R^{13}-N(R^{10})C(=O)OR^{10}$, $-R^{13}-N(R^{10})C(=O)-R^{13}-N(R^{10})R^{11}$, $-R^{13}-N(R^{10})-R^{13}-C(=O)OR^{10}$, $-R^{13}-N(R^{10})C(=O)-R^{14}-S(O)_tN(R^{10})R^{11}$, $-R^{13}-N(R^{10})C(=O)-R^{13}-N(R^{10})C(=O)R^{10}$, $-R^{13}-N(R^{10})C(=O)-R^{13}-N(R^{10})-R^{14}-N(R^{10})R^{11}$, $-R^{13}-N(R^{10})S(O)_tN(R^{10})R^{11}$, and $-R^{13}-O-R^{14}-C(=O)OR^{10}$; each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-B) are those wherein r is 0 to 4; q is 0 to 2; $R^{1a}$ is hydrogen, $-R^{13}-OR^{10}$, $-R^{13}-C(=O)OR^{10}$, $-R^{13}-C(=O)R^{10}$, alkyl, halo, haloalkyl, cyano, optionally substituted cycloalkyl, optionally substituted cycloalkylalkyl, aryl (optionally substituted with one or more halo groups), optionally substituted aralkyl, heteroaryl (optionally substituted with one or more alkyl groups), optionally substituted heteroarylalkyl, optionally substituted heterocyclyl, and optionally substituted heterocyclylalkyl; $R^{1b}$, $R^{1c}$, $R^{1d}$ and $R^{1e}$ are each independently hydrogen or halo; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; each $R^{6a}$, $R^{6b}$ and $R^{6c}$ are each independently selected from hydrogen, alkyl, haloalkyl or hydroxyalkyl; $R^7$ and $R^{5a}$, together with the nitrogen and carbon to which they are attached, form an optionally substituted 5- to 7-membered N-heterocyclyl; or $R^7$ and $R^{5a}$, together with the nitrogen and carbon to which they are attached, form an optionally substituted 5- to 7-membered N-heterocyclyl and $R^2$ and $R^{5c}$, together with the nitrogen and carbon to which are they are attached, form an optionally substituted 5- to 7-membered N-heterocyclyl; or $R^7$ and $R^{5b}$, together with the nitrogen and carbon to which they are attached, form an optionally substituted 5- to 7-membered N-heterocyclyl; or $R^7$ and $R^{5c}$, together with the nitrogen and carbon to which they are attached, form an optionally substituted 5- to 7-membered N-heterocyclyl or an optionally substituted 6- to 10-membered bridged N-heterocyclyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(O)$_t$N($R^{10}$)$R^{11}$, —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(O)$_t$N($R^{10}$)$R^{11}$, and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-B) are those wherein r is 0 to 4; q is 0 to 2; $R^{1a}$ is hydrogen, halo, or heteroaryl (optionally substituted with one or more alkyl groups); $R^{1b}$, $R^{1c}$, $R^{1d}$ and $R^{1e}$ are each independently hydrogen or halo; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12}$—, or an optionally substituted straight or branched alkylene chain; each $R^{6a}$, $R^{6b}$ and $R^{6c}$ are each independently selected from hydrogen, alkyl, haloalkyl or hydroxyalkyl; $R^7$ and $R^{5a}$, together with the nitrogen and carbon to which they are attached, form an optionally substituted pyrrolidinyl or an optionally substituted piperidinyl; or $R^7$ and $R^{5b}$, together with the nitrogen and carbon to which they are attached, form an optionally substituted pyrrolidinyl; or $R^7$ and $R^{5c}$, together with the nitrogen and carbon to which they are attached, form an optionally substituted piperidinyl or an optionally substituted 6- to 10-membered bridged N-heterocyclyl; $R^8$ is selected from the group consisting of hydrogen, alkyl, optionally substituted heteroaryl, or optionally substituted heterocyclyl; or $R^8$ is aralkyl optionally substituted with —$R^{13}$—C(=O)$OR^{10}$ or —$R^{13}$—C(=O)—$R^{13}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Specific embodiments of these compounds include the following:

4-[[[1-[(4-phenoxyphenyl)methyl]piperidin-4-yl]amino]methyl]benzoic acid;

4-[[methyl[[(R)-1-[(4-phenoxyphenyl)methyl]-3-pyrrolidinyl]methyl]amino]methyl]benzoic acid;

4-[[methyl[[(S)-1-[(4-phenoxyphenyl)methyl]-3-pyrrolidinyl]methyl]amino]methyl]benzoic acid;

4-[[[1-[[4-(4-chlorophenoxy)phenyl]methyl]piperidin-4-yl]amino]methyl]benzoic acid;

4-[[[[(RS)-1-[[4-(4-bromophenoxy)phenyl]methyl]-2-piperidinyl]methyl]methylamino]methyl]benzoic acid;

4-[[[[(RS)-1-[[4-[2-(4-fluorophenyl)ethoxy]phenyl]methyl]-2-piperidinyl]methyl]methylamino]methyl]benzoic acid;

4-[[[(3-exo)-8-[[4-(4-bromophenoxy)phenyl]methyl]-8-azabicyclo[3.2.1]oct-3-yl]methylamino]methyl]benzoic acid;

4-[[[[(R)-1-[[4-(4-bromophenoxy)phenyl]methyl]-2-pyrrolidinyl]methyl]methylamino]methyl]benzoic acid;

4-[[[1-[[4-(4-bromophenoxy)phenyl]methyl]-4-methyl-4-piperidinyl]methylamino]methyl]benzoic acid;

4-[[[1-[[4-(4-bromophenoxy)phenyl]methyl]-4-piperidinyl]methylamino]methyl]benzoic acid;

4-[[[[(R)-1-[[4-(4-bromophenoxy)phenyl]methyl]-2-piperidinyl]methyl]methylamino]methyl]benzoic acid;
4-[[methyl[[(R)-1-[[4-[4-(2-oxazolyl)phenoxy]phenyl]methyl]-2-piperidinyl]methyl]amino]methyl]benzoic acid;
4-[[methyl[[(S)-1-[[4-[4-(2-oxazolyl)phenoxy]phenyl]methyl]-2-piperidinyl]methyl]amino]methyl]benzoic acid;
4-[[methyl[(3-exo)-8-[[4-[4-(2-oxazolyl)phenoxy]phenyl]methyl]-8-azabicyclo[3.2.1]oct-3-yl]amino]methyl]benzoic acid;
4-[[[[(R)-1-[[4-[4-(2-oxazolyl)phenoxy]phenyl]methyl]-2-pyrrolidinyl]methyl]methylamino]methyl]benzoic acid;
6-[[[1-[[4-(4-chlorophenoxy)phenyl]methyl]-4-piperidinyl]methyl]amino]-3-pyridinecarboxylic acid;
1-[(4-phenoxyphenyl)methyl]-4-piperidinemethanamine;
ethyl 1,6-dihydro-6-oxo-2-[[[1-[(4-phenoxyphenyl)methyl]-4-piperidinyl]methyl]amino]-5-pyrimidinecarboxylate; and
1,6-dihydro-6-oxo-2-[[[1-[(4-phenoxyphenyl)methyl]-4-piperidinyl]methyl]amino]-5-pyrimidinecarboxylic acid.

C. Another aspect of the invention are the compounds of Formula (I) having Formula (I-C):

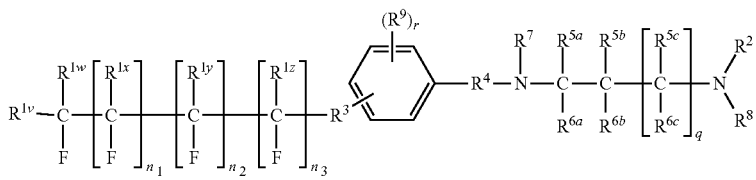

wherein the substituents are as described above in the Summary.

Accordingly, one embodiment of the compounds of Formula (I-C) are those wherein $n_1$, $n_2$ and $n_3$ are each independently 0 to 2; r is 0 to 4; q is 0 to 2; $R^{1v}$, $R^{1w}$, $R^{1x}$, $R^{1y}$ and $R^{1z}$ are each independently hydrogen or fluoro; $R^2$ and $R^7$, together with the nitrogens to which they are attached and one of $R^{5a}$, $R^{5b}$ and $R^{5c}$, form an optionally substituted 6- to 10-membered bridged N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—O$R^{10}$, —$R^{13}$—O—$R^{14}$—C(=O)O$R^{10}$, —$R^{13}$—C(=O)$R^{10}$, —$R^{13}$—C(=O)O$R^{10}$, —$R^{13}$—C(=O)—$R^{14}$—C(=O)O$R^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—O$R^{10}$, —$R^{13}$—C(=O)$R^{10}$, —$R^{13}$—C(=O)O$R^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)O$R^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)O$R^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-C) having the following formula (I-C-1):

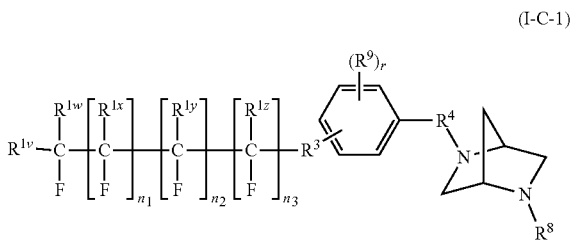

wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$R^{10}$, —$R^1$—C(=O)$R^{10}$, —$R^{13}$—C(O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-C-1) wherein $n_1$, $n_2$ and $n_3$ are each independently 1 to 3; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—O—, or an optionally substituted straight or branched alkylene chain; $R^4$ is a direct bond, —O—$R^{12a}$— or an optionally substituted straight or branched alkylene chain; $R^8$ is aralkyl optionally substituted with one or more of —$R^{13}$—$OR^{10}$, —$R^{13}$—C(=O)$OR^{10}$ and —$R^{13}$—C(=O)N($R^{10}$)$R^{11}$; each $R^9$ is independently alkyl, halo or —O—$R^{10}$; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; and each $R^{13}$ is a direct bond or an optionally substituted straight or branched alkylene chain.

Another embodiment are those compounds of formula (I-C-1) wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—O—, or an alkylene chain; $R^4$ is a direct bond, —O—$R^{12a}$— or an optionally substituted straight or branched alkylene chain; each $R^{5a}$, $R^{5b}$, $R^{6a}$ and $R^{6b}$ is hydrogen; $R^8$ is benzyl substituted with one or more of —$R^{13}$—$OR^{10}$ and —$R^{13}$—C(=O)$OR^{10}$; each $R^9$ is independently —O—$R^{10}$ or halo; $R^{10}$ is hydrogen, alkyl or optionally substituted aryl; $R^{12}$ is $C_{1-6}$alkylene; $R^{12a}$ is methylene or ethylene; and each $R^{13}$ is a direct bond or an optionally substituted straight or branched alkylene chain.

Specific embodiments of the compounds of formula (I-C-1) include the following:

4-[[(1S,4S)-5-[[4-(2,2,3,3,3-pentafluoropropoxy)phenyl]methyl]-2,5-diazabicyclo[2.2.1]hept-2-yl]methyl]benzoic acid;

4-[[(1S,4S)-5-[[4-(2-fluoroethoxy)phenyl]methyl]-2,5-diazabicyclo[2.2.1]hept-2-yl]methyl]benzoic acid;

4-[[(1S,4S)-5-[[4-(2,2,3,3-tetrafluoropropoxy)phenyl]methyl]-2,5-diazabicyclo[2.2.1]hept-2-yl]methyl]benzoic acid;

4-[[(1S,4S)-5-[[4-(2,2,3,3,4,4,4-heptafluorobutoxy)phenyl]methyl]-2,5-diazabicyclo[2.2.1]hept-2-yl]methyl]benzoic acid;

4-[[(1S,4S)-5-[[4-[(7,7,8,8,8-pentafluorooctyl)oxy]phenyl]methyl]-2,5-diazabicyclo[2.2.1]hept-2-yl]methyl]benzoic acid;

4-[[(1S,4S)-5-[[4-(2,2,2-trifluoroethoxy)phenyl]methyl]-2,5-diazabicyclo[2.2.1]hept-2-yl]methyl]benzoic acid;

4-[[(1S,4S)-5-[[4-(trifluoromethyl)phenyl]methyl]-2,5-diazabicyclo[2.2.1]hept-2-yl]methyl]benzoic acid;

4-[[(1S,4S)-5-[[4-(trifluoromethoxy)phenyl]methyl]-2,5-diazabicyclo[2.2.1]hept-2-yl]methyl]benzoic acid;

4-[[(1S,4S)-5-[[4-(difluoromethoxy)phenyl]methyl]-2,5-diazabicyclo[2.2.1]hept-2-yl]methyl]benzoic acid;

4-[[(1S,4S)-5-[[4-(1,1,2,2-tetrafluoroethoxy)phenyl]methyl]-2,5-diazabicyclo[2.2.1]hept-2-yl]methyl]benzoic acid;

4-[[(1S,4S)-5-[[4-(2,2,3,4,4,4-hexafluorobutoxy)phenyl]methyl]-2,5-diazabicyclo[2.2.1]hept-2-yl]methyl]benzoic acid;

4-[[(1S,4S)-5-[[4-(3,3,4,4,5,5,6,6,6-nonafluorohexyl)phenyl]methyl]-2,5-diazabicyclo[2.2.1]hept-2-yl]methyl]benzoic acid;

4-[[(1S,4S)-5-[[4-(3,3,4,4,4-pentafluorobutyl)phenyl]methyl]-2,5-diazabicyclo[2.2.1]hept-2-yl]methyl]benzoic acid;

4-[[(1S,4S)-5-[[4-(4,4,5,5,5-pentafluoropentyl)phenyl]methyl]-2,5-diazabicyclo[2.2.1]hept-2-yl]methyl]benzoic acid;

4-[[(1S,4S)-5-[[4-(4,4,4-trifluorobutoxy)phenyl]methyl]-2,5-diazabicyclo[2.2.1]hept-2-yl]methyl]benzoic acid;

4-[[(1S,4S)-5-[[4-(3,3,3-trifluoropropoxy)phenyl]methyl]-2,5-diazabicyclo[2.2.1]hept-2-yl]methyl]benzoic acid;

4-[[(1S,4S)-5-[[4-(1,1,2,3,3,3-hexafluoropropoxy)phenyl]methyl]-2,5-diazabicyclo[2.2.1]hept-2-yl]methyl]benzoic acid;

methyl 4-[[(1S,4S)-5-[[4-(3,3,4,4,4-pentafluorobutyl)phenyl]methyl]-2,5-diazabicyclo[2.2.1]hept-2-yl]methyl]benzoate;

methyl 2-methoxy-4-[[(1S,4S)-5-[[4-(2,2,3,3-tetrafluoropropoxy)phenyl]methyl]-2,5-diazabicyclo[2.2.1]hept-2-yl]methyl]benzoate;

methyl 2-methoxy-4-[[(1S,4S)-5-[[4-(2,2,3,3,4,4,4-heptafluorobutoxy)phenyl]methyl]-2,5-diazabicyclo[2.2.1]hept-2-yl]methyl]benzoate;

3-methoxy-4-[[(1S,4S)-5-[[4-(2,2,3,3-tetrafluoropropoxy)phenyl]methyl]-2,5-diazabicyclo[2.2.1]hept-2-yl]methyl]benzoic acid;

4-[[(1S,4S)-5-[[4-(2,2,3,3,4,4,4-heptafluorobutoxy)phenyl]methyl]-2,5-diazabicyclo[2.2.1]hept-2-yl]methyl]-3-methoxybenzoic acid;

3-methoxy-4-[[(1S,4S)-5-[[4-(2,2,3,3,3-pentafluoropropoxy)phenyl]methyl]-2,5-diazabicyclo[2.2.1]hept-2-yl]methyl]benzoic acid;

2-methoxy-4-[[(1S,4S)-5-[[4-(2,2,3,3-tetrafluoropropoxy)phenyl]methyl]-2,5-diazabicyclo[2.2.1]hept-2-yl]methyl]benzoic acid;

2-methoxy-4-[[(1S,4S)-5-[[4-(2,2,3,3,3-pentafluoropropoxy)phenyl]methyl]-2,5-diazabicyclo[2.2.1]hept-2-yl]methyl]benzoic acid; and 4-[[(1S,4S)-5-[[4-(2,2,3,3,4,4,4-heptafluorobutoxy)phenyl]methyl]-2,5-diazabicyclo[2.2.1]hept-2-yl]methyl]-2-methoxybenzoic acid.

Another embodiment of the compounds of formula (I-C) are those wherein $n_1$, $n_2$ and $n_3$ are each independently 0 to 2; r is 0 to 4; q is 0 to 2; $R^{1v}$, $R^{1w}$, $R^{1x}$, $R^{1y}$ and $R^{1z}$ are each independently hydrogen or fluoro; $R^2$ and $R^7$, together with the nitrogens to which they are attached, form an optionally substituted 5- to 7-membered N-heterocyclyl; $R^3$ is a direct bond, $-O-$, $-R^{12}-O-$, $-O-R^{12}-$, $-O-R^{12}-O-$, an optionally substituted straight or branched alkylene chain, an optionally substituted straight or branched alkenylene chain, or an optionally substituted straight or branched alkynylene chain; $R^4$ is a direct bond, $-O-R^{12a}-$, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{14}-C(=O)OR^{10}$, $-R^{13}-C(=O)R^{10}$, $-R^{13}-C(=O)OR^{10}$, $-R^{13}-C(=O)-R^{14}-C(=O)OR^{10}$, $-R^{13}-C(=O)-R^{13}-N(R^{10})R^{11}$, $-R^{13}-C(=O)-R^{14}-S(=O)_tN(R^{10})R^{11}$ (where t is 1 or 2), or $-R^{14}-S(=O)_pR^{10}$ (where p is 0, 1 or 2); and $-R^{14}-S(=O), R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{10}$, $-R^{13}-C(=O)OR^{10}$, $-R^{13}-C(=O)-R^{13}-N(R^{10})R^{11}$, $-R^{13}-C(=O)N(R^{10})-R^{14}-N(R^{10})R^{11}$, $-R^{13}-S(=O)_tN(R^{10})R^{11}$ (where t is 1 or 2), $-R^{13}-N(R^{10})R^{11}$, $-R^{13}-N(R^{10})C(=O)R^{10}$, $-R^{13}-N(R^{10})C(=O)-R^{13}-N(R^{10})R^{11}$, $-R^{13}-N(R^{10})-R^{14}-C(=O)OR^{10}$, $-R^{13}-N(R^{10})C(=O)-R^{14}-S(=O)_tN(R^{10})R^{11}$ (where t is 1 or 2), $-R^{13}-N(R^{10})C(=O)-R^{13}-N(R^{10})C(=O)R^{10}$, $-R^{13}-N(R^{10})C(=O)-R^{13}-N(R^{10})R^{14}-N(R^{10})R^{11}$, $-R^{13}-N(R^{10})S(=O)_tN(R^{10})R^{11}$ (where t is 1 or 2), and $-R^{13}-O-R^{14}-C(=O)OR^{10}$; each $R^9$ is independently $-O-R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{2a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I) having the following formula (I-C-2):

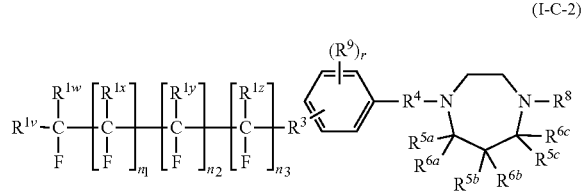

(I-C-2)

wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, $-O-$, $-R^{12}-O-$, $-O-R^{12}-$, $-O-R^{12}-O-$, an optionally substituted straight or branched alkylene chain, an optionally substituted straight or branched alkenylene chain, or an optionally substituted straight or branched alkynylene chain; $R^4$ is a direct bond, $-O-R^{12}-$, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, $-R^{13}-OR^{10}$, $-R^{13}-O-R^{14}-C(=O)OR^{10}$, $-R^{13}-C(=O)R^{10}$, $-R^{13}-C(=O)OR^{10}$, $-R^{13}-C(=O)-R^{14}-C(=O)OR^{10}$, $-R^{13}-C(=O)-R^{13}-N(R^{10})R^{11}$, $-R^{13}-C(=O)-R^{14}-S(=O)_tN(R^{10})R^{11}$ (where t is 1 or 2), or $-R^{14}-S(=O), R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, $-R^{13}-OR^{10}$, $-R^{13}-C(=O)R^{10}$, $-R^{13}-C(=O)OR^{10}$, $-R^{13}-C(=O)-R^{13}-N(R^{10})R^{11}$, $-R^{13}-C(=O)N(R^{10})-R^{14}-$ N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$R^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)O$R^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12}$, is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-C-2) are those wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is aralkyl optionally substituted with one or more substituents selected from the group consisting of halo, nitro, cyano, optionally substituted heteroaryl, hydroxyiminoalkyl, —$R^{13}$—O$R^{10}$, —$R^{13}$—C(=O)$R^{11}$, —$R^{13}$—C(=O)O$R^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)O$R^{14}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)O$R^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-C-2) are those wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is benzyl optionally substituted with one or more substituents selected from the group consisting of halo, nitro, cyano, optionally substituted heteroaryl, hydroxyiminoalkyl, —$R^{13}$—O$R^{10}$, —$R^{13}$—C(=O)$R^{10}$, —$R^{13}$—C(=O)O$R^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)O$R^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)O$R^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-C-2) are those wherein $n_1$, $n_2$ and $n_3$ are each independently 0 to 2; r is 0; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—, —O—$R^{12}$—O—, or an optionally substituted straight or branched $C_{1-6}$alkylene chain; $R^4$ is a direct bond, —O—$R^{12a}$—, or an optionally substituted straight or branched methylene, ethylene or propylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^e$ is benzyl substituted with one or more of —$R^{13}$—O$R^{10}$ and —$R^{13}$—C(=O)O$R^{10}$; each $R^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is a $C_{1-6}$alkylene chain (optionally substituted with one or more substituents selected from the group consisting of —O$R^{10}$); $R^{12a}$ is a methylene, ethylene or propylene chain (optionally substituted with one or more substituents selected from the group consisting of —O$R^{10}$); and each $R^{13}$ is a direct bond or an optionally substituted straight or branched alkylene chain.

Specific embodiments of these compounds include the following:
4-[[hexahydro-4-[[4-(2,2,3,3,3-pentafluoropropoxy)phenyl]methyl]-1H-1,4-diazepin-1-yl]methyl]benzoic acid; and
methyl 4-[[hexahydro-4-[[4-(2,2,3,3,3-pentafluoropropoxy)phenyl]methyl]-1H-1,4-diazepin-1-yl]methyl]benzoate.

Another embodiment of the compounds of formula (I-C-2) are those wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^2$ and $R^7$, together with the nitrogens to which they are attached, form hexahydro-1H-diazepinyl (optionally substituted with oxo); $R^3$ is a direct bond, —O—, —$R^{12}$—O—, —O—$R^{12}$—, —O—$R^{12}$—O—, or an optionally substituted straight or branched methylene or ethylene chain; $R^4$ is a direct bond, —O—$R^{12a}$—, or an optionally substituted straight or branched methylene, ethylene or propylene chain; each $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is benzyl substituted with optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is a $C_{1-6}$ alkylene chain (optionally substituted with one or more substituents selected from the group consisting of —$OR^{10}$); $R^{12a}$ is a methylene, ethylene or propylene chain (optionally substituted with one or more substituents selected from the group consisting of —$OR^{10}$); each $R^{13}$ is a direct bond or an optionally substituted straight or branched alkylene chain; and each $R^{14}$ is an optionally substituted straight or branched alkylene chain.

Another embodiment of the compounds of formula (I-C) are those wherein $n_1$, $n_2$ and $n_3$ are each independently 0 to 2; r is 0 to 4; q is 0 to 2; $R^{1v}$, $R^{1w}$, $R^{1x}$, $R^{1y}$ and $R^{1z}$ are each independently hydrogen or fluoro; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; or $R^{5a}$ and $R^{5b}$, together with the carbons to which they are attached, form an optionally substituted 3- to 7-membered cycloalkyl; or $R^{5a}$ and $R^{5c}$, together with the carbons to which they are attached, form an optionally substituted 4- to 7-membered cycloalkyl; or $R^{5b}$ and $R^{6b}$, together with the carbon to which they are attached, form an optionally substituted 3- to 7-membered cycloalkyl; $R^1$ is selected from the group consisting of hydrogen, —$R^{14}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{14}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of the invention are those compounds of formula (I-C) wherein $n_1$, $n_2$ and $n_3$ are each independently 0 to 2; r is 0 to 4; q is 0 to 2; $R^{1v}$, $R^{1w}$, $R^{1x}$, $R^{1y}$ and $R^{1z}$ are each independently hydrogen or fluoro; $R^2$ is hydrogen, alkyl, haloalkyl, hydroxyalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —R$^{12}$—O—, —O—R$^{12}$—, —O—R$^{12}$—O—, or an optionally substituted straight or branched alkylene chain; R$^4$ is a direct bond, —O—R$^{12a}$—, or an optionally substituted straight or branched alkylene chain; R$^{5a}$, R$^{5b}$, R$^{5c}$, R$^{6a}$, R$^{6b}$ and R$^{6c}$ are each independently selected from hydrogen, alkyl, haloalkyl or hydroxyalkyl; or R$^{5a}$ and R$^{5b}$, together with the carbons to which they are attached, form an optionally substituted 3- to 7-membered cycloalkyl; or R$^{5a}$ and R$^{5c}$, together with the carbons to which they are attached, form an optionally substituted 4- to 7-membered cycloalkyl; or R$^{5b}$ and R$^{6b}$, together with the carbon to which they are attached, form an optionally substituted 3- to 7-membered cycloalkyl; R$^1$ is selected from the group consisting of hydrogen, —R$^{13}$—C(=O)OR$^{10}$, alkyl, haloalkyl, and optionally substituted aralkyl; R$^8$ is selected from the group consisting of hydrogen, alkyl, or —R$^{13}$—C(=O)R$^{10}$; or R$^8$ is aralkyl optionally substituted with one or more of —R$^{13}$—OR$^{10}$ and —R$^{13}$—C(=O)OR$^{10}$; each R$^9$ is independently —O—R$^{10}$, alkyl, hydroxyalkyl, halo, haloalkyl, aryl or aralkyl; each R$^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; R$^{12}$ is an optionally substituted straight or branched alkylene chain; R$^{12a}$ is an optionally substituted straight or branched alkylene chain; and each R$^{13}$ is a direct bond or an optionally substituted straight or branched alkylene chain.

Another embodiment of this aspect of the invention are compounds of formula (I-C) having the following formula (I-C-3):

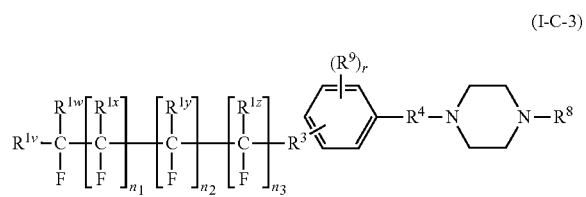

(I-C-3)

wherein $n_1$, $n_2$ and $n_3$ are each independently 0 to 2; r is 0 to 4; R$^{1v}$, R$^{1w}$, R$^{1x}$, R$^{1y}$ and R$^{1z}$ are each independently hydrogen or fluoro; R$^3$ is a direct bond, —O—, —R$^{12}$—O—, —O—R$^{12}$—, —O—R$^{12}$—O—, an optionally substituted straight or branched alkylene chain, an optionally substituted straight or branched alkenylene chain, or an optionally substituted straight or branched alkynylene chain; R$^4$ is a direct bond, —O—R$^{12a}$—, an optionally substituted straight or branched alkylene chain, an optionally substituted straight or branched alkenylene chain, or an optionally substituted straight or branched alkynylene chain; R$^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —R$^{13}$—OR$^{10}$, —R$^{13}$—O—R$^{14}$—C(=O)OR$^{10}$, —R$^{13}$—C(=O)R$^{10}$, —R$^{13}$—C(=O)OR$^{10}$, —R$^{13}$—C(=O)—R$^{14}$—C(=O)OR$^{10}$, —R$^{13}$—C(=O)—R$^{13}$—N(R$^{10}$)R$^{11}$, —R$^{13}$—C(=O)—R$^{14}$—S(=O)$_t$N(R$^{10}$)R$^{11}$ (where t is 1 or 2), or —R$^{14}$—S(=O)$_p$R$^{10}$ (where p is 0, 1 or 2); or R$^8$ is aralkyl optionally substituted with one or more substituents selected from the group consisting of halo, nitro, cyano, optionally substituted heteroaryl, hydroxyiminoalkyl, —R$^{13}$—OR$^{10}$, —R$^{13}$—C(=O)R$^{10}$, —R$^{13}$—C(=O)OR$^{10}$, —R$^{13}$—C(=O)—R$^{13}$—N(R$^{10}$)R$^{11}$, —R$^{13}$—C(=O)N(R$^{10}$)—R$^4$—N(R$^{10}$)R$^{11}$, —R$^{13}$—S(=O)$_t$N(R$^{10}$)R$^{11}$ (where t is 1 or 2), —R$^{13}$—N(R$^{10}$)R$^{11}$, —R$^{13}$—N(R$^{10}$)C(=O)R$^{10}$, —R$^{13}$—N(R$^{10}$)C(=O)—R$^{13}$—N(R$^{10}$)R$^{11}$, —R$^{13}$—N(R$^{10}$)—R$^{14}$—C(=O)OR$^{10}$, —R$^{13}$—N(R$^{10}$)C(=O)—R$^{14}$—S(=O)$_t$N(R$^{10}$)R$^{11}$ (where t is 1 or 2), —R$^{13}$—N(R$^{10}$)C(=O)—R$^{13}$—N(R$^{10}$)C(=O)R$^{10}$, —R$^{13}$—N(R$^{10}$)C(=O)—R$^{13}$—N(R$^{10}$)—R$^{14}$—N(R$^{10}$)R$^{11}$, —R$^{13}$—N(R$^{10}$)S(=O)$_t$N(R$^{10}$)R$^1$ (where t is 1 or 2), and —R$^{13}$—O—R$^{14}$—C(=O)OR$^{10}$; each R$^9$ is independently —O—R$^{10}$, alkyl, hydroxyalkyl, halo, haloalkyl, aryl or aralkyl; each R$^{10}$ and R$^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or R$^{10}$ and R$^{11}$, together with the nitrogen to which they are attached, form an optionally substituted N-heterocyclyl or an optionally substituted N-heteroaryl; R$^{12}$ is an optionally substituted straight or branched alkylene chain, an optionally substituted straight or branched alkenylene chain, or an optionally substituted straight or branched alkynylene chain; R$^{12a}$ is an optionally substituted straight or branched alkylene chain, an optionally substituted straight or branched alkenylene chain, or an optionally substituted straight or branched alkynylene chain; each R$^{13}$ is a direct bond or an optionally substituted straight or branched alkylene chain, an optionally substituted straight or branched alkenylene chain, or an optionally substituted straight or branched alkynylene chain; and each R$^{14}$ is an optionally substituted straight or branched alkylene chain, an optionally substituted straight or branched alkenylene chain, or an optionally substituted straight or branched alkynylene chain.

Another embodiment of the compounds of formula (I-C-3) are those wherein $n_1$, $n_2$ and $n_3$ are each independently 0 to 2; r is 0 to 4; R$^{1v}$, R$^{1w}$, R$^{1x}$, R$^{1y}$ and R$^{1z}$ are each independently hydrogen or fluoro; R$^3$ is a direct bond, —O—, —R$^{12}$—O—, —O—R$^{12}$—, —O—R$^{12}$—O—, or an optionally substituted straight or branched alkylene chain; R$^4$ is a direct bond, —O—R$^{12a}$—, or an optionally substituted straight or branched alkylene chain; R$^8$ is selected from the group consisting of —R$^{13}$—C(=O)—R$^{14}$—C(=O)OR$^{10}$ or —R$^{13}$—C(=O)—R$^{14}$—S(=O)$_t$N(R$^{10}$)R$^{11}$ (where t is 1 or 2); or R$^6$ is aralkyl optionally substituted with one or more substituents selected from the group consisting of —R$^{13}$OR$^{10}$, —R$^{13}$—C(=O)OR$^{10}$, —R$^{13}$—C(=O)—R$^{13}$—N(R$^{10}$)R$^{11}$, —R$^{13}$—N(R$^{10}$)C(=O)R$^{10}$, and —R$^{13}$—N(R$^{10}$)C(=O)—R$^{13}$—N(R$^{10}$)R$^{11}$; each R$^9$ is independently —O—R$^{10}$, alkyl, hydroxyalkyl, halo, haloalkyl, aryl or aralkyl; each R$^{10}$ and R$^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or R$^{10}$ and R$^{11}$, together with the nitrogen to which they are attached, form an optionally substituted N-heterocyclyl or an optionally substituted N-heteroaryl; R$^{12}$ is an optionally substituted straight or branched alkylene chain; R$^{12a}$ is an optionally substituted straight or branched alkylene chain; each R$^{13}$ is a direct bond or an optionally substituted straight or branched alkylene chain; and each R$^{14}$ is an optionally substituted straight or branched alkylene chain.

Another embodiment of the compounds of the formula (I-C) are those wherein $n_1$, $n_2$ and $n_3$ are each independently 0 to 2; r is 0 to 4; q is 0 to 2; $R^{1v}$, $R^{1w}$, $R^{1x}$, $R^{1y}$ and $R^{1z}$ are each independently hydrogen or fluoro; $R^2$ and $R^{5a}$, together with the nitrogen and carbon to which they are attached, form an optionally substituted 5- to 7-membered N-heterocyclyl or an optionally substituted 6- to 10-membered bridged N-heterocyclyl; or $R^2$ and $R^{5b}$, together with the nitrogen and carbon to which they are attached, form an optionally substituted 5- to 7-membered N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5b}$ and $R^{6b}$ together, and $R^{5c}$ and $R^{6c}$ together can be an oxo group; or $R^{5b}$ and $R^{6b}$, together with the carbon to which they are attached, form an optionally substituted 3- to 7-membered cycloalkyl; $R^1$ is selected from the group consisting of hydrogen, —$R^{14}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{14}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-C) are those wherein $n_1$, $n_2$ and $n_3$ are each independently 0 to 2; r is 0 to 4; q is 0 to 2; $R^{1v}$, $R^{1w}$, $R^{1x}$, $R^{1y}$ and $R^{1z}$ are each independently hydrogen or fluoro; $R^2$ and $R^{5a}$, together with the nitrogen and carbon to which they are attached, form an optionally substituted piperidinyl, an optionally substituted pyrrolidinyl, or an optionally substituted 6- to 10-membered bridged N-heterocyclyl; or $R^2$ and $R^{5b}$, together with the nitrogen and carbon to which they are attached, form an optionally substituted pyrrolidinyl or an optionally substituted piperidinyl; $R^3$ is a direct bond, —O—$R^{12}$—, or an optionally substituted straight or branched alkylene chain; $R^4$ is a direct bond, —O—$R^{12a}$—, or an optionally substituted straight or branched alkylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^1$ is selected from the group consisting of hydrogen, —$R^{14}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{14}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen or aralkyl optionally substituted with one or more substituents selected from the group consisting of —$R^{13}$—$OR^{10}$, —$R^{13}$—C(=O)$OR^{10}$, —$R^{13}$—C(=O)—$R^{13}$—N($R^{10}$)$R^{11}$, or —$R^{13}$—C(=O)N($R^{10}$)—$R^{14}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

More specific embodiments of this aspect of the invention are compounds of formula (I) having the following formulas (I-C-4) and (I-C-5):

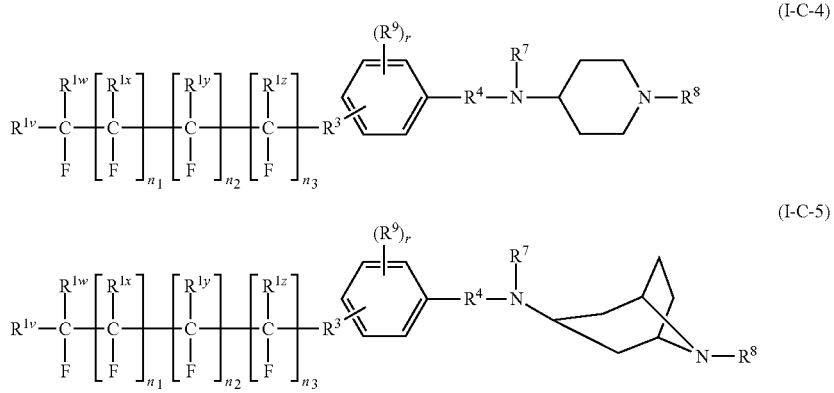

(I-C-4)

(I-C-5)

wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$ $R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{1'}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{2a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Specific embodiments of the compounds of formulas (I-C-4) and (I-C-5) are those compounds wherein $n_1$, $n_2$ and $n_3$ are each independently 0 to 2; r is 0 to 4; $R^{1v}$, $R^{1w}$, $R^{1x}$, $R^{1y}$ and $R^{1z}$ are each independently hydrogen or fluoro; $R^3$ is a direct bond, —O—, —$R^{12}$—O—, —O—$R^{12}$—, —O—$R^{12}$—O—, or an optionally substituted straight or branched alkylene chain; $R^4$ is a direct bond; $R^8$ is selected from the group consisting of —$R^{13}$—C(=O)—$R^{14}$—C(=O)$OR^{10}$ or —$R^{13}$—C(=O)—$R^{14}$—S(=O)$_t$N($R^{10}$)$R^{11}$ (where t is 1 or 2); or $R^8$ is aralkyl optionally substituted with one or more substituents selected from the group consisting of —$R^{13}$$OR^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)$R^{10}$, and —$R^{13}$—N($R^{10}$)C(=O)—$R^{13}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Other specific embodiments of the compounds of formulas (I-C-4) and (I-C-5) are those compounds wherein $n_1$, $n_2$ and $n_3$ are each independently 0 to 2; r is 0; $R^{1v}$, $R^{1w}$, $R^{1x}$, $R^{1y}$ and $R^{1z}$ are each independently hydrogen or fluoro; $R^3$ is a direct bond, —O—, —$R^2$—O—, —O—$R^{12}$—, —O—$R^{12}$—O—, or an optionally substituted straight or branched alkylene chain; $R^4$ is a direct bond; $R^8$ is benzyl substituted with one or more of —$R^{13}$—$OR^{10}$ and —$R^{13}$—

C(=O)OR$^{10}$; each R$^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; R$^{12}$ is a C$_{1-6}$ alkylene chain (optionally substituted with one or more substituents selected from the group consisting of —OR$^{10}$); R$^{12a}$ is a methylene, ethylene or propylene chain (optionally substituted with one or more substituents selected from the group consisting of —OR$^{10}$); and each R$^{13}$ is a direct bond or an optionally substituted straight or branched alkylene chain.

Specific examples of this embodiment include the following compounds:

4-[[4-[[4-(2,2,3,3,4,4,4-heptafluorobutoxy)phenyl]amino]-1-piperidinyl]methyl]benzoic acid;

4-[[(3-exo)-3-[[4-(2,2,3,3,4,4,4-heptafluorobutoxy)phenyl]amino]-8-azabicyclo[3.2.1]oct-8-yl]methyl]benzoic acid;

4-[[(3-exo)-3-[[4-(2,2,3,3,3-pentafluoropropoxy)phenyl]amino]-8-azabicyclo[3.2.1]oct-8-yl]methyl]benzoic acid; and methyl 4-[[(3-exo)-3-[[4-(2,2,3,3,4,4,4-heptafluorobutoxy)phenyl]amino]-8-azabicyclo[3.2.1]oct-8-yl]methyl]benzoate.

Another embodiment of the compounds of formula (I-C) are those wherein n$_1$, n$_2$ and n$_3$ are each independently 0 to 2; r is 0 to 4; q is 0 to 2; R$^{1v}$, R$^{1w}$, R$^{1x}$, R$^{1y}$ and R$^{1z}$ are each independently hydrogen or fluoro; R$^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; R$^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —R$^{13}$—OR$^{10}$, —R$^{13}$—O—R$^{14}$—C(=O)OR$^{10}$, —R$^{13}$—C(=O)R$^{10}$, —R$^{13}$—C(=O)OR$^{10}$, —R-$^{13}$C(=O)—R$^{14}$—C(=O)OR$^{10}$, —R$^{13}$—C(=O)—R$^{13}$—N(R$^{10}$)R$^{11}$, —R$^{13}$—C(=O)—R$^{14}$—S(=O)$_t$N(R$^{10}$)R$^{11}$ (where t is 1 or 2), or —R$^{14}$—S(=O)$_p$R$^{10}$ (where p is 0, 1 or 2); or R$^8$ is aralkyl optionally substituted with one or more substituents selected from the group consisting of halo, nitro, cyano, optionally substituted heteroaryl, hydroxyiminoalkyl, —R$^{13}$—OR$^{10}$, —R$^{13}$—C(=O)R$^{10}$, —R$^{13}$—C(=O)OR$^{10}$, —R$^{13}$—C(=O)—R$^{13}$—N(R$^{10}$)R$^{11}$, —R$^{13}$—C(=O)N(R$^{10}$)—R$^{14}$—N(R$^{10}$)R$^{11}$, —R$^{13}$—S(=O)$_t$N(R$^{10}$)R$^{11}$ (where t is 1 or 2), —R$^{13}$—N(R$^{10}$)R$^{11}$, —R$^{13}$—N(R$^{10}$)C(=O)R$^{10}$, —R$^{13}$—N(R$^{10}$)C(=O)—R$^{13}$—N(R$^{10}$)R$^{11}$, —R$^{13}$—N(R$^{10}$)—R$^{13}$—C(=O)OR$^{10}$, —R$^{13}$—N(R$^{10}$)C(=O)—R$^{14}$—S(=O)$_t$N(R$^{10}$)R$^{11}$ (where t is 1 or 2), —R$^{13}$—N(R$^{10}$)C(=O)—R$^{13}$—N(R$^{10}$)C(=O)R$^{10}$, —R$^{13}$—N(R$^{10}$)C(=O)—R$^{13}$—N(R$^{10}$)—R$^{14}$—N(R$^{10}$)R$^{11}$, —R$^{13}$—N(R$^{10}$)S(=O)$_t$N(R$^{10}$)R$^{11}$ (where t is 1 or 2), and —R$^{13}$—O—R$^{14}$—C(=O)OR$^{10}$; or R$^2$ and R$^8$, together with the nitrogen to which they are attached, form an optionally substituted N-heterocyclyl or an optionally substituted N-heteroaryl; R$^3$ is a direct bond, —O—, —R$^{12}$—O—, —O—R$^{12}$—, —O—R$^{12}$—O—, an optionally substituted straight or branched alkylene chain, an optionally substituted straight or branched alkenylene chain, or an optionally substituted straight or branched alkynylene chain; R$^4$ is a direct bond, —O—R$^{12a}$—, an optionally substituted straight or branched alkylene chain, an optionally substituted straight or branched alkenylene chain, or an optionally substituted straight or branched alkynylene chain; R$^7$ and R$^{5a}$, together with the nitrogen and carbon to which they are attached, form an optionally substituted 5- to 7-membered N-heterocyclyl; or R$^7$ and R$^{5a}$, together with the nitrogen and carbon to which they are attached, form an optionally substituted 5- to 7-membered N-heterocyclyl and R$^2$ and R$^{5c}$, together with the nitrogen and carbon to which are they are attached, form an optionally substituted 5- to 7-membered N-heterocyclyl; or R$^7$ and R$^{5b}$, together with the nitrogen and carbon to which they are attached, form an optionally substituted 5- to 7-membered N-heterocyclyl; or R$^7$ and R$^{5c}$, together with the nitrogen and carbon to which they are attached, form an optionally substituted 5- to 7-membered N-heterocyclyl or an optionally substituted 6- to 10-membered bridged N-heterocyclyl; R$^{5a}$, R$^{5b}$, R$^{5c}$, R$^{6a}$, R$^{6b}$ and R$^{6c}$ are each independently selected from hydrogen, alkyl, haloalkyl or hydroxyalkyl; each R$^9$ is independently —O—R$^{10}$, alkyl, hydroxyalkyl, halo, haloalkyl, aryl or aralkyl; each R$^{10}$ and R$^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or R$^{10}$ and R$^{11}$, together with the nitrogen to which they are attached, form an optionally substituted N-heterocyclyl or an optionally substituted N-heteroaryl; R$^{12}$ is an optionally substituted straight or branched alkylene chain, an optionally substituted straight or branched alkenylene chain, or an optionally substituted straight or branched alkynylene chain; R$^{12a}$ is an optionally substituted straight or branched alkylene chain, an optionally substituted straight or branched alkenylene chain, or an optionally substituted straight or branched alkynylene chain; each R$^{13}$ is a direct bond, an optionally substituted straight or branched alkylene chain, an optionally substituted straight or branched alkenylene chain, or an optionally substituted straight or branched alkynylene chain; and each R$^{14}$ is an optionally substituted straight or branched alkylene chain, an optionally substituted straight or branched alkenylene chain, or an optionally substituted straight or branched alkynylene chain.

Another embodiment of the compounds of formula (I-C) are those wherein n$_1$, n$_2$ and n$_3$ are each independently 0 to 2; r is 0 to 4; q is 0 to 2; R$^{1v}$, R$^{1w}$, R$^{1x}$, R$^{1y}$ and R$^{1z}$ are each independently hydrogen or fluoro; R$^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; R$^8$ is selected from the group consisting of hydrogen, alkyl, optionally substituted heteroaryl, or optionally substituted heterocyclyl; or R$^8$ is aralkyl optionally substituted with —R$^{13}$—OR$^{10}$, —R$^{13}$—C(=O)OR$^{10}$ or —R$^{13}$—C(=O)—R$^{13}$—N(R$^{10}$)R$^{11}$; or R$^2$ and R$^8$, together with the nitrogen to which they are attached, form an optionally substituted N-heterocyclyl or an optionally substituted N-heteroaryl; R$^3$ is a direct bond, —O—, —R$^{12}$—O—, —O—R$^{12}$—, —O—R$^{12}$—O—, or an optionally substituted straight or branched alkylene chain; R$^4$ is a direct bond, —O—R$^{12a}$—, or an optionally substituted straight or branched alkylene chain; R$^7$ and R$^{5a}$, together with the nitrogen and carbon to which they are attached, form an optionally substituted pyrrolidinyl or an optionally substituted piperidinyl; or R$^7$ and R$^{5b}$, together with the nitrogen and carbon to which they are attached, form an optionally substituted pyrrolidinyl; or $R^7$ and $R^{5c}$, together with the nitrogen and carbon to which they are attached, form an optionally substituted piperidinyl or an optionally substituted 6- to 10-membered bridged N-heterocyclyl; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain; $R^{12a}$ is an optionally substituted straight or branched alkylene chain; and each $R^{13}$ is a direct bond or an optionally substituted straight or branched alkylene chain.

D. Another aspect of the invention are the compounds of Formula (I) having Formula (I-D):

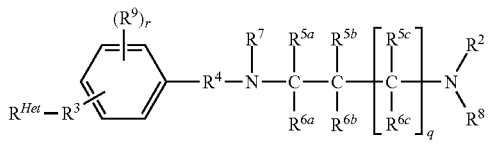

(I-D)

wherein $R^{Het}$ is an optionally substituted heteroaryl as defined in the Definitions hereinabove, and the remaining substituents are as described above in the Summary.

Accordingly, one embodiment of the compounds of Formula (I-D) are those wherein r is 0 to 4; q is 0 to 2; $R^{Het}$ is an optionally substituted heteroaryl; $R^2$ and $R^7$, together with the nitrogens to which they are attached and one of $R^{5a}$, $R^{5b}$ and $R^{5c}$, form an optionally substituted 6- to 10-membered bridged N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^6$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-D) having the following formula (I-D-1):

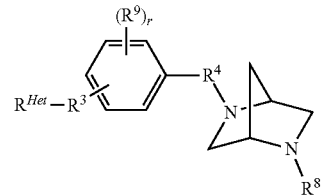

(I-D-1)

wherein; r is 0 to 4; $R^{Het}$ is an optionally substituted heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^4$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)
$R^{10}$, —$R^{13}$—C(=O)$OR^{10}$, —$R^{13}$—C(=O)—$R^{13}$—N($R^{10}$)
$R^{11}$, —$R^{13}$—C(=O)N($R^{10}$)—$R^{14}$—N($R^{10}$)$R^{11}$, —$R^{13}$—S
(=O)$_t$N($R^{10}$)$R^{11}$ (where t is 1 or 2), —$R^{13}$—N($R^{10}$)$R^{11}$,
—$R^{13}$—N($R^{10}$)C(=O)$R^{10}$, —$R^{13}$—N($R^{10}$)C(=O)—
$R^{13}$—N($R^{10}$)$R^{11}$, —$R^{13}$—N($R^{10}$)—$R^{13}$—C(=O)$OR^{10}$,
—$R^{13}$—N($R^{10}$)C(=O)—$R^{14}$—S(=O)$_t$N($R^{10}$)$R^{11}$ (where t
is 1 or 2), —$R^{13}$—N($R^{10}$)C(=O)—$R^{13}$—N($R^{10}$)C(=O)
$R^{10}$, —$R^{13}$—N($R^{10}$)C(=O)—$R^{13}$—N($R^{10}$)—$R^{14}$—N($R^{10}$)
$R^{11}$, —$R^{13}$—N($R^{10}$)S(=O)$_t$N($R^{10}$)$R^{11}$ (where t is 1 or 2),
and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I-D-1) wherein r is 0 to 4; $R^{Het}$ is an optionally substituted heteroaryl; $R^3$ is a direct bond, —O—, —$R^{12}$—O—, —O—$R^{12}$—O—, or an optionally substituted straight or branched alkylene chain; $R^4$ is a direct bond, —O—$R^{12a}$— or an optionally substituted straight or branched alkylene chain; $R^8$ is aralkyl optionally substituted with one or more of —$R^{13}$—$OR^{10}$, —$R^{13}$—C(=O)$OR^{10}$ and —$R^{13}$—C(=O)N($R^{10}$)$R^{11}$; each $R^9$ is independently alkyl, halo or —O—$R^{10}$; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain; $R^{12a}$ is an optionally substituted straight or branched alkylene chain; and each $R^{13}$ is a direct bond or an optionally substituted straight or branched alkylene chain.

Another embodiment are those compounds of formula (I-D-1) wherein; r is 0 to 4; $R^{Het}$ is an optionally substituted monocyclic or bicyclic heteroaryl; $R^3$ is a direct bond, —O—, —$R^{12}$—O—, —O—$R^1$—O—, or an alkylene chain; $R^4$ is a direct bond, —O—$R^{12a}$— or an optionally substituted straight or branched alkylene chain; each $R^{5a}$, $R^{5b}$, $R^{6a}$ and $R^{6b}$ is hydrogen; $R^8$ is benzyl substituted with one or more of —$R^{13}$—$OR^{10}$ and —$R^{13}$—C(=O)$OR^{10}$; each $R^9$ is independently —O—$R^{10}$ or halo; $R^{10}$ is hydrogen, alkyl or optionally substituted aryl; $R^{12}$ is $C_{1-6}$alkylene; $R^{12a}$ is methylene or ethylene; and each $R^{13}$ is a direct bond or an optionally substituted straight or branched alkylene chain.

Specific embodiments of the compounds of formula (I-D-1) include the following:
4-[[(1S,4S)-5-[[4-(thiazol-2-yloxy)phenyl]methyl]-2,5-diazabicyclo[2.2.1]hept-2-yl]methyl]benzoic acid;
4-[[(1S,4S)-5-[[4-(benzothiazol-2-yloxy)phenyl]methyl]-2,5-diazabicyclo[2.2.1]hept-2-yl]methyl]benzoic acid;
4-[[(1S,4S)-5-[[4-(2-methylbenzothiazol-5-yloxy)phenyl]methyl]-2,5-diazabicyclo[2.2.1]hept-2-yl]methyl]benzoic acid;
4-[[(1S,4S)-5-[[4-(2-methylbenzothiazol-6-yloxy)phenyl]methyl]-2,5-diazabicyclo[2.2.1]hept-2-yl]methyl]benzoic acid;
methyl 4-[[(1S,4S)-5-[[4-(thiazol-4-ylmethoxy)phenyl]methyl]-2,5-diazabicyclo[2.2.1]hept-2-yl]methyl]benzoate;
4-[[(1S,4S)-5-[[4-(thiazol-4-ylmethoxy)phenyl]methyl]-2,5-diazabicyclo[2.2.1]hept-2-yl]methyl]benzoic acid;
4-[[(1S,4S)-5-[[4-(oxazol-4-ylmethoxy)phenyl]methyl]-2,5-diazabicyclo[2.2.1]hept-2-yl]methyl]benzoic acid; and
methyl 4-[[(1S,4S)-5-[[4-(oxazol-4-ylmethoxy)phenyl]methyl]-2,5-diazabicyclo[2.2.1]hept-2-yl]methyl]benzoate.

Another embodiment of the compounds of formula (I-D) are those wherein r is 0 to 4; q is 0 to 2; $R^{Het}$ is an optionally substituted heteroaryl; $R^2$ and $R^7$, together with the nitrogens to which they are attached, form an optionally substituted 5- to 7-membered N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{18}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; each $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment are those compounds of formula (I) having the following formula (I-D-2):

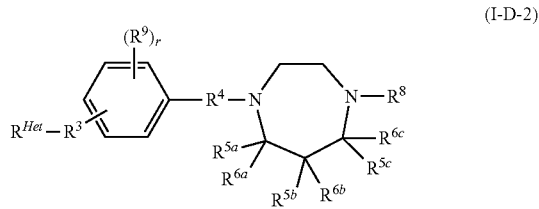

(I-D-2)

wherein r is 0 to 4; $R^{Het}$ is an optionally substituted heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5a}$ and $R^{6a}$ together, $R^{5b}$ and $R^{6b}$ together, and $R^{5c}$ and $R^{6c}$ together can be an oxo group; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N ($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-D-2) are those wherein r is 0 to 4; $R^{Het}$ is an optionally substituted heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{11}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of formula (I-D-2) are those wherein r is 0 to 4; $R^{Het}$ is an optionally substituted heteroaryl; $R^3$ is a direct bond, —O—, —$R^{12}$—

O—, —O—R$^{12}$—, —O—R$^{12}$—O—, or an optionally substituted straight or branched alkylene chain; R$^4$ is a direct bond, —O—R$^{12a}$—, or an optionally substituted straight or branched alkylene chain; R$^{5a}$, R$^{5b}$, R$^{5c}$, R$^{6a}$, R$^{6b}$ and R$^{6c}$ are each independently selected from hydrogen, alkyl, haloalkyl or hydroxyalkyl; R$^8$ is benzyl optionally substituted with one or more substituents selected from the group consisting of halo, nitro, cyano, optionally substituted heteroaryl, hydroxyiminoalkyl, —R$^{13}$—OR$^{10}$, —R$^{13}$—C(=O)R$^{10}$, —R$^{13}$—C(=O)OR$^{10}$, —R$^{13}$—C(=O)—R$^{13}$—N(R$^{10}$)R$^{11}$, —R$^{13}$—C(=O)N(R$^{10}$)—R$^{14}$—N(R$^{10}$)R$^{11}$, —R$^{13}$—S(=O)$_t$N(R$^{10}$)R$^{11}$ (where t is 1 or 2), —R$^{13}$—N(R$^{10}$)R$^{11}$, —R$^{13}$—N(R$^{10}$)C(=O)R$^{10}$, —R$^{13}$—N(R$^{10}$)C(=O)—R$^{13}$—N(R$^{10}$)R$^{11}$, —R$^{13}$—N(R$^{10}$)—R$^{14}$—C(=O)OR$^{10}$, —R$^{13}$—N(R$^{10}$)C(=O)—R$^{14}$—S(=O)$_t$N(R$^{10}$)R$^{11}$ (where t is 1 or 2), —R$^{13}$—N(R$^{10}$)C(=O)—R$^{13}$—N(R$^{10}$)C(=O)R$^{10}$, —R$^{13}$—N(R$^{10}$)C(=O)—R$^{13}$—N(R$^{10}$)—R$^{14}$—N(R$^{10}$)R$^{11}$, —R$^{13}$—N(R$^{10}$)S(=O)$_t$N(R$^{10}$)R$^{11}$ (where t is 1 or 2), and —R$^{13}$—O—R$^{14}$—C(=O)OR$^{10}$; each R$^9$ is independently —O—R$^{10}$, alkyl, hydroxyalkyl, halo, haloalkyl, aryl or aralkyl; each R$^{10}$ and R$^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; R$^{12}$ is an optionally substituted straight or branched alkylene chain; R$^{12a}$ is an optionally substituted straight or branched alkylene chain; each R$^{13}$ is a direct bond or an optionally substituted straight or branched alkylene chain; and each R$^{14}$ is an optionally substituted straight or branched alkylene chain.

Another embodiment of the compounds of formula (I-D-2) are those wherein r is 0; R$^{Het}$ is an optionally substituted heteroaryl; R$^3$ is a direct bond, —O—, —R$^{12}$—O—, —O—R$^{12}$—, —O—R$^{12}$—O—, or an optionally substituted straight or branched C$_{1-6}$alkylene chain; R$^4$ is a direct bond, —O—R$^{12a}$—, or an optionally substituted straight or branched methylene, ethylene or propylene chain; R$^{5a}$, R$^{5b}$, R$^{5c}$, R$^{6a}$, R$^{6b}$ and R$^{6c}$ are each independently selected from hydrogen, alkyl, haloalkyl or hydroxyalkyl; R$^8$ is benzyl substituted with one or more of —R$^{13}$—OR$^{10}$ and —R$^{13}$—C(=O)OR$^{10}$; each R$^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; R$^{12}$ is a C$_{1-6}$alkylene chain (optionally substituted with one or more substituents selected from the group consisting of —OR$^{10}$); R$^{12a}$ is a methylene, ethylene or propylene chain (optionally substituted with one or more substituents selected from the group consisting of —OR$^{10}$); and each R$^{13}$ is a direct bond or an optionally substituted straight or branched alkylene chain.

Another embodiment of the compounds of formula (I-D-2) are those wherein r is 0 to 4; R$^{Het}$ is an optionally substituted heteroaryl; R$^2$ and R$^7$, together with the nitrogens to which they are attached, form hexahydro-1H-diazepinyl (optionally substituted with oxo); R$^3$ is a direct bond, —O—, —R$^{12}$—O—, —O—R$^{12}$—, —O—R$^{12}$—O—, or an optionally substituted straight or branched methylene or ethylene chain; R$^4$ is a direct bond, —O—R$^{12a}$—, or an optionally substituted straight or branched methylene, ethylene or propylene chain; each R$^{5a}$, R$^{5b}$, R$^{5c}$, R$^{6a}$, R$^{6b}$ and R$^{6c}$ are each independently selected from hydrogen, alkyl, haloalkyl or hydroxyalkyl; R$^8$ is benzyl substituted with optionally substituted with one or more substituents selected from the group consisting of halo, nitro, cyano, optionally substituted heteroaryl, hydroxyiminoalkyl, —R$^{13}$—OR$^{10}$, —R$^{13}$—C(=O)R$^{10}$, —R$^{13}$—C(=O)—R$^{13}$—N(R$^{10}$)R$^{11}$, —R$^{13}$—C(=O)N(R$^{10}$)—R$^{14}$—N(R$^{10}$)R$^{11}$, —R$^{13}$—S(=O)$_t$N(R$^{10}$)R$^{11}$ (where t is 1 or 2), —R$^{13}$—N(R$^{10}$)R$^{17}$, —R$^{13}$—N(R$^{10}$)C(=O)R$^{10}$, —R$^{13}$—N(R$^{10}$)C(=O)—R$^{13}$—N(R$^{10}$)R$^{11}$, —R$^{13}$—N(R$^{10}$)—R$^{14}$—C(=O)OR$^{10}$, —R$^{13}$—N(R$^{10}$)C(=O)—R$^{14}$—S(=O)$_t$N(R$^{10}$)R$^{11}$ (where t is 1 or 2), —R$^{13}$—N(R$^{10}$)C(=O)—R$^{13}$—N(R$^{10}$)C(=O)R$^{10}$, —R$^{13}$—N(R$^{10}$)C(=O)—R$^{13}$—N(R$^{10}$)—R$^{14}$—N(R$^{10}$)R$^{11}$, —R$^{13}$—N(R$^{10}$)S(=O)$_t$N(R$^{10}$)R$^{11}$ (where t is 1 or 2), and —R$^{13}$—O—R$^{14}$—C(=O)OR$^{10}$; each R$^{10}$ and R$^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; R$^{12}$ is a C$_{1-6}$alkylene chain (optionally substituted with one or more substituents selected from the group consisting of —OR$^{10}$); R$^{12a}$ is a methylene, ethylene or propylene chain (optionally substituted with one or more substituents selected from the group consisting of —OR$^{10}$); each R$^{13}$ is a direct bond or an optionally substituted straight or branched alkylene chain; and each R$^{14}$ is an optionally substituted straight or branched alkylene chain.

Another embodiment of the compounds of formula (I-D) are those wherein r is 0 to 4; q is 0 to 2; R$^{Het}$ is an optionally substituted heteroaryl; R$^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or R$^2$ and R$^8$, together with the nitrogen to which they are attached, form an optionally substituted N-heterocyclyl or an optionally substituted N-heteroaryl; R$^3$ is a direct bond, —O—, —R$^{12}$—O—, —O—R$^{12}$—, —O—R$^{12}$—O—, an optionally substituted straight or branched alkylene chain, an optionally substituted straight or branched alkenylene chain, or an optionally substituted straight or branched alkynylene chain; R$^4$ is a direct bond, —O—R$^{12a}$—, an optionally substituted straight or branched alkylene chain, an optionally substituted straight or branched alkenylene chain, or an optionally substituted straight or branched alkynylene chain; R$^{5a}$, R$^{5b}$, R$^{5c}$, R$^{6a}$, R$^{6b}$ and R$^{6c}$ are each independently selected from hydrogen, alkyl, haloalkyl or hydroxyalkyl; or any one of R$^{5a}$ and R$^{6a}$ together, R$^{5b}$ and R$^{6b}$ together, and R$^{5c}$ and R$^{6c}$ together can be an oxo group; or R$^{5a}$ and R$^{5b}$, together with the carbons to which they are attached, form an optionally substituted 3- to 7-membered cycloalkyl; or R$^{5a}$ and R$^{5c}$, together with the carbons to which they are attached, form an optionally substituted 4- to 7-membered cycloalkyl; or R$^{5b}$ and R$^{6b}$, together with the carbon to which they are attached, form an optionally substituted 3- to 7-membered cycloalkyl; R$^1$ is selected from the group consisting of hydrogen, —R$^{14}$—OR$^{10}$, —R$^{13}$—C(=O)R$^{10}$, —R$^{13}$—C(=O)OR$^{10}$, —R$^{13}$—C(=O)—R$^{13}$—N(R$^{10}$)R$^{11}$, —R$^{14}$—N(R$^{10}$)C(=O)N(R$^{10}$)R$^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; R$^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{1'}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_1$N($R^{10}$)$R^{1'}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of the invention are those compounds of formula (I-D) wherein r is 0 to 4; q is 0 to 2; $R^{Het}$ is an optionally substituted heteroaryl; $R^2$ is hydrogen, alkyl, haloalkyl, hydroxyalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{12a}$—, or an optionally substituted straight or branched alkylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or $R^{5a}$ and $R^{5b}$, together with the carbons to which they are attached, form an optionally substituted 3- to 7-membered cycloalkyl; or $R^{5a}$ and $R^{5c}$, together with the carbons to which they are attached, form an optionally substituted 4- to 7-membered cycloalkyl; or $R^{5b}$ and $R^{6b}$, together with the carbon to which they are attached, form an optionally substituted 3- to 7-membered cycloalkyl; $R^1$ is selected from the group consisting of hydrogen, —$R^{13}$—C(=O)$OR^{10}$, alkyl, haloalkyl, and optionally substituted aralkyl; $R^8$ is selected from the group consisting of hydrogen, alkyl, or —$R^{13}$—C(=O)$R^{10}$; or $R^8$ is aralkyl optionally substituted with one or more of —$R^{13}$—$OR^{10}$ and —$R^{13}$—C(=O)$OR^{10}$; each $R^9$ is independently —O—$R^{10}$, alkyl, hydroxyalkyl, halo, haloalkyl, aryl or aralkyl; each $R^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is an optionally substituted straight or branched alkylene chain; $R^{12a}$ is an optionally substituted straight or branched alkylene chain; and each $R^{13}$ is a direct bond or an optionally substituted straight or branched alkylene chain.

Another embodiment of this aspect of the invention are compounds of formula (I) having the following formula (I-D-3):

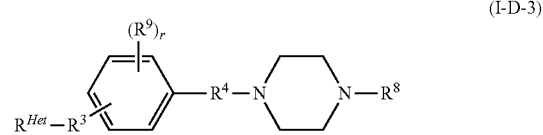

(I-D-3)

wherein r is 0 to 4; $R^{Het}$ is an optionally substituted heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^e$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12}$, is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-D-3) are those wherein r is 0 to 4; $R^{Het}$ is an optionally substituted heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond, —O—$R^{1a}$—, or an optionally substituted straight or branched alkylene chain; $R^8$ is selected from the group consisting of —$R^{13}$—C(=O)—$R^{14}$—C(=O)O$R^{10}$ or —$R^{13}$—C(=O)—$R^{14}$—S(=O)$_t$N($R^{10}$)$R^{11}$ (where t is 1 or 2); or $R^8$ is aralkyl optionally substituted with one or more substituents selected from the group consisting of —$R^{13}$O$R^{10}$, —$R^{13}$—C(=O)O$R^{10}$, —$R^{13}$—C(=O)—$R^{13}$—N($R^{10}$)$R^{11}$, —$R^{13}$—N($R^{10}$)C(=O)$R^{10}$, and —$R^{13}$—N($R^{10}$)C(=O)—$R^{13}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

Another embodiment of the compounds of the formula (I-D) are those wherein; r is 0 to 4; q is 0 to 2; $R^{Het}$ is an optionally substituted heteroaryl; $R^2$ and $R^{5a}$, together with the nitrogen and carbon to which they are attached, form an optionally substituted 5- to 7-membered N-heterocyclyl or an optionally substituted 6- to 10-membered bridged N-heterocyclyl; or $R^2$ and $R^{5b}$, together with the nitrogen and carbon to which they are attached, form an optionally substituted 5- to 7-membered N-heterocyclyl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{1a}$—, an optionally substituted straight or branched alkylene chain, an optionally substituted straight or branched alkenylene chain, or an optionally substituted straight or branched alkynylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; or any one of $R^{5b}$ and $R^{6b}$ together, and $R^{5c}$ and $R^{6c}$ together can be an oxo group; or $R^{5b}$ and $R^{6b}$, together with the carbon to which they are attached, form an optionally substituted 3- to 7-membered cycloalkyl; $R^1$ is selected from the group consisting of hydrogen, —$R^{14}$—O$R^{10}$, —$R^{13}$—C(=O)$R^{10}$, —$R^{13}$—C(=O)O$R^{10}$, —$R^{13}$—C(=O)—$R^{13}$—N($R^{10}$)$R^{11}$, —$R^{14}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—O$R^{10}$, —$R^{13}$—O—$R^{14}$—C(=O)O$R^{10}$, —$R^{13}$—C(=O)$R^{10}$, —$R^{13}$—C(=O)O$R^{10}$, —$R^{13}$—C(=O)—$R^{14}$—C(=O)O$R^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$ $R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—O$R^{10}$, —$R^{13}$—C(=O)$R^{10}$, —$R^{13}$—C(=O)O$R^{10}$, —$R^{13}$—C(=O)—$R^{13}$—N($R^{10}$)$R^{11}$, —$R^{13}$—C(=O)N($R^{10}$)—$R^4$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)O$R^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)O$R^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-D) are those wherein r is 0 to 4; q is 0 to 2; $R^{Het}$ is an optionally substituted heteroaryl; $R^2$ and $R^{5a}$, together with the nitrogen and carbon to which they are attached, form an optionally substituted piperidinyl, an optionally substituted pyrrolidinyl, or an optionally substituted 6- to 10-membered bridged N-heterocyclyl; or $R^2$ and $R^{5b}$, together with the nitrogen and carbon to which they are attached, form an optionally substituted pyrrolidinyl or an optionally substituted piperidinyl; $R^3$ is a direct bond, —O—$R^{12}$—, or an optionally substituted straight or branched alkylene chain;

$R^4$ is a direct bond, —O—$R^{12a}$—, or an optionally substituted straight or branched alkylene chain; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; $R^7$ is selected from the group consisting of hydrogen, —$R^{14}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{14}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, and optionally substituted heterocyclylalkyl; $R^8$ is hydrogen or aralkyl optionally substituted with one or more substituents selected from the group consisting of —$R^{13}$—$OR^{10}$, —$R^{13}$—C(=O)$OR^{10}$, —$R^{13}$—C(=O)—$R^{13}$—N($R^{10}$)$R^{11}$, or —$R^{13}$—C(=O)N($R^{10}$)—$R^{14}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

More specific embodiments of this aspect of the invention are compounds of formula (I) having the following formulas (I-D-4) and (I-D-5):

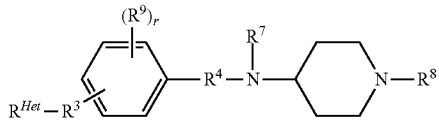

(I-D-4)

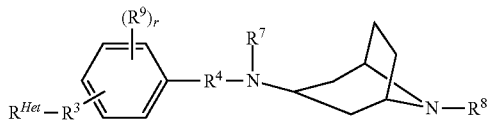

(I-D-5)

wherein r is 0 to 4; $R^{Het}$ is an optionally substituted heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O), $R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$OR^{10}$, —$R^{13}$—N($R^{10}$)C(=O)—$R^{13}$—N($R^{10}$)$R^{11}$, —$R^{13}$—N($R^{10}$)—$R^{14}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^1$ (where t is 1 or 2), and —$R^{13}$—O—$R^{14}$—C(=O)$OR^{10}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond or an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Specific embodiments of the compounds of formulas (I-D-4) and (I-D-5) are those compounds wherein r is 0 to 4; $R^{Het}$ is an optionally substituted heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond; $R^8$ is selected from the group consisting of —$R^{13}$—C(=O)—$R^{14}$—C(=O)$OR^{10}$ or —$R^{13}$—C(=O)—$R^{14}$—S(=O)$_t$N($R^{10}$)$R^{11}$ (where t is 1 or 2); or $R^e$ is aralkyl optionally substituted with one or more substituents selected from the group consisting of —$R^{13}OR^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)$R^{10}$, and —$R^{13}$—N($R^{10}$)C(=O)—$R^{13}$—N($R^{10}$)$R^{11}$; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain; $R^{12a}$ is an optionally substituted straight or branched alkylene chain; each $R^{13}$ is a direct bond or an optionally substituted straight or branched alkylene chain; and each $R^{14}$ is an optionally substituted straight or branched alkylene chain.

More specific embodiments of the compounds of formulas (I-D-4) and (1-D-5) are those compounds wherein; r is 0; $R^{Het}$ is an optionally substituted monocyclic or bicyclic heteroaryl; $R^3$ is a direct bond, —O—, —$R^{12}$—O—, —O—$R^{12}$—, —O—$R^{12}$—O—, or an optionally substituted straight or branched alkylene chain; $R^4$ is a direct bond; $R^8$ is benzyl substituted with one or more of —$R^{13}$—$OR^{10}$ and —$R^{13}$—C(=O)$OR^{10}$; each $R^{10}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; $R^{12}$ is a $C_{1-6}$alkylene chain (optionally substituted with one or more substituents selected from the group consisting of —$OR^{10}$); $R^{12a}$ is a methylene, ethylene or propylene chain (optionally substituted with one or more substituents selected from the group consisting of —$OR^{10}$); and each $R^{13}$ is a direct bond or an optionally substituted straight or branched alkylene chain.

Specific examples of these embodiments include the following compounds:

4-[[4-[[4-(benzothiazol-2-yloxy)phenyl]amino]-1-piperidinyl]methyl]benzoic acid;
4-[[(3-exo)-3-[[4-(benzothiazol-2-yloxy)phenyl]amino]-8-azabicyclo[3.2.1]oct-8-yl]methyl]benzoic acid;
4-[[(3-exo)-3-[[4-(thiazol-4-ylmethoxy)phenyl]amino]-8-azabicyclo[3.2.1]oct-8-yl]methyl]benzoic acid;
methyl 4-[[(3-exo)-3-[[4-(thiazol-4-ylmethoxy)phenyl]amino]-8-azabicyclo[3.2.1]oct-8-yl]methyl]benzoate;
4-[[(3-exo)-3-[[4-(pyrazol-1-ylmethyl)phenyl]amino]-8-azabicyclo[3.2.1]oct-8-yl]methyl]benzoic acid;
4-[[(3-exo)-3-[[4-(pyridin-4-ylmethyl)phenyl]amino]-8-azabicyclo[3.2.1]oct-8-yl]methyl]benzoic acid;
4-[[(3-exo)-3-[[4-(oxazol-2-ylmethoxy)phenyl]amino]-8-azabicyclo[3.2.1]oct-8-yl]methyl]benzoic acid;
4-[[(3-exo)-3-[[4-(1,2,4-triazol-1-ylmethyl)phenyl]amino]-8-azabicyclo[3.2.1]oct-8-yl]methyl]benzoic acid; and
4-[[(3-exo)-3-[N-oxazol-2-ylmethyl[4-(oxazol-2-ylmethoxy)phenyl]amino]-8-azabicyclo[3.2.1]oct-8-yl]methyl]benzoic acid.

Another embodiment of the compounds of formula (I-D) are those wherein r is 0 to 4; q is 0 to 2; $R^{Het}$ is an optionally substituted monocyclic or bicyclic heteroaryl; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; $R^8$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted heteroaryl, optionally substituted heteroarylalkyl, optionally substituted heterocyclyl, optionally substituted heterocyclylalkyl, —$R^{13}$—$OR^{10}$, —$R^{13}$—O—$R^{14}$—C(=O)$OR^{10}$, —$R^{13}$—C(=O)$R^{10}$, —$R^{13}$—C(=O)$OR^{10}$, —$R^{13}$—C(=O)—$R^{14}$—C(=O)$OR^{10}$, —$R^{13}$—C(=O)—$R^{13}$—N($R^{10}$)$R^{11}$, —$R^{13}$—C(=O)—$R^{14}$—S(=O)$_t$N($R^{10}$)$R^{11}$ (where t is 1 or 2), or —$R^{14}$—S(=O)$_p$$R^{10}$ (where p is 0, 1 or 2); or $R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$; or $R^2$ and $R^8$, together with the nitrogen to which they are attached, form an optionally substituted N-heterocyclyl or an optionally substituted N-heteroaryl; $R^3$ is a direct bond, —O—, —$R^{12}$—O—, —O—$R^{12}$—, —O—$R^{12}$—O—, an optionally substituted straight or branched alkylene chain, an optionally substituted straight or branched alkenylene chain, or an optionally substituted straight or branched alkynylene chain; $R^4$ is a direct bond, —O—$R^{12a}$—, an optionally substituted straight or branched alkylene chain, an optionally substituted straight or branched alkenylene chain, or an optionally substituted straight or branched alkynylene chain; $R^7$ and $R^{5a}$, together with the nitrogen and carbon to which they are attached, form an optionally substituted 5- to 7-membered N-heterocyclyl; or $R^7$ and $R^{5a}$, together with the nitrogen and carbon to which they are attached, form an optionally substituted 5- to 7-membered N-heterocyclyl and $R^2$ and $R^{5c}$, together with the nitrogen and carbon to which are they are attached, form an optionally substituted 5- to 7-membered N-heterocyclyl; or $R^7$ and $R^{5b}$, together with the nitrogen and carbon to which they are attached, form an optionally substituted 5- to 7-membered N-heterocyclyl; or $R^7$ and $R^{5c}$, together with the nitrogen and carbon to which they are attached, form an optionally substituted 5- to 7-membered N-heterocyclyl or an optionally substituted 6- to 10-membered bridged N-heterocyclyl; $R^{5a}$, $R^{5b}$, $R^{5c}$, $R^{6a}$, $R^{6b}$ and $R^{6c}$ are each independently selected from hydrogen, alkyl, haloalkyl or hydroxyalkyl; each $R^9$ is independently —O—$R^{10}$, alkyl, hydroxyalkyl, halo, haloalkyl, aryl or aralkyl; each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or $R^{10}$ and $R^{11}$, together with the nitrogen to which they are attached, form an optionally substituted N-heterocyclyl or an optionally substituted N-heteroaryl; $R^{12}$ is an optionally substituted straight or branched alkylene chain, an optionally substituted straight or branched alkenylene chain, or an optionally substituted straight or branched alkynylene chain; $R^{12a}$ is an optionally substituted straight or branched alkylene chain, an optionally substituted straight or branched alkenylene chain, or an optionally substituted straight or branched alkynylene chain; each $R^{13}$ is a direct bond, an optionally substituted straight or branched alkylene chain, an optionally substituted straight or branched alkenylene chain, or an optionally substituted straight or branched alkynylene chain; and each $R^{14}$ is an optionally substituted straight or branched alkylene chain, an optionally substituted straight or branched alkenylene chain, or an optionally substituted straight or branched alkynylene chain.

Another embodiment of the compounds of formula (I-D) are those wherein r is 0 to 4; q is 0 to 2; $R^{Het}$ is an optionally substituted monocyclic or bicyclic heteroaryl; $R^2$ is hydrogen, alkyl, haloalkyl, haloalkenyl, haloalkynyl, hydroxyalkyl, optionally substituted cycloalkyl, optionally substituted cycloalkylalkyl, optionally substituted aryl, optionally substituted aralkyl, optionally substituted heteroaryl, optionally substituted heteroarylalkyl, optionally substituted heterocyclyl and optionally substituted heterocyclylalkyl; $R^8$ is selected from the group consisting of hydrogen, alkyl, optionally substituted heteroaryl, or optionally substituted heterocyclyl; or R⁸ is aralkyl optionally substituted with —R¹³—OR¹⁰, —R¹³—C(=O)OR¹⁰ or —R¹³—C(=O)—R¹—N(R¹⁰)R¹¹; or R² and R⁸, together with the nitrogen to which they are attached, form an optionally substituted N-heterocyclyl or an optionally substituted N-heteroaryl; R³ is a direct bond, —O—, —R¹²—O—, —O—R¹²—, —O—R¹²—O—, or an optionally substituted straight or branched alkylene chain; R⁴ is a direct bond, —O—R¹²ᵃ—, or an optionally substituted straight or branched alkylene chain; R⁷ and R⁵ᶜ, together with the nitrogen and carbon to which they are attached, form an optionally substituted pyrrolidinyl or an optionally substituted piperidinyl; or R¹ and R⁵ᵇ, together with the nitrogen and carbon to which they are attached, form an optionally substituted pyrrolidinyl; or R⁷ and R⁵ᶜ, together with the nitrogen and carbon to which they are attached, form an optionally substituted piperidinyl or an optionally substituted 6- to 10-membered bridged N-heterocyclyl; R⁵ᵃ, R⁵ᵇ, R⁵ᶜ, R⁶ᵃ, R⁶ᵇ and R⁶ᶜ are each independently selected from hydrogen, alkyl, haloalkyl or hydroxyalkyl; each R⁹ is independently —O—R¹⁰, alkyl, hydroxyalkyl, halo, haloalkyl, aryl or aralkyl; each R¹⁰ and R¹¹ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl; or R¹⁰ and R¹¹, together with the nitrogen to which they are attached, form an optionally substituted N-heterocyclyl or an optionally substituted N-heteroaryl; R¹² is an optionally substituted straight or branched alkylene chain; R¹²ᵃ is an optionally substituted straight or branched alkylene chain; and each R¹³ is a direct bond or an optionally substituted straight or branched alkylene chain.

Another aspect of the invention, as set forth above in the Summary, are methods of treating a disease or disorder ameliorated by the inhibition of LTA₄-h activity in a mammal, wherein the method comprises administering to a mammal in need thereof a therapeutically effective amount of compound of Formula (I), as set forth above in the Summary.

Of this aspect, one embodiment is wherein the disease or disorder is selected from the group consisting of acute inflammation, chronic inflammation, anaphylactic reactions, allergic reactions, allergic contact dermatitis, allergic rhinitis, chemical and non-specific irritant contact dermatitis, urticaria, atopic dermatitis, psoriasis, fistulas associated with Crohn's disease, pouchitis, septic or endotoxic shock, hemorrhagic shock, shock-like syndromes, capillary leak syndromes induced by immunotherapy of cancer, acute respiratory distress syndrome, scleroderma lung disease, traumatic shock, immune- and pathogen-induced pneumonias, immune complex-mediated pulmonary injury and chronic obstructive pulmonary disease, inflammatory bowel diseases, ulcerative colitis, Crohn's disease, post-surgical trauma, gastrointestinal ulcers, diseases associated with ischemia-reperfusion injury, acute myocardial ischemia, infarction, acute renal failure, ischemic bowel disease, acute hemorrhagic or ischemic stroke, immune-complex-mediated glomerulonephritis, autoimmune diseases, insulin-dependent diabetes mellitus, multiple sclerosis, rheumatoid arthritis, osteoarthritis, systemic lupus erythematosus, acute and chronic organ transplant rejection, transplant arteriosclerosis, transplant fibrosis, cardiovascular disorders, hypertension, atherosclerosis, aneurysm, critical leg ischemia, peripheral arterial occlusive disease, Reynaud's syndrome, diabetic nephropathy, neuropathy, retinopathy, macular degeneration, glaucoma, neurodegenerative disorders, delayed neurodegeneration in stroke, Alzheimer's disease, Parkinson's disease, encephalitis, HIV dementia, inflammatory pain, neuropathic pain, arthritic pain, periodontal disease, gingivitis, ear infections, migraine, benign prostatic hyperplasia, cancer, leukemias, lymphomas, prostate cancer, breast cancer, lung cancer, malignant melanoma, renal carcinoma, head tumors, neck tumors and colorectal cancer.

The various embodiments described above are described in more detail herein.

Preparation of the Compounds of the Invention

The following Reaction Schemes illustrate methods to make compounds of this invention, i.e., compounds of formula (I):

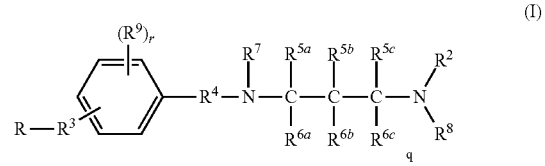

where R, r, q, R², R³, R⁴, R⁵ᵃ, R⁵ᵇ, R⁵ᶜ, R⁶ᵃ, R⁶ᵇ, R⁶ᶜ, R⁷, R⁸, and R⁹ are described above in the Summary, as single stereoisomers or as mixtures of stereoisomers, and the pharmaceutically acceptable salts, solvates, clathrates, polymorphs, ammonium ions, N-oxides or prodrugs thereof. It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(=O)—R″ (where R″ is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (I) not specifically illustrated below by using the appropriate starting components and modifying the parameters of the synthesis as needed. In general, compounds employed as initial starting materials in the synthesis of the compounds of the invention are well known and commercially available, e.g., from Sigma Aldrich, Lancaster Synthesis, Inc., Maybridge, Matrix Scientific, TCI, and Fluorochem USA, etc. To the extent that the compounds employed as initial starting materials are not commercially available, the compounds may be readily synthesized using specific references provided, or by standard procedures commonly employed by those of ordinary skill in the art and/or found in general references text (see, for example, *Comprehensive Organic Transformations*, VCH Publishers Inc., 1989; *Compendium of Organic Synthetic Methods*, Volumes 1-10, 1974-2002, Wiley Interscience; *Advanced Organic Chemistry: Reactions, Mechanisms, and Structure*, 5th edition, Wiley Interscience, 2001; *Advanced Organic Chemistry*, 4th Edition, Part B, Reactions and Synthesis, Kluwer Academic/Plenum Publishers, 2000, etc., and references cited therein).

In the following Reaction Schemes and description thereof, the following common abbreviations are used:
DMF for N,N-dimethylformamide
THF for tetrahydrofuran
TFA for trifluoroacetic acid
EtOAc for ethyl acetate
TMS for trimethylsilyl
TLC for thin layer chromatography
MeOH for methanol
NaOH for sodium hydroxide
Boc for t-butoxycarbonyl A. Preparation of Compounds of Formula (Ia)

Compounds of formula (Ia) are compounds of formula (I) wherein R, r, $R^3$ and $R^9$ are as described above in the Summary of the Invention; $R^2$ and $R^7$, together with the nitrogens to which they are attached, form an optionally substituted 5- to 7-membered N-heterocyclyl, or $R^2$ and $R^7$, together with the nitrogens to which they are attached and one of $R^{5a}$, $R^{5b}$ and $R^{5c}$, form an optionally substituted 6- to 10-membered bridged N-heterocyclyl; $R^4$ is a straight or branched alkylene chain; and $R^8$ is optionally substituted aralkyl. Compounds of formula (Ia) can be prepared as described below in Reaction Scheme 1A wherein a is 0 to 5; R, r, $R^3$ and $R^9$ are as described above in the Summary; $R^{4a}$ is a straight or branched alkylene chain; $R^{8a}$ is a straight or branched alkylene chain; each $R^{8b}$ is independently hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})S(O)_tR^{15}$ (where t is 1 or 2), $-R^{16}-S(O)_tOR^{15}$ (where t is 1 or 2), $-R^{16}-S(O)_pR^{15}$ (where p is 0, 1 or 2), or $-R^{16}-S(O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; and each X is independently bromo or chloro:

REACTION SCHEME 1A

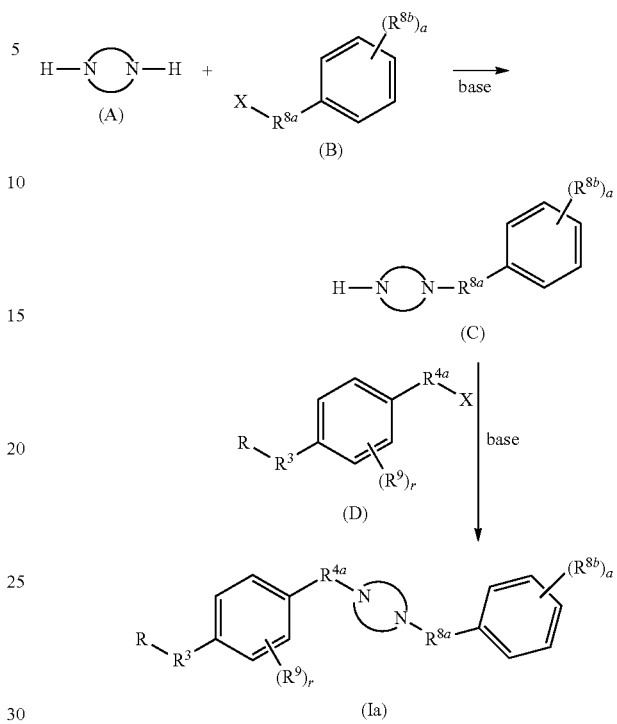

Compounds of formula (A) are optionally substituted N-heterocyclylics or optionally substituted bridged N-heterocyclics and include, for example, the following optionally substituted compounds:

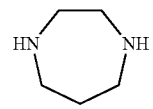

hexahydro-1H-1,4-diazepine

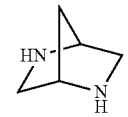

2,5-diazabicyclo[2.2.1]heptane

piperazine

Compounds of formula (A) are commercially available, or can be prepared by methods known to one skilled in the art. Compounds of formula (B) are also commercially available, or can be prepared according to methods known to one skilled in the art, or by methods disclosed herein. For example, as set forth in the following reaction scheme, compounds of formula (B) can be prepared by treating a compound of formula (Ba), which is commercially available, with the appropriate brominating or chlorinating agent under standard conditions to form a compound of formula (B) where X is bromo or chloro:

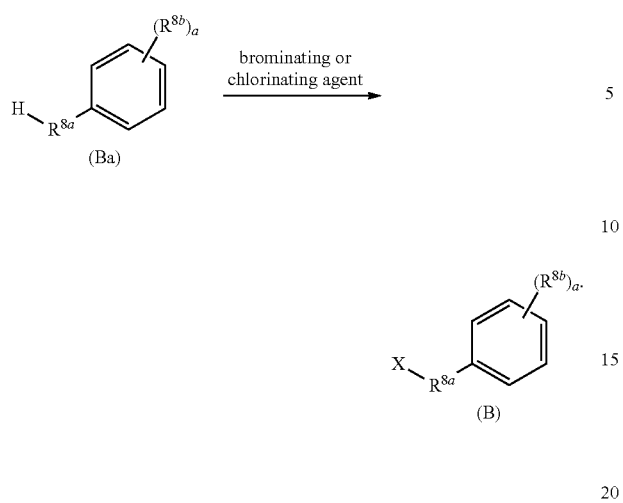

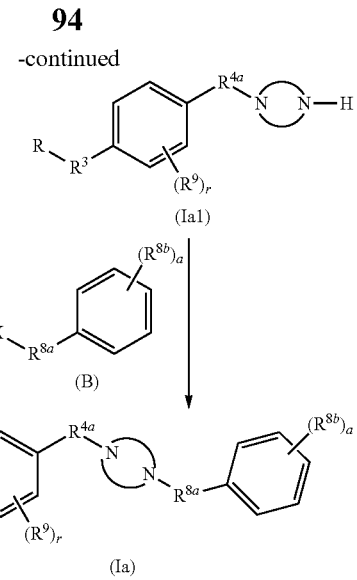

Compounds of formula (D) are commercially available or can be prepared according to methods known to one skilled in the art or by methods disclosed herein.

In general, compounds of formula (Ia), as set forth above in Reaction Scheme 1A, are prepared by reacting a compound of formula (A) with an equivalent amount of a compound of formula (B) at ambient temperatures in the presence of base to generate compounds of formula (C), which are isolated from the reaction mixture by standard isolation techniques, such as chromatography. Compounds of formula (C) can then be coupled with compounds of formula (D) at ambient temperature in the presence of base to generate compounds of formula (Ia), which can be isolated from the reaction mixture by standard isolation techniques, such as chromatography.

Alternatively, one of the nitrogens in the compound of formula (A) can first be protected under standard nitrogen-protecting techniques. The nitrogen-protected compound of formula (A) can then be treated with the compound of formula (B) as described above to form the corresponding nitrogen-protected compound of formula (C). Prior to the reaction with the compound of formula (D) to generate the compound of formula (Ia1), the nitrogen-protecting group can be removed from the compound of formula (C) under standard nitrogen deprotection procedures to form the free base.

Alternatively, compounds of formula (Ia) are prepared by the method described below in Reaction Scheme 1B wherein a, R, r, $R^3$, $R^{4a}$, $R^{8a}$, $R^{8b}$, and $R^9$ are as described above for Reaction Scheme 1A and each X is independently bromo or chloro:

REACTION SCHEME 1B

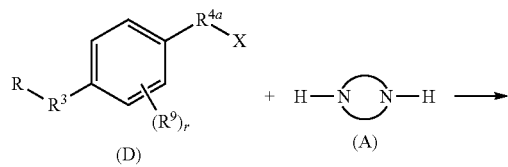

Compounds of formula (D), (A) and (B) are commercially available or can be prepared by methods known to one skilled in the art or by methods disclosed herein.

Compounds of formula (Ia1) are compounds of formula (Ia) wherein R, r, $R^3$, and $R^9$ are as described above in the Summary of the Invention; $R^2$ and $R^7$, together with the nitrogens to which they are attached, form an optionally substituted 5- to 7-membered N-heterocyclyl, or $R^2$ and $R^7$, together with the nitrogens to which they are attached and one of $R^{5a}$, $R^{5b}$ and $R^{5c}$, form an optionally substituted 6- to 10-membered bridged N-heterocyclyl; $R^{4a}$ is a straight or branched alkylene chain; and $R^8$ is hydrogen.

In general, compounds of formula (Ia) are prepared by the method shown in Reaction Scheme 1B by reacting a compound of formula (D) with a compound of formula (A) under standard alkylation conditions to provide a compound of formula (Ia1), which can be isolated from the reaction mixture by standard isolation techniques. The compound of formula (Ia1) is then treated with an equivalent amount of a compound of formula (B) under standard alkylation conditions to form a compound of formula (Ia), which can be isolated from the reaction mixture by standard isolation techniques.

B. Preparation of Compounds of Formula (Ib)

Compounds of formula (Ib) are compounds of formula (I) wherein R, r, $R^3$, and $R^9$ are as described above in the Summary of the Invention; $R^2$ and $R^7$, together with the nitrogens to which they are attached, form an optionally substituted 5- to 7-membered N-heterocyclyl, or $R^2$ and $R^7$, together with the nitrogens to which they are attached and one of $R^{5a}$, $R^{5b}$ and $R^{5c}$, form an optionally substituted 6- to 10-membered bridged N-heterocyclyl; $R^4$ is methylene and $R^8$ is optionally substituted aralkyl. Compounds of formula (Ia) can be prepared as described below in Reaction Scheme 2 wherein a is 0 to 5; R, r, $R^3$, and $R^9$ are as described above in the Summary of the Invention; $R^{8a}$ is a straight or branched alkylene chain; each $R^{8b}$ is independently hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})S(O)_tR^{15}$ (where t is 1 or 2), $-R^{16}-S(O)_tOR^{15}$ (where t is 1 or 2), $-R^{16}-S(O)_tR^{15}$ (where p is 0, 1 or 2), or —$R^{16}$—S(O)$_t$N($R^{15}$)$_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; and X is bromo or chloro:

REACTION SCHEME 2

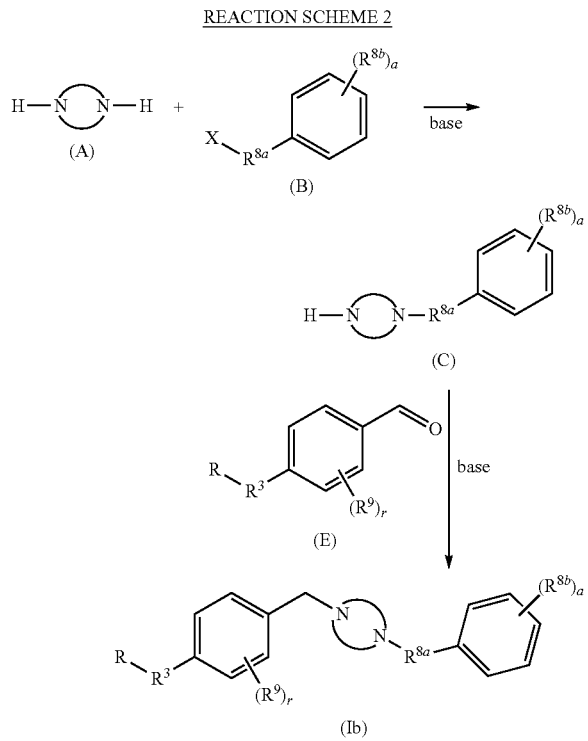

Compounds of formula (A) and formula (B) are commercially available or can be prepared according to methods known to one skilled in the art or by methods disclosed herein. Compounds of formula (E) are commercially available or can be prepared by methods known to one skilled in the art.

In general, a compound of formula (C) is prepared in a manner similar to that described above in Reaction Scheme 1A. The compound of formula (C) is then treated with a compound of formula (E) under standard reductive amination conditions to yield a compound of formula (Ib), which can be isolated from the reaction mixture by standard isolation techniques.

Compounds of formula (Ib) wherein $R^{8b}$ is a carboxylic acid ester group can be hydrolyzed under the appropriate hydrolysis conditions to yield compounds of formula (Ib) wherein $R^{8b}$ is a carboxylic acid group.

Compounds of formula (E) where $R^3$ is —O—, —$R^{12}$—O—, or —O—$R^{12}$—O—, i.e., compounds of formula (Ea) as set forth below in Reaction Scheme 2A, can be prepared by reacting a compound of formula (Eb) where R is as defined above in the Summary and $R^{3a}$ is —O—, —$R^1$—O—, or —O—$R^{12}$—O—, with a compound of formula (Ec) where r and $R^9$ are as defined above in the Summary under standard Williamson ether synthesis conditions to yield a compound of formula (Ea):

REACTION SCHEME 2A

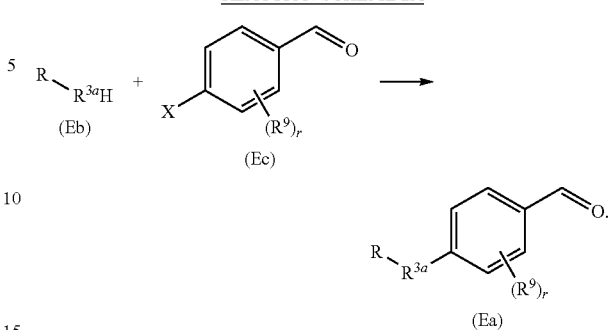

C. Preparation of Compounds of Formula (Ic) Compounds of formula (Ic) are compounds of formula (I) wherein R, r, $R^3$ and $R^9$ are described above in the Summary and $R^4$ is —O—$R^{12a}$— (where $R^{12a}$ is as defined above in the Summary); $R^8$ is an optionally substituted benzyl group; and $R^2$ and $R^7$, together with the nitrogens to which they are attached, form an optionally substituted 5- to 7-membered N-heterocyclyl, or $R^2$ and $R^7$, together with the nitrogens to which they are attached and one of $R^{5a}$, $R^{5b}$ and $R^{5c}$, form an optionally substituted 6- to 10-membered bridged N-heterocyclyl. Compounds of formula (Ic) can be prepared as described below in Reaction Scheme 3 wherein a is 0 to 5; R, r, $R^3$, $R^9$, and $R^{12a}$ are as described above in the Summary; $R^{8a}$ is a straight or branched alkylene chain; each $R^{8b}$ is independently hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—OC(=O)—$R^{15}$, —$R^{16}$—N($R^{15}$)$_2$, —$R^{16}$—C(=O)$R^{15}$, —$R^{16}$—C(=O)$OR^{15}$, —$R^{16}$—C(=O)N($R^{15}$)$_2$, —$R^{16}$—N($R^{15}$)C(=O)$OR^{15}$, —$R^{16}$—N($R^{15}$)C(=O)$R^{15}$, —$R^{16}$—N($R^{15}$) S(O)$_t$$R^{15}$ (where t is 1 or 2), —$R^{16}$—S(O)$_t$$OR^{15}$ (where t is 1 or 2), —$R^{16}$—S(O), $R^{15}$ (where p is 0, 1 or 2), or —$R^{16}$—S(O)$_t$N($R^{15}$)$_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; and each X is independently bromo or chloro:

REACTION SCHEME 3

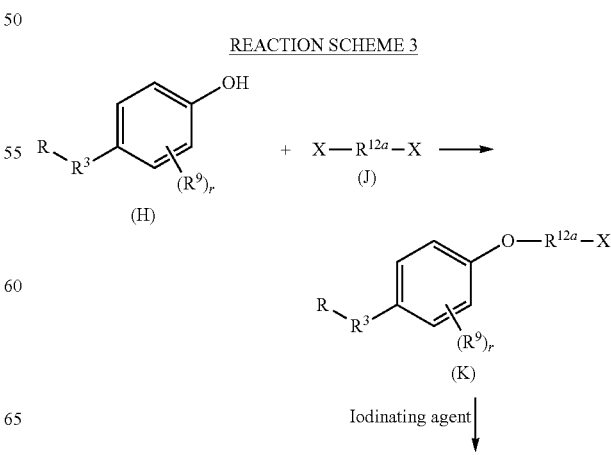

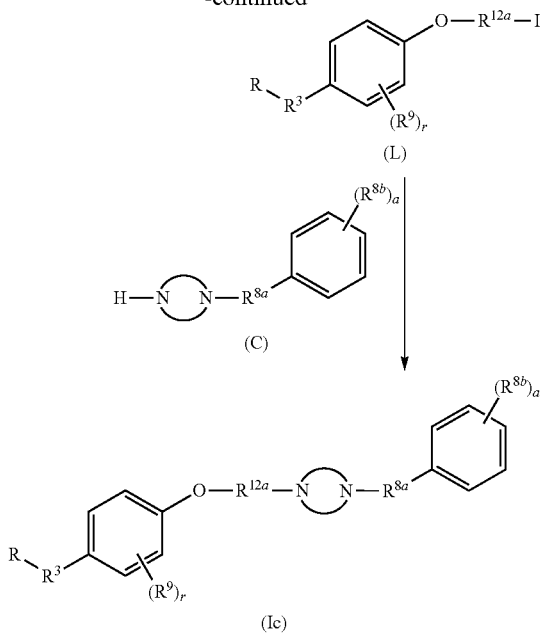

Compounds of formulas (H), (J) and (C) are commercially available or can be prepared according to methods known to one skilled in the art or by methods disclosed herein.

In general, compounds of formula (Ic) are prepared by first reacting a compound of formula (H) with a compound of formula (J) under standard Williamson ether synthesis conditions, preferably in the presence of cesium carbonate and acetonitrile, to produce a compound of formula (K), which is isolated from the reaction mixture by standard isolation techniques. The compound of formula (K) is then treated with an iodinating agent such as sodium iodide, preferably in acetone or butanone, to effect the halide exchange in order to provide a compound of formula (L), which is isolated from the reaction mixture by standard isolation techniques. The compound of formula (L) is then treated with a compound of formula (C) under standard alkylation conditions, preferably in the presence of a base such as triethylamine, to provide a compound of formula (Ic), which is isolated from the reaction mixture by standard isolation techniques.

Compounds of formula (Ic) wherein $R^{8b}$ is a carboxylic acid ester group can be hydrolyzed under the appropriate hydrolysis conditions to yield compounds of formula (Ic) wherein $R^{8b}$ is a carboxylic acid group.

D. Preparation of Compounds of Formula (Id)

Compounds of formula (Id) are compounds of formula (I) where R, r, q, $R^2$, $R^3$, $R^{5a}$, $R^{5b}$, $R^{5c}$, $R^{6a}$, $R^{6b}$, $R^{6c}$, $R^1$, and $R^9$ are as described above in the Summary; $R^4$ is methylene; and $R^8$ is optionally substituted aralkyl; provided that $R^2$ together with the nitrogen to which it is attached cannot form a heterocyclic structure with any other substituent, $R^7$ together with the nitrogen to which it is attached cannot form a heterocyclic structure with any other substituents, and $R^2$ and $R^7$ together with the nitrogens to which they are attached cannot form a heterocyclic ring. Compounds of formula (Id) can be prepared as described below in Reaction Scheme 4 wherein a is 0 to 5; R, r, q, $R^3$, $R^{5a}$, $R^{5b}$, $R^{5c}$, $R^{6a}$, $R^{6b}$, $R^{6c}$ and $R^9$ are as described above in the Summary; $R^2$ and $R^7$ are as described above in the Summary except that neither $R^2$ or $R^7$ can form a heterocyclic structure with any other substituent; $R^{8a}$ is a straight or branched alkylene chain; each $R^{8b}$ is independently hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R')_2$, $-R^{16}-N(R')C(=O)OR^1$, $-R^{16}-N(R^{15})C(=O)R^{15}$, $-R^{16}-N(R^{15})S(O)_tR^{15}$ (where t is 1 or 2), $-R^{16}-S(O)_tOR^{15}$ (where t is 1 or 2), $-R^{16}-S(O)_pR^{15}$ (where p is 0, 1 or 2), or $-R^{16}-S(O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; and X is bromo or chloro:

REACTION SCHEME 4

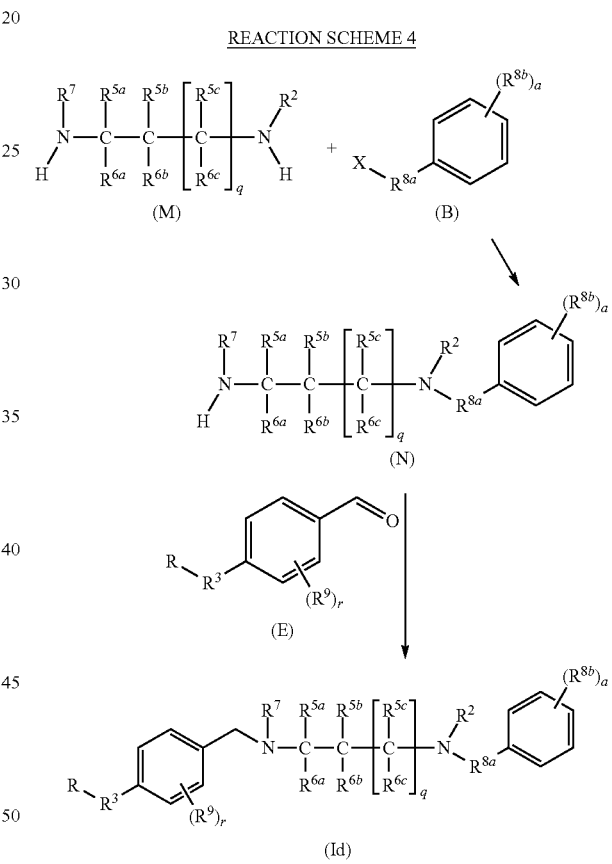

Compounds of formula S (M), (B) and (E) are commercially available or can be prepared according to methods known to one skilled in the art or by methods disclosed herein.

In general, compounds of formula (Id) are prepared by first treating a compound of formula (M) with a compound of formula (B) at elevated temperatures, preferably at reflux temperature, under standard amine alkylation conditions, such as the presence of a polar aprotic solvent and base, such as triethylamine. The compound of formula (N) is then isolated from the reaction conditions by standard isolation techniques. The compound of formula (N) is then treated with a compound of formula (E) under standard reductive amination conditions, preferably in an aprotic solvent in the presence of a selective reducing agent, such as sodium triacetoxyborohydride, at ambient temperature, to afford a compound of formula (Id), which is isolated from the reaction mixture by standard isolation techniques.

Compounds of formula (Id) wherein $R^{8b}$ is a carboxylic acid ester group can be hydrolyzed under the appropriate hydrolysis conditions to yield compounds of formula (Id) wherein $R^{8b}$ is a carboxylic acid group.

E. Preparation of Compounds of Formula (Ie)

Compounds of formula (Ie) are compounds of formula (I) where r, q, R, $R^3$, $R^{5b}$, $R^{5c}$, $R^{6a}$, $R^{6b}$, $R^{6c}$ and $R^9$ are as described above in the Summary; $R^2$ and $R^{5a}$, together with the nitrogen and carbon to which they are attached, form an optionally substituted piperidinyl; $R^4$ is methylene; $R^7$ is methyl and $R^8$ is optionally substituted aralkyl. Compounds of formula (Ie) are prepared as described below in Reaction Scheme 5 wherein a is 0 to 5; r, R, $R^3$ and $R^9$ are as described above in the Summary; $R^{4a}$ is methylene; $R^{8a}$ is a straight or branched alkylene chain; each $R^{5b}$ is independently hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—OC(=O)—$R^{15}$, —$R^{16}$—$N(R^{15})_2$, —$R^{16}$—C(=O)$R^{15}$, —$R^{16}$—C(=O)$OR^{15}$, —$R^{16}$—C(=O)$N(R^{15})_2$, —$R^{16}$—$N(R^{15})C$(=O)$OR^{15}$, —$R^{16}$—N$(R^{15})C$(=O)$R^{15}$, —$R^{16}$—$N(R^{15})$ S(O)$_t R^{15}$ (where t is 1 or 2), —$R^{16}$—S(O)$_t OR^{15}$ (where t is 1 or 2), —$R^{11}$—S(O)$_p R^{15}$ (where p is 0, 1 or 2), or —$R^{16}$—S(O)$_t N(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; PG is a nitrogen protecting group; and X is bromo or chloro:

REACTION SCHEME 5

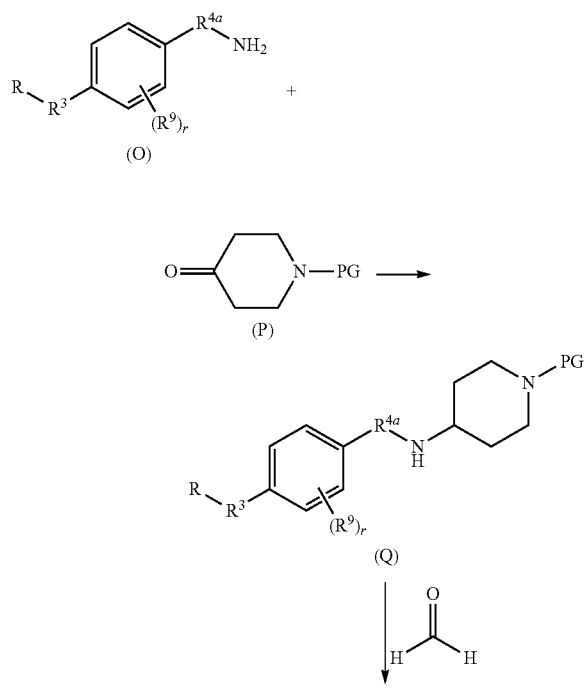

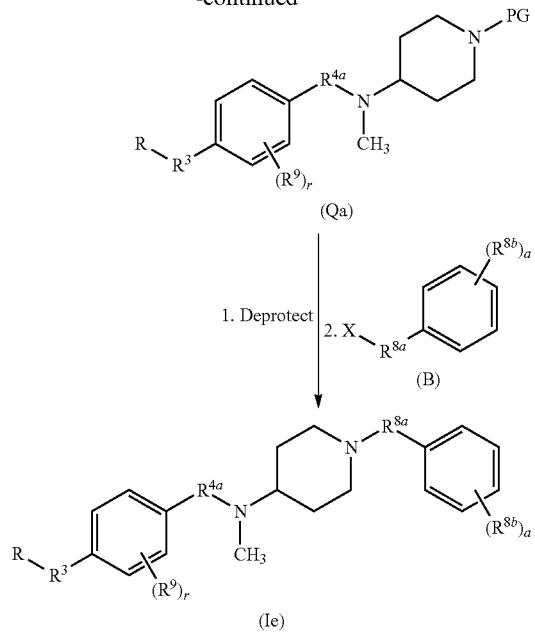

Compounds of formulas (O), (P) and (B) are commercially available, or can be prepared by methods known to one skilled in the art or by methods disclosed herein.

In general, compounds of formula (Ie) are prepared by first treating a compound of formula (O) with a compound of formula (P) under standard reductive amination conditions, preferably in an aprotic solvent in the presence of a selective reducing agent, such as sodium triacetoxyborohydride, and preferably at ambient temperature, to afford a compound of formula (Q), which is isolated from the reaction mixture by standard isolation techniques. The compound of formula (Q) is then treated with formaldehyde under standard reductive amination conditions to form a compound of formula (Qa), which is isolated from the reaction mixture by standard isolation techniques. The compound of formula (Qa) is then subjected to standard nitrogen-deprotection techniques and the treated with a compound of formula (B) under standard alkylation conditions at ambient temperatures to form a compound of formula (Ie), which is isolated from the reaction mixture by standard isolation techniques.

Compounds of formula (Ie) wherein $R^{8b}$ is a carboxylic acid ester group can be hydrolyzed under the appropriate hydrolysis conditions to yield compounds of formula (Ie) wherein $R^{8b}$ is a carboxylic acid group.

F. Preparation of Compounds of Formula (If)

Compounds of formula (If) are compounds of formula (I) where r, q, R, $R^3$, $R^{5b}$, $R^{5c}$, $R^{6a}$, $R^{6b}$, $R^{6c}$ and $R^9$ are as described above in the Summary; $R^2$ is methyl; $R^7$ and $R^{5a}$, together with the nitrogen and carbon to which they are attached, form an optionally substituted piperidinyl; $R^4$ is methylene; $R^7$ is methyl; and $R^8$ is optionally substituted aralkyl.

Compounds of formula (If) are prepared as described below in Reaction Scheme 6 wherein a is 0 to 5; r, R, $R^3$ and $R^9$ are as described above in the Summary; each $R^{8b}$ is independently hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{16}$—$OR^{15}$, —$R^{16}$—OC (=O)—R¹⁵, —R¹⁶—N(R¹⁵)₂, —R¹⁶—C(=O)R¹⁵, —R¹⁶—C(=O)OR¹⁵, —R¹⁶—C(=O)N(R¹⁵)₂, —R¹⁶—N(R¹⁵)C(=O)OR¹⁵, —R¹⁶—N(R¹⁵)C(=O)R¹⁵, —R¹⁶—N(R¹⁵) S(O)ₜR¹⁵ (where t is 1 or 2), —R¹⁶—S(O)OR¹⁵ (where t is 1 or 2), —R¹⁶—S(O)ₚR¹⁵ (where p is 0, 1 or 2), or —R¹⁶—S(O)ₜN(R¹⁵)₂ (where t is 1 or 2), where each R¹⁵ is independently hydrogen, alkyl, haloalkyl, cycloalkyl, cycloalkylalkyl, aryl, aralkyl, heterocyclyl, heterocyclylalkyl, heteroaryl or heteroarylalkyl, and each R¹⁶ is independently a direct bond or a straight or branched alkylene or alkenylene chain; and PG is a nitrogen protecting group:

REACTION SCHEME 6

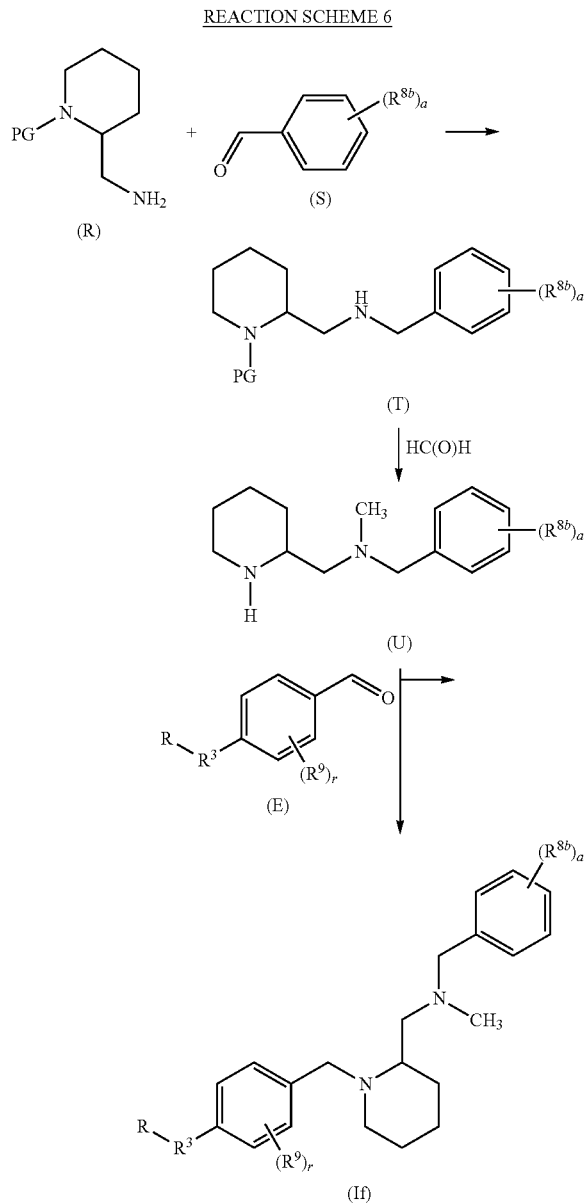

Compounds of formula (R), (S) and (E) are commercially available, or can be prepared by methods known to one skilled in the art or by methods disclosed herein.

In general, compounds of formula (If) are prepared by first treating a compound of formula (R) with a compound of formula (S) under standard reductive amination conditions, preferably in an aprotic solvent in the presence of a selective reducing agent, such as sodium triacetoxyborohydride, at ambient temperature, to form a compound of formula (T), which is isolated from the reaction mixture by standard isolation techniques. The compound of formula (T) is then treated with formaldehyde under standard reductive amination conditions to yield a product, which is then treated under appropriate nitrogen deprotection conditions to yield a compound of formula (U), which is isolated from the reaction mixture by standard isolation techniques, such as organic extraction and flash chromatography. The compound of formula (U) is then treated with a compound of formula (E) under standard reductive amination conditions to yield a compound of formula (If), which is isolated from the reaction mixture by standard isolation techniques.

Compounds of formula (if) wherein R⁸ᵇ is a carboxylic acid ester group can be hydrolyzed under the appropriate hydrolysis conditions to yield compounds of formula (If) wherein R⁸ᵇ is a carboxylic acid group.

G. Preparation of Compounds of Formula (Ig) Compounds of formula (Ig) are compounds of formula (I) where r, q, R, R³, R⁵ᵇ, R⁵ᶜ, R⁶ᵃ, R⁶ᵇ, R⁶ᶜ and R⁹ are as described above in the Summary; R² is methyl, R⁷ and R⁵ᵃ together with the nitrogen and carbon to which they are attached, form an optionally substituted pyrrolidinyl; R⁴ is methylene; and R⁸ is optionally substituted aralkyl. Compounds of formula (Ig) are prepared as described below in Reaction Scheme 7 wherein a is 1 to 5; r, R, R³ and R⁹ are as described above in the Summary; each R⁸ᵇ is hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —R¹⁶—OR¹⁵, —R¹⁶—OC(=O)—R¹⁵, —R¹⁶—N(R¹⁵)₂, —R¹⁶—C(=O)R¹⁵, —R¹⁶—C(=O)OR¹⁵, —R¹⁶—C(=O)N(R¹⁵)₂, —R¹⁶—N(R¹⁵)C(=O)OR¹⁵, —R¹⁶—N(R¹⁵)C(=O)R¹⁵, —R¹⁶—N(R¹⁵) S(O)ₜR¹⁵ (where t is 1 or 2), —R¹⁶—S(O) OR¹⁵ (where t is 1 or 2), —R¹⁶—S(O)ₚR¹⁵ (where p is 0, 1 or 2), and —R¹⁶—S(O)ₜN(R¹⁵)₂ (where t is 1 or 2), where each R¹⁵ is independently hydrogen, alkyl, haloalkyl, cycloalkyl, cycloalkylalkyl, aryl, aralkyl, heterocyclyl, heterocyclylalkyl, heteroaryl or heteroarylalkyl, and each R¹⁶ is independently a direct bond or a straight or branched alkylene or alkenylene chain; and PG is a nitrogen protecting group:

REACTION SCHEME 7

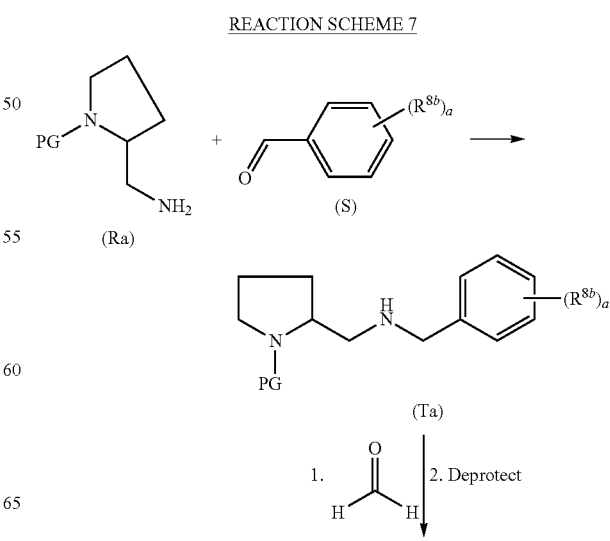

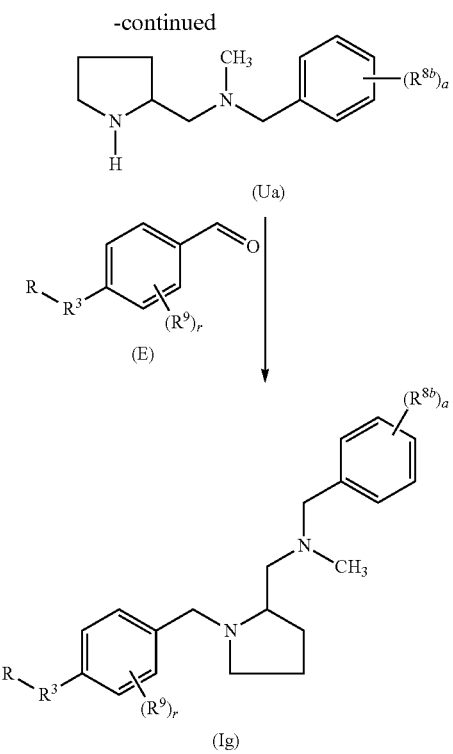

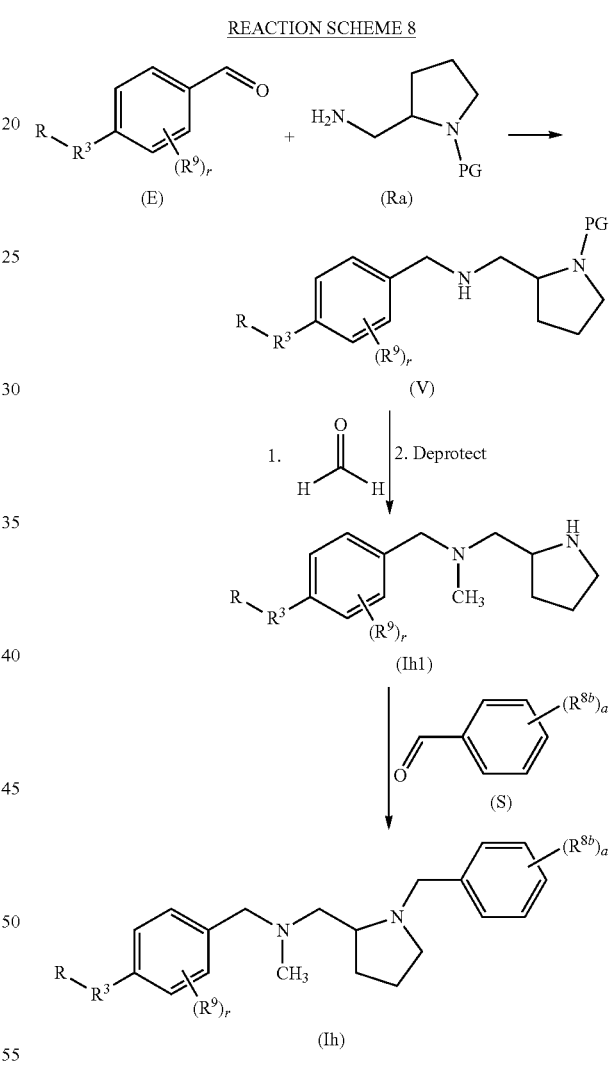

heterocyclyl, heterocyclylalkyl, heteroaryl, heteroarylalkyl, $-R^{16}-OR^{15}$, $-R^{16}-OC(=O)-R^{15}$, $-R^{16}-N(R'S)_2$, $-R^{16}-C(=O)R'S$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})S(O)_tR^{15}$ (where t is 1 or 2), $-R^{16}-S(O)_tOR^{15}$ (where t is 1 or 2), $-R^{16}-S(O)_pR^{15}$ (where p is 0, 1 or 2), and $-R^{16}-S(O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; and PG is a nitrogen protecting group:

Compounds of formula (Ra), (S) and (E) are commercially available, or can be prepared by methods known to one skilled in the art or by methods disclosed herein.

In general, compounds of formula (Ig) are prepared by first treating a compound of formula (Ra) with a compound of formula (S) under standard reductive amination conditions, preferably in an aprotic solvent in the presence of a selective reducing agent, such as sodium triacetoxyborohydride, at ambient temperature, to form a compound of formula (Ta), which is isolated from the reaction mixture by standard isolation techniques. The compound of formula (Ta) is then treated with formaldehyde under standard reductive amination conditions to yield a product, which is then treated under appropriate nitrogen deprotection conditions to yield a compound of formula (Ua), which is isolated from the reaction mixture by standard isolation techniques, such as organic extraction and flash chromatography. The compound of formula (Ua) is then treated with a compound of formula (E) under standard reductive amination conditions to yield a compound of formula (Ig), which is isolated from the reaction mixture by standard isolation techniques.

Compounds of formula (Ig) wherein $R^{8b}$ is a carboxylic acid ester group can be hydrolyzed under the appropriate hydrolysis conditions to yield compounds of formula (Ig) wherein $R^{8b}$ is a carboxylic acid group.

H. Preparation of Compounds of Formula (Ih1) and (Ih)

Compounds of formula (Ih1) and (Ih) are compounds of formula (I) where r, q, R, $R^3$, $R^{5a}$, $R^{5c}$, $R^{6a}$, $R^{6b}$, $R^{6c}$ and $R^9$ are as described above in the Summary; $R^2$ and $R^{5b}$, together with the nitrogen and carbon to which they are attached, form an optionally substituted pyrrolidinyl; $R^4$ is methylene; $R^7$ is methyl; and $R^8$ is optionally substituted aralkyl.

Compounds of formula (Ih) are prepared as described below in Reaction Scheme 8 wherein a is 1 to 5; r, R, $R^3$ and $R^9$ are as described above in the Summary; each $R^{8b}$ is hydrogen, alkyl, alkenyl, alkynyl, halo, haloalkyl, haloalkenyl, cyano, nitro, aryl, aralkyl, cycloalkyl, cycloalkylalkyl, Compounds of formula (Ra), (S) and (E) are commercially available, or can be prepared by methods known to one skilled in the art or by methods disclosed herein.

In general, compounds of formula (Ig) are prepared by first treating a compound of formula (E) with a compound of formula (Ra) under standard reductive amination conditions, preferably in an aprotic solvent in the presence of a selective reducing agent, such as sodium triacetoxyborohydride, at ambient temperature, to form a compound of formula (V), which is isolated from the reaction mixture by standard isolation techniques. The compound of formula (V) is then treated with formaldehyde under standard reductive amination conditions to yield a product, which is then treated under appropriate nitrogen deprotection conditions to yield a compound of formula (Ih1), which is isolated from the reaction mixture by standard isolation techniques, such as organic extraction and flash chromatography. The compound of formula (Ih1) is then treated with a compound of formula (S) under standard reductive amination conditions to yield a compound of formula (Ih), which is isolated from the reaction mixture by standard isolation techniques.

Compounds of formula (Ih) wherein $R^{8b}$ is a carboxylic acid ester group can be hydrolyzed under the appropriate hydrolysis conditions to yield compounds of formula (Ih) wherein $R^{8b}$ is a carboxylic acid group.

I. Preparation of Compounds of Formula (Ii)

Compounds of formula (Ii) are compounds of formula (I) where r, q, R, $R^3$, $R^{5b}$, $R^{5c}$, $R^{6a}$, $R^{6b}$, $R^{6c}$ and $R^9$ are as described above in the Summary; $R^2$ and $R^{5a}$, together with the nitrogen and carbon to which they are attached, form an optionally substituted azabicyclo[3.2.1]octan-3-onyl; $R^4$ is methylene; $R^7$ is hydrogen; and $R^8$ is optionally substituted aralkyl. Compounds of formula (Ii) are prepared as described below in Reaction Scheme 9 wherein a is 1 to 5; r, R, $R^3$ and $R^9$ are as described above in the Summary; $R^{4a}$ is methylene; $R^{8a}$ is a straight or branched alkylene chain; each $R^{8b}$ is hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})S(O)_tR^{15}$ (where t is 1 or 2), $-R^{16}-S(O)_tOR^{15}$ (where t is 1 or 2), $-R^{16}-S(O)_pR^{15}$ (where p is 0, 1 or 2), and $-R^{16}-S(O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; PG is a nitrogen protecting group and X is bromo or chloro:

REACTION SCHEME 9

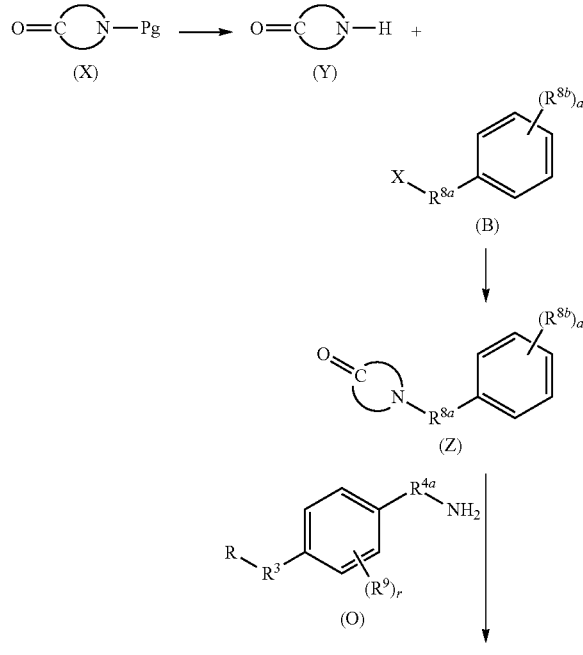

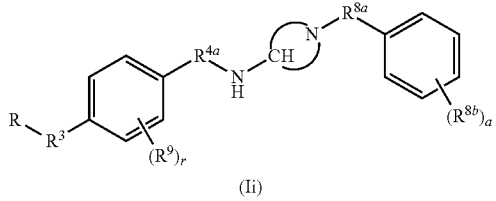

(Ii)

Compounds of formula (Y) are optionally substituted N-heterocyclics or optionally substituted bridged N-heterocyclics and include, for example, the following optionally substituted compounds:

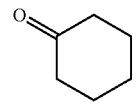

4-piperidone

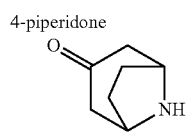

8-azabicyclo[3.2.1]octan-3-one

Compounds of formulas (B), (X), (Y) and (O) are commercially available, or can be prepared by methods known to one skilled in the art or by methods disclosed herein.

In general, compounds of formula (Ii) are prepared by first deprotecting the compound of formula (X) under standard nitrogen deprotection conditions to yield a compound of formula (Y), which is then treated with a compound of formula (B) under standard alkylation conditions to yield a compound of formula (Z), which is isolated from the reaction mixture by standard isolation techniques. The compound of formula (Z) is then treated with a compound of formula (O) under standard reductive amination conditions to yield a compound of formula (Ii), which is isolated from the reaction mixture by standard isolation techniques.

Compounds of formula (Ii) wherein $R^{8b}$ is a carboxylic acid ester group can be hydrolyzed under the appropriate hydrolysis conditions to yield compounds of formula (Ii) wherein $R^{8b}$ is a carboxylic acid group.

J. Preparation of Compounds of Formula (Ij)

Compounds of formula (Ij) are compounds of formula (I) where q is 1, r, R, $R^3$, $R^{5b}$, $R^{5a}$, $R^{6a}$, $R^{6b}$, $R^{6c}$ and $R^9$ are as described above in the Summary; $R^7$ and $R^{5c}$, together with the nitrogen and carbon to which they are attached, form an optionally substituted azabicyclo[3.2.1]octan-3-onyl; $R^4$ is methylene; $R^2$ is methyl; and $R^8$ is optionally substituted aralkyl. Compounds of formula (Ii) are prepared as described below in Reaction Scheme 10A wherein a is 1 to 5; r, R, $R^3$ and $R^9$ are as described above in the Summary; $R^{8a}$ is a straight or branched alkylene chain; each $R^{8b}$ is hydrogen, alkyl, alkenyl, alkynyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, $-R^{16}-OR^{15}$, $-R^{16}-OC(=O)-R^{15}$, $-R^{16}-N(R^{15})_2$, $-R^{16}-C(=O)R^{15}$, $-R^{16}-C(=O)OR^{15}$, $-R^{16}-C(=O)N(R^{15})_2$, $-R^{16}-N(R^{15})C(=O)OR^{15}$, $-R^{16}-N(R^{15})C(=O)R^{15}$, $-R^{16}-N(R^{15})S(O)_tR^{15}$ (where t is 1 or 2), $-R^{16}-S(O)_tOR^{15}$ (where t is 1 or 2), $-R^{16}-S(O)_pR^{15}$ (where p is 0, 1 or 2), and $-R^{16}-S(O)_tN(R^{15})_2$ (where t is 1 or 2), where each $R^{15}$ is independently hydrogen, alkyl, haloalkyl, cycloalkyl, cycloalkylalkyl, aryl, aralkyl, heterocyclyl, heterocyclylalkyl, heteroaryl or heteroarylalkyl, and each $R^{16}$ is independently a direct bond or a straight or branched alkylene or alkenylene chain; and PG is a nitrogen-protecting group:

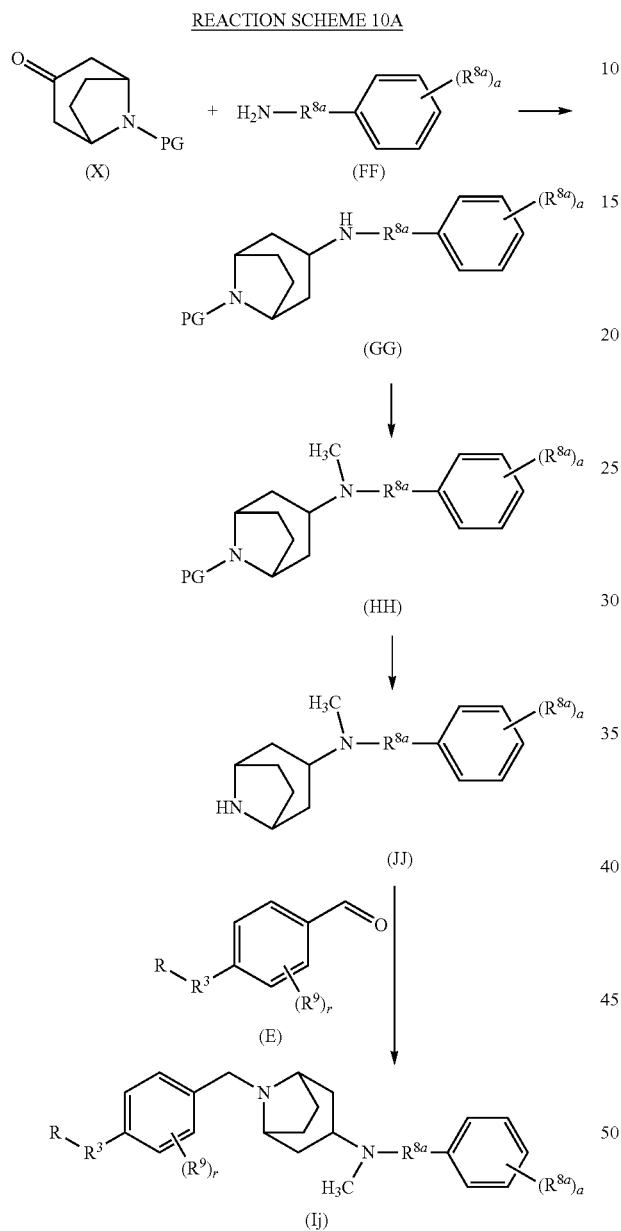

Compounds of formulas (E), (X) and (FF) are commercially available, or can be prepared by methods known to one skilled in the art or by methods disclosed herein In general, compounds of formula (Ij) are treated with a compound of formula (FF) under standard reductive amination conditions to yield a compound of formula (GG), which is isolated from the reaction mixture by standard isolation techniques. The compound of formula (GG) is then treated with formaldehyde under standard reductive amination conditions to yield a compound of formula (HH), which is isolated from the reaction mixture by standard isolation techniques. The compound of formula (HH) is then treated under standard nitrogen deprotection procedures to yield the compound of formula (JJ). The compound of formula (JJ) is then treated with a compound of formula (E) under standard reductive amination conditions to yield the compound of formula (Ij), which is isolated from the reaction mixture by standard isolation techniques.

Compounds of formula (Ij) wherein $R^{8b}$ is a carboxylic acid ester group can be hydrolyzed under the appropriate hydrolysis conditions to yield compounds of formula (Ij) wherein $R^{8b}$ is a carboxylic acid group.

Compounds of formula (E) where R is 2-oxazolylphenoxy can be prepared as described below in Reaction Scheme 10B wherein r and $R^9$ are as defined above in Reaction Scheme 10A and X is bromo or chloro:

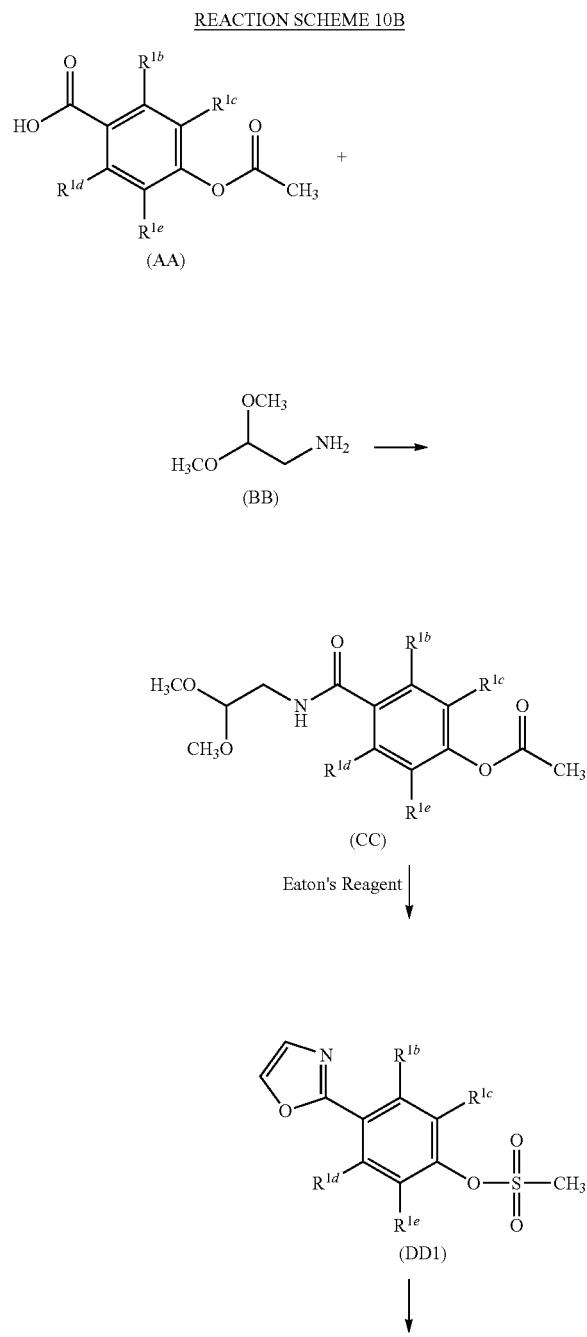

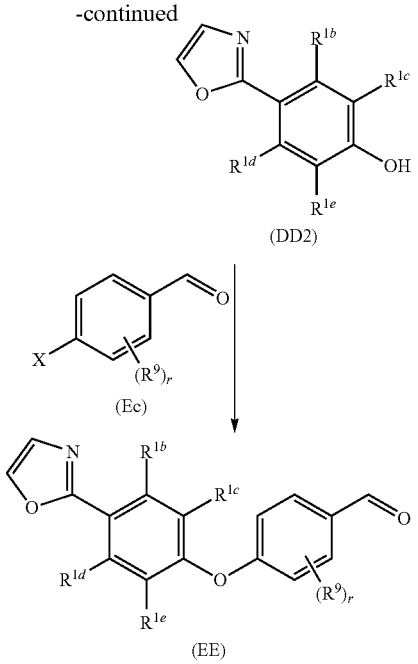

Compounds of formulas (AA), (BB) and (Ec) are commercially available, or can be prepared by methods known to one skilled in the art or by methods disclosed herein.

In general, compounds of formula (EE) are prepared by first treating a compound of formula (AA) with a compound of formula (BB) under standard acylation conditions to produce a compound of formula (CC), which is isolated from the reaction mixture by standard isolation techniques. Compound of formula (CC) is then treated with Eaton's reagent under conditions similar to those described in Pandit, C. R. et al, "Preparation of 2-Substituted Oxazoles", Synth. Commun. 32, 2427-2432 (2002) to form a compound of formula (DD1), which is isolated from the reaction conditions by standard isolation techniques. The compound of formula (DD1) is then hydrolyzed under base hydrolysis conditions to yield a compound of formula (DD2), which is isolated from the reaction conditions by standard isolation techniques. The compound of formula (DD2) is then reacted with a compound of formula (Ec) under standard nucleophilic aromatic substitution conditions to yield a compound of formula (EE), which is isolated from the reaction mixture by standard isolation techniques.

It is understood that other compounds of the invention, not specifically disclosed in the above Reaction Schemes, may be similarly prepared with the appropriate starting materials by one skilled in the art.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the invention are intended to be within the scope of the invention. Furthermore, all compounds of the invention which contain an ester group can be converted to the corresponding acid by methods known to one skilled in the art or by methods described herein.

To prepare the cyclodextrin clathrates of this invention, the compounds of formula (I), as defined above in the Summary of the Invention, can be dissolved in a pharmacologically acceptable solvent, e.g., in an alcohol, preferably ethanol, in a ketone, e.g., acetone or in an ether, e.g., diethyl ether, and mixed with aqueous solutions of α-cyclodextrin, β-cyclodextrin or γ-cyclodextrin, preferably ρ-cyclodextrin, at 20° C. to 80° C.; or the acids of the compounds of formula (I) as defined above in the Summary of the Invention in the form of the aqueous solutions of their salts (e.g., sodium or potassium salts) can be admixed with a cyclodextrin and after solution with the equivalent amount of an acid (e.g., HCl or $H_2SO_4$) to afford the corresponding cyclodextrin clathrate.

At this point or after cooling, the corresponding cyclodextrin clathrates separate in the form of crystals. However, it is also possible to convert oily and also crystalline compounds of formula (I), as defined above in the Summary of the Invention, by rather long stirring (e.g., for 1 hour to 14 days) at ambient temperature, by treatment with an aqueous solution of cyclodextrins, into the corresponding cyclodextrin clathrate form. The clathrates can then be isolated as solid, free-flowing crystals by suctioning off the solvents and drying.

Cyclodextrins used in this invention are commercially available, for example, from Aldrich Chemical Co., or can be prepared by methods known to those skilled in the art. See, for example, Croft, A. P. et al., "Synthesis of Chemically Modified Cyclodextrins", Tetrahedron (1983), Vol. 39, No. 9, pp. 1417-1474. Suitable cyclodextrins will include a wide variety of those which produce clathrates of the compounds of formula (I) as set forth above. See, for example, J. E. F. Reynolds (ed.) Martindale, The Extra Pharmacopoeia 28th ed. The Pharmaceutical Press, London 1982, p. 333 and 389-390; and O.-A. Neumueller (ed.), Roempps Chemie-Lexikon, 8. Aufl. Franckh'sche Verlagshandlung, Stuttgart 1981, p. 763-764, 841, 1053-1054.

By selection of the suitable amounts of cyclodextrins and water it is possible to obtain the new clathrates in a stoichiometric composition with a reproducible content of effective substance. The clathrates can be used in a dry hygroscopic form or in a water-containing, but less hygroscopic form. A typical molar ratio of cyclodextrin to a compound of formula (I) is 2:1 (cyclodextrin:compound).

The following specific Synthetic Preparations (for the preparation of starting materials and intermediates) and Synthetic Examples (for the preparation of the compounds of the invention) and the Biological Examples (for the assays used to demonstrate the utility of the compounds of the invention) are provided as a guide to assist in the practice of the invention, and are not intended as a limitation on the scope of the invention. Where one or more NMR's are given for a particular compound, each NMR may represent a single stereoisomer, a non-racemic mixture of stereoisomers or a racemic mixture of the stereoisomers of the compound.

Synthetic Preparation 1

Compound of Formula (C)

A. A suspension of 1,1-dimethylethyl (1S,4S)-2,5-diazabicyclo[2.2.1]heptane-2-carboxylate (28.2 g, 142.2 mmol, Aldrich), methyl 4-(bromomethyl)benzoate (35.8 g, 156.5 mmol, 1.1 equiv., Aldrich #34, 815-5), and potassium carbonate (78.6 g, 569 mmol, 4 equiv.) in DMF (700 mL) was stirred at ambient temperature for 21 hours. The reaction was then poured into 2 L ice water and allowed to stand for 20 minutes. The solid was filtered off and rinsed with water and hexanes (to remove any residual methyl 4-(bromomethyl)benzoate) to provide 41.7 g (85%) of the pure product, 1,1-dimethylethyl (1S,4S)-5-[[4-(methoxycarbonyl)phenyl]methyl]-2,5-diazabicyclo[2.2.1]heptane-2-carboxylate, as a white powder; $^1$H NMR (CDCl$_3$) δ 7.98 (d, 2H), 7.42 (d, 2H), 4.38/4.25 (sbr, 1H), 3.91 (s, 3H), 3.79/3.78 (s, 2H), 3.61/3.50 (dbr, 1H), 3.44 (dbr, 1H), 3.17 (m, 1H), 2.90/2.86 (dbr, 1H), 2.71/2.52 (dbr, 1H), 1.87/1.68 (m, 2H), 1.47 (s, 9H) ppm.

1,1-Dimethylethyl (1S,4S)-5-[[4-(methoxycarbonyl)phenyl]methyl]-2,5-diazabicyclo[2.2.1]heptane-2-carboxylate (44.1 g, 127.3 mmol) was slurried in HCl (2 M in water, 0.6 L). The solid went into solution over 2 hours, and the solution was stirred for another 16 hours. The reaction was cooled to −5 C and saturated K$_2$CO$_3$ was added slowly enough to keep the temperature below 0 C to prevent ester hydrolysis. Once the pH was 11, the solution was extracted with CH$_2$Cl$_2$ until no product was observed in the water layer by TLC (3×). The combined organic fractions were concentrated under vacuum to obtain pure methyl 4-[[(1S,4S)-2,5-diazabicyclo[2.2.1]hept-2-yl]methyl]benzoate (30.3 g, 97%) as the freebase; $^1$H NMR (CD$_3$OD) δ 7.98 (d, 2H), 7.49 (d, 2H), 4.00 (sbr, 1H), 3.90 (s, 3H), 3.88 (d, 1H), 3.80 (d, 1H), 3.57 (sbr, 1H), 3.39 (ddbr, 1H), 3.03 (ddbr, 1H), 2.88 (ddbr, 1H), 2.72 (ddbr, 1H), 2.09 (dbr, 1H), 1.75 (dbr, 1H) ppm.

B. Following the above procedure, 1,1-dimethylethyl (1S,4S)-2,5-diazabicyclo[2.2.1]heptane-2-carboxylate and methyl 3-methoxy-4-(bromomethyl)benzoate are reacted together to give methyl 3-methoxy-4-[[(1S,4S)-2,5-diazabicyclo[2.2.1]hept-2-yl]methyl]benzoate.

C. In like manner, 1,1-dimethylethyl (1S,4S)-2,5-diazabicyclo[2.2.1]heptane-2-carboxylate and methyl 2-methoxy-4-(bromomethyl)benzoate are reacted together to give methyl 2-methoxy-4-[[(1S,4S)-2,5-diazabicyclo[2.2.1]hept-2-yl]methyl]benzoate.

D. Alternatively, a mixture of hexahydro-1H-1,4-diazepine (17.47 g, 174.4 mmol) and methyl 4-(bromomethyl)benzoate (5.0 g, 21.8 mmol) was heated with triethylamine (24 mL, 174.4 mmol) in tetrahydrofuran (872 mL) to reflux for three hours. After cooling, the mixture was treated with saturated sodium bicarbonate solution. The mixture was extracted with ethyl acetate. The organic layer was washed with brine, dried over sodium sulfate, and concentrated under reduced pressure. Flash chromatography gave 3.04 g of methyl 4-[(hexahydro-1H-1,4-diazepin-1-yl)methyl]benzoate, $^1$H NMR (300 MHz, CDCl$_3$) δ 7.98 (d, 2H), 7.42 (d, 2H), 3.90 (s, 3H), 3.70 (s, 2H), 2.97 (m, 2H), 2.91 (m, 2H), 2.67 (m, 2H), 2.66 (m, 2H), 1.77 (m, 2H)

Synthetic Preparation 2

Compound of Formula (E)

A. A slurry of 4-acetoxybenzoic acid (100 g, 555.1 mmol) in CH$_2$Cl$_2$ (50 mL) was treated with a catalytic amount of DMF (0.5 mL) and cooled in ice bath. The reaction was stirred as neat oxalyl chloride (51 mL, 582.82 mmol, 1.05 equiv.) was added dropwise. The reaction was allowed to warm to ambient temperature and stirred overnight. The reaction mixture was concentrated under reduced pressure to give 4-(chlorocarbonyl)phenyl acetate (110 g, 100% th.; 110% pract.), which was used in the next step without further purification; $^1$H NMR (CDCL$_3$) δ 8.09 (d, 2H), 7.20 (d, 2H), 2.28 (s, 3H) ppm.

B. To a solution of 4-(chlorocarbonyl)phenyl acetate (45.6 g, 0.23 mol) in sulfolane (200 mL) was added 2-TMS-1,2,3-triazole (1.1 eq., 34 mL) over one minute. After stirring for 5 minutes under nitrogen, the reaction was exothermic and the temperature was increased to between 35° C. and 40° C. The reaction mixture was placed under vacuum for 10 minutes to remove the chlorotrimethylsilane (b.p.=57° C.). The reaction mixture was heated at 150° C. for 2.5 hours. After 10 minutes, gas evolution was observed. After cooling, the reaction mixture was poured into water (1.2 L) and extracted with ether (3×). The combined organic layers were washed with water (3×) and brine, dried and concentrated to give 4-(2-oxazolyl)phenyl acetate (44.8 g, 96% th.; 98% pract) as a solid; $^1$H NMR (CDCl$_3$) δ 8.05 (d, 2H), 7.70 (s, 1H), 7.20 (m, 3H), 2.35 (s, 3H) ppm.

C. To a solution of 4-(2-oxazolyl)phenyl acetate (44.7 g, 22 mmol) in methanol (500 ml) was added an aqueous solution of potassium carbonate KOH (176 g in 800 mL, 5.8 eq.). The reaction was stirred at ambient temperature for 1 hour under nitrogen.

Methanol was removed under reduced pressure and the residue was treated with concentrated hydrochloric acid to give a slurry with a pH of 6. The precipitated solid was isolated by filtration and dried to give 35 g. Recrystallization from methanol gave 4-(2-oxazolyl)phenol (28 g, 79% th.; 63% pract); $^1$H NMR (DMSO) δ 10.05 (s, 1H), 8.10 (s, 1H), 7.75 (d, 2H), 7.20 (s, 1H), 6.85 (d, 2H) ppm.

D. To a solution of 4-(2-oxazolyl)phenol (4.1 g, 25.44 mmol) in DMF (98 ml), K$_2$CO$_3$ (3.52 g, 25.44 mmol, 1 equiv.) was added. The reaction was stirred at ambient temperature for 30 min. Then, 4-fluorobenzaldehyde (2.73 mL, 25.44 mmol, 1 equiv., Aldrich #12, 837-6) was added and stirring was continued at 150° C. for 4 hours. After cooling, saturated NaHCO$_3$ was added to the reaction mixture. The reaction mixture was extracted with ethyl acetate. The organic layer was washed with brine, dried over Na$_2$SO$_4$, and concentrated under reduced pressure. Flashmaster chromatography on 50 g of silica gel using a gradient of 100% hexane→50% hexane+50% ethyl acetate gave 6.4 g of 4-[4-(2-oxazolyl)phenoxy]benzaldehyde still containing 20 mol % DMF. Further drying led to the pure product (6.05 g; 90% th.; 148% pract.); $^1$H NMR (CDCl$_3$) δ 9.95 (s, 1H), 8.09 (d, 2H), 7.89 (d, 2H), 7.72 (d, 1H), 7.24 (d, 1H), 7.16 (d, 2H), 7.13 (d, 2H) ppm.

Synthetic Preparation 3

Compound of Formula (E)

The mixture of 4-bromophenol (10 g, 57.8 mmol), 4-fluorobenzaldehyde (7.17 g, 57.9 mmol), and potassium carbonate (12 g, 86.7 mmol) in DMF was heated at 170° C. for 4 hours. After cooling to ambient temperature, the reaction mixture was poured into ice-water. The resulting solid, 4-(4-bromophenoxy)benzaldehyde, was isolated by filtration (15 g, 94%), $^1$H NMR (CDCl$_3$) δ 9.95 (s, 1H), 7.85 (d, 2H), 6.62 (d, 2H), 7.17 (d, 2H), 6.96 (d, 2H) ppm.

Synthetic Preparation 4

Compounds of Formula (E)

A. To sodium hydride (288 mg as 55-60% mineral oil dispersion, 6 mmol) in N,N-dimethylformamide (2 mL), a solution of 2,2,3,3-tetrafluoro-1-propanol (535 µL, 6 mmol) in N,N-dimethylformamide (8 mL) was added dropwise. The reaction mixture was stirred for thirty minutes at room temperature. Then, 4-fluorobenzaldehyde (429 µL, 4 mmol) was added slowly, and the reaction was heated to 80° C. for three hours. After cooling, saturated sodium bicarbonate solution was added. The mixture was extracted with ethyl acetate. The organic layer was washed with brine, dried over sodium sulfate, and concentrated under reduced pressure. Flash chromatography gave 674 mg of 4-(2,2,3,3-tetrafluoropropoxy)benzaldehyde; $^1$H NMR (300 MHz, CDCl$_3$) δ 9.93 (s, 1H), 7.88 (d, 2H), 7.06 (d, 2H), 6.06 (tt, 1H), 4.44 (tt, 2H) ppm.

B. Following the above procedure, a solution of 2,2,3,3,4,4,4-heptafluoro-1-butanol (750 µL, 6 mmol) in N,N-dimethylformamide (8 mL) and 4-fluorobenzaldehyde (429 µL, 4 mmol) were reacted together with sodium hydride (288 mg as 55-60% mineral oil dispersion, 6 mmol) in N,N-dimethylformamide (2 mL). Flash chromatography gave 117 mg of 4-(2,2,3,3,4,4,4-heptafluorobutoxy)benzaldehyde; $^1$H NMR (300 MHz, CDCl$_3$) δ 9.93 (s, 1H), 7.89 (d, 2H), 7.08 (d, 2H), 4.54 (tt, 2H) ppm.

Synthetic Preparation 5

Compound of Formula (E)

To a solution of oxalyl chloride (80.2 µL, 0.93 mmol) in dichloromethane (8 mL) at −78° C., dimethyl sulfoxide (132.2 µL, 1.86 mmol) was added dropwise. After 15 minutes, 4-(3,3,4,4,5,5,6,6,6-nonafluorohexyl)benzenemethanol (300 mg, 0.85 mmol) was added. After 30 minutes, triethylamine (590 µL, 4.23 mmol) was added. The reaction was then allowed to warm to room temperature. Saturated sodium bicarbonate solution was added. The mixture was extracted with dichloromethane. The organic layer was washed with brine, dried over sodium sulfate, and concentrated under reduced pressure. Flash chromatography gave 122 mg of 4-(3,3,4,4,5,5,6,6,6-nonafluorohexyl)benzaldehyde; $^1$H NMR (300 MHz, CDCl$_3$) δ 10.00 (s, 1H), 7.85 (d, 2H), 7.40 (d, 2H), 3.01 (m, 2H), 2.41 (m, 2H) ppm.

Synthetic Preparation 6

Compound of Formula (E)

At −78° C., pentafluoroiodoethane (2.09 g, 8.51 mmol)) was condensed into a pressure bottle. Toluene (5 mL), 4-ethenylbenzenemethanol acetate (1 g, 5.67 mmol), and tributyltin hydride (1.53 mL, 5.67 mmol) were added. The pressure bottle was sealed and irradiated for hours using a 75 W lamp. The solvent was removed in vacuo. Flash chromatography of the residue gave 525 mg of 4-(3,3,4,4,4-pentafluorobutyl)benzenemethanol acetate; $^1$H NMR (300 MHz, CDCl$_3$) δ 7.32 (d, 2H), 7.21 (d, 2H), 5.09 (s, 2H), 2.91 (m, 2H), 2.32 (m, 2H), 2.10 (s, 3H) ppm.

4-(3,3,4,4,4-Pentafluorobutyl)benzenemethanol acetate (525 mg, 1.42 mmol) was heated to reflux with aqueous potassium hydroxide solution (40%; 399 µL, 2.84 mmol) in methanol (6 mL) for two hours. The residue was acidified with 1 M aqueous hydrochloric acid, and extracted with ethyl acetate. The combined organic layers were concentrated under reduced pressure. Flash chromatography gave 314 mg of 4-(3,3,4,4,4-pentafluorobutyl)benzenemethanol; $^1$H NMR (300 MHz, CDCl$_3$) δ 7.33 (d, 2H), 7.21 (d, 2H), 4.68 (dbr, 2H), 2.91 (m, 2H), 2.32 (m, 2H), 1.71 (tbr, 1H) ppm.

In a similar manner as described in Synthetic Preparation 3, 4-(3,3,4,4,4-pentafluorobutyl)benzaldehyde was prepared from oxalyl chloride (105 µL, 1.22 mmol) in dichloromethane (10.5 mL), dimethyl sulfoxide (173.6 µL, 2.45 mmol), 4-(3,3,4,4,4-pentafluorobutyl)benzenemethanol (314 mg, 1.11 mmol), and triethylamine (770 µL, 5.56 mmol). Flash chromatography gave 213 mg of the title compound; $^1$H NMR (300 MHz, CDCl$_3$) δ 10.00 (s, 1H), 7.85 (d, 2H), 7.39 (d, 2H), 3.00 (m, 2H), 2.37 (m, 2H) ppm.

Synthetic Preparation 7

Compound of Formula (E)

A solution of tosyl chloride (46 g, 0.24 mol) in pyridine (350 mL) was stirred as 2,2-3,3,3-pentafluoropropanol (25 g, 0.17 mol) was added. The reaction mixture was stirred at RT for 1.5 h before the addition of ice (300 g). After an additional 40 min, the resulting solid was isolated by filtration and dried in vacuo to afford 20.75 g of 2,2,3,3,3-pentafluoropropyl 4-methylbenzenesulfonate.

A solution of 4-hydroxybenzaldehyde (2 g, 16.7 mmol) in DMF (33 mL) was stirred as solid potassium carbonate (4.1 g, 29.7 mmol) was added, and the reaction mixture was then stirred at RT. After 30 min, solid 2,2,3,3,3-pentafluoropropyl 4-methylbenzenesulfonate (5 g, 16.4 mmol) was added into the reaction mixture. The mixture was stirred and heated at 100° C. for 7 h. The reaction mixture was allowed to cool, diluted with ethyl acetate, washed with water (3×) and brine, and concentrated. Purification by flash chromatography on silica gel using a gradient of ethyl acetate in hexane afforded 4-(2,2,3,3,3-pentafluoropropoxy)benzaldehyde (1.26 g).

Synthetic Preparation 8

Compound of Formula (K)

A solution of 4-(benzyl)phenol (638 mg, 3.46 mmol), 1-bromo-2-chloroethane (2.3 mL, 27.7 mmol) and cesium carbonate (4.5 g, 27.7 mmol) in 35 mL of acetonitrile was heated at reflux for 12 hours. After cooling, water was added. The mixture was extracted with ethyl acetate. The organic layer was washed with brine, dried over sodium sulfate, and concentrated under reduced pressure. Flash chromatography gave 734 mg of 1-(2-chloroethoxy)-4-(benzyl)benzene, $^1$H NMR (300 MHz, CDCl$_3$) δ 7.29 (dd, 2H), 7.19 (dd, 1H), 7.18 (d, 2H), 7.12 (d, 2H), 6.85 (d, 2H), 4.21 (t, 2H), 3.93 (s, 2H), 3.80 (t, 2H) ppm.

Synthetic Preparation 9

Compound of Formula (L)

A solution of 1-(2-chloroethoxy)-4-(benzyl)benzene (734 mg, 2.97 mmol) and sodium iodide (1.78 g, 11.9 mmol) in 2-butanone (30 mL) was heated at reflux for 16 hours. After cooling, water was added. The mixture was extracted with ethyl acetate. The organic layer was washed with brine, dried over sodium sulfate, and concentrated under reduced pressure. Flash chromatography gave 732 mg of 1-(2-iodoethoxy)-4-(benzyl)benzene, $^1$H NMR (300 MHz, CDCl$_3$) δ 7.29 (dd, 2H), 7.19 (dd, 1H), 7.18 (d, 2H), 7.11 (d, 2H), 6.84 (d, 2H), 4.23 (t, 2H), 3.94 (s, 2H), 3.41 (t, 2H) ppm.

Synthetic Preparation 10

Compound of Formula (N)

A mixture of methyl 4-(bromomethyl)benzoate (2 g, 8.73 mmol) and N,N'-dimethylethan-1,2-diamine (7.5 mL, 70 mmol) was heated with triethylamine (9.8 mL, 70 mmol) in tetrahydrofuran (80 mL) to reflux for two hours. After cooling, the mixture was treated with saturated sodium bicarbonate solution. The mixture was extracted with ethyl acetate. The organic layer was washed with brine, dried over sodium sulfate, and concentrated under reduced pressure. Flash chromatography gave 1.28 g of methyl 4-[(methyl(2-(methylamino)ethyl)amino)methyl]benzoate, $^1$H NMR (300 MHz, CD$_3$OD) δ 7.97 (d, 2H), 7.45 (d, 2H), 3.59 (s, 2H), 2.67 (m, 2H), 2.54 (m, 2H), 2.35 (s, 3H), 2.22 (s, 3H) ppm.

Synthetic Preparation 11

Compounds of formula (O)

A. A solution of 4-(2-oxazolyl)phenol (10.8 g, 11.2 mmol) in DMSO (9 mL) was stirred as potassium tert-butoxide (1.5 g, 13.4 mmol) and 4-fluoro-nitrobenzene (1.3 mL, 12.3 mmol) were added sequentially. The reaction was stirred for 17 hours at ambient temperature. The reaction was poured into a cold aqueous sodium hydroxide solution (1 N). The solid was isolated by filtration to give 2.6 g of 2-[4-(4-nitrophenoxy)phenyl]oxazole.

B. A slurry of 2-[4-(4-nitrophenoxy)phenyl]oxazole (2.6 g, 9.2 mmol) in a mixture of ethyl acetate (20 mL) and methanol (100 mL) was placed under a nitrogen atmosphere before the addition of catalyst palladium (10% on C, 0.65 g). The reaction mixture was placed under a hydrogen atmosphere at atmospheric pressure. After 3 hours, the reaction mixture was filtered through a pad of Celite and washed with methanol. The filtrate was concentrated to give the 2.4 g of 4-[4-(2-oxazolyl)phenoxy]benzenamine.

Synthetic Preparation 12

Compounds of Formula (O)

A solution of 2,2,3,3,4,4,4-heptafluorobutanol (5.7 g, 28.5 mmol) in DMF (100 mL) was stirred and cooled to −5° C. as sodium hydride (0.72 g, 30 mmol) was added. After 1 h at −5° C., the reaction was treated with 4-fluoronitrobenzene (4.1 g, 29 mmol). The reaction was allowed to warm to ambient temperature, concentrated, and slurried in methylene chloride (200 mL). The slurry was washed with an 1 N aqueous potassium hydroxide solution (2×) and brine solution, dried over basic alumina, treated with charcoal, filtered, and concentrated to give 4-(2',2',3',3',4',4',4'-heptafluorobutanoxy)nitrobenzene.

A solution of 4-(2',2',3',3',4',4',4'-heptafluorobutanoxy)nitrobenzene (9 g, 28 mmol) in methanol (100 mL) was degassed with nitrogen, treated with 10% palladium on carbon, and placed under an atmosphere of hydrogen (50 psi) for 1 h. The reaction mixture was filtered and the filtrate was concentrated to give 7.6 g of 4-(2',2',3',3',4',4',4'-heptafluorobutanoxy)aminobenzene.

Synthetic Preparation 13

Compounds of Formula (Qa) and (Q)

A. A solution of phenoxyphenylethanamine (2 g, 9.4 mmol) and 1-Boc-piperidin-4-one (1.9 g, 9.4 mmol) in dichloroethane (30 mL) was stirred as acetic acid (675 mg, 11.26 mmol) and sodium triacetoxyborohydride (2.4 g, 11.3 mmol) were added sequentially. The reaction was stirred at ambient temperature for 17 hours. The reaction was concentrated to give 1,1-dimethylethyl 4-((2-(4-phenoxyphenyl)ethyl)amino)-1-piperidinecarboxylate.

B. A solution of 1,1-dimethylethyl 4-((2-(4-phenoxyphenyl)ethyl)amino)-1-piperidinecarboxylate (about 9.4 mmol) in a mixture of methanol and dichloroethane (30 mL) was treated with a formaldehyde (37% solution in water). After the addition of sodium cyanoborohydride (710 mg, 11.26 mmol), the reaction was stirred for 17 hours. The reaction was concentrated. Purification on silica gel using a gradient of ethyl acetate in hexane gave 1,1-dimethylethyl 4-(methyl (2-(4-phenoxyphenyl)ethyl)amino)-1-piperidinecarboxylate.

C. In a similar manner as described above in Paragraph A, a solution of 1,1-dimethylethyl 4-oxo-1-piperidinecarboxylate (1 g, 4.5 mmol) and 4-(4-chlorophenoxy)aniline (1 g, 5 mmol) in dichloromethane was stirred as acetic acid (0.39 g, 6.5 mmol) was added. After 15 minutes, sodium triacetoxyborohydride (2 g, 9.4 mmol) was added and the reaction was stirred for 3 days. The reaction was treated with aqueous sodium bicarbonate. The organic layer was washed with water, dried, and concentrated. Purification by flash chromatography on silica gel using a gradient of ethyl acetate in hexane gave 1.3 g of 1,1-dimethylethyl 4-[[4-(4-chlorophenoxy)phenyl]amino]-1-piperidinecarboxylate.

Synthetic Preparation 14

Compound of Formula (T)

A solution of 1-Boc-2-aminomethylpiperidine (429 mg, 2 mmol) and methyl 4-formylbenzoate (329 mg, 2 mmol) in dichloroethane (10 mL) was stirred as acetic acid (180 mg, 3 mmol) and sodium triacetoxyborohydride (487 mg, 2.3 mmol) were added sequentially. The reaction was stirred at ambient temperature for 17 hours. The reaction was poured into water and extracted with methylene chloride (2×). The organic phase was dried over sodium sulfate, filtered, and concentrated. Purification on silica gel using a gradient of ethyl acetate in hexane gave 0.7 g of 1,1-dimethylethyl 2-((4-(methoxycarbonyl)phenylmethylamino)methyl)-1-piperidinecarboxylate.

Synthetic Preparation 15

Compound of Formula (U)

A. A solution of 1,1-dimethylethyl 2-((4-(methoxycarbonyl)phenylmethylamino)methyl)-1-piperidinecarboxylate (0.7 g, 2 mmol) in dichloroethane (10 mL) was treated with acetic acid (180 mg, 3 mmol) and formaldehyde (37% solution in water). After the addition of sodium triacetoxyborohydride (487 mg, 2.3 mmol) the reaction was stirred for 3 days. The reaction was poured into water and extracted with methylene chloride (2×). The organic phase was dried over sodium sulfate, filtered, and concentrated. Purification on silica gel using a gradient of ethyl acetate in hexane gave 0.38 g of 1,1-dimethylethyl 2-(((4-(methoxycarbonyl)phenylmethyl)(methyl)amino)methyl)-1-piperidinecarboxylate.

B. A solution of 1,1-dimethylethyl 2-(((4-(methoxycarbonyl)phenylmethyl)(methyl)amino)methyl)piperidine-1-carboxylate in dichloromethane (6 mL) was treated with a solution of 4 N hydrochloric acid in dioxane (6 mL). The reaction was stirred overnight. Solvent was removed under reduced pressure and the product, methyl 4-((methyl(piperidin-2-ylmethyl)amino)methyl)benzoate, was isolated as the hydrochloride salt.

Synthetic Preparation 16

Compound of Formula (Ta)

A solution of 1,1-dimethylethyl 2-(aminomethyl)-1-pyrrolidinecarboxylate (1000 mg, 5 mmol) and methyl 4-formylbenzoate (820 mg, 5 mmol) in dichloroethane was stirred as acetic acid (450 mg, 7.5 mmol) and sodium triacetoxyborohydride (1271 mg, 6 mmol) were added sequentially at ambient temperature. After stirring at ambient temperature for 17 hours, treated with a saturated aqueous solution of sodium bicarbonate and extracted with EtOAc. The combined organic extracts were dried and concentrated. Purification by flash chromatography afforded 1,1-dimethylethyl 2-[[[[4-(methoxycarbonyl)phenyl]methyl]amino]methyl]-1-pyrrolidinecarboxylate (800 mg), $^1$H NMR (CDCl$_3$) 7.98 (d, 2H), 3.37 (d, 2H), 3.91 (s, 3H), 3.82 (s, 2H), 3.36 (m, 2H), 2.72 (m, 1H), 1.82 (m, 3H), 1.44 (m, 2H) ppm.

Synthetic Preparation 17

Compound of Formula (Ua)

A. A solution of 1,1-dimethylethyl 2-[[[[4-(methoxycarbonyl)phenyl]methyl]amino]methyl]-1-pyrrolidinecarboxylate in dichloroethane was stirred as acetic acid (400 mg, 6.65 mmol), formaldehyde (37% solution in water), and sodium triacetoxyborohydride (1100 mg, 5.18 mmol) were added sequentially. The reaction was stirred at ambient temperature for 17 hours, treated with a saturated aqueous solution of sodium bicarbonate and extracted with EtOAc. The combined organic layers were dried and concentrated. Purification by flash chromatography afforded 1,1-dimethylethyl 2-[[[[4-(methoxycarbonyl)phenyl]methyl]methylamino]methyl]-1-pyrrolidinecarboxylate (670 mg).

B. A solution of 1,1-dimethylethyl 2-[[[[4-(methoxycarbonyl)phenyl]methyl]methylamino]methyl]-1-pyrrolidinecarboxylate in dichloromethane was treated with 4 N HCl (2 mL) and stirred at ambient temperature for 4 hours. The reaction was concentrated to give methyl 4-[[methyl(2-pyrrolidinylmethyl)amino]methyl]benzoate as a hydrochloride salt.

Synthetic Preparation 18

Compound of Formula (V)

A solution of 1,1-dimethyl (R)-2-(aminomethyl)pyrrolidinecarboxylate (400 mg, 2 mmol) and 4-(4-bromophenoxy)benzaldehyde (400 mg, 2 mmol) and 4-(4-bromophenoxy)benzaldehyde (554 mg, 2 mmol) in dichloroethane (10 mL) was stirred as acetic acid (180 mg, 3 mmol) and sodium triacetoxyborohydride (508 mg, 1.2 mmol) were added. The reaction was stirred for 17 hours. The reaction was treated with a saturated aqueous solution of sodium bicarbonate and extracted with ethyl acetate (2×). The combined organic extracts were dried and concentrated. Purification by flash chromatography on silica gel using a mixture of ethyl acetate in hexane gave 0.9 g of 1,1-dimethylethyl 2-[[[[4-(4-bromophenoxy)phenyl]methyl]amino]methyl]-1-pyrrolidinecarboxylate.

Synthetic Preparation 19

Compound of Formula (V)

A solution of 1,1-dimethyl (R)-2-(aminomethyl)pyrrolidinecarboxylate (2 mmol) and 4-(4-2,2,3,3,3-pentafluoropropoxy)benzaldehyde (2 mmol) in dichloroethane (10 mL) is stirred, as acetic acid (3 mmol) and sodium triacetoxyborohydride (1.2 mmol) are added. The reaction is stirred for 17 hours. The reaction is treated with a saturated aqueous solution of sodium bicarbonate and extracted with ethyl acetate (2×). The combined organic extracts are dried and concentrated. Purification by flash chromatography on silica gel using a mixture of ethyl acetate in hexane gives 1,1-dimethylethyl 2-[[[[4-(2,2,3,3,3-pentafluoropropoxy)phenyl]methyl]amino]methyl]-1-pyrrolidinecarboxylate.

Synthetic Preparation 20

Compound of Formula (Y)

A solution of N-Boc nortropinone (0.73 g, 3.24 mmol) in a minimal amount of dichloromethane (1 mL) was treated with a solution of 4 M hydrochloric acid in dioxane (3.2 mL, 12.8 mmol). After stirring for 2.5 days, the reaction was complete by TLC analysis. Solvent was removed under reduced pressure to give 0.52 g of 8-azabicyclo[3.2.1]octan-3-one.

Synthetic Preparation 21

Compound of Formula (Z)

A slurry of 8-azabicyclo[3.2.1]octan-3-one hydrochloride salt (0.52 g, 3.2 mmol) and methyl 4-(bromomethyl)benzoate (0.75 g, 3.3 mmol) in 30 mL of acetonitrile was stirred as solid potassium carbonate (1.9 g, 13.6 mmol) was added. After 4 days, the reaction was filtered. The filtrate was concentrated. Purification by chromatography on silica gel using hexane gave 0.66 g of methyl 4-[(3-oxo-8-azabicyclo[3.2.1]oct-8-yl)methyl]-benzoate.

Synthetic Preparation 22

Compound of Formula (CC)

A solution of 4-(chlorocarbonyl)phenyl acetate (110 g, 553.87 mmol) in $CH_2Cl_2$ (500 mL) was cooled in an ice bath and treated with triethylamine (115 mL, 830 mmol, 1.5 equiv.) and 2,2-dimethoxyethanamine (63.36 mL, 581.56 mmol, 1.05 equiv.). The reaction mixture was allowed to warm to ambient temperature and the reaction was followed by TLC ($CH_2Cl_2$). The reaction mixture was concentrated under reduced pressure, diluted with ethyl acetate and filtered. The filtrate was washed with water. The aqueous layer was extracted with ethyl acetate (2×). The combined organic layers were washed with water, dilute mono-potassium phosphate (pH=5.4, pH of solution about 7), water, and brine, dried, and concentrated to give 120 g (81% th.; 109% pract.) of 4-(2,2-dimethoxyethylcarbamoyl)phenyl acetate as a light brown waxy solid with no further purification; $^1$H NMR (CDCl$_3$) δ 7.79 (d, 2H), 7.15 (d, 2H), 6.32 (br. t, 1H), 4.47 (t, 1H), 3.58 (d, 2H), 3.41 (s, 6H), 2.30 (s, 3H) ppm.

Synthetic Preparation 23

Compound of Formula (DD1)

In a similar manner as described in Pandit, C. R. et al., "Preparation of 2-Substituted Oxazoles", *Synth. Commun.* 32, 2427-2432 (2002), 4-(2,2-dimethoxyethylcarbamoyl)phenyl acetate (43 g, 160.88 mmol) was stirred and treated with Eaton's reagent (380 ml; 7.7 wt. % phosphorus pentoxide in methanesulfonic acid, Aldrich #38, 081-4). After 15 minutes, the internal temperature of the reaction was raised to about 130° C. and held for about 3 hours.

The reaction was followed by TLC analysis (2:1 EtOAc:Hex) with only a single new UV active spot observed. The reaction mixture was allowed to cool to about 40° C. and was then cooled in an ice bath to about 3° C. The reaction was poured into 2 L of ice water and extracted with ethyl acetate (1.4 L). The organic layer was washed with water (1 L). The combined aqueous layers were extracted with ethyl acetate (2×1 L). The combined organic layers were washed with water (2×) and brine, dried, treated with silica gel and charcoal, and concentrated. The residue was dissolved in methylene chloride and treated with hexane until a precipitate was seen. The mixture was treated with charcoal, filtered, and concentrated to give 53.3 g of 4-(oxazol-2-yl) phenyl methanesulfonate (>100% th.; 90% pract.) which contained 1.2 equivalents of methyl methanesulfonic acid; $^1$H NMR (CDCl$_3$) δ 8.07 (d, 2H), 7.71 (d, 1H), 7.36 (d, 2H), 7.22 (d, 1H), 3.16 (s, 3H) ppm.

Synthetic Preparation 24

Compound of Formula (DD2)

To a solution of 4-(oxazol-2-yl)phenyl methanesulfonate (11.2 g, 46.81 mmol) in THF (200 mL), a freshly prepared aqueous solution of KOH (40 wt. %, 13.2 mL, 93.6 mmol, 2 equiv.) was added. The reaction mixture was stirred at 80° C. for 4 hours and at ambient temperature overnight. Another 2 equiv. of aqueous solution of KOH (40 wt. %, 13.2 mL, 93.6 mmol) was then added and the reaction mixture was continuously stirred at 80° C. for 3 hours. After cooling, the reaction mixture was cautiously brought to pH 5 with 1 M aqueous HCl. The mixture was extracted with ethyl acetate. The organic layer was washed with brine, dried over $Na_2SO_4$, and concentrated under reduced pressure. Flashmaster chromatography on 50 g of silica gel using a gradient of 100% $CH_2Cl_2 \rightarrow 90\%$ $CH_2Cl_2$+10% methanol gave 4.25 g (56% th.; 38% pract.) of 4-(oxazol-2-yl)phenol; $^1$H NMR (CD$_3$OD) δ 7.86 (d, 1H), 7.84 (d, 2H), 7.20 (d, 1H), 6.88 (d, 2H) ppm.

Synthetic Preparation 25

Compound of Formula (EE)

A solution of 4-(2-oxazolyl)phenol (15.7 g, 97 mmol) in DMF (120 mL) was treated with cesium carbonate (41 g, 126 mmol) and 4-fluorobenzaldehyde (13.3 g, 107 mmol). The reaction was heated at 110° C. for 2.5 hours. The reaction mixture was cooled and poured onto a mixture of ice and water. The product was isolated by extraction with methylene chloride (3x). The combined organic layers were washed with water and brine, dried, and concentrated. The residue was recrystallized from aqueous ethanol to give 19.7 g of 4-[4-(2-oxazolyl)phenoxy]-benzaldehyde.

Synthetic Preparation 26

Compound of Formula (GG)

A solution of N-Boc nortropinone (2.4 g, 10.9 mmol) and methyl 4-aminomethylbenzoate (1.6 g, 10.9 mmol) in dichloroethane (20 mL) was stirred as acetic acid (0.85 g, 14.2 mmol) was added. After 1 hour, sodium triacetoxyborohydride (2.7 g, 13.1 mmol) was added and the reaction was stirred for 17 hours. The reaction was treated with a saturated aqueous solution of sodium bicarbonate and extracted with ethyl acetate (2x). The combined organic extracts were dried and concentrated. Purification by flash chromatography on silica gel using a gradient of ethyl acetate in hexane gave 3.6 g of 1,1-dimethylethyl 3-[[[4-(methoxycarbonyl)phenyl]methyl]amino]-8-azabicyclo[3.2.1]octane-8-carboxylate.

Synthetic Preparation 27

Compound of Formula (HH)

A solution of 1,1-dimethylethyl 3-[[[4-(methoxycarbonyl)phenyl]methyl]amino]-8-azabicyclo[3.2.1]octane-8-carboxylate (2.1 g, 5.7 mmol) and formaldehyde (1 mL of 37% solution in water) in dichloroethane (20 mL) was stirred as acetic acid (0.37 g, 6.9 mmol) and sodium triacetoxyborohydride (1.7 g, 8 mmol) were added. The reaction was stirred for 17 hours. The reaction was treated with a saturated aqueous solution of sodium bicarbonate and extracted with ethyl acetate (2x). The combined organic extracts were dried and concentrated. Purification by flash chromatography on silica gel using a gradient of ethyl acetate in hexane gave 1.7 g of 1,1-dimethylethyl 3-[[[4-(methoxycarbonyl)phenyl]methyl]methylamino]-8-azabicyclo[3.2.1]octane-8-carboxylate.

Synthetic Preparation 28

Compound of Formula (JJ)

1,1-Dimethylethyl 3-[[[4-(methoxycarbonyl)phenyl]methyl]methylamino]-8-azabicyclo[3.2.1]octane-8-carboxylate (1.7 g, 4.4 mmol) in a solution of 4 N hydrochloric acid in dioxane (10 mL) was stirred overnight. Solvent was removed under reduced pressure and methyl 4-[[(8-azabicyclo[3.2.1]oct-3-yl)methylamino]-methyl]benzoate (0.8 g) was isolated as the hydrochloride salt.

Synthetic Preparation 29

Compound of Formula (K)

A. A solution of 2-aminoacetaldehyde dimethylacetal (12.3 mL, 112 mmol) in a mixture of acetone (50 mL) and aqueous potassium bicarbonate (12 g, 122 mmol in 110 mL of water) was stirred and cooled to −5° C., as a solution of 4-iodobenzoyl chloride (25 g, 94 mmol) was added dropwise. The cooling bath was removed and the reaction stirred for 3 hours. The reaction was concentrated and diluted with water. The resulting solid was isolated by filtration and dried to give 30.5 g of N-(2,2-dimethoxyethyl)-4-iodobenzamide, $^1$H NMR (400 MHz, CDCl$_3$) δ 7.78 (d, 2H), 7.46 (d, 2H), 6.34 (s, 1H), 4.44 (t, 1H), 3.58 (t, 2H), 3.42 (s, 6H) ppm.

B. A solution of N-(2,2-dimethoxyethyl)-4-iodobenzamide (10 g, 30 mmol) in Eaton's reagent (100 mL) was heated at 135° C. for 17 hours. The reaction was allowed to cool and poured into ice water. The brown solid was isolated by filtration. Purification on silica gel eluting with dichloromethane gave 6.7 g of 2-(4-Iodophenyl)oxazole, $^1$H NMR (400 MHz, CDCl$_3$) δ 7.79 (q, 4H), 7.72 (s, 1H), 7.27 (s, 1H).

C A Schlenk Flask was charged with tetrakis(triphenylphosphine)palladium(0) (0.42 g, 0.37 mmol), nitrogen, THF (20 ML), 2-(4-iodophenyl)oxazole (1 g, 3.7 mmol), and 4-methoxybenzyl zinc chloride (0.5 M in THF, 9.6 mL, 4.8 mmol). After 3 hours, the filtrate was concentrated. The resulting solid was treated with a mixture of ethyl acetate and a dilute aqueous ammonium chloride solution. The mixture was filtered and the organic layer was dried and concentrated. Purification on silica gel using a gradient of dichloromethane in hexane gave 0.8 g of 2-[4-[(4-methoxyphenyl)methyl]phenyl]oxazole, $^1$H NMR (400 MHz, CDCl$_3$) δ 7.97 (d, 2H), 7.68 (s, 1H), 7.27 (d, 2H), 7.22 (s, 1H), 7.13 (d, 2H), 6.82 (d, 2H), 3.96 (s, 2H), 3.78 (s, 3H).

D. A solution of 2-[4-[(4-methoxyphenyl)methyl]phenyl]oxazole (0.4 g, 1.5 mmol) in dichloromethane (15 mL) was stirred and cooled to −78° C. as a solution of borontribromide in dichloromethane (1 N, 15 mL, 15 mmol) was added over 5 minutes. The cooling bath was removed and the reaction was allowed to warm to ambient temperature over 3 days. The reaction was diluted with methanol and concentrated, repeat twice. Purification on silica gel using a gradient of ethyl acetate in dichloromethane and hexane gave 0.22 g of 4-[[4-(2-oxazolyl)phenyl]methyl]phenol, $^1$H NMR (400 MHz, DMSO-d$_6$) δ 9.19 (s, 1H), 8.17 (s, 1H), 7.88 (s, 2H), 7.35 (d, 2H), 7.02 (s, 2H), 6.66 (d, 2H), 3.84 (s, 2H).

E. A solution of 4-[[4-(2-oxazol yl)phenyl]methyl]phenol (2.2 g, 8.75 mmol) and 2-chloroethylbromide (10 g, 70 mmol) in acetonitrile as stirred as cesium carbonate (22.8 g, 70 mmol) was added. The reaction was heated at reflux for 3 days. The reaction was diluted with water. The product, 2-[4-[[4-(2-chloroethoxy)phenyl]methyl]phenyl]oxazole (2.7 g), was isolated by filtration, $^1$H NMR (400 MHz, CDCl$_3$) δ 7.97 (d, 2H), 7.68 (s, 1H), 7.35 (m, 2H), 7.21 (s, 1H), 7.13 (d, 2H), 6.82 (d, 2H), 4.22 (t, 2H), 3.96 (s, 2H), 3.79 (t, 2H).

Synthetic Preparation 30

Compound of Formula (L)

A solution of 2-[4-[[4-(2-chloroethoxy)phenyl]methyl] phenyl]oxazole (1.7 g, 4.4 mmol) in 2-butanone (18 mL) was stirred as sodium iodide (7 g, 44 mmol) was added. The reaction was heated at reflux for 2 days. The reaction was concentrated. The residue was dissolved in ethyl acetate and washed with water. The combined organic layers were dried and concentrated. The residue was recrystallized from methanol to give 1.4 g of 2-[4-[[4-(2-iodoethoxy)phenyl] methyl]phenyl]oxazole, $^1$H NMR (400 MHz, CDCl$_3$) δ 7.97 (d, 2H), 7.68 (s, 1H), 7.27 (d, 2H), 7.21 (s, 1H), 7.13 (d, 2H), 6.82 (d, 2H), 4.22 (t, 2H), 3.96 (s, 2H), 3.39 (t, 2H).

Synthetic Example 1

Compounds of Formula (Ia)

A. 4-[4-(2-oxazolyl)phenoxy]benzaldehyde (10.2 g, 38.5 mmol) and methyl 4-[[(1S,4S)-2,5-diazabicyclo[2.2.1]hept-2-yl]methyl]benzoate (9.9 g, 40.4 mmol, 1.05 equiv.) were dissolved in dichloroethane (200 mL). After 75 minutes, sodium triacetoxyborohydride (9.8 g, 46.1 mmol, 1.2 equiv.) was added. The reaction mixture was stirred overnight at ambient temperature. Then, 1 N NaOH was added. The reaction mixture was separated and the aqueous layer was extracted with CH$_2$Cl$_2$. The combined organic layers were washed with 0.5 M H$_2$SO$_4$, and MeOH was added to the mixture until the precipitated gummy solid dissolved. The layers were separated and the aqueous layer was cooled to −5 C and saturated K$_2$CO$_3$ was added slowly enough to keep the temperature below 0 C to prevent ester hydrolysis. Once the pH was 11, the solution was extracted with EtOAc (2×), and the combined EtOAc fractions were dried and concentrated to give 19.0 g (100%) of methyl 4-[[(1S,4S)-5-[[4-[4-(2-oxazolyl)phenoxy]phenyl]methyl]-2,5-diazabicyclo [2.2.1]hept-2-yl]methyl]benzoate as the free base, which was 98% pure by HPLC; $^1$H NMR (300 MHz, CDCl$_3$) δ 8.02 (d, 2H), 8.02 (d, 2H), 7.69 (d, 1H), 7.47 (d, 2H), 7.40 (d, 2H), 7.22 (d, 1H), 7.08 (d, 2H), 7.05 (d, 2H), 3.92 (s, 3H), 3.84 (d, 1H), 3.78 (d, 1H), 3.77 (d, 1H), 3.71 (d, 1H), 3.35 (s, 1H), 3.31 (s, 1H), 2.89 (d, 1H), 2.88 (d, 1H), 2.71 (dd, 1H), 2.70 (dd, 1H), 1.79 (s, 2H) ppm.

B. Methyl 4-[[(1S,4S)-5-[[4-[4-(2-oxazolyl)phenoxy] phenyl]methyl]-2,5-diazabicyclo[2.2.1]hept-2-yl]methyl] benzoate (21.0 g, 42.4 mmol) was dissolved in MeOH (200 mL) and THF (200 mL) and aqueous NaOH (1 M, 200 mL, 5 equiv.) was added. The reaction mixture was stirred overnight at ambient temperature, and then adjusted to pH 8 with 6 M HCl. The solution was concentrated under reduced pressure. The residue was diluted with water and extracted with 5% MeOH/CH$_2$Cl$_2$ (2×). The combined organic layers were concentrated under reduced pressure. The resulting solid was redissolved in 3/1 MeOH/water and concentrated under reduced pressure to remove the residual CH$_2$Cl$_2$. This procedure gave 18.2 g (89%) of the pure product, 4-[[(1S, 4S)-5-[[4-[4-(2-oxazolyl)phenoxy]phenyl]methyl]-2,5-diazabicyclo[2.2.1]hept-2-yl]methyl]benzoic acid, with 0.5 eq water; $^1$H NMR (300 MHz, CD$_3$OD) δ 8.00 (d, 2H), 7.96 (d, 1H), 7.93 (d, 2H), 7.45 (d, 2H), 7.40 (d, 2H), 7.27 (d, 1H), 7.08 (d, 2H), 7.06 (d, 2H), 3.93 (d, 1H), 3.89 (d, 1H), 3.83 (d, 1H), 3.80 (d, 1H), 3.53 (s, 2H), 3.06 (d, 1H), 3.04 (d, 1H), 2.80 (dd, 2H), 1.93 (s, 2H) ppm.

Synthetic Example 2

Compounds of Formula (Ia1) and (Ia)

A mixture of hexahydro-1H-1,4-diazepine (3.44 g, 34.4 mmol) and 1-(chloromethyl)-4-(benzyloxy)benzene (2.0 g, 8.6 mmol) was treated with triethylamine (4.8 ml, 34.4 mmol) in 100 mL tetrahydrofuran and heated at reflux for 4 h. After cooling, the mixture was treated with saturated sodium bicarbonate solution. The mixture was extracted with ethyl acetate. The combined organic layer was washed with brine, dried over sodium sulfate, and concentrated under reduced pressure. Flash chromatography gave 2.0 g of hexahydro-1-[[4-(phenylmethoxy)phenyl]methyl]-1H-1,4-diazepine; $^1$H NMR (300 MHz, CDCl$_3$) δ 7.44 (d, 2H), 7.39 (dd, 2H), 7.32 (dd, 1H), 7.26 (d, 2H), 6.93 (d, 2H), 5.05 (s, 2H), 3.60 (s, 2H), 2.96 (m, 2H), 2.89 (m, 2H), 2.68 (m, 2H), 2.65 (m, 2H), 1.75 (m, 2H) ppm.

Synthetic Example 3

Compounds of Formula (Ia)

A solution of methyl 4-[[hexahydro-4-[(4-phenoxyphenyl)methyl]-1H-1,4-diazepin-1-yl]methyl]benzoate (260 mg, 0.60 mmol) in tetrahydrofuran (6 mL) was cautiously added to lithium alanate (45.5 mg, 1.2 mmol) in tetrahydrofuran (12 mL) at 0° C. The reaction was stirred overnight at ambient temperature. The mixture was treated with saturated sodium bicarbonate solution and extracted with ethyl acetate. The organic layer was washed with brine, dried over sodium sulfate, and concentrated under reduced pressure. Flash chromatography gave 190 mg of [4-[[hexahydro-4-[(4-phenoxyphenyl)methyl]-1H-1,4-diazepin-1-yl]methyl] phenyl]methanol; $^1$H NMR (300 MHz, CDCl$_3$) δ 7.33 (m, 4H), 7.33 (dd, 2H), 7.29 (d, 2H), 7.09 (dd, 1H), 7.00 (d, 2H), 6.95 (d, 2H), 4.68 (s, 2H), 3.64 (s, 2H), 3.61 (s, 2H), 2.73 (m, 4H), 2.67 (s, 4H), 1.80 (m, 2H) ppm.

Synthetic Example 4

Compounds of Formula (Ia)

A. A solution of hexahydro-1-[[4-(phenylmethoxy)phenyl]methyl]-1H-1,4-diazepine (150 mg, 0.506 mmol) and methyl 3-bromopropanoate (0.22 mL, 2.0 mmol) in THF (6 mL) was treated with triethylamine (0.28 mL, 2 mmol) and the reaction was heated at reflux for 4 hours. The reaction was allowed to cool and treated with an aqueous bicarbonate solution.

The combined ethyl acetate extracts were washed with water, dried and concentrated to give 0.1 g of methyl hexahydro-4-[[4-(phenylmethoxy)phenyl]methyl]-1H-1,4-diazepine-1-propanoate; $^1$H NMR (300 MHz, CDCl$_3$) δ 7.44 (d, 2H), 7.39 (dd, 2H), 7.32 (dd, 1H), 7.24 (d, 2H), 6.93 (d, 2H), 5.05 (s, 2H), 3.67 (s, 3H), 3.56 (s, 2H), 2.85 (t, 2H), 2.48 (t, 2H), 2.77-2.58 (m, 8H), 1.77 (m, 2H) ppm.

B. A solution of methyl hexahydro-4-[[4-(phenylmethoxy)phenyl]methyl]-1H-1,4-diazepine-1-propanoate (0.1 g, 0.27 mmol) in methanol (2 mL) was treated with aqueous sodium hydroxide (2 M, 1 mL). After 2 hours at ambient temperature, the reaction was diluted with water, neutralized with 1 N hydrochloric acid, and extracted with n-butanol. The combined extracts were dried and concentrated to give 0.1 g of hexahydro-4-[[4-(phenylmethoxy) phenyl]methyl]-1H-1,4-diazepine-1-propanoic acid; $^1$H NMR (300 MHz, CD$_3$OD) δ 7.41 (d, 2H), 7.36 (dd, 2H), 7.34 (d, 2H), 7.29 (dd, 1H), 6.98 (d, 2H), 5.05 (s, 2H), 3.81 (s, 2H), 3.25 (m, 2H), 3.23 (m, 2H), 3.20 (t, 2H), 3.00 (m, 2H), 2.91 (m, 2H), 2.56 (t, 2H), 2.02 (m, 2H) ppm.

C. In a manner similar as described above in Paragraph A, a solution of hexahydro-1-[[4-(phenylmethoxy)phenyl]methyl]-1H-1,4-diazepine (150 mg, 0.506 mmol) and methyl 4-bromobutanoate (0.29 mL, 2.0 mmol) in THF (6 mL) was treated with triethylamine (0.28 mL, 2 mmol) and the reaction was heated at reflux for 4 hours. The reaction was allowed to cool and treated with an aqueous bicarbonate solution. The combined ethyl acetate extracts were washed with water, dried and concentrated to give 0.16 g of methyl hexahydro-4-[[4-(phenylmethoxy)phenyl]methyl]-1H-1,4-diazepine-1-butanoate.

D. In a manner similar as described above in Paragraph B, a solution of methyl 4-(4-(4-(benzyloxy)benzyl)-hexahydro-1H-diazepin-1-yl)butanoate (0.16 g, 0.4 mmol) in methanol (2 mL) was treated with aqueous sodium hydroxide (2M, 1 mL). After 2 hours at ambient temperature, the reaction was diluted with water, neutralized with 1 N hydrochloric acid, and extracted with n-butanol. The combined extracts were dried and concentrated to give 0.13 g of hexahydro-4-[[4-(phenylmethoxy)phenyl]methyl]-1H-1,4-diazepine-1-butanoic acid; $^1$H NMR (300 MHz, CD$_3$OD) δ 7.41 (d, 2H), 7.35 (dd, 2H), 7.30 (d, 2H), 7.28 (dd, 1H), 6.96 (d, 2H), 5.03 (s, 2H), 3.69 (s, 2H), 3.26 (m, 2H), 3.19 (m, 2H), 3.04 (t, 2H), 2.89 (m, 2H), 2.81 (m, 2H), 2.40 (t, 2H), 2.01 (m, 2H), 1.86 (m, 2H) ppm.

Synthetic Example 5

Compounds of Formula (Ic)

A mixture of methyl 4-[(hexahydro-1H-diazepin-1-yl)methyl]benzoate (109 mg, 0.44 mmol) and 1-(2-iodoethoxy)-4-(benzyl)benzene (120 mg, 0.44 mmol) in THE (4 mL) was treated with triethylamine (112 µl, 0.80 mmol) and heated at reflux for 5 hours. After cooling, the mixture was treated with saturated sodium bicarbonate solution. The mixture was extracted with ethyl acetate. The organic layer was washed with brine, dried over sodium sulfate, and concentrated under reduced pressure. Flash chromatography gave 55 mg of methyl 4-[[hexahydro-4-[2-[4-(phenylmethyl)phenoxy]ethyl]-1H-1,4-diazepin-1-yl]methyl]benzoate; $^1$H NMR (300 MHz, CDCl$_3$) δ 7.98 (d, 2H), 7.42 (d, 2H), 7.28 (dd, 2H), 7.17 (d, 2H), 7.18 (dd, 1H), 7.09 (d, 2H), 6.82 (d, 2H), 4.05 (t, 2H), 3.92 (s, 2H), 3.91 (s, 3H), 3.69 (s, 2H), 2.97 (t, 2H), 2.88 (m, 2H), 2.84 (m, 2H), 2.69 (m, 4H), 1.81 (m, 2H) ppm.

B. A solution of methyl 4-[[hexahydro-4-[2-[4-(phenylmethyl)phenoxy]ethyl]-1H-1,4-diazepin-1-yl]methyl]benzoate (55 mg, 0.12 mmol) in methanol (4 mL) was stirred as a solution of aqueous sodium hydroxide (0.60 mL, 2 M) was added. The reaction was stirred for 17 hours at ambient temperature. The reaction was concentrated under reduced pressure. The residue was diluted with water, adjusted to pH 8 with 1 M aqueous hydrochloric acid, and extracted with butanol. The combined organic layers were concentrated under reduced pressure. Flash chromatography gave 46 mg of 4-[[hexahydro-4-[2-[4-(phenylmethyl)phenoxy]ethyl]-1H-1,4-diazepin-1-yl]methyl]benzoic acid; $^1$H NMR (300 MHz, CD$_3$OD) δ 7.94 (d, 2H), 7.36 (d, 2H), 7.21 (dd, 2H), 7.13 (d, 2H), 7.12 (dd, 1H), 7.07 (d, 2H), 6.82 (d, 2H), 4.08 (t, 2H), 3.82 (s, 2H), 3.75 (s, 2H), 3.05 (t, 2H), 2.99 (m, 4H), 2.81 (m, 2H), 2.80 (m, 2H), 1.88 (m, 2H) ppm.

Synthetic Example 6

Compounds of Formula (Id)

A. A solution of 4-[4-(2-oxazolyl)phenoxy]benzaldehyde (100 mg, 0.38 mmol) and methyl 4-[(methyl(2-(methylamino)ethyl)amino)methyl]benzoate (90 mg, 0.38 mmol) in dichloromethane (4 mL) was stirred for 15 minutes before the addition of sodium triacetoxyborohydride (160 mg, 76 mmol). The reaction mixture was stirred overnight at ambient temperature. Saturated sodium bicarbonate solution was then added. The mixture was stirred for 30 minutes and then extracted with dichloromethane. The combined organic layers were washed with water, dried over sodium sulfate, and concentrated under reduced pressure. Flash chromatography gave 120 mg of methyl 4-[[methyl[2-[methyl[[4-[4-(2-oxazolyl)phenoxy]phenyl]methyl]amino]ethyl]amino]methyl]benzoate; $^1$H NMR (300 MHz, CDCl$_3$) δ 7.99 (d, 2H), 7.97 (d, 2H), 7.68 (d, 1H), 7.38 (d, 2H), 7.29 (d, 2H), 7.20 (d, 1H), 7.03 (d, 2H), 6.99 (d, 2H), 3.89 (s, 3H), 3.56 (s, 2H), 3.49 (s, 2H), 2.56 (m, 4H), 2.22 (s, 3H), 2.21 (s, 3H) ppm.

B. Methyl 4-[[methyl[2-[methyl[[4-[4-(2-oxazolyl)phenoxy]phenyl]methyl]amino]-ethyl]amino]methyl]benzoate (120 mg 0.25 mmol) was stirred with aqueous sodium hydroxide solution (1.25 mL, 2 M) in methanol (3 mL) overnight at ambient temperature, and then concentrated under reduced pressure. The residue was diluted with water, adjusted to pH 8 with 1 M aqueous hydrochloric acid, and extracted with butanol. The combined organic layers were concentrated under reduced pressure. Flash chromatography gave 41 mg of 4-[[methyl[2-[methyl[[4-[4-(2-oxazolyl)phenoxy]phenyl]methyl]amino]ethyl]amino]methyl]benzoic acid; $^1$H NMR (300 MHz, CD$_3$OD) δ 7.98 (d, 2H), 7.96 (d, 2H), 7.95 (d, 1H), 7.41 (d, 2H), 7.38 (d, 2H), 7.26 (d, 1H), 7.06 (d, 4H), 3.80 (s, 2H), 3.78 (s, 2H), 2.86 (m, 4H), 2.40 (s, 3H), 2.39 (s, 3H) ppm.

Synthetic Example 7

Compounds of Formula (Ie)

A. A solution of 1,1-dimethylethyl 4-(methyl(2-(4-phenoxyphenyl)ethyl)amino)-1-piperidinecarboxylate (290 mg, 0.71 mmol) in dichloroethane was added a solution of hydrogen chloride in dioxane (4N). The reaction was stirred at ambient temperature for 4 hours. The reaction mixture was concentrated to dryness to give N-methyl-N-[2-(4-phenoxyphenyl)ethyl]-4-piperidinamine.

B. A solution of N-methyl-N-[2-(4-phenoxyphenyl)ethyl]-4-piperidinamine (about 0.7 mmol) in DMF (5 mL) and diisopropylethylamine (5 mL) was stirred as methyl 4-(bromomethyl)benzoate (163 mg, 0.71 mmol) was added. The reaction was stirred for 54 hours at ambient temperature. The reaction was diluted with ethyl acetate, washed with brine, dried, and concentrated to give methyl 4-[[4-[methyl[2-(4-phenoxyphenyl)ethyl]amino]-1-piperidinyl]methyl]benzoate; 1H NMR (CDCl$_3$) 7.76 (d, 2H), 7.37 (d, 2H), 7.28 (td, 2H), 7.14 (d, 2H), 7.06 (dt, 1H), 6.95 (dt, 2H), 6.92 (dd, 2H), 3.84 (s, 3H), 3.55 (s, 2H), 2.87 (m, 2H), 2.71 (m, 3H), 2.51 (m, 1H), 2.01 (s, 3H), 1.98 (m, 2H), 1.76 (m, 2H), 1.62 (m, 2H) ppm.

C. A solution of methyl 4-[4-[methyl[2-(4-phenoxyphenyl)ethyl]amino]-1-piperidinyl]methyl]benzoate (about 0.71 mmol) in aqueous THF was treated with an aqueous solution of lithium hydroxide. The reaction was acidified with TFA. Purification by preparatory HPLC gave 40 mg of 4-[[4-[methyl[2-(4-phenoxyphenyl)ethyl]amino]-1-piperidinyl]methyl]benzoic acid; 1H NMR (400 MHz, DMSO-d$_6$) δ 7.95 (d, 2H), 7.56 (dbr, 2H), 7.32 (ddd, 2H), 7.26 (d, 2H), 7.07 (tt, 1H), 6.88-6.96 (m, 4H), 4.27 (br, 2H), 3.25 (br, 3H), 2.86 (br, 4H), 2.72 (s, 3H), 2.14 (br, 2H) 1.85 (br, 2H) ppm.

D. In a similar manner as described above in Paragraph A, a solution of 1,1-dimethylethyl 4-[[4-(4-chlorophenoxy)phenyl]amino]-1-piperidinecarboxylate (1.34 g, 3.3 mmol) in dichloromethane (10 mL) was stirred as a solution of 4 M hydrochloric acid in dioxane (3.3 mL, 13.3 mmol) was added. The reaction was stirred for 17 hours. Solvent was removed to yield 1.14 g of N-[4-(4-chlorophenoxy)phenyl]-4-piperidinamine hydrochloride salt.

E. A slurry of N-[4-(4-chlorophenoxy)phenyl]-4-piperidinamine, hydrochloride salt (0.3 g, 0.8 mmol) in acetonitrile (9 mL) was stirred as methyl 4-(2-bromoethyl)benzoate (0.2 g, 0.8 mmol), potassium carbonate (0.34 g, 2.5 mmol), and potassium iodide (19 mg, 0.11 mmol) were added sequentially. The reaction was heated at reflux for 2 days. The cooled reaction mixture was filtered and concentrated. Purification by reverse phase preparative HPLC using a gradient of acetonitrile in water (plus 0.1% TFA) gave 0.13 g of methyl 4-[2-[4-[[4-(4-chlorophenoxy)phenyl]amino]-1-piperidinyl]ethyl]benzoate trifluoroacetic acid salt.

F. A solution of methyl 4-[2-[4-[[4-(4-chlorophenoxy)phenyl]amino]-1-piperidinyl]ethyl]benzoate trifluoroacetic acid salt (0.13 g, 0.18 mmol) in THF (4 mL) and methanol was stirred as an aqueous solution of lithium hydroxide (84 mg, 2 mmol) in 4 mL of water was added. The reaction was stirred for 17 hours and acidified with TFA. Purification by reverse phase preparative HPLC using a gradient of acetonitrile in water (plus 0.1% TFA) gave 66 mg of 4-[2-[4-[[4-(4-chlorophenoxy)phenyl]amino]-1-piperidinyl]ethyl]benzoic acid; $^1$H NMR (400 MHz, DMSO-$d_6$) δ 7.85 (d, 2H), 7.44 (d, 2H), 7.35 (d, 2H), 6.86 (d, 4H), 6.64 (d, 2H), 3.62 (dbr, 2H), 3.37 (m, 3H), 3.08 (m, 4H), 2.14 (dbr, 2H), 1.56 (qbr, 2H) ppm.

Synthetic Example 8

Compounds of Formula (If)

A slurry of methyl 4-((methyl(piperidin-2-ylmethyl)amino)methyl)benzoate hydrochloride salt (200 mg, 0.58 mmol) in dichloroethane (6 mL) was stirred as diisopropylethylamine (225 mg, 1.74 mmol) was added. After 30 minutes, 4-(4-bromophenoxy)benzaldehyde (160 mg, 0.58 mmol) was added to the reaction mixture. After 20 minutes, solid triacetoxyborohydride (147 mg, 0.7 mmol) was added and the reaction was stirred for 17 hours. Solvent was removed under reduced pressure. The residue was dissolved in a mixture of THF and methanol and treated with lithium hydroxide to give a basic solution. The reaction was stirred for 17 hours, concentrated to dryness, and purified by reverse phase preparative HPLC using a gradient of acetonitrile in water containing 0.1% TFA. Relevant fractions were combined to give 40 mg of 4-[[[[(RS)-1-[[4-(4-bromophenoxy)phenyl]methyl]-2-piperidinyl]methyl]methylamino]methyl]benzoic acid; $^1$NMR (400 MHz, DMSO-$d_6$) δ 7.93 (d, 2H), 7.57 (d, 2H), 7.52 (m, 4H), 7.06 (d, 2H), 6.96 (d, 2H), 4.61 (dbr, 2H), 4.18 (dbr, 2H), 3.24 (m, 1H), 2.34 (s, 3H), 2.00 (m, 1H), 1.63 (m, 5H) ppm.

Synthetic Example 9

Compounds of Formula (Ig)

A. A solution of methyl 4-[[methyl(2-pyrrolidinylmethyl)amino]methyl]benzoate hydrochloride salt (310 mg, 1.04 mmol) and 4-(4-bromophenoxy)benzaldehyde (301 mg, 1.1 mmol) in dichloroethane was stirred as diisopropylethylamine (DIEA, 1 mL) and sodium triacetoxyborohydride (286 mg, 1.35 mmol) were added sequentially at ambient temperature. After stirring at ambient temperature for 17 hours, the reaction mixture was treated with a saturated aqueous solution of sodium bicarbonate and extracted with EtOAc. The combined organic layers were dried and concentrated. Purification by flash chromatography afforded methyl 4-[[[[(R)-1-[[4-(4-bromophenoxy)phenyl]methyl]-2-pyrrolidinyl]methyl]methylamino]methyl]benzoate (510 mg, 94%); $^1$NMR (400 MHz, DMSO-$d_6$) δ 7.98 (d, 2H), 7.42 (dd, 2H), 7.24 (d, 2H), 6.91 (d, 2H), 6.83 (d, 2H), 3.82 (s, 3H), 4.16 (d, 1H), 3.55 (dd, 2H), 3.23 (d, 1H), 2.90 (m, 1H), 2.42 (m, 1H), 2.55 (dd, 1H), 2.38 (dd, 1H), 2.11 (s, 3H), 2.17 (m, 1H), 1.99 (m, 1H), 1.63 (m, 3H) ppm.

B. A solution of methyl 4-[[[[(R)-1-[[4-(4-bromophenoxy)phenyl]methyl]-2-pyrrolidinyl]methyl]methylamino]methyl]benzoate (510 mg, 0.98 mmol) in THF (10 mL) and MeOH (10 mL) was stirred as lithium hydroxide (400 mg) in water was added. The reaction mixture was stirred at ambient temperature for 3 days. The reaction mixture was neutralized with 1 N HCl and concentrated. Purification by reverse phase preparative chromatography afforded 4-[[[[(R)-1-[[4-(4-bromophenoxy)phenyl]methyl]-2-pyrrolidinyl]methyl]methylamino]methyl]benzoic acid as a TFA salt (400 mg); $^1$H NMR (400 MHz, DMSO-$d_6$) δ 7.95 (d, 2H), 7.57 (m, 4H), 7.16 (d, 2H), 6.94 (d, 2H), 4.23 (m, 1H), 3.39 (m, 4H), 3.27 (m, 2H), 2.32 (m, 1H), 2.21 (s, 3H), 1.82 (m, 4H), 1.23 (m, 2H) ppm.

Synthetic Example 10

Compounds of Formula (Ih1)

A. A solution of 1,1-dimethylethyl 2-[[[[4-(4-bromophenoxy)phenyl]methyl]amino]-methyl]-1-pyrrolidinecarboxylate (900 mg, 1.9 mmol) in dichloroethane (10 mL) was stirred as acetic acid (180 mg, 3 mmol), formaldehyde (37% solution in water) and sodium triacetoxyborohydride (508 mg, 2.4 mmol) were added. The reaction was stirred for 17 hours. The reaction was treated with a saturated aqueous solution of sodium bicarbonate and extracted with ethyl acetate (2×). The combined organic extracts were dried and concentrated. Purification by flash chromatography on silica gel using a mixture of ethyl acetate in hexane gave 0.67 g of 1,1-dimethylethyl (R)-2-[[methyl[[4-(4-bromophenoxy)phenyl]methyl]amino]methyl]-1-pyrrolidinecarboxylate.

B. A solution of 1,1-dimethylethyl (R)-2-[[methyl[[4-(4-bromophenoxy)phenyl]methyl]amino]methyl]-1-pyrrolidinecarboxylate (670 mg, 1.8 mmol) in a solution of 4 N hydrochloric acid in dioxane (6 mL) was stirred overnight. Solvent was removed under reduced pressure and 870 mg of (R)—N-[[4-(4-bromophenoxy)phenyl]methyl]-N-methyl-2-pyrrolidinemethanamine was isolated as the hydrochloride salt.

Synthetic Example 11

Compounds of Formula (Ih)

A. A solution of (R)—N-[[4-(4-bromophenoxy)phenyl]methyl]-N-methyl-2-pyrrolidinemethanamine hydrochloride salt (0.87 g, 2 mmol) and methyl 4-formylbenzoate (346 mg, 2.11 mmol) in dichloroethane (20 mL) was stirred as diisopropylethylamine (0.12 mL, 3 mmol) and sodium triacetoxyborohydride (536 mg, 2.53 mmol) were added sequentially. The reaction was stirred at ambient temperature overnight. The reaction was treated with a saturated aqueous solution of sodium bicarbonate and extracted with ethyl acetate (2×). The combined organic extracts were dried and concentrated. Purification by flash chromatography on silica gel gave 0.9 g of methyl 4-[[(R)-2-[[[[4-(4-bromophenoxy)phenyl]methyl]methylamino]methyl]-1-pyrrolidinyl]methyl]benzoate.

B. A solution of methyl 4-[[(R)-2-[[[[4-(4-bromophenoxy)phenyl]methyl]methylamino]methyl]-1-pyrrolidinyl]methyl]benzoate in a mixture of THF and methanol and treated with an aqueous solution of lithium hydroxide (400 mg). The reaction was stirred for 3 days. After acidification with 1 N hydrochloric acid, purification by reverse phase preparative HPLC using a gradient of acetonitrile in water containing 0.1% TFA give 270 mg of 4-[[(R)-2-[[[[4-(4-bromophenoxy)phenyl]methyl]methylamino]methyl]-1-pyrrolidinyl]methyl]benzoic acid; $^1$NMR (400 MHz, DMSO-$d_6$) δ 7.98 (d, 2H), 7.61 (d, 2H), 7.54 (d, 2H), 7.40 (d, 2H), 7.07 (d, 2H), 6.96 (d, 2H), 4.46 (m, 1H), 4.17 (dbr, 1H), 3.18 (m, 4H), 3.02 (m, 2H), 2.37 (sbr, 3H), 2.25 (m, 1H), 1.82 (m, 4H), 1.21 (m, 2H) ppm.

Synthetic Example 12

Compounds of Formula (Ii)

A. A solution of methyl 4-[(3-oxo-8-azabicyclo[3.2.1]oct-8-yl)methyl]-benzoate (0.3 g, 1.1 mmol) and 4-phenoxybenzenemethaneamine (0.23 g, 1.15 mmol) in dichloromethane (6.5 mL) was stirred as acetic acid (0.09 g, 1.5 mmol) was added. After 15 minutes, sodium triacetoxyborohydride (0.45 g, 2.15 mmol) was added and the reaction was stirred for 2.5 days. The reaction was treated with a saturated aqueous solution of sodium bicarbonate and extracted with dichloromethane (2×). The combined organic extracts were washed with water, dried and concentrated. Purification by flash chromatography on silica gel using a gradient of methanol in dichloromethane gave 0.2 g of methyl 4-[[(3-exo)-3-[[(4-phenoxyphenyl)methyl]amino]-8-azabicyclo[3.2.1]oct-8-yl]methyl]benzoate.

B. A solution of methyl 4-[[(3-exo)-3-[[(4-phenoxyphenyl)methyl]amino]-8-azabicyclo[3.2.1]oct-8-yl]methyl]benzoate (0.2 g, 0.46 mmol) in THF (7 mL) was diluted with water (7 mL) and treated with lithium hydroxide monohydrate (0.2 g, 5 mmol). After 15 hours, the reaction was concentrated. The residue was neutralized with 1 N hydrochloric acid and extracted with a 3 to 1 mixture of dichloromethane and isopropanol (5×). The combined organic layers were dried and concentrated to give 0.15 g of 4-[[(3-exo)-3-[[(4-phenoxyphenyl)methyl]amino]-8-azabicyclo[3.2.1]oct-8-yl]methyl]benzoic acid; $^1$H NMR (400 MHz, DMSO-$d_6$. 45° C.) δ 7.94 (d, 2H), 7.65 (d, 2H), 7.31 (m, 2H), 7.24 (m, 2H), 7.09 (t, 1H), 6.92 (m, 4H), 4.09 (sbr, 2H), 3.71 (sbr, 4H), 3.18 (s, 1H), 2.74 (dbr, 2H), 2.51 (dbr, 2H), 2.18 (sbr, 2H), 1.78 (dbr, 2H).

Synthetic Example 13

Compounds of Formula (Ij)

A. A solution of methyl 4-[(8-azabicyclo[3.2.1]oct-3-ylmethylamino)methyl]-benzoate (0.33 g, 1.1 mmol) and 4-[4-(2-oxazolyl)phenoxy]-benzaldehyde (0.3, 1.1 mmol) in dichloroethane (20 mL) was stirred as sodium triacetoxyborohydride (0.3 g, 1.4 mmol) was added. The reaction was stirred for 17 hours. The reaction was treated with 1 N sodium hydroxide and extracted with dichloromethane (2×). The combined organic extracts were dried and concentrated. Purification by flash chromatography on silica gel using a gradient of ethyl acetate in dichloromethane gave 0.47 g of methyl 4-[[methyl[(3-exo)-8-[[4-[4-(2-oxazolyl)phenoxy]phenyl]methyl]-8-azabicyclo[3.2.1]oct-3-yl]amino]methyl]benzoate.

B. A slurry of methyl 4-[[methyl[(3-exo)-8-[[4-[4-(2-oxazolyl)phenoxy]phenyl]-methyl]-8-azabicyclo[3.2.1]oct-3-yl]amino]methyl]benzoate (0.47 g, 0.9 mmol) in a mixture of methanol and THF was treated with a 1 N sodium hydroxide solution (4 mL, 4.4 mmol). The reaction was stirred for 17 h at ambient temperature, acidified with 1 N hydrochloric acid to a pH between 5 and 6, and concentrated. The residue was dissolved in dichloromethane, washed with water, dried and concentrated to give 0.37 g of 4-[[methyl[(3-exo)-8-[[4-[4-(2-oxazolyl)phenoxy]phenyl]methyl]-8-azabicyclo[3.2.1]oct-3-yl]amino]methyl]benzoic acid; $^1$H NMR (400 MHz, DMSO-$d_6$) δ 8.17 (d, 1H), 7.97 (dt, 2H), 7.89 (d, 2H), 7.50 (d, 2H), 7.38 (d, 2H), 7.33 (d, 1H), 7.12/7.07 (m, 4H), 3.70 (s, 2H), 3.55 (s, 2H), 2.54/2.49 (m, 1H), 2.12/1.94 (m, 13H) ppm.

Synthetic Example 14

Compound of Formula (I)

A. A solution of 2-(4-morpholinyl)ethanamine (1 g, 7.4 mmol) in dichloromethane was stirred as a solution of 2-[4-[[4-(2-iodoethoxy)phenyl]methyl]phenyl]oxazole (0.3 g, 0.74 mmol) in dichloromethane was added dropwise and the reaction was heated at reflux for 17 hours. The reaction was concentrated. The residue was dissolved in ethyl acetate and washed with water. The combined organic layers were dried and concentrated. Purification by chromatography on silica gel using a gradient of methanol in dichloromethane gave 0.26 g of N-[2-[4-[[4-(2-oxazolyl)phenyl]methyl]phenoxy]ethyl]-4-morpholineethanamine; $^1$H NMR (400 MHz, CDCl$_3$) δ 7.97 (d, 2H), 7.68 (s, 1H), 7.27 (d, 2H), 7.21 (s, 1H), 7.13 (d, 2H), 6.82 (d, 2H), 4.08 (t, 2H), 3.96 (s, 2H), 3.67 (m, 4H), 3.03 (t, 2H), 2.78 (t, 2H), 2.51 (t, 2H), 2.43 (m, 4H) ppm.

B. A solution of N-[2-[4-[[4-(2-oxazolyl)phenyl]methyl]phenoxy]ethyl]-4-morpholineethanamine (0.25 g, 0.6 mmol) and methyl 4-formylbenzoate (0.11 g, 0.66 mmol) in dichloroethane (5 mL) was stirred as sodium triacetoxyborohydride (0.16 g, 0.74 mmol) was added and stirred for 17 h. The reaction was diluted with water and extracted with ethyl acetate. The combined organic extracts were dried and concentrated. Purification by chromatography on silica gel using a gradient of methanol in dichloromethane gave 0.28 g of methyl 4-[[[2-(4-morpholinyl)ethyl][2-[4-[[4-(2-oxazolyl)phenyl]methyl]phenoxy]ethyl]amino]-methyl]benzoate; $^1$H NMR (400 MHz, CDCl$_3$) δ 7.97 (m, 4H), 7.68 (s, 1H), 7.42 (d, 2H), 7.27 (d, 2H), 7.21 (s, 1H), 7.08 (d, 2H), 6.78 (d, 2H), 4.03 (t, 2H), 3.96 (s, 2H), 3.92 (s, 3H), 3.79 (s, 2H), 3.66 (m, 4H), 2.92 (t, 2H), 2.73 (t, 2H), 2.47 (m, 2H) 2.42 (m, 4H) ppm.

C. A solution of methyl 4-[[[2-(4-morpholinyl)ethyl][2-[4-[[4-(2-oxazolyl)phenyl]methyl]phenoxy]ethyl]amino]methyl]benzoate (0.22 g, 4 mmol) in methanol (13 mL) was stirred as a 1.2 N aqueous solution of sodium hydroxide (3 mL) was added. The reaction was stirred for 17 h and concentrated. Purification of the aqueous mixture after acidification on reverse phase HPLC using a gradient of acetonitrile in water (plus 0.1% TFA) gave 0.12 g of 4-[[[2-(4-morpholinyl)ethyl][2-[4-[[4-(2-oxazolyl)phenyl]methyl]phenoxy]ethyl]-amino]methyl]benzoic acid; $^1$H NMR (400 MHz, DMSO-$d_6$) δ 8.22 (s, 1H), 7.97 (m, 4H), 7.48 (d, 2H), 7.38 (m, 3H), 7.18 (d, 2H), 6.82 (d, 2H), 4.03 (t, 2H), 3.96

(s, 2H), 3.88 (s, 2H), 3.54 (m, 4H), 2.86 (t, 2H), 2.68 (t, 2H), 2.42 (m, 2H) 2.36 (m, 4H) ppm.

Synthetic Example 15

Further Compounds of Formula (I)

Following the general procedures described herein and exemplified in Synthetic Examples 1-14, the following compounds, as well as other compounds encompassed within Formula (I), can be synthesized utilizing the appropriate starting materials:

4-[[(1S,4S)-5-[2-[4-(phenylmethyl)phenoxy]ethyl]-2,5-diazabicyclo[2.2.1]hept-2-yl]methyl]benzoic acid; $^1$H NMR (300 MHz, CD$_3$OD) δ 7.92 (d, 2H), 7.38 (d, 2H), 7.24 (dd, 2H), 7.16 (d, 2H), 7.14 (dd, 1H), 7.10 (d, 2H), 6.86 (d, 2H), 4.10 (t, 2H), 3.89 (d, 1H), 3.89 (s, 2H), 3.81 (d, 1H), 3.67 (s, 1H), 3.49 (s, 1H), 3.14 (dt, 1H), 3.08 (d, 1H), 3.04 (d, 1H), 3.03 (dt, 1H), 2.94 (dd, 1H), 2.78 (dd, 1H), 1.95 (d, 1H), 1.87 (d, 1H) ppm;

4-[[(1S,4S)-5-[(4-phenoxyphenyl)methyl]-2,5-diazabicyclo[2.2.1]hept-2-yl]methyl]benzoic acid; $^1$H NMR (300 MHz, CD$_3$OD) δ 7.92 (d, 2H), 7.40 (d, 2H), 7.40 (d, 2H), 7.35 (dd, 2H), 7.11 (dd, 1H), 6.99 (d, 2H), 6.96 (d, 2H), 3.94 (d, 1H), 3.91 (d, 1H), 3.84 (d, 1H), 3.82 (d, 1H), 3.59 (s, 1H), 3.56 (s, 1H), 3.09 (d, 1H), 3.07 (d, 1H), 2.83 (dd, 1H), 2.81 (dd, 1H), 1.96 (s, 2H) ppm;

4-[[(1S,4S)-5-[[4-(4-fluorophenoxy)phenyl]methyl]-2,5-diazabicyclo[2.2.1]hept-2-yl]methyl]benzoic acid; $^1$H NMR (300 MHz, Pyridine-d$_6$) δ 8.50 (d, 2H), 7.49 (d, 2H), 7.60 (d, 2H), 7.13 (dd, 2H), 7.09 (d, 2H), 7.06 (dd, 2H), 3.80 (d, 1H), 3.75 (d, 1H), 3.71 (d, 1H), 3.66 (d, 1H), 3.26 (s, 1H), 3.24 (s, 1H), 2.87 (d, 2H), 2.63 (dd, 1H), 2.61 (dd, 1H), 1.69 (s, 2H) ppm;

4-[[(1S,4S)-5-[[4-(2-phenylethoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.33 (d, 2H), 7.31-7.25 (m, 4H), 7.20 (m, 1H), 6.91 (d, 2H), 4.18 (t, 2H), 3.96 (d, 1H), 3.91 (d, 1H), 3.86 (d, 1H), 3.80 (d, 1H), 3.68 (s, 1H), 3.57 (s, 1H), 3.17 (d, 1H), 3.06 (t, 2H), 3.04 (d, 1H), 2.89 (dd, 1H), 2.79 (dd, 1H), 1.99 (s, 2H) ppm 4-[[(1S,4S)-5-[[4-(2-phenylethoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.33 (d, 2H), 7.31-7.25 (m, 4H), 7.20 (m, 1H), 6.91 (d, 2H), 4.18 (t, 2H), 3.96 (d, 1H), 3.91 (d, 1H), 3.86 (d, 1H), 3.80 (d, 1H), 3.68 (s, 1H), 3.57 (s, 1H), 3.17 (d, 1H), 3.06 (t, 2H), 3.04 (d, 1H), 2.89 (dd, 1H), 2.79 (dd, 1H), 1.99 (s, 2H) ppm;

4-[[(1S,4S)-5-[3-(4-phenoxyphenyl)propyl]-2,5-diazabicyclo[2.2.1]hept-2-yl]methyl]benzoic acid; $^1$H NMR (300 MHz, Pyridine-d$_5$) δ 8.49 (d, 2H), 7.60 (d, 2H), 7.34 (dd, 2H), 7.26 (d, 2H), 7.11 (d, 2H), 7.09 (dd, 1H), 7.08 (d, 2H), 3.79 (d, 1H), 3.70 (d, 1H), 3.26 (s, 1H), 3.23 (s, 1H), 2.84 (d, 1H), 2.81 (d, 1H), 2.69 (t, 2H), 2.66 (dd, 1H), 2.62 (m, 1H), 2.60 (dd, 1H), 2.46 (dt, 1H), 1.80 (m, 2H), 1.66 (m, 2H) ppm;

4-[[(1S,4S)-5-[[4-(4-chlorophenoxy)phenyl]methyl]-2,5-diazabicyclo[2.2.1]hept-2-yl]methyl]benzoic acid; $^1$H NMR (300 MHz, Pyridine-d$_5$) δ 8.50 (d, 2H), 7.60 (d, 2H), 7.50 (d, 2H), 7.35 (d, 2H), 7.11 (d, 2H), 7.02 (d, 2H), 3.80 (d, 1H), 3.76 (d, 1H), 3.71 (d, 1H), 3.66 (d, 1H), 3.26 (s, 1H), 3.24 (s, 1H), 2.87 (d, 2H), 2.63 (dd, 1H), 2.61 (dd, 1H), 1.69 (s, 2H) ppm;

4-[[(1S,4S)-5-[2-(4-phenoxyphenyl)ethyl]-2,5-diazabicyclo[2.2.1]hept-2-yl]methyl]benzoic acid; $^1$H NMR (300 MHz, Pyridine-d$_5$) δ 8.47 (d, 2H), 7.60 (d, 2H), 7.34 (dd, 2H), 7.29 (d, 2H), 7.09 (d, 2H), 7.09 (dd, 1H), 7.10 (d, 2H), 3.79 (d, 1H), 3.70 (d, 1H), 3.29 (s, 1H), 3.23 (s, 1H), 2.60 (dd, 1H), 2.91-2.68 (m, 7H), 1.68 (d, 1H), 1.63 (d, 1H) ppm;

4-[[(1S,4S)-5-[[4-(2-phenoxyethoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.38 (d, 2H), 7.32 (d, 2H), 7.27 (dd, 2H), 6.96 (d, 2H), 6.96 (d, 2H), 6.93 (dd, 1H), 4.31 (s, 4H), 3.84 (d, 1H), 3.79 (d, 1H), 3.76 (d, 1H), 3.71 (d, 1H), 3.44 (s, 1H), 3.41 (s, 1H), 2.98 (d, 1H), 2.97 (d, 1H), 2.73 (dd, 1H), 2.70 (dd, 1H), 1.85 (m, 2H) ppm;

4-[[(1S,4S)-5-[[4-(4-bromophenoxy)phenyl]methyl]-2,5-diazabicyclo[2.2.1]hept-2-yl]methyl]benzoic acid; $^1$H NMR (300 MHz, CD$_3$OD) δ 7.92 (d, 2H), 7.47 (d, 2H), 7.40 (d, 2H), 7.39 (d, 2H), 6.97 (d, 2H), 6.91 (d, 2H), 3.87 (d, 1H), 3.82 (d, 1H), 3.80 (d, 1H), 3.75 (d, 1H), 3.45 (s, 2H), 3.00 (d, 2H), 2.99 (d, 1H), 2.74 (dd, 2H), 1.87 (m, 2H) ppm;

4-[[(1S,4S)-5-[2-[4-[(4-chlorophenyl)methyl]phenoxy]ethyl]-2,5-diazabicyclo[2.2.1]hept-2-yl]methyl]benzoic acid; $^1$H NMR (300 MHz, Pyridine-d$_5$) δ 8.45 (d, 2H), 7.59 (d, 2H), 7.32 (d, 2H), 7.17 (d, 2H), 7.15 (d, 2H), 7.04 (d, 2H), 4.10 (t, 2H), 3.84 (s, 2H), 3.76 (d, 1H), 3.69 (d, 1H), 3.33 (s, 1H), 3.21 (s, 1H), 3.00 (dt, 1H), 2.92 (d, 1H), 2.89 (dt, 1H), 2.80 (d, 1H), 2.77 (dd, 1H), 2.60 (dd, 1H), 1.67 (d, 1H), 1.64 (d, 1H) ppm;

4-[[(1S,4S)-5-[2-[4-[(4-fluorophenyl)methyl]phenoxy]ethyl]-2,5-diazabicyclo[2.2.1]hept-2-yl]methyl]benzoic acid; $^1$H NMR (300 MHz, Pyridine-d$_5$) δ 8.46 (d, 2H), 7.59 (d, 2H), 7.19 (dd, 2H), 7.17 (d, 2H), 7.07 (dd, 2H), 7.04 (d, 2H), 4.09 (t, 2H), 3.86 (s, 2H), 3.76 (d, 1H), 3.69 (d, 1H), 3.32 (s, 1H), 3.21 (s, 1H), 2.99 (dt, 1H), 2.91 (d, 1H), 2.88 (dt, 1H), 2.80 (d, 1H), 2.77 (dd, 1H), 2.60 (dd, 1H), 1.67 (d, 1H), 1.63 (d, 1H) ppm;

4-[[(1S,4S)-5-[[4-[(2'-fluoro[1,1'-biphenyl]-4-yl)oxy]phenyl]methyl]-2,5-diazabicyclo[2.2.1]hept-2-yl]methyl]benzoic acid; $^1$H NMR (300 MHz, CD$_3$OD) δ 7.93 (d, 2H), 7.52 (dd, 2H), 7.46 (dd, 1H), 7.40 (d, 2H), 7.38 (d, 2H), 7.34 (m, 1H), 7.22 (dd, 1H), 7.06 (dd, 1H), 7.04 (d, 2H), 7.01 (d, 2H), 3.83 (d, 1H), 3.78 (d, 1H), 3.76 (d, 1H), 3.72 (d, 1H), 3.40 (s, 1H), 3.39 (s, 1H), 2.97 (d, 2H), 2.70 (dd, 2H), 1.83 (m, 2H) ppm;

4-[[(1S,4S)-5-[[4-[4-(3-furanyl)phenoxy]phenyl]methyl]-2,5-diazabicyclo[2.2.1]hept-2-yl]methyl]benzoic acid; $^1$H NMR (300 MHz, CD$_3$OD) δ 7.92 (d, 2H), 7.85 (s, 1H), 7.54 (dd, 1H), 7.53 (d, 2H), 7.39 (d, 4H), 6.99 (d, 2H), 6.98 (d, 2H), 6.77 (dd, 1H), 3.89 (d, 1H), 3.85 (d, 1H), 3.80 (d, 1H), 3.77 (d, 1H), 3.49 (s, 1H), 3.47 (s, 1H), 3.02 (d, 2H), 2.77 (dd, 1H), 2.75 (dd, 1H), 1.89 (m, 2H) ppm;

4-[[(1S,4S)-5-[[4-[4-(trifluoromethyl)phenoxy]phenyl]methyl]-2,5-diazabicyclo[2.2.1]hept-2-yl]methyl]benzoic acid; $^1$H NMR (300 MHz, CD$_3$OD) δ 7.93 (d, 2H), 7.64 (d, 2H), 7.47 (d, 2H), 7.41 (d, 2H), 7.10 (d, 2H), 7.06 (d, 2H), 3.97 (d, 1H), 3.93 (d, 1H), 3.87 (d, 1H), 3.83 (d, 1H), 3.58 (s, 2H), 3.10 (d, 1H), 3.08 (d, 1H), 2.83 (dd, 2H), 1.97 (m, 2H) ppm;

4-[[(1S,4S)-5-[[4-(4-acetylphenoxy)phenyl]methyl]-2,5-diazabicyclo[2.2.1]hept-2-yl]methyl]benzoic acid;

4-[[(1S,4S)-5-[[4-[4-(3-thienyl)phenoxy]phenyl]methyl]-2,5-diazabicyclo[2.2.1]hept-2-yl]methyl]benzoic acid; $^1$H NMR (300 MHz, DMSO-d$_6$) δ 7.84 (d, 2H), 7.79 (dd, 1H), 7.71 (d, 2H), 7.62 (dd, 1H), 7.51 (dd, 1H), 7.35 (d, 2H), 7.35 (d, 2H), 7.02 (d, 2H), 6.97 (d, 2H), 3.75 (d, 1H), 3.71 (d, 1H), 3.66 (d, 1H), 3.62 (d, 1H), 3.25 (s, 2H), 2.71 (d, 2H), 2.58 (dd, 2H), 1.66 (s, 2H) ppm;

4-[[(1S,4S)-5-[[4-[4-(3,5-dimethyl-4-isoxazolyl)phenoxy] phenyl]methyl]-2,5-diazabicyclo[2.2.1]hept-2-yl]methyl] benzoic acid;

4-[[(1S,4S)-5-[(3-fluoro-4-phenoxyphenyl)methyl]-2,5-diazabicyclo[2.2.1]hept-2-yl]methyl]benzoic acid;

4-[[(1S,4S)-5-[[3-(2-phenylethoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.32-7.25 (m, 4H), 7.21 (dd, 1H), 6.93 (d, 1H), 7.20 (m, 1H), 6.97 (s, 1H), 6.81 (d, 1H), 4.18 (t, 2H), 3.84 (d, 1H), 3.77 (d, 1H), 3.75 (d, 1H), 3.69 (d, 1H), 3.39 (s, 2H), 3.06 (t, 2H), 2.96 (d, 1H), 2.95 (d, 1H), 2.69 (dd, 2H), 1.83 (s, 2H) ppm;

4-[[(1S,4S)-5-[(4-fluoro-2-phenoxyphenyl)methyl]-2,5-diazabicyclo[2.2.1]hept-2-yl]methyl]benzoic acid;

4-[[(1S,4S)-5-[(3-phenoxyphenyl)methyl]-2,5-diazabicyclo[2.2.1]hept-2-yl]methyl]benzoic acid; $^1$H NMR (300 MHz, CD$_3$OD) δ 7.91 (d, 2H), 7.35 (d, 2H), 7.34 (dd, 2H), 7.30 (dd, 1H), 7.11 (d, 1H), 7.10 (dd, 1H), 7.03 (m, 1H), 6.98 (d, 2H), 6.87 (d, 1H), 3.79 (d, 1H), 3.76 (d, 1H), 3.72 (d, 1H), 3.67 (d, 1H), 3.33 (s, 2H), 2.91 (d, 1H), 2.88 (d, 1H), 2.67 (dd, 1H), 2.63 (dd, 1H), 1.79 (d, 1H), 1.78 (d, 1H) ppm;

4-[[(1S,4S)-5-[(2-fluoro-4-phenoxyphenyl)methyl]-2,5-diazabicyclo[2.2.1]hept-2-yl]methyl]benzoic acid; $^1$H NMR (300 MHz, CD$_3$OD) δ 7.92 (d, 2H), 7.44 (dd, 1H), 7.39 (dd, 2H), 7.38 (d, 2H), 7.17 (dd, 1H), 7.03 (d, 2H), 6.77 (dd, 1H), 6.69 (dd, 1H), 3.86 (d, 1H), 3.81 (d, 1H), 3.78 (d, 1H), 3.73 (d, 1H), 3.42 (s, 2H), 3.02 (d, 1H), 2.97 (d, 1H), 2.74 (dd, 1H), 2.73 (dd, 1H), 1.86 (d, 1H), 1.83 (d, 1H) ppm;

4-[[(1S,4S)-5-[(2,4-diphenoxyphenyl)methyl]-2,5-diazabicyclo[2.2.1]hept-2-yl]methyl]benzoic acid; $^1$H NMR (300 MHz, CD$_3$OD) δ 7.89 (d, 2H), 7.51 (d, 1H), 7.32 (dd, 4H), 7.31 (d, 2H), 7.09 (dd, 1H), 7.08 (dd, 1H), 6.97 (d, 2H), 6.94 (d, 2H), 6.76 (dd, 1H), 6.45 (d, 1H), 3.81 (d, 1H), 3.75 (d, 1H), 3.71 (d, 1H), 3.69 (d, 1H), 3.39 (s, 1H), 3.32 (s, 1H), 2.98 (d, 1H), 2.87 (d, 1H), 2.71 (dd, 1H), 2.66 (dd, 1H), 1.78 (d, 1H), 1.75 (d, 1H) ppm;

4-[[(1S,4S)-5-([1,1'-biphenyl]-4-ylmethyl)-2,5-diazabicyclo[2.2.1]hept-2-yl]methyl]benzoic acid; $^1$H NMR (300 MHz, CD$_3$OD) δ 7.93 (d, 2H), 7.61 (d, 2H), 7.61 (d, 2H), 7.48 (d, 2H), 7.43 (dd, 2H), 7.40 (d, 2H), 7.32 (dd, 1H), 3.97 (d, 2H), 3.88 (d, 1H), 3.87 (d, 1H), 3.61 (s, 1H), 3.59 (s, 1H), 3.11 (d, 2H), 2.86 (dd, 1H), 2.83 (dd, 1H), 1.98 (s, 2H) ppm;

4-[[(1S,4S)-5-[(4-phenoxyphenyl)methyl]-2,5-diazabicyclo[2.2.1]hept-2-yl]methyl]benzeneacetic acid; $^1$H NMR (300 MHz, CD$_3$OD) δ 7.37 (d, 2H), 7.34 (dd, 2H), 7.30 (s, 4H), 7.11 (dd, 1H), 6.97 (d, 2H), 6.94 (d, 2H), 3.88 (d, 1H), 3.85 (d, 1H), 3.80 (d, 1H), 3.75 (d, 1H), 3.57 (s, 1H), 3.53 (s, 1H), 3.47 (s, 2H), 3.07 (d, 1H), 3.03 (d, 1H), 2.80 (dd, 1H), 2.77 (dd, 1H), 1.93 (s, 2H) ppm;

4-[[(1S,4S)-5-[[4-(2-phenoxyethoxy)phenyl]methyl]-2,5-diazabicyclo[2.2.1]hept-2-yl]methyl]benzeneacetic acid; $^1$H NMR (300 MHz, CD$_3$OD) δ 7.32 (d, 2H), 7.29 (s, 4H), 7.27 (dd, 2H), 6.96 (d, 2H), 6.96 (d, 1H), 6.93 (dd, 1H), 4.31 (s, 4H), 3.85 (d, 1H), 3.84 (d, 1H), 3.77 (d, 1H), 3.75 (d, 1H), 3.53 (s, 2H), 3.46 (s, 2H), 3.04 (d, 1H), 3.03 (d, 1H), 2.78 (dd, 1H), 1.92 (s, 2H) ppm;

4-[[(1S,4S)-5-[[4-(2-phenylethoxy)phenyl]methyl]-2,5-diazabicyclo[2.2.1]hept-2-yl]methyl]benzeneacetic acid; $^1$H NMR (300 MHz, CD$_3$OD) δ 7.38-7.15 (m, 5H), 7.27 (s, 4H), 7.25 (d, 2H), 6.86 (d, 2H), 4.16 (t, 2H), 3.74 (d, 1H), 3.70 (d, 1H), 3.67 (d, 1H), 3.63 (d, 1H), 3.45 (s, 2H), 3.34 (s, 2H), 3.04 (t, 2H), 2.91 (d, 1H), 2.90 (d, 1H), 2.64 (dd, 2H), 1.78 (s, 2H) ppm;

4-[[(1S,4S)-5-[[4-[4-(2-thiazolyl)phenoxy]phenyl]methyl]-2,5-diazabicyclo[2.2.1]hept-2-yl]methyl]benzoic acid; $^1$H NMR (400 MHz, DMSO-d$_6$) δ 8.00 (m, 4H), 7.80 (d, 1H), 7.55 (d, 1H), 7.50 (m, 4H), 7.10 (m, 4H), 4.20 (m, 1H), 4.10 (m, 2H), 4.00 (m, 2H), 3.84 (m, 1H), 3.40 (d, 1H), 3.25 (m, 1H), 3.10 (m, 1H), 3.00 (m, 1H), 2.20 (s, 2H) ppm; and methyl 4-[[(1S,4S)-5-[[4-[4-(2-thiazolyl)phenoxy]phenyl] methyl]-2,5-diazabicyclo[2.2.1]hept-2-yl]methyl]benzoate; $^1$H NMR (400 MHz, CDCl$_3$) δ 8.00 (d, 2H), 7.90 (d, 2H), 7.80 (d, 1H), 7.45 (d, 2H), 7.35 (d, 2H), 7.30 (d, 1H), 7.05 (m, 4H), 3.90 (s, 3H), 3.80 (m, 4H), 3.30 (d, 2H), 2.86 (m, 2H), 2.70 (m, 2H), 1.80 (s, 2H) ppm;

methyl hexahydro-4-[[4-(phenylmethoxy)phenyl]methyl]-1H-1,4-diazepine-1-acetate; H NMR (300 MHz, CDCl$_3$) δ 7.43 (d, 2H), 7.38 (dd, 2H), 7.31 (dd, 1H), 7.25 (d, 2H), 6.92 (d, 2H), 5.04 (s, 2H), 3.70 (s, 3H), 3.58 (s, 2H), 3.41 (s, 2H), 2.86 (m, 2H), 2.84 (m, 2H), 2.69 (m, 4H), 1.81 (m, 2H) ppm;

ethyl hexahydro-4-[[4-(phenylmethoxy)phenyl]methyl]-1H-1,4-diazepine-1-butanoate;

hexahydro-δ-oxo-4-[[4-(phenylmethoxy)phenyl]methyl]-1H-1,4-diazepine-1-butanesulfonamide; $^1$H NMR (300 MHz, CDCl$_3$): δ 7.43 (d, 2H), 7.38 (dd, 2H), 7.32 (dd, 1H), 7.22 (d, 2H), 6.93/6.92 (d, 2H), 5.31 (s, 2H), 5.05/5.04 (s, 2H), 3.61 (m, 2H), 3.56/3.55 (s, 2H), 3.48 (m, 2H), 3.21 (m, 2H), 2.53/2.50 (t, 2H), 2.64 (m, 2H), 2.59 (m, 2H), 2.21 (m, 2H), 1.83 (m, 2H) ppm;

hexahydro-1-[[4-(phenylmethoxy)phenyl]methyl]-4-[2-(phenylsulfonyl)ethyl]-1H-1,4-diazepine; $^1$H NMR (300 MHz, CDCl$_3$) δ 7.91 (d, 2H), 7.64 (dd, 1H), 7.55 (dd, 2H), 7.44 (d, 2H), 7.38 (dd, 2H), 7.32 (dd, 1H), 7.20 (d, 2H), 6.92 (d, 2H), 5.05 (s, 2H), 3.51 (s, 2H), 3.28 (m, 2H), 2.95 (m, 2H), 2.62 (m, 2H), 2.57 (m, 4H), 2.52 (m, 2H), 1.66 (m, 2H) ppm;

4-[[hexahydro-4-[[4-(phenylmethoxy)phenyl]methyl]-1H-1,4-diazepin-1-yl]methyl]benzoic acid; $^1$H NMR (300 MHz, CD$_3$OD) δ 7.90 (d, 2H), 7.43 (d, 2H), 7.36 (dd, 2H), 7.33 (d, 2H), 7.29 (dd, 1H), 7.24 (d, 2H), 6.94 (d, 2H), 5.07 (s, 2H), 3.67 (s, 2H), 3.58 (s, 2H), 2.74 (m, 4H), 2.70 (m, 4H), 1.80 (m, 2H) ppm;

4-[[hexahydro-4-[(4-phenoxyphenyl)methyl]-1H-1,4-diazepin-1-yl]methyl]benzoic acid; $^1$H NMR (300 MHz, CD$_3$OD) δ 7.98 (d, 2H), 7.42 (d, 2H), 7.41 (d, 2H), 7.33 (dd, 2H), 7.11 (dd, 1H), 6.96 (d, 2H), 6.93 (d, 2H), 3.96 (s, 2H), 3.87 (s, 2H), 3.06 (m, 2H), 3.04 (m, 2H), 2.94 (m, 2H), 2.92 (m, 2H), 1.99 (m, 2H) ppm;

4-[[hexahydro-4-[3-[4-(phenylmethyl)phenoxy]propyl]-1H-1,4-diazepin-1-yl]methyl]benzoic acid; $^1$H NMR (300 MHz, CD$_3$OD) δ 7.92 (d, 2H), 7.37 (d, 2H), 7.23 (dd, 2H), 7.15 (d, 2H), 7.14 (dd, 1H), 7.09 (d, 2H), 6.83 (d, 2H), 4.03 (t, 2H), 3.88 (s, 2H), 3.79 (s, 2H), 3.27 (m, 2H), 3.17 (m, 4H), 2.90 (m, 2H), 2.84 (m, 2H), 2.12 (m, 2H), 2.01 (m, 2H) ppm;

4-[[4-[[4-(4-fluorophenoxy)phenyl]methyl]hexahydro-1H-1,4-diazepin-1-yl]methyl]benzoic acid; $^1$H NMR (300 MHz, CD$_3$OD) δ 7.93 (d, 2H), 7.38 (d, 2H), 7.38 (d, 2H), 7.11 (dd, 2H), 7.02 (dd, 2H), 6.95 (d, 2H), 3.89 (s, 2H), 3.88 (s, 2H), 3.04-2.87 (m, 8H), 1.97 (m, 2H) ppm;

4-[[hexahydro-4-[[4-[4-(1H-pyrrol-1-yl)phenoxy]phenyl] methyl]-1H-1,4-diazepin-1-yl]methyl]benzoic acid; $^1$H NMR (300 MHz, CD$_3$OD) δ 7.91 (d, 2H), 7.35 (d, 4H), 7.46 (d, 2H), 7.13 (t, 2H), 7.07 (d, 2H), 6.98 (d, 2H), 6.27 (t, 2H), 3.75 (s, 2H), 3.72 (s, 2H), 2.82 (m, 4H), 2.79 (s, 4H), 1.87 (m, 2H) ppm;

4-[[hexahydro-4-[[4-[(RS)-2-hydroxy-2-phenylethoxy]phenyl]methyl]-1H-1,4-diazepin-1-yl]methyl]benzoic acid;

¹H NMR (300 MHz, CD₃OD) δ 7.93 (d, 2H), 7.45 (d, 2H), 7.39-7.24 (m, 3H), 7.36 (d, 2H), 7.32 (d, 2H), 6.92 (d, 2H), 5.01 (t, 1H), 4.06 (d, 2H), 3.91 (s, 2H), 3.78 (s, 2H), 3.04 (m, 2H), 2.97 (m, 2H), 2.83 (m, 4H), 1.94 (m, 2H) ppm;

4-[[hexahydro-4-[[4-(2-phenylethyl)phenyl]methyl]-1H-1,4-diazepin-1-yl]methyl]benzoic acid; ¹H NMR (300 MHz, CD₃OD) δ 7.93 (d, 2H), 7.38 (d, 2H), 7.29 (d, 2H), 7.24-7.08 (m, 5H), 7.13 (d, 2H), 3.91 (s, 2H), 3.83 (s, 2H), 3.02 (m, 2H), 2.95 (m, 2H), 2.89 (s, 4H), 2.88 (m, 4H), 1.95 (m, 2H) ppm;

4-[[hexahydro-4-[[4-(2-phenylethoxy)phenyl]methyl]-1H-1,4-diazepin-1-yl]methyl]benzoic acid; ¹H NMR (300 MHz, CD₃OD) δ 7.92 (d, 2H), 7.36 (d, 2H), 7.31 (d, 2H), 7.29-7.15 (m, 5H), 6.90 (d, 2H), 4.16 (t, 2H), 3.93 (s, 2H), 3.78 (s, 2H), 3.06 (m, 2H), 3.04 (t, 2H), 3.00 (m, 2H), 2.84 (m, 4H), 1.95 (m, 2H) ppm;

4-[[hexahydro-4-[[4-(2-phenoxyethoxy)phenyl]methyl]-1H-1,4-diazepin-1-yl]methyl]benzoic acid; ¹H NMR (300 MHz, DMSO-d₆) δ 7.85 (d, 2H), 7.35 (d, 2H), 7.22 (d, 2H), 7.30 (dd, 2H), 6.95 (dd, 1H), 6.92 (d, 2H), 6.98 (d, 2H), 4.29 (s, 4H), 3.64 (s, 2H), 3.53 (s, 2H), 2.64 (m, 2H), 2.63 (m, 2H), 2.58 (s, 4H), 1.69 (m, 2H) ppm;

4-[[hexahydro-4-[3-(4-phenoxyphenyl)propyl]-1H-1,4-diazepin-1-yl]methyl]benzoic acid; ¹H NMR (300 MHz, CD₃OD) δ 7.92 (d, 2H), 7.37 (d, 2H), 7.33 (dd, 2H), 7.21 (d, 2H), 7.09 (dd, 1H), 6.94 (d, 2H), 6.91 (d, 2H), 3.77 (s, 2H), 3.29 (m, 2H), 3.20 (m, 2H), 3.05 (m, 2H), 2.88 (m, 2H), 2.82 (t, 2H), 2.67 (t, 2H), 2.01 (m, 2H), 1.99 (m, 2H) ppm;

4-[[hexahydro-4-[2-(4-phenoxyphenyl)ethyl]-1H-1,4-diazepin-1-yl]methyl]benzoic acid; ¹H NMR (300 MHz, CD₃OD) δ 7.99 (d, 2H), 7.29 (d, 2H), 7.32 (dd, 2H), 7.14 (d, 2H), 7.07 (dd, 1H), 6.96 (d, 2H), 6.91 (d, 2H), 3.77 (s, 2H), 3.12 (m, 4H), 3.01 (m, 2H), 2.91 (m, 4H), 2.84 (m, 2H), 2.02 (m, 2H) ppm;

4-[[4-[[4-(4-bromophenoxy)phenyl]methyl]hexahydro-1H-1,4-diazepin-1-yl]methyl]benzoic acid; ¹H NMR (300 MHz, CD₃OD) δ 7.92 (d, 2H), 7.48 (d, 2H), 7.39 (d, 2H), 7.38 (d, 2H), 6.98 (d, 2H), 6.91 (d, 2H), 3.84 (s, 2H), 3.82 (s, 2H), 2.93 (m, 2H), 2.91 (m, 2H), 2.89 (s, 4H), 1.93 (m, 2H) ppm;

4-[[hexahydro-4-[[4-[(4'-methoxy[1,1'-biphenyl]-4-yl)oxy]phenyl]methyl]-1H-1,4-diazepin-1-yl]methyl]benzoic acid;

4-[[4-[[4-[(4'-fluoro[1,1'-biphenyl]-4-yl)oxy]phenyl]methyl]-hexahydro-1H-1,4-diazepin-1-yl]methyl]benzoic acid;

4-[[4-[[4-[(2'-fluoro[1,1'-biphenyl]-4-yl)oxy]phenyl]methyl]-hexahydro-1H-1,4-diazepin-1-yl]methyl]benzoic acid; ¹H NMR (300 MHz, CD₃OD) δ 7.93 (d, 2H), 7.54 (dd, 2H), 7.47 (dd, 1H), 7.41 (d, 2H), 7.38 (d, 2H), 7.35 (m, 1H), 7.24 (dd, 1H), 7.17 (m, 1H), 7.07 (d, 2H), 7.04 (d, 2H), 3.88 (s, 2H), 3.87 (s, 2H), 2.98 (m, 2H), 2.96 (m, 2H), 2.93 (m, 4H), 1.96 (m, 2H) ppm;

4-[[4-[[4-[4-(3-furanyl)phenoxy]phenyl]methyl]-hexahydro-1H-1,4-diazepin-1-yl]methyl]benzoic acid; ¹H NMR (300 MHz, CD₃OD) δ 7.91 (d, 2H), 7.85 (s, 1H), 7.54 (d, 2H), 7.54 (dd, 2H), 7.36 (d, 4H), 7.00 (d, 2H), 6.97 (d, 2H), 6.78 (dd, 1H), 3.78 (s, 2H), 3.76 (s, 2H), 2.87 (m, 2H), 2.85 (m, 2H), 2.82 (s, 4H), 1.89 (m, 2H) ppm;

4-[[hexahydro-4-[[4-[4-(3-thienyl)phenoxy]phenyl]methyl]-1H-1,4-diazepin-1-yl]methyl]benzoic acid; ¹H NMR (300 MHz, DMSO-d₆) δ 7.85 (d, 2H), 7.81 (dd, 1H), 7.72 (d, 2H), 7.63 (dd, 1H), 7.53 (dd, 1H), 7.35 (d, 2H), 7.33 (d, 2H), 7.03 (d, 2H), 6.99 (d, 2H), 3.65 (s, 2H), 3.59 (s, 2H), 2.66 (m, 4H), 2.82 (s, 4H), 1.72 (m, 2H) ppm;

4-[[4-[[4-[(4'-cyano[1,1'-biphenyl]-4-yl)oxy]phenyl]methyl]-hexahydro-1H-1,4-diazepin-1-yl]methyl]benzoic acid;

4-[[hexahydro-4-[[4-[4-(1,1-dimethylethyl)phenoxy]phenyl]methyl]-1H-1,4-diazepin-1-yl]methyl]benzoic acid;

4-[[4-[[4-[(1,3-benzodioxol-5-yl)oxy]phenyl]methyl]-hexahydro-1H-1,4-diazepin-1-yl]methyl]benzoic acid; ¹H NMR (300 MHz, CD₃OD) δ 7.92 (d, 2H), 7.37 (d, 2H), 7.34 (d, 2H), 6.91 (d, 2H), 6.79 (d, 1H), 6.56 (d, 1H), 6.47 (dd, 1H), 5.96 (s, 2H), 3.81 (s, 4H), 2.96-2.81 (m, 8H), 1.92 (m, 2H) ppm;

4-[[4-[[4-[(2,3-dihydro-2,2,3,3-tetrafluoro-1,4-benzodioxin-6-yl)oxy]phenyl]methyl]hexahydro-1H-1,4-diazepin-1-yl]methyl]benzoic acid;

4-[[hexahydro-4-[[4-[4-(trifluoromethyl)phenoxy]phenyl]methyl]-1H-1,4-diazepin-1-yl]methyl]benzoic acid; ¹H NMR (300 MHz, CD₃OD) δ 7.92 (d, 2H), 7.63 (d, 2H), 7.42 (d, 2H), 7.36 (d, 2H), 7.09 (d, 2H), 7.05 (d, 2H), 3.77 (s, 2H), 3.74 (s, 2H), 2.84 (m, 4H), 2.80 (s, 4H), 1.88 (m, 2H) ppm;

4-[[4-[[4-(2,4-difluorophenoxy)phenyl]methyl]-hexahydro-1H-1,4-diazepin-1-yl]methyl]benzoic acid; ¹H NMR (300 MHz, CD₃OD) δ 7.92 (d, 2H), 7.38 (d, 2H), 7.36 (d, 2H), 7.17 (ddd, 1H), 7.14 (ddd, 1H), 6.98 (dddd, 1H), 6.91 (d, 2H), 3.86 (s, 2H), 3.84 (s, 2H), 2.95 (m, 2H), 2.91 (m, 2H), 2.90 (s, 4H), 1.94 (m, 2H) ppm;

4-[[4-[[4-(3,4-difluorophenoxy)phenyl]methyl]-hexahydro-1H-1,4-diazepin-1-yl]methyl]benzoic acid; ¹H NMR (300 MHz, CD₃OD) δ 7.93 (d, 2H), 7.42 (d, 2H), 7.39 (d, 2H), 7.25 (ddd, 1H), 7.00 (d, 2H), 6.93 (ddd, 1H), 6.79 (dddd, 1H), 3.89 (s, 2H), 3.87 (s, 2H), 2.96 (m, 2H), 2.95 (m, 2H), 2.93 (s, 4H), 1.96 (m, 2H) ppm;

4-[[hexahydro-4-[[4-(3,4,5-trifluorophenoxy)phenyl]methyl]-1H-1,4-diazepin-1-yl]methyl]benzoic acid; ¹H NMR (300 MHz, CD₃OD) δ 7.92 (d, 2H), 7.43 (d, 2H), 7.38 (d, 2H), 7.03 (d, 2H), 6.75 (m, 2H), 3.82 (s, 2H), 3.78 (s, 2H), 2.89 (m, 2H), 2.87 (m, 2H), 2.85 (s, 4H), 1.91 (m, 2H) ppm;

4-[[4-[[4-(4-chlorophenoxy)phenyl]methyl]hexahydro-1H-1,4-diazepin-1-yl]methyl]benzoic acid; ¹H NMR (300 MHz, CD₃OD) δ 7.91 (d, 2H), 7.35 (d, 4H), 7.33 (d, 2H), 6.96 (d, 4H), 3.72 (s, 2H), 3.68 (s, 2H), 2.80 (m, 4H), 2.76 (s, 4H), 1.85 (m, 2H) ppm;

4-[[4-[[4-([1,1'-biphenyl]-4-yloxy)phenyl]methyl]hexahydro-1H-1,4-diazepin-1-yl]methyl]benzoic acid; ¹H NMR (300 MHz, CD₃OD) δ 7.91 (d, 2H), 7.61 (d, 2H), 7.59 (d, 2H), 7.42 (dd, 2H), 7.35 (d, 4H), 7.34 (dd, 1H), 7.06 (d, 2H), 6.99 (d, 2H), 3.72 (s, 2H), 3.69 (s, 2H), 2.81 (m, 2H), 2.79 (m, 2H), 2.77 (s, 4H), 1.85 (m, 2H) ppm;

4-[[hexahydro-4-[[4-(2,3,4-trifluorophenoxy)phenyl]methyl]-1H-1,4-diazepin-1-yl]methyl]benzoic acid; ¹H NMR (300 MHz, CD₃OD) δ 7.91 (d, 2H), 7.36 (d, 2H), 7.35 (d, 2H), 7.12 (dddd, 1H), 6.95 (d, 2H), 6.92 (m, 1H), 3.73 (s, 2H), 3.68 (s, 2H), 2.79 (m, 4H), 2.76 (s, 4H), 1.85 (m, 2H) ppm;

4-[[4-[[4-(4-acetylphenoxy)phenyl]methyl]hexahydro-1H-1,4-diazepin-1-yl]methyl]benzoic acid; ¹H NMR (300 MHz, CD₃OD) δ 8.00 (d, 2H), 7.91 (d, 2H), 7.42 (d, 2H), 7.35 (d, 2H), 7.05 (d, 2H), 7.02 (d, 2H), 3.73 (s, 2H), 3.71 (s, 2H), 2.81 (m, 4H), 2.77 (s, 4H), 2.57 (s, 3H), 1.86 (m, 2H) ppm;

4-[[4-[[4-(2-oxazolyl)phenoxy]phenyl]methyl]-hexahydro-1H-1,4-diazepin-1-yl]methyl]benzoic acid; ¹H NMR (300 MHz, CD₃OD δ 7.99 (d, 2H), 7.94 (d, 2H), 7.94 (d, 1H), 7.44 (d, 2H), 7.39 (d, 2H), 7.26 (d, 1H), 7.07 (d, 2H), 7.05 (d, 2H), 3.92 (s, 4H), 3.01 (m, 2H), 2.98 (m, 2H), 2.97 (m, 4H), 1.98 (m, 2H) ppm;

4-[[4-[[4-[2-(4-fluorophenyl)ethoxy]phenyl]methyl]hexahydro-1H-1,4-diazepin-1-yl]methyl]benzoic acid; $^1$H NMR (400 Mz, DMSO-d$_6$) δ 7.86 (d, 2H), 7.37 (d, 2H), 7.33 (dd, 2H), 7.17 (d, 2H), 7.10 (tt, 2H), 6.83 (d, 2H), 4.11 (t, 2H), 3.63 (s, 2H), 3.52 (s, 2H), 2.98 (t, 2H), 2.61 (t, 4H), 2.56 (s, 4H), 1.67 (t, 2H) ppm;

4-[[hexahydro-4-[2-(4-phenoxyphenoxy)ethyl]-1H-1,4-diazepin-1-yl]methyl]benzoic acid; $^1$H NMR (400 Mz, DMSO-d$_6$) δ 7.98 (d, 2H), 7.58 (d, 2H), 7.35 (t, 2H), 7.06 (t, 1H), 7.00 (s, 4H), 6.90 (d, 2H), 4.24 (tbr, 4H), 3.80/3.00 (mbr, 10H), 2.05 (sbr, 2H) ppm;

4-[[hexahydro-4-[3-[4-[4-(trifluoromethyl)phenoxy]phenoxy]propyl]-1H-1,4-diazepin-1-yl]methyl]benzoic acid; $^1$H NMR (400 Mz, CD$_3$OD) δ 8.08 (d, 2H), 7.62 (d, 2H), 7.58 (d, 2H), 7.06 (s, 4H), 7.00 (d, 2H), 4.45 (s, 2H), 4.38 (mbr, 2H), 3.92 (mbr, 2H), 3.76-3.62 (mbr, 6H), 3.42 (mbr, 2H), 2.33 (sbr, 2H) ppm;

4-[[hexahydro-4-[[4-(phenylmethoxy)phenyl]methyl]-1H-1,4-diazepin-1-yl]methyl]benzoic acid; $^1$H NMR (300 MHz, CD$_3$OD) δ 7.90 (d, 2H), 7.43 (d, 2H), 7.36 (dd, 2H), 7.33 (d, 2H), 7.29 (dd, 1H), 7.24 (d, 2H), 6.94 (d, 2H), 5.07 (s, 2H), 3.67 (s, 2H), 3.58 (s, 2H), 2.74 (m, 4H), 2.70 (m, 4H), 1.80 (m, 2H) ppm;

4-[[hexahydro-7-oxo-4-[(4-phenoxyphenyl)methyl]-1H-1,4-diazepin-1-yl]methyl]benzoic acid;

4-[[hexahydro-δ-oxo-4-[(4-phenoxyphenyl)methyl]-1H-1,4-diazepin-1-yl]methyl]benzoic acid;

3-[[hexahydro-4-[(4-phenoxyphenyl)methyl]-1H-1,4-diazepin-1-yl]methyl]benzoic acid; $^1$H NMR (300 MHz, DMSO-d$_6$) δ 7.90 (s, 1H), 7.79 (d, 1H), 7.51 (d, 1H), 7.40 (dd, 1H), 7.38 (dd, 2H), 7.32 (d, 2H), 7.12 (dd, 1H), 6.99 (d, 2H), 6.94 (d, 2H), 3.66 (s, 2H), 3.59 (s, 2H), 2.66 (m, 4H), 2.61 (s, 4H), 1.72 (m, 2H) ppm; and 3-[[hexahydro-4-[[4-(phenylmethoxy)phenyl]methyl]-1H-1,4-diazepin-1-yl]methyl]benzoic acid; $^1$H NMR (300 MHz, CD$_3$OD) δ 7.99 (s, 1H), 7.91 (d, 1H), 7.49 (d, 1H), 7.40 (d, 2H), 7.40 (d, 2H), 7.39 (dd, 1H), 7.34 (dd, 2H), 7.28 (dd, 1H), 7.01 (d, 2H), 5.07 (s, 2H), 4.10 (s, 2H), 3.87 (s, 2H), 3.22 (m, 2H), 3.15 (m, 2H), 2.96 (m, 2H), 2.92 (m, 2H), 2.04 (m, 2H) ppm;

4-[[hexahydro-4-[(4-phenoxyphenyl)methyl]-1H-1,4-diazepin-1-yl]methyl]-α,α-dimethylbenzenemethanol;

4-[[hexahydro-4-[(4-phenoxyphenyl)methyl]-1H-hexahydro-1H-diazepin-1-yl]methyl]benzonitrile;

(E)-4-[[hexahydro-4-[(4-phenoxyphenyl)methyl]-1H-hexahydro-1H-diazepin-1-yl]methyl]benzaldehyde oxime;

1-[4-[[hexahydro-4-[(4-phenoxyphenyl)methyl]-1H-1,4-diazepin-1-yl]methyl]phenyl]ethanone; $^1$H NMR (300 MHz, CDCl$_3$) δ 7.91 (d, 2H), 7.45 (d, 2H), 7.33 (dd, 2H), 7.29 (d, 2H), 7.09 (dd, 1H), 7.00 (d, 2H), 6.95 (d, 2H), 3.70 (s, 2H), 3.62 (s, 2H), 2.74 (m, 2H), 2.73 (m, 2H), 2.67 (s, 2H), 2.59 (s, 3H), 1.81 (m, 2H) ppm;

N-[2-[[hexahydro-4-[[4-(phenylmethoxy)phenyl]methyl]-1H-1,4-diazepin-1-yl]methyl]phenyl]acetamide; $^1$H NMR (300 MHz, CDCl$_3$) δ 11.01 (s, 1H), 8.28 (d, 1H), 7.44 (d, 2H), 7.39 (dd, 2H), 7.33 (dd, 2H), 7.28 (dd, 1H), 7.24 (d, 2H), 7.05 (d, 1H), 6.98 (dd, 1H), 6.93 (d, 2H), 5.06 (s, 2H), 3.68 (s, 2H), 3.58 (s, 2H), 2.16 (s, 3H), 2.72 (m, 4H), 2.66 (s, 4H), 1.83 (m, 2H) ppm;

N-[4-[[hexahydro-4-[[4-(phenylmethoxy)phenyl]methyl]-1H-1,4-diazepin-1-yl]methyl]phenyl]acetamide;

2-amino-N-[3-[[hexahydro-4-[[4-(phenylmethoxy)phenyl]methyl]-1H-1,4-diazepin-1-yl]methyl]phenyl]acetamide;

2-amino-N-[2-[[hexahydro-4-[[4-(phenylmethoxy)phenyl]methyl]-1H-1,4-diazepin-1-yl]methyl]phenyl]acetamide; $^1$H NMR (300 MHz, CD$_3$OD) δ 8.10 (d, 1H), 7.42 (d, 2H), 7.35 (dd, 2H), 7.28 (dd, 1H), 7.23 (dd, 1H), 7.22 (d, 2H), 7.14 (d, 1H), 7.03 (dd, 1H), 6.94 (d, 2H), 5.04 (s, 2H), 3.64 (s, 2H), 3.57 (s, 2H), 3.40 (s, 2H), 2.75 (m, 2H), 2.71 (m, 2H), 2.65 (m, 4H), 1.81 (m, 2H) ppm;

2-(acetylamino)-N-[2-[[hexahydro-4-[[4-(phenylmethoxy)phenyl]methyl]-1H-1,4-diazepin-1-yl]methyl]phenyl]acetamide; $^1$H NMR (300 MHz, CDCl$_3$) δ 11.39 (s, 1H), 8.21 (d, 1H), 7.44 (d, 2H), 7.38 (dd, 2H), 7.32 (dd, 1H), 7.28 (dd, 1H), 7.23 (d, 2H), 7.07 (d, 1H), 7.00 (dd, 1H), 6.92 (d, 2H), 6.49 (m, 1H), 5.05 (s, 2H), 4.08 (d, 2H), 3.69 (s, 2H), 3.58 (s, 2H), 2.73 (m, 2H), 2.71 (m, 2H), 2.66 (m, 4H), 2.07 (s, 3H), 1.83 (m, 2H) ppm;

N-[2-[[hexahydro-4-[[4-(phenylmethoxy)phenyl]methyl]-1H-1,4-diazepin-1-yl]methyl]phenyl]-5-methyl-2-thiophenecarboxamide; $^1$H NMR (300 MHz, CDCl$_3$) δ 11.35 (s, 1H), 8.36 (d, 1H), 7.55 (d, 1H), 7.44 (d, 2H), 7.39 (dd, 2H), 7.32 (dd, 2H), 7.31 (dd, 1H), 7.23 (d, 2H), 7.10 (d, 1H), 7.00 (dd, 1H), 6.92 (d, 2H), 6.77 (d, 1H), 5.05 (s, 2H), 3.74 (s, 2H), 3.58 (s, 2H), 2.79 (m, 2H), 2.72 (m, 6H), 2.54 (s, 3H), 1.85 (m, 2H) ppm;

N-[4-[[hexahydro-4-[[4-(phenylmethoxy)phenyl]methyl]-1H-1,4-diazepin-1-yl]methyl]phenyl]-2-methyl-3-pyridinecarboxamide; $^1$H NMR (300 MHz, CDCl$_3$) δ 8.57 (dd, 1H), 7.75 (d, 1H), 7.63 (s, 1H), 7.55 (d, 2H), 7.43 (d, 2H), 7.38 (dd, 2H), 7.35 (dd, 2H), 7.32 (dd, 1H), 7.25 (d, 2H), 7.19 (dd, 4.6 Hz, 1H), 6.92 (d, 2H), 5.05 (s, 2H), 3.63 (s, 2H), 3.58 (s, 2H), 2.71 (m, 4H), 2.71 (s, 3H), 2.66 (s, 4H), 1.79 (m, 2H) ppm;

N-[3-[[hexahydro-4-[[4-(phenylmethoxy)phenyl]methyl]-1H-1,4-diazepin-1-yl]methyl]phenyl]-N'-(2-hydroxyethyl)urea; $^1$H NMR (300 MHz, CDCl$_3$) δ 7.98 (s, 1H), 7.42 (d, 2H), 7.37 (dd, 2H), 7.31 (dd, 1H), 7.29 (s, 1H), 7.22 (d, 1H), 7.20 (d, 1H), 7.13 (dd, 1H), 6.90 (d, 2H), 6.88 (d, 1H), 6.09 (t, 1H), 5.02 (s, 2H), 3.60 (t, 2H), 3.52 (s, 2H), 3.51 (s, 2H), 3.30 (dt, 2H), 2.66 (m, 4H), 2.62 (s, 4H), 1.73 (m, 2H) ppm;

N-[3-[[hexahydro-4-[[4-(phenylmethoxy)phenyl]methyl]-1H-1,4-diazepin-1-yl]methyl]phenyl]-N'-(3-hydroxypropyl)urea; $^1$H NMR (300 MHz, CDCl$_3$) δ 7.59 (s, 1H), 7.42 (d, 2H), 7.38 (dd, 2H), 7.32 (dd, 1H), 7.26 (s, 1H), 7.22 (d, 2H), 7.16 (dd, 1H), 6.94 (d, 1H), 6.91 (d, 2H), 5.96 (t, 1H), 5.03 (s, 2H), 3.64 (t, 2H), 3.55 (s, 2H), 3.54 (s, 2H), 3.34 (dt, 2H), 2.68 (m, 4H), 2.63 (s, 4H), 1.75 (m, 2H), 1.64 (m, 2H) ppm;

N-[3-[[hexahydro-4-[[4-(phenylmethoxy)phenyl]methyl]-1H-1,4-diazepin-1-yl]methyl]phenyl]-N'-[3-(1H-imidazol-1-yl)propyl]urea; $^1$H NMR (300 MHz, CDCl$_3$) δ 8.07 (s, 1H), 7.43 (s, 1H), 7.42 (d, 2H), 7.37 (dd, 2H), 7.34 (s, 1H), 7.31 (dd, 1H), 7.21 (d, 2H), 7.21 (d, 1H), 7.16 (dd, 1H), 7.02 (s, 1H), 6.96 (d, 1H), 6.90 (d, 2H), 6.90 (s, 1H), 6.15 (t, 1H), 5.02 (s, 2H), 3.93 (t, 2H), 3.55 (s, 2H), 3.54 (s, 2H), 3.14 (td, 2H), 2.67 (m, 4H), 2.62 (s, 4H), 1.91 (m, 2H), 1.74 (m, 2H) ppm;

N-[3-[[hexahydro-4-[[4-(phenylmethoxy)phenyl]methyl]-1H-1,4-diazepin-1-yl]methyl]phenyl]-N'-[2-(1H-imidazol-4-yl)ethyl]urea; $^1$H NMR (300 MHz, CDCl$_3$) δ 8.35 (s, 1H), 7.30 (s, 1H), 7.41 (d, 2H), 7.36 (dd, 2H), 7.34 (s, 1H), 7.32 (dd, 1H), 7.18 (d, 2H), 7.15 (d, 1H), 7.10 (dd, 1H), 6.89 (d, 2H), 6.87 (d, 1H), 6.64 (s, 1H), 6.11 (t, 1H), 5.01 (s, 2H), 3.51 (s, 2H), 3.49 (s, 2H), 3.40 (m, 2H), 2.67 (m, 2H), 2.65 (m, 4H), 2.61 (s, 4H), 1.71 (m, 2H) ppm;

N-[3-[[hexahydro-4-[[4-(phenylmethoxy)phenyl]methyl]-1H-1,4-diazepin-1-yl]methyl]phenyl]-N'-[3-(4-morpholinyl)propyl]urea; $^1$H NMR (300 MHz, CDCl$_3$) δ 7.43 (d, 2H), 7.38 (dd, 2H), 7.31 (dd, 1H), 7.26 (s, 1H), 7.23 (d, 2H), 7.23 (d, 1H), 7.21 (s, 1H), 7.19 (dd, 1H), 7.00 (d, 1H), 6.91 (d, 2H), 5.78 (m, 1H), 5.04 (s, 2H), 3.60 (m, 4H), 3.57 (s, 2H), 3.56 (s, 2H), 3.28 (m, 2H), 2.69 (m, 4H), 2.64 (s, 4H), 2.38 (m, 2H), 2.37 (m, 4H), 1.76 (m, 2H), 1.66 (m, 2H) ppm;

N-[4-[[hexahydro-4-[[4-(phenylmethoxy)phenyl]methyl]-1H-1,4-diazepin-1-yl]methyl]phenyl]-N'-(2-hydroxyethyl)urea; $^1$H NMR (300 MHz, CD$_3$OD) δ 7.41 (d, 2H), 7.36 (d, 2H), 7.34 (dd, 2H), 7.28 (dd, 1H), 7.24 (d, 2H), 7.22 (d, 2H), 6.94 (d, 2H), 5.03 (s, 2H), 3.64 (t, 2H), 3.63 (s, 4H), 3.33 (t, 2H), 2.78 (m, 4H), 2.74 (s, 4H), 1.83 (m, 2H) ppm;

N-[4-[[hexahydro-4-[[4-(phenylmethoxy)phenyl]methyl]-1H-1,4-diazepin-1-yl]methyl]phenyl]-N'-(3-hydroxypropyl)urea; $^1$H NMR (300 MHz, CD$_3$OD) δ 7.43 (d, 2H), 7.37 (dd, 2H), 7.35 (d, 2H), 7.30 (dd, 1H), 7.26 (d, 2H), 7.23 (d, 2H), 6.95 (d, 2H), 5.05 (s, 2H), 3.65 (t, 2H), 3.64 (s, 4H), 3.32 (t, 2H), 2.79 (m, 4H), 2.74 (s, 4H), 1.83 (m, 2H), 1.75 (m, 2H) ppm;

N-[4-[[hexahydro-4-[[4-(phenylmethoxy)phenyl]methyl]-1H-1,4-diazepin-1-yl]methyl]phenyl]-N'-[3-(1H-imidazol-1-yl)propyl]urea; $^1$H NMR (300 MHz, CD$_3$OD) δ 7.66 (s, 1H), 7.40 (d, 2H), 7.37 (d, 2H), 7.34 (dd, 2H), 7.29 (dd, 1H), 7.24 (d, 2H), 7.22 (d, 2H), 7.13 (s, 1H), 6.95 (s, 1H), 6.93 (d, 2H), 5.03 (s, 2H), 4.06 (t, 2H), 3.66 (s, 4H), 3.18 (t, 2H), 2.80 (m, 4H), 2.75 (s, 4H), 1.98 (m, 2H), 1.84 (m, 2H) ppm;

N-[4-[[hexahydro-4-[[4-(phenylmethoxy)phenyl]methyl]-1H-1,4-diazepin-1-yl]methyl]phenyl]-N'-[2-(1H-imidazol-4-yl)ethyl]urea; $^1$H NMR (300 MHz, CD$_3$OD) δ 7.58 (s, 1H), 7.40 (d, 2H), 7.35 (d, 2H), 7.34 (dd, 2H), 7.30 (dd, 1H), 7.27 (d, 2H), 7.22 (d, 2H), 6.86 (s, 1H), 6.95 (d, 2H), 5.04 (s, 2H), 3.72 (s, 2H), 3.71 (s, 2H), 3.45 (t, 2H), 2.86 (m, 4H), 2.82 (s, 4H), 2.79 (t, 2H), 1.82 (m, 2H) ppm;

N-[2-[[hexahydro-4-[[4-(phenylmethoxy)phenyl]methyl]-1H-1,4-diazepin-1-yl]methyl]phenyl]-N'-[3-(1H-imidazol-1-yl)propyl]urea; $^1$H NMR (300 MHz, CDCl$_3$) δ 10.21 (s, 1H), 7.99 (d, 1H), 7.42 (d, 2H), 7.42 (s, 1H), 7.38 (dd, 2H), 7.31 (dd, 1H), 7.22 (dd, 1H), 7.20 (d, 2H), 7.00 (d, 1H), 6.91 (d, 2H), 6.88 (dd, 1H), 6.75 (s, 1H), 5.67 (m, 1H), 5.03 (s, 2H), 3.62 (s, 2H), 3.54 (s, 2H), 3.52 (m, 2H), 2.82 (t, 2H), 2.65 (m, 4H), 2.62 (s, 4H), 1.74 (m, 2H) ppm;

N-[2-[[hexahydro-4-[[4-(phenylmethoxy)phenyl]methyl]-1H-1,4-diazepin-1-yl]methyl]phenyl]-N'-[3-(4-morpholinyl)propyl]urea; $^1$H NMR (300 MHz, CD$_3$OD) δ 9.99 (s, 1H), 8.01 (d, 1H), 7.43 (d, 2H), 7.38 (dd, 2H), 7.32 (dd, 1H), 7.24 (dd, 1H), 7.22 (d, 2H), 7.02 (d, 1H), 6.93 (d, 2H), 6.89 (dd, 1H), 5.36 (t, 1H), 5.05 (s, 2H), 3.67 (s, 2H), 3.65 (m, 4H), 3.58 (s, 2H), 3.32 (td, 2H), 2.69 (m, 4H), 2.66 (s, 4H), 2.44 (m, 2H), 2.41 (m, 4H), 1.79 (m, 2H), 1.72 (m, 2H) ppm;

3-amino-N-[2-[[hexahydro-4-[[4-(phenylmethoxy)phenyl]methyl]-1H-1,4-diazepin-1-yl]methyl]phenyl]propanamide; $^1$H NMR (300 MHz, CDCl$_3$) δ 11.00 (s, 1H), 8.26 (d, 1H), 7.44 (d, 2H), 7.39 (dd, 2H), 7.32 (dd, 1H), 7.27 (dd, 1H), 7.23 (d, 1H), 7.05 (d, 1H), 6.97 (dd, 1H), 6.92 (d, 2H), 5.05 (s, 2H), 3.67 (s, 2H), 3.57 (s, 2H), 3.09 (t, 2H), 2.72 (m, 2H), 2.71 (m, 2H), 2.65 (s, 4H), 2.50 (t, 2H), 1.82 (m, 2H) ppm;

N-[2-[[hexahydro-4-[[4-(phenylmethoxy)phenyl]methyl]-1H-1,4-diazepin-1-yl]methyl]phenyl]-N'-(2-hydroxyethyl)urea; $^1$H NMR (300 MHz, CDCl$_3$) δ 10.39 (s, 1H), 8.01 (d, 1H), 7.43 (d, 2H), 7.39 (dd, 2H), 7.32 (dd, 1H), 7.24 (dd, 1H), 7.22 (dd, 1H), 7.01 (d, 1H), 6.93 (d, 2H), 6.89 (dd, 1H), 5.53 (t, 1H), 5.05 (s, 2H), 3.72 (t, 2H), 3.67 (s, 2H), 3.60 (s, 2H), 3.38 (dt, 2H), 2.68 (m, 8H), 1.78 (m, 2H) ppm;

2-amino-N-[2-[[hexahydro-4-[[4-(phenylmethoxy)phenyl]methyl]-1H-1,4-diazepin-1-yl]methyl]phenyl]-2-methylpropanamide; $^1$H NMR (300 MHz, CD$_3$OD) δ 8.06 (d, 1H), 7.43 (d, 2H), 7.36 (dd, 2H), 7.32 (dd, 1H), 7.26 (dd, 1H), 7.23 (d, 2H), 7.16 (d, 1H), 7.03 (dd, 1H), 6.94 (d, 2H), 5.06 (s, 2H), 3.63 (s, 2H), 3.59 (s, 2H), 2.82-2.61 (m, 8H), 1.82 (m, 2H), 1.40 (s, 6H) ppm;

2-amino-N-[4-[[hexahydro-4-[[4-(phenylmethoxy)phenyl]methyl]-1H-1,4-diazepin-1-yl]methyl]phenyl]acetamide; $^1$H NMR (300 MHz, CD$_3$OD) δ 7.53 (d, 2H), 7.42 (d, 2H), 7.36 (dd, 2H), 7.32 (dd, 1H), 7.28 (d, 2H), 7.23 (d, 2H), 6.94 (d, 2H), 5.06 (s, 2H), 3.60 (s, 2H), 3.57 (s, 2H), 3.41 (s, 2H), 2.73 (m, 4H), 2.68 (s, 4H), 1.79 (m, 2H) ppm;

(S)-α-amino-N-[4-[[hexahydro-4-[[4-(phenylmethoxy)phenyl]methyl]-1H-1,4-diazepin-1-yl]methyl]phenyl]benzenepropanamide; $^1$H NMR (300 MHz, CD$_3$OD) δ 7.43 (d, 2H), 7.43 (d, 2H), 7.36 (dd, 2H), 7.33-7.17 (m, 5H), 7.32 (dd, 1H), 7.27 (d, 2H), 7.24 (d, 2H), 6.94 (d, 2H), 5.06 (s, 2H), 3.67 (dd, 1H), 3.60 (s, 2H), 3.59 (s, 2H), 3.07 (dd, 1H), 2.90 (dd, 1H), 2.73 (m, 4H), 2.69 (s, 4H), 1.80 (m, 2H) ppm;

2-(acetylamino)-N-[4-[[hexahydro-4-[[4-(phenylmethoxy)phenyl]methyl]-1H-1,4-diazepin-1-yl]methyl]phenyl]acetamide; $^1$H NMR (300 MHz, CDCl$_3$) δ 8.83 (s, 1H), 7.48 (d, 2H), 7.43 (d, 2H), 7.38 (dd, 2H), 7.32 (dd, 1H), 7.28 (d, 2H), 7.24 (d, 2H), 6.91 (d, 2H), 6.75 (t, 1H), 5.04 (s, 2H), 4.12 (d, 2H), 3.60 (s, 2H), 3.58 (s, 2H), 2.71 (m, 2H), 2.70 (m, 2H), 2.65 (s, 4H), 2.09 (s, 3H), 1.78 (m, 2H) ppm;

2-(dimethylamino)-N-[4-[[hexahydro-4-[[4-(phenylmethoxy)phenyl]methyl]-1H-1,4-diazepin-1-yl]methyl]phenyl]acetamide; N-(2-aminoethyl)-N'-[2-[[hexahydro-4-[[4-(phenylmethoxy)phenyl]methyl]-1H-1,4-diazepin-1-yl]methyl]phenyl]urea; $^1$H NMR (300 MHz, CD$_3$OD) δ 7.83 (d, 1H), 7.40 (d, 2H), 7.34 (dd, 2H), 7.27 (dd, 1H), 7.22 (d, 2H), 7.20 (dd, 1H), 7.07 (d, 1H), 6.93 (d, 2H), 6.91 (dd, 1H), 5.02 (s, 2H), 3.58 (s, 2H), 3.56 (s, 2H), 3.26 (t, 2H), 2.76 (t, 2H), 2.67 (m, 2H), 2.64 (s, 4H), 2.63 (m, 2H), 1.75 (m, 2H) ppm;

(S)-2-amino-5-oxo-5-[[4-[[hexahydro-4-[[4-(phenylmethoxy)phenyl]methyl]-1H-1,4-diazepin-1-yl]methyl]phenyl]amino]pentanoic acid; $^1$H NMR (300 MHz, CD$_3$OD) δ 7.59 (d, 2H), 7.43 (d, 2H), 7.37 (dd, 2H), 7.36 (d, 4H), 7.30 (dd, 1H), 7.04 (d, 2H), 5.10 (s, 2H), 4.06 (s, 2H), 3.91 (s, 2H), 3.71 (t, 1H), 3.18 (m, 2H), 3.15 (m, 2H), 3.03 (m, 2H), 3.01 (m, 2H), 2.64 (t, 2H), 2.19 (m, 2H), 2.04 (m, 2H) ppm;

4-(aminosulfonyl)-N-[2-[[hexahydro-4-[[4-(phenylmethoxy)phenyl]methyl]-1H-1,4-diazepin-1-yl]methyl]phenyl]butanamide; $^1$H NMR (300 MHz, CD$_3$Cl) δ 11.16 (s, 1H), 8.20 (d, 1H), 7.44 (d, 2H), 7.38 (dd, 2H), 7.32 (dd, 1H), 7.27 (dd, 1H), 7.22 (d, 1H), 7.05 (d, 1H), 6.98 (dd, 1H), 6.93 (d, 2H), 5.05 (s, 2H), 4.92 (s, 2H), 3.68 (s, 2H), 3.59 (s, 2H), 3.23 (t, 1H), 2.71 (m, 4H), 2.66 (s, 4H), 2.56 (t, 2H), 2.28 (m, 2H), 1.82 (m, 2H) ppm;

3-amino-N-[4-[[hexahydro-4-[[4-(phenylmethoxy)phenyl]methyl]-1H-1,4-diazepin-1-yl]methyl]phenyl]propanamide; $^1$H NMR (300 MHz, CD$_3$OD) δ 7.52 (d, 2H), 7.43 (d, 2H), 7.36 (dd, 2H), 7.32 (dd, 1H), 7.28 (d, 2H), 7.23 (d, 2H), 6.94 (d, 2H), 5.06 (s, 2H), 3.60 (s, 2H), 3.58 (s, 2H), 3.04 (t, 2H), 2.73 (m, 4H), 2.69 (s, 4H), 2.59 (t, 2H), 1.80 (m, 2H) ppm;

(S)—N-[4-[[hexahydro-4-[[4-(phenylmethoxy)phenyl]methyl]-1H-1,4-diazepin-1-yl]methyl]phenyl]pyrrolidine-2-carboxamide; $^1$H NMR (300 MHz, CD$_3$OD) δ 7.53 (d, 2H), 7.43 (d, 2H), 7.36 (dd, 2H), 7.31 (dd, 1H), 7.28 (d, 2H), 7.23 (d, 2H), 6.93 (d, 2H), 5.06 (s, 2H), 3.75 (dd, 1H), 3.59 (s, 2H), 3.56 (s, 2H), 3.04 (m, 1H), 2.96 (m, 1H), 2.72 (m, 4H), 2.67 (s, 4H), 2.20 (m, 1H), 1.87 (m, 1H), 1.79 (m, 2H), 1.78 (m, 2H) ppm;

2-[[3-[[hexahydro-4-[[4-(phenylmethoxy)phenyl]methyl]-1H-1,4-diazepin-1-yl]methyl]phenyl]amino]acetic acid; $^1$H NMR (300 MHz, CD$_3$OD) δ 7.40 (d, 2H), 7.34 (dd, 2H), 7.30 (d, 2H), 7.28 (dd, 1H), 7.08 (dd, 1H), 6.96 (d, 2H), 6.62 (s, 1H), 6.60 (d, 1H), 6.57 (d, 1H), 5.04 (s, 2H), 3.85 (s, 2H), 3.79 (s, 2H), 3.66 (s, 2H), 2.98 (m, 2H), 2.96 (m, 2H), 2.92 (s, 4H), 1.93 (m, 2H) ppm;

2-[[4-[[hexahydro-4-[[4-(phenylmethoxy)phenyl]methyl]-1H-1,4-diazepin-1-yl]methyl]phenyl]amino]acetic acid; $^1$H NMR (300 MHz, CD$_3$OD) δ 7.40 (d, 2H), 7.34 (dd, 2H), 7.28 (dd, 1H), 7.25 (d, 2H), 7.14 (d, 2H), 6.95 (d, 2H), 6.57 (d, 2H), 5.04 (s, 2H), 3.95 (s, 2H), 3.68 (s, 2H), 3.66 (s, 2H), 3.15 (m, 2H), 3.05 (m, 2H), 2.81 (m, 4H), 1.94 (m, 2H) ppm;

4-[[hexahydro-4-[[4-(phenylmethoxy)phenyl]methyl]-1H-1,4-diazepin-1-yl]methyl]benzenemethanol; N-[3-[[hexahydro-4-[[4-(phenylmethoxy)phenyl]methyl]-1H-1,4-diazepin-1-yl]methyl]phenyl]sulfamide; $^1$H NMR (300 MHz, CDCl$_3$) δ 7.52 (d, 1H), 7.43 (d, 2H), 7.42 (s, 1H), 7.39 (dd, 2H), 7.32 (dd, 1H), 7.23 (d, 2H), 7.06 (d, 1H), 6.99 (dd, 1H), 6.92 (d, 2H), 5.05 (s, 2H), 3.73 (s, 2H), 3.56 (s, 2H), 2.76 (m, 2H), 2.71 (m, 2H), 2.64 (s, 4H), 1.85 (m, 2H) ppm;

2-[4-[[hexahydro-4-[[4-(phenylmethoxy)phenyl]methyl]-1H-1,4-diazepin-1-yl]methyl]phenoxy]acetic acid; $^1$H NMR (300 MHz, CD$_3$OD) δ 7.43 (d, 2H), 7.37 (dd, 2H), 7.33 (d, 2H), 7.32 (dd, 1H), 7.31 (d, 2H), 7.00 (d, 2H), 6.93 (d, 2H), 5.09 (s, 2H), 4.41 (s, 2H), 3.93 (s, 2H), 3.90 (s, 2H), 3.04 (m, 4H), 3.01 (m, 4H), 2.01 (m, 2H) ppm; and 2-[3-[[hexahydro-4-[[4-(phenylmethoxy)phenyl]methyl]-1H-1,4-diazepin-1-yl]methyl]phenoxy]acetic acid; $^1$H NMR (300 MHz, CD$_3$OD) δ 7.43 (d, 2H), 7.38 (d, 2H), 7.37 (dd, 2H), 7.30 (dd, 1H), 7.22 (dd, 1H), 7.03 (d, 2H), 6.99 (s, 1H), 6.88 (d, 1H), 6.87 (d, 1H), 5.04 (s, 2H), 4.41 (s, 2H), 4.07 (s, 2H), 3.81 (s, 2H), 3.18 (m, 2H), 3.07 (m, 2H), 2.93 (m, 2H), 2.89 (m, 2H), 2.00 (m, 2H) ppm;

4-[[methyl[2-[methyl[[4-(phenylmethoxy)phenyl]methyl]amino]ethyl]amino]methyl]benzoic acid; $^1$H NMR (300 MHz, CD$_3$OD) δ 7.95 (d, 2H), 7.41 (d, 2H), 7.37 (d, 2H), 7.35 (dd, 2H), 7.34 (dd, 1H), 7.28 (dd, 1H), 7.01 (d, 2H), 5.07 (s, 2H), 3.97 (s, 2H), 3.69 (s, 2H), 3.01 (t, 2H), 2.80 (t, 2H), 2.55 (s, 3H), 2.28 (s, 3H) ppm;

4-[[methyl[3-[methyl[[4-(phenylmethoxy)phenyl]methyl]amino]propyl]amino]methyl]benzoic acid; $^1$H NMR (300 MHz, CD$_3$OD) δ 7.99 (d, 2H), 7.43 (d, 4H), 7.43 (d, 2H), 7.35 (dd, 2H), 7.29 (dd, 1H), 7.04 (d, 2H), 5.09 (s, 2H), 4.18 (s, 2H), 3.91 (s, 2H), 3.10 (m, 2H), 2.81 (m, 2H), 2.71 (s, 3H), 2.45 (s, 3H), 2.09 (m, 2H) ppm;

4-[[methyl[3-[methyl[[4-(2-phenoxyethoxy)phenyl]methyl]amino]propyl]amino]methyl]benzoic acid; $^1$H NMR (300 MHz, CD$_3$OD) δ7.92 (d, 2H), 7.29 (d, 2H), 7.27 (dd, 2H), 7.24 (d, 2H), 6.96 (d, 2H), 6.96 (d, 2H), 6.93 (dd, 1H), 4.31 (s, 4H), 3.60 (s, 2H), 3.58 (s, 2H), 2.53 (m, 2H), 2.46 (m, 2H), 2.30 (s, 3H), 2.24 (s, 3H), 1.79 (m, 2H) ppm;

4-[[methyl[2-[methyl[[4-(2-phenylethoxy)phenyl]methyl]amino]ethyl]amino]methyl]benzoic acid; $^1$H NMR (300 MHz, CD$_3$OD) δ 7.94 (d, 2H), 7.35 (d, 2H), 7.32-7.24 (m, 4H), 7.29 (d, 2H), 7.19 (m, 1H), 6.93 (d, 2H), 4.17 (t, 2H), 3.90 (s, 2H), 3.67 (s, 2H), 3.05 (t, 2H), 2.96 (m, 2H), 2.76 (m, 2H), 2.50 (s, 3H), 2.29 (s, 3H) ppm;

4-[[methyl[3-[methyl[[4-(2-phenylethoxy)phenyl]methyl]amino]propyl]amino]methyl]benzoic acid; $^1$H NMR (300 MHz, CD$_3$OD) δ 7.94 (d, 2H), 7.32-7.22 (m, 4H), 7.28 (d, 2H), 7.26 (d, 2H), 7.17 (m, 1H), 6.88 (d, 2H), 4.13 (t, 2H), 3.79 (s, 2H), 3.60 (s, 2H), 3.03 (t, 2H), 2.72 (m, 2H), 2.51 (m, 2H), 2.42 (s, 3H), 2.24 (s, 3H), 1.85 (m, 2H) ppm;

4-[[methyl[2-[methyl[[4-(2-phenoxyethoxy)phenyl]methyl]amino]ethyl]amino]methyl]benzoic acid; $^1$H NMR (300 MHz, CD$_3$OD) δ 7.92 (d, 2H), 7.30 (d, 2H), 7.27 (dd, 2H), 7.22 (d, 2H), 6.96 (d, 2H), 6.95 (d, 2H), 6.93 (dd, 1H), 4.31 (s, 4H), 3.57 (s, 2H), 3.54 (s, 2H), 2.60 (m, 4H), 2.25 (s, 3H), 2.23 (s, 3H) ppm;

4-[[methyl[3-[methyl[[4-[4-(2-oxazolyl)phenoxy]phenyl]methyl]amino]propyl]amino]methyl]benzoic acid; $^1$H NMR (300 MHz, CD$_3$OD) δ 7.99 (d, 2H), 7.94 (d, 2H), 7.94 (d, 1H), 7.37 (d, 2H), 7.32 (d, 2H), 7.26 (d, 1H), 7.08 (d, 2H), 7.05 (d, 2H), 3.72 (s, 4H), 2.64 (m, 2H), 2.62 (m, 2H), 2.36 (s, 3H), 2.35 (s, 3H), 1.86 (m, 2H) ppm;

4-[[[4-[[(4-phenoxyphenyl)methyl]amino]cyclohexyl]amino]methyl]benzoic acid;

4-[[methyl[2,2-dimethyl-3-[[[4-[4-(2-oxazolyl)phenoxy]phenyl]methyl]amino]propyl]amino]methyl]-benzoic acid; $^1$H NMR (300 MHz, CD$_3$OD) δ 8.00 (d, 2H), 7.95 (d, 1H), 7.89 (d, 2H), 7.36 (d, 2H), 7.21 (d, 2H), 7.27 (d, 1H), 7.10 (d, 2H), 7.03 (d, 2H), 4.09 (s, 2H), 3.68 (s, 2H), 3.01 (s, 2H), 2.72 (s, 2H), 2.30 (s, 3H), 1.07 (s, 6H) ppm;

4-[[methyl[2,2-dimethyl-3-[methyl[[4-(2-phenoxyethoxy)phenyl]methyl]amino]propyl]amino]methyl]-benzoic acid; $^1$H NMR (300 MHz, CD$_3$OD) δ 7.95 (d, 2H), 7.25 (m, 7H), 6.96 (d, 2H), 6.94 (d, 2H), 4.30 (s, 4H), 3.90 (s, 2H), 3.74 (s, 2H), 2.84 (s, 2H), 2.63 (s, 2H), 2.56 (s, 3H), 2.36 (s, 3H), 1.02 (s, 6H) ppm;

4-[[methyl[2,2-dimethyl-3-[methyl[[4-[4-(2-oxazolyl)phenoxy]phenyl]methyl]amino]propyl]amino]-methyl]benzoic acid; $^1$H NMR (300 MHz, CD$_3$OD) δ 7.99 (d, 2H), 7.96 (d, 2H), 7.95 (d, 1H), 7.37 (d, 2H), 7.32 (d, 2H), 7.26 (d, 1H), 7.08 (d, 2H), 7.04 (d, 2H), 3.80 (s, 2H), 3.83 (s, 2H), 2.71 (s, 2H), 2.66 (s, 2H), 2.48 (s, 3H), 2.41 (s, 3H), 1.02 (s, 6H) ppm;

4-[[methyl[2,2-dimethyl-3-[methyl[[4-(2-phenylethoxy)phenyl]methyl]amino]propyl]amino]methyl]-benzoic acid; $^1$H NMR (300 MHz, CD$_3$OD) δ 7.96 (d, 2H), 7.26 (m, 8H), 7.18 (m, 1H), 6.90 (d, 2H), 4.18 (t, 2H), 3.96 (s, 2H), 3.74 (s, 2H), 3.06 (t, 2H), 2.91 (s, 2H), 2.64 (s, 2H), 2.62 (s, 3H), 2.36 (s, 3H), 1.03 (s, 6H) ppm;

N-[2-[[[4-(phenylmethoxy)phenyl]methyl]amino]ethyl]-4-(1H-imidazol-1-yl)benzamide;

4-[[[[4-(4-bromophenoxy)phenyl]methyl][2-(1-pyrrolidinyl)ethyl]amino]methyl]benzoic acid; $^1$H NMR (400 MHz, DMSO-d$_6$) δ 7.96 (d, 2H), 7.59 (m, 4H), 7.45 (d, 2H), 7.17 (d, 2H), 6.92 (d, 2H), 3.72 (m, 4H), 3.61 (sbr, 2H), 3.37 (t, 2H), 3.21 (sbr, 2H), 2.72 (m, 2H), 1.86 (sbr, 4H) ppm;

1,1-dimethylethyl (2-aminoethyl)[(4-phenoxyphenyl)methyl]carbamate; $^1$H NMR (400 MHz, DMSO-d$_6$) δ 7.38/7.34 (m, 2H), 7.22 (d, 2H), 7.12/7.09 (m, 1H), 6.98/6.95 (m, 4H), 4.35 (s, 2H), 3.15/3.05 (m, 2H), 2.60 (t, 2H), 1.96 (br s), 1.39/1.36 (m, 9H) ppm;

N-[(4-phenoxyphenyl)methyl]-1,2-ethanediamine; $^1$H NMR (400 MHz, DMSO-d$_6$) δ 8.99 (br s, 1H), 7.96 (br s, 2H), 7.50 (d, 2H), 7.42 (t, 2H), 7.18 (t, 1H), 7.08 (d, 2H), 7.01 (d, 2H), 4.19 (s, 2H), 3.13 (d, 4H) ppm;

N-[5-[(4-phenoxyphenyl)methyl]pentyl]-4-(2H-tetrazol-5-yl)benzamide; $^1$H NMR (400 MHz, DMSO-d$_6$) δ 8.70 (br s, 1H), 8.63 (t, 1H), 8.12 (d, 2H), 8.03 (d, 2H), 7.48 (d, 2H), 7.41 (t, 2H), 7.17 (t, 1H), 7.06 (d, 2H), 7.01 (d, 2H), 4.12 (br s, 2H), 3.29 (q, 2H), 2.91 (br s, 2H), 1.65 (m, 2H), 1.56 (m, 2H), 1.37 (m, 2H) ppm;

N-[3-[[(4-phenoxyphenyl)methyl]propyl]-4-(2H-tetrazol-5-yl)benzamide; $^1$H NMR (400 MHz, DMSO-d$_6$) δ 8.81 (t, 1H), 8.73 (br s, 1H), 8.14 (d, 2H), 8.04 (d, 2H), 7.49 (d, 2H), 7.40 (t, 2H), 7.16 (t, 1H), 7.05 (d, 2H), 7.00, (d, 2H), 4.15 (br s, 2H), 3.37 (q, 2H), 2.99 (br s, 2H), 1.90 (m, 2H) ppm;

methyl 4-[[[2-(4-morpholinyl)ethyl][(4-phenoxyphenyl)methyl]amino]methyl]benzoate;

4-[[[2-(4-morpholinyl)ethyl][(4-phenoxyphenyl)methyl]amino]methyl]benzoic acid;

N-[[4-(phenylmethoxy)phenyl]methyl]-1,2-ethanediamine; $^1$H NMR (400 MHz, DMSO-d$_6$) δ 7.38 (m, 4H), 7.28 (m, 1H), 7.22 (m, 2H), 6.92 (m, 2H), 5.05 (s, 2H), 2.65 (t, 2H), 2.53 (t, 2H), 2.48 (t, 2H) ppm;

N-[[4-[(4-methylphenyl)methoxy]phenyl]methyl]-1,2-ethanediamine; $^1$H NMR (400 MHz, DMSO-d$_6$) δ 7.32 (d, 2H), 7.15 (m, 4H), 6.90 (d, 2H), 5.00 (s, 2H), 2.55 (m, 2H), 2.46 (m, 2H), 2.43 (m, 2H), 2.28 (s, 3H) ppm;

N-[[4-(2-naphthalenylmethoxy)phenyl]methyl]-1,2-ethanediamine; $^1$H NMR (400 MHz, DMSO-d$_6$) δ 7.92 (m, 4H), 7.52 (m, 5H), 7.18 (d, 2H), 5.28 (s, 2H), 4.12 (s, 2H), 3.16 (m, 4H) ppm;

(S)-4-methyl-N-[[4-(phenylmethoxy)phenyl]methyl]-1,2-pentanediamine; $^1$H NMR (400 MHz, DMSO-d$_6$) δ 7.2 (m, 10H), 5.07 (s, 2H), 3.65 (m, 2H), 3.56 (m, 1H), 3.11 (m, 1H), 1.63 (m, 2H), 1.32 (m, 1H), 0.93 (M, 6H) (400 MHz, DMSO-d$_6$) δ 7.2 (m, 10H), 5.07 (s, 2H), 3.65 (m, 2H), 3.56 (m, 1H), 3.11 (m, 1H), 1.63 (m, 2H), 1.32 (m, 1H), 0.93 (M, 6H) ppm;

N-methyl-N'-[[4-(phenylmethoxy)phenyl]methyl]-1,2-ethanediamine; $^1$H NMR (400 MHz, DMSO-d$_6$) δ 7.38 (m, 4H), 7.28 (m, 1H), 7.22 (m, 2H), 6.92 (m, 2H), 5.05 (s, 2H), 3.6 (s, 2H), 2.58 (m, 4H), 2.26 (s, 3H) ppm;

3-[[methyl[2-[methyl[[4-(phenylmethoxy)phenyl]methyl]amino]ethyl]amino]methyl]benzoic acid; $^1$H NMR (300 MHz, CD$_3$OD) δ 7.99 (s, 1H), 7.94 (d, 1H), 7.47 (d, 1H), 7.40 (d, 2H), 7.39 (dd, 1H), 7.37 (d, 2H), 7.34 (dd, 2H), 7.28 (dd, 1H), 7.03 (d, 2H), 5.07 (s, 2H), 4.02 (s, 2H), 3.72 (s, 2H), 3.08 (t, 2H), 2.84 (t, 2H), 2.59 (s, 3H), 2.29 (s, 3H) ppm;

4-(1H-imidazol-1-yl)-N-[2-[[(4-phenoxyphenyl)methyl]amino]ethyl]benzamide; $^1$H NMR (400 MHz, DMSO-d$_6$) δ 9.50 (s, 1H), 8.89 (t, 2H), 8.27 (s, 1H), 8.07 (d, 2H), 7.93 (d, 2H), 7.79 (s, 1H), 7.52 (d, 2H), 7.41 (t, 2H), 7.18 (t, 1H), 7.07 (d, 2H), 7.02 (d, 2H), 4.20 (br s, 2H), 3.62 (q, 2H), 3.14 (br s, 2H) ppm;

4-fluoro-N-[2-[[(4-phenoxyphenyl)methyl]amino]ethyl]benzamide; $^1$H NMR (400 MHz, DMSO-d$_6$) δ 8.82 (br s, 1H), 8.69 (t, 1H), 7.92 (m, 2H), 7.51 (d, 2H), 7.41 (t, 2H), 7.32 (t, 2H), 7.18 (t, 1H), 7.06 (d, 2H), 7.01 (d, 2H), 4.19 (br s, 2H), 3.56 (q, 2H), 3.11 (br s, 2H) ppm;

4-cyano-N-[2-[[(4-phenoxyphenyl)methyl]amino]ethyl]benzamide; $^1$H NMR (400 MHz, DMSO-d) δ 8.89 (t, 1H), 8.80 (br s, 1H), 8.00 (s, 4H), 7.51 (d, 2H), 7.41 (t, 2H), 7.18 (t, 1H), 7.06 (d, 2H), 7.01 (d, 2H), 4.19 (br s, 2H), 3.60 (q, 2H), 3.13 (br s, 2H) ppm;

4-[[[2-[[(4-phenoxyphenyl)methyl]amino]ethyl]amino]carbonyl]benzoic acid; $^1$H NMR (400 MHz, DMSO-d$_6$) δ 8.81 (t, 2H), 8.04 (d, 2H), 7.95 (d, 2H), 7.51 (d, 2H), 7.41 (t, 2H), 7.18 (t, 1H), 7.06 (d, 2H), 7.02 (d, 2H), 4.19 (s, 2H), 3.60 (q, 2H), 3.13 (bm, 2H) ppm;

4-(4-methyl-1H-imidazol-1-yl)-N-[2-[[(4-phenoxyphenyl)methyl]amino]ethyl]benzamide; NMR obtained on mixture: Major isomer $^1$H NMR (400 MHz, DMSO-d$_6$) δ 9.47 (s, 1H), 8.92 (bm, 1H), 8.85 (t, 1H), 8.07 (t, 2H), 7.88 (d, 2H), 7.78 (d, 1H), 7.52 (d, 2H), 7.41 (t, 2H), 7.18 (t, 1H), 7.07 (d, 2H), 7.02 (d, 2H), 4.20 (br s, 2H), 3.62 (q, 2H), 3.14 (br s, 2H), 2.33 (d, 3H); Minor isomer: $^1$H NMR (400 MHz, DMSO-d$_6$) δ 9.30 (s, 1H), 8.92 (bm, 1H), 8.85 (t, 1H), 8.07 (t, 2H), 8.02 (br s, 2H), 7.62 (br s, 1H), 7.52 (d, 2H), 7.41 (t, 2H), 7.18 (t, 1H), 7.07 (d, 2H), 7.02 (d, 2H), 4.20 (br s, 2H), 3.62 (q, 2H), 3.14 (br s, 2H), 2.20 (d, 3H) ppm;

4-(2-methyl-1H-imidazol-1-yl)-N-[2-[[(4-phenoxyphenyl)methyl]amino]ethyl]benzamide; $^1$H NMR (400 MHz, DMSO-d$_6$) δ 8.90 (t, 2H), 8.08 (d, 2H), 7.92 (d, 1H), 7.80 (d, 1H), 7.76 (d, 1H), 7.52 (d, 2H), 7.41 (t, 2H), 7.18 (t, 1H), 7.07 (d, 2H), 7.02 (d, 2H), 4.21 (br s, 2H), 3.62 (q, 2H), 3.14 (br s, 2H), 2.53 (s, 3H) ppm;

N-[2-[[(4-phenoxyphenyl)methyl]amino]ethyl]-4-(2H-tetrazol-5-yl)benzamide; $^1$H NMR (400 MHz, DMSO-d$_6$) δ 8.83 (t, 2H), 8.16 (d, 2H), 8.06 (d, 2H), 7.52 (d, 2H), 7.41 (t, 2H), 7.18 (t, 1H), 7.07 (d, 2H), 7.02 (d, 2H), 4.20 (br s, 2H), 3.62 (q, 2H), 3.14 (br s, 2H) ppm; and N-[2-[[(4-phenoxyphenyl)methyl]amino]ethyl]-3-(2H-tetrazol-5-yl)benzamide; $^1$H NMR 400 MHz, DMSO-d$_6$): δ 8.89 (t, 1H), 8.81 (br s, 1H), 8.58 (t, 1H), 8.19 (d, 1H), 8.04 (d, 1H), 7.74 (t, 1H), 7.52 (d, 2H), 7.41 (t, 2H), 7.17 (t, 1H), 7.07 (d, 2H), 7.01 (d, 2H), 4.20 (br s, 2H), 3.63 (q, 2H), 3.15 (br s, 2H) ppm;

4-[[4-[[4-(phenylmethoxy)phenyl]methyl]-1-piperazinyl]methyl]benzoic acid; $^1$H NMR (300 MHz, CD$_3$OD) δ 7.90 (d, 2H), 7.43 (d, 2H), 7.36 (dd, 2H), 7.32 (d, 2H), 7.30 (dd, 1H), 7.23 (d, 2H), 6.94 (d, 2H), 5.07 (s, 2H), 3.55 (s, 2H), 3.47 (s, 2H), 2.50 (m, 8H) ppm;

4-[[4-[[4-(2-phenoxyethoxy)phenyl]methyl]-1-piperazinyl]methyl]benzoic acid; $^1$H NMR (300 MHz, CD$_3$OD) δ 7.90 (d, 2H), 7.31 (d, 2H), 7.27 (dd, 2H), 7.24 (d, 2H), 6.96 (d, 2H), 6.93 (d, 2H), 6.92 (dd, 1H), 4.31 (s, 4H), 3.55 (s, 2H), 3.47 (s, 2H), 2.50 (m, 8H) ppm;

4-[[4-[[4-(2-phenylethoxy)phenyl]methyl]-1-piperazinyl]methyl]benzoic acid; $^1$H NMR (300 MHz, CD$_3$OD) δ 7.89 (d, 2H), 7.34-7.26 (m, 4H), 7.31 (d, 2H), 7.20 (d, 2H), 7.20 (m, 1H), 6.86 (d, 2H), 4.17 (t, 2H), 3.54 (s, 2H), 3.45 (s, 2H), 3.05 (t, 2H), 2.49 (m, 8H) ppm;

4-[[4-[[4-[4-(2-oxazotyl)phenoxy]phenyl]methyl]-1-piperazinyl]methyl]benzoic acid; $^1$H NMR (300 MHz, CD$_3$OD) δ 7.99 (d, 2H), 7.96 (d, 2H), 7.95 (d, 1H), 7.40 (d, 2H), 7.39 (d, 2H), 7.26 (d, 1H), 7.07 (d, 2H), 7.05 (d, 2H), 3.71 (s, 4H), 2.70 (m, 8H) ppm;

N-[2-[[4-[[4-(phenylmethoxy)phenyl]methyl]-1-piperazinyl]methyl]phenyl]-2-thiophenecarboxamide; $^1$H NMR (300 MHz, CDCl$_3$) δ 11.18 (s, 1H), 8.36 (d, 1H), 7.70 (dd, 1H), 7.52 (dd, 1H), 7.44 (d, 2H), 7.39 (dd, 2H), 7.33 (dd, 2H), 7.23 (d, 2H), 7.13 (d, 1H), 7.12 (dd, 1H), 7.03 (dd, 1H), 6.94 (d, 2H), 5.05 (s, 2H), 3.64 (s, 2H), 3.51 (s, 2H), 2.56 (m, 8H) ppm;

N-(2-hydroxyethyl)-N'-[2-[[4-[[4-(phenylmethoxy)phenyl]methyl]-1-piperazinyl]methyl]phenyl]urea; $^1$H NMR (300 MHz, CDCl$_3$) δ 9.63 (s, 1H), 7.90 (d, 1H), 7.43 (d, 2H), 7.38 (dd, 2H), 7.32 (dd, 2H), 7.26 (dd, 1H), 7.21 (d, 2H), 7.06 (d, 1H), 6.94 (dd, 1H), 6.93 (d, 2H), 5.05 (s, 2H), 4.92 (t, 1H), 3.77 (t, 2H), 3.55 (s, 2H), 3.47 (s, 2H), 3.44 (dt, 2H), 2.47 (m, 8H) ppm;

(S)-2-amino-N-[3-[[4-[[4-(phenylmethoxy)phenyl]methyl]-1-piperazinyl]methyl]phenyl]propanamide; $^1$H NMR (300 MHz, CDCl$_3$) δ 9.45 (s, 1H), 7.59 (d, 1H), 7.46 (s, 1H), 7.43 (d, 2H), 7.38 (dd, 2H), 7.32 (dd, 1H), 7.26 (dd, 1H), 7.21 (d, 2H), 7.04 (d, 1H), 6.92 (d, 2H), 5.05 (s, 2H), 3.61 (q, 1H), 3.49 (s, 2H), 3.46 (s, 2H), 2.48 (m, 8H), 1.43 (d, 3H) ppm;

3-amino-N-[3-[[4-[[4-(phenylmethoxy)phenyl]methyl]-1-piperazinyl]methyl]phenyl]propanamide; $^1$H NMR (300 MHz, CDCl$_3$) δ 9.84 (s, 1H), 7.47 (d, 1H), 7.44 (s, 1H), 7.42 (d, 2H), 7.37 (dd, 2H), 7.31 (dd, 1H), 7.22 (dd, 1H), 7.20 (d, 2H), 7.01 (d, 1H), 6.91 (d, 2H), 5.04 (s, 2H), 3.47 (s, 2H), 3.45 (s, 2H), 3.10 (m, 2H), 2.48 (m, 10H) ppm;

(S)-4-amino-5-oxo-5-[4-[[4-(phenylmethoxy)phenyl]methyl]-1-piperazinyl]pentanoic acid; $^1$H NMR (300 MHz, CD$_3$OD) δ 7.43 (d, 2H), 7.37 (dd, 2H), 7.30 (dd, 1H), 7.25 (d, 2H), 6.96 (d, 2H), 5.08 (s, 2H), 4.31 (dd, 1H), 3.67-3.54 (m, 4H), 3.51 (s, 2H), 2.50 (m, 2H), 2.46 (m, 2H), 2.40 (m, 2H), 2.00 (m, 1H), 1.89 (m, 1H) ppm;

δ-oxo-4-[[4-(phenylmethoxy)phenyl]methyl]-1-piperazinebutanesulfonamide; $^1$H NMR (300 MHz, CDCl$_3$) δ 7.43 (d, 2H), 7.38 (dd, 2H), 7.32 (dd, 1H), 7.21 (d, 2H), 6.93 (d, 2H), 5.36 (s, 2H), 5.05 (s, 2H), 3.59 (m, 2H), 3.45 (s, 2H), 3.44 (m, 2H), 3.20 (t, 2H), 2.50 (t, 2H), 2.41 (m, 2H), 2.39 (m, 2H), 2.18 (m, 2H) ppm;

3-[[4-[[4-(phenylmethoxy)phenyl]methyl]-1-piperazinyl]methyl]benzoic acid; $^1$H NMR (300 MHz, CD$_3$OD) δ 7.90 (s, 1H), 7.86 (d, 1H), 7.42 (d, 2H), 7.37 (d, 1H), 7.36 (dd, 2H), 7.31 (dd, 1H), 7.29 (dd, 1H), 7.24 (d, 2H), 6.96 (d, 2H), 5.07 (s, 2H), 3.60 (s, 2H), 3.53 (s, 2H), 2.56 (m, 8H) ppm;

4-[[4-[methyl[(4-phenoxyphenyl)methyl]amino]-1-piperidinyl]methyl]benzoic acid; $^1$H NMR (300 MHz, CD$_3$OD) δ 7.93 (d, 2H), 7.35 (d, 2H), 7.34 (dd, 2H), 7.33 (d, 2H), 7.11 (dd, 1H), 6.97 (d, 2H), 6.94 (d, 2H), 3.70 (s, 2H), 3.63 (s, 2H), 3.05 (d, 2H), 2.63 (m, 1H), 2.29 (s, 3H), 2.13 (dd, 2H), 1.91 (d, 2H), 1.74 (dddd, 2H) ppm;

4-[[4-[methyl[2-[4-(phenylmethyl)phenoxy]ethyl]amino]-1-piperidinyl]methyl]benzoic acid; $^1$H NMR (300 MHz, CD$_3$OD) δ 7.93 (d, 2H), 7.33 (d, 2H), 7.23 (dd, 2H), 7.15 (d, 2H), 7.13 (dd, 2H), 7.08 (d, 2H), 6.83 (d, 2H), 4.05 (t, 2H), 3.87 (s, 2H), 3.56 (s, 2H), 2.99 (d, 2H), 2.92 (t, 2H), 2.56 (m, 1H), 2.40 (s, 3H), 2.07 (dd, 2H), 1.84 (d, 2H), 1.61 (dddd, 2H) ppm;

4-[[4-[[[4-(4-bromophenoxy)phenyl]methyl]amino]-1-piperidinyl]methyl]benzoic acid; $^1$H NMR (400 MHz, DMSO-d$_6$) δ 9.15 (br, 1H), 8.06 (dbr, 2H), 7.62 (m, 3H), 7.57 (d, 2H), 7.16 (d, 2H), 7.02 (d, 2H), 4.38 (sbr, 1H), 4.22 (sbr, 2H), 3.41 (br, 4H), 3.07 (sbr, 2H), 2.15 (sbr, 2H), 1.83 (sbr, 2H) ppm;

4-[[4-[[[4-(4-bromophenoxy)phenyl]methyl]methylamino]-1-piperidinyl]methyl]benzoic acid; $^1$H NMR (400 MHz, DMSO-d$_6$) δ 8.01 (d, 2H), 7.60 (d, 2H), 7.57 (dd, 2H), 7.52 (d, 2H), 7.08 (d, 2H), 6.99 (dt, 2H), 4.37 (br, 2H), 4.21 (br, 1H), 3.44 (m, 4H), 2.98 (br, 2H), 2.58 (s, 3H), 2.22 (m, 2H), 2.01 (br, 2H) ppm;

4-[[(RS)-2-[[[[4-(4-bromophenoxy)phenyl]methyl]methylamino]methyl]-1-piperidinyl]methyl]benzoic acid; $^1$H NMR (400 MHz, DMSO-d$_6$) δ 7.98 (d, 2H), 7.60 (d, 2H), 7.58 (d, 2H), 7.43 (d, 2H), 7.08 (d, 2H), 6.92 (d, 2H), 4.46 (dbr, 2H), 4.21 (dbr, 2H), 3.44 (m, 4H), 2.98 (m, 3H), 2.52 (s, 3H), 1.98 (m, 1H), 1.62 (m, 5H) ppm;

4-[[4-[[[4-(4-bromophenoxy)phenyl]methyl][(methylamino)carbonyl]amino]-1-piperidinyl]methyl]benzoic acid; $^1$H NMR (400 MHz, CD$_3$OD) δ 8.05 (d, 2H), 7.60 (d, 2H), 7.45 (d, 2H), 7.22 (d, 2H), 6.98 (d, 2H), 6.82 (d, 2H), 4.43 (s, 2H), 4.35 (s, 2H), 4.24 (t, 1H), 3.46 (d, 2H), 3.11 (t, 2H), 2.70 (s, 3H), 2.03 (qbr, 2H), 1.88 (d, 2H) ppm;

4-[[4-[(4-phenoxyphenyl)amino]-1-piperidinyl]methyl]benzoic acid; $^1$H NMR (400 MHz, DMSO-d$_6$) δ 9.78 (sbr, 1H), 8.01 (d, 2H), 7.62 (d, 2H), 7.24 (t, 2H), 6.99 (t, 1H), 6.82 (m, 4H), 6.63 (d, 2H), 4.36 (s, 2H), 6.63 (d, 2H), 4.36 (s, 2H), 3.41 (dbr, 2H), 3.23 (sbr, 1H), 3.08 (sbr, 2H), 2.14 (dbr, 2H), 1.53 (qbr, 2H) ppm;

4-[[4-[methyl(4-phenoxyphenyl)amino]-1-piperidinyl]methyl]benzoic acid;

4-[[4-[[4-(4-chlorophenoxy)phenyl]amino]-1-piperidinyl]methyl]benzoic acid; $^1$H NMR (400 MHz, DMSO-d$_6$) δ 10.04 (sbr, 1H), 8.01 (d, 2H), 7.60 (d, 2H), 7.39 (d, 2H), 7.23 (sbr, 2H), 7.13 (d, 2H), 6.96 (d, 2H), 4.34 (s, 2H), 3.57 (tbr, 1H), 3.44 (dbr, 2H), 2.98 (tbr, 2H), 2.09 (dbr, 2H), 1.81 (qbr, 2H) ppm;

4-[[4-[[4-(2-phenylethoxy)phenyl]amino]-1-piperidinyl]methyl]benzoic acid; $^1$H NMR (400 MHz, DMSO-d$_6$) δ 11.0 (s, 1H), 8.00 (m, 2H), 7.70 (m, 2H), 7.30 (m, 4H), 7.20 (m, 1H), 6.80 (m, 4H), 4.30 (m, 2H), 4.10 (m, 2H), 3.40 (m, 5H), 2.95 (m, 3H), 2.05 (m, 2H), 1.85 (m, 2H) ppm;

4-[[4-[[(4-phenoxyphenyl)methyl]amino]-1-piperidinyl]methyl]benzoic acid; $^1$H NMR (300 MHz, Pyridine-d$_5$) δ 8.47 (d, 2H), 7.55 (d, 2H), 7.49 (d, 2H), 7.35 (dd, 2H), 7.20 (dd, 1H), 7.12 (d, 2H), 7.12 (d, 2H), 3.85 (s, 2H), 3.50 (s, 2H), 2.83 (d, 2H), 2.57 (m, 1H), 2.00 (dd, 2H), 1.91 (d, 2H), 1.56 (dddd, 2H) ppm;

4-[[(S)-3-[[methyl[(4-phenoxyphenyl)methyl]amino]methyl]-1-pyrrolidinyl]methyl]benzoic acid; $^1$H NMR (300 MHz, CD$_3$OD) δ 7.93 (d, 2H), 7.35 (d, 2H), 7.33 (dd, 2H), 7.27 (d, 2H), 7.09 (dd, 1H), 6.96 (d, 2H), 6.92 (d, 2H), 3.73 (d, 1H), 3.71 (d, 1H), 3.49 (d, 1H), 3.45 (d, 1H), 2.90 (dd, 1H), 2.73 (m, 1H), 2.59 (m, 1H), 2.50 (m, 1H), 2.37 (m, 2H), 2.33 (m, 1H), 2.20 (s, 3H), 2.02 (m, 1H), 1.49 (m, 1H) ppm;

4-[[(R)-3-[[methyl[(4-phenoxyphenyl)methyl]amino]methyl]-1-pyrrolidinyl]methyl]benzoic acid;

4-[[(3-exo)-3-[[[4-(4-bromophenoxy)phenyl]methyl]methylamino]-8-azabicyclo[3.2.1]oct-8-yl]methyl]benzoic acid; $^1$H NMR (400 MHz, CD$_3$OD) δ 8.12 (d, 2H), 7.61 (d, 2H), 7.53 (d, 2H), 7.43 (d, 2H), 7.03 (d, 2H), 6.95 (d, 2H), 4.22 (s, 2H), 4.15 (sbr, 2H), 3.96 (sbr, 2H), 2.64/2.43 (mbr, 8H), 2.34/2.22 (mbr, 4H) ppm;

4-[[4-[[(methylamino)carbonyl][2-(4-phenoxyphenyl)ethyl]amino]-1-piperidinyl]methyl]benzoic acid; $^1$H NMR (400 MHz, CD$_3$OD) δ 8.15 (d, 2H), 7.63 (d, 2H), 7.31 (t, 2H), 7.23 (d, 2H), 7.09 (t, 1H), 6.91 (d, 4H), 4.38 (s, 2H), 4.07 (tt, 2H), 3.50 (dbr, 2H), 3.64 (dbr, 2H), 3.11 (t, 2H), 2.82 (t, 2H), 2.74 (s, 3H), 2.12 (dq, 2H), 1.80 (dbr, 4H) ppm;

4-[[4-[acetyl[2-[4-(4-bromophenoxy)phenyl]ethyl]amino]-1-piperidinyl]methyl]benzoic acid; $^1$H NMR (400 MHz, DMSO-d$_6$) δ 7.98 (dt, 2H), 7.59 (t, 2H), 7.46 (t, 2H), 7.21 (dd, 2H), 6.97 (dd, 2H), 6.92 (dd, 2H), 4.39 (m, 4H), 4.04 (m, 1H), 3.37 (m, 2H), 3.12 (m, 2H), 1.98 (s, 3H), 1.94 (m, 2H), 1.75 (m, 2H) ppm;

4-[[(RS)-3-[methyl[2-(4-phenoxyphenoxy)ethyl]amino]-1-pyrrolidinyl]methyl]benzoic acid; $^1$H NMR (400 MHz, DMSO-d$_6$) δ 7.97 (d, 2H), 7.56 (dbr, 2H), 7.33 (t, 2H), 7.06 (t, 1H), 6.98 (m, 4H), 6.89 (d, 2H), 4.23 (sbr, 4H), 4.20/3.00 (mbr, 7H), 2.79 (s, 3H), 2.20/2.00 (mbr, 2H) ppm;

methyl 4-[[4-[[4-(4-chlorophenoxy)phenyl]amino]-1-piperidinyl]methyl]benzoate;

4-[[4-[[4-(4-chlorophenoxy)phenyl]amino]-1-piperidinyl]methyl]-N-(2-hydroxyethyl)benzamide; $^1$H NMR (400 MHz, DMSO-d$_6$) δ 8.37 (t, 1H), 7.79 (d, 2H), 7.36 (d, 2H), 7.29 (d, 2H), 6.81 (dd, 4H), 6.56 (d, 2H), 5.41 (d, 1H), 4.69 (t, 1H), 3.49 (m, 4H), 3.32 (m, 2H), 3.14 (sbr, 1H), 2.74 (dbr, 2H), 2.06 (tbr, 2H), 1.84 (dbr, 2H), 1.37 (tbr, 2H) ppm;

N-[4-(4-chlorophenoxy)phenyl]-4-piperidinamine;

4-[[4-[[4-(4-chlorophenoxy)phenyl]amino]-1-piperidinyl]methyl]-N-[2-(dimethylamino)ethyl]benzamide; ¹H NMR (400 MHz, DMSO-d₆) δ 0.08 (s, 1H), 9.64 (s, 1H), 8.80 (t, 1H), 7.94 (d, 2H), 7.61 (d, 2H), 7.32 (d, 2H), 6.83 (d, 4H), 6.82 (d, 2H), 4.34 (s, 2H), 3.61 (q, 2H), 3.38 (dbr, 2H), 3.27 (m, 3H), 3.06 (m, 2H), 2.82 (s, 6H), 2.11 (dbr, 2H), 1.54 (qbr, 2H) ppm;

4-[3-[4-[[4-(4-chlorophenoxy)phenyl]amino]-1-piperidinyl]propyl]benzoic acid; ¹H NMR (400 MHz, DMSO-d₆) δ 7.86 (d, 2H), 7.38 (m, 4H), 6.83 (m, 4H), 6.62 (m, 2H), 3.52 (dbr, 2H), 3.39 (m, 1H), 3.08 (m, 4H), 2.71 (m, 2H), 2.11 (dbr, 2H), 1.96 (m, 2H), 1.56 (qbr, 2H) ppm;

4-[[(3-exo)-3-[[4-(4-chlorophenoxy)phenyl]amino]-8-azabicyclo[3.2.1]oct-8-yl]methyl]benzoic acid; ¹H NMR (400 MHz, DMSO-d₆) δ 9.61 (sbr, 1H), 7.98 (d, 2H), 7.69 (d, 2H), 7.36 (d, 2H), 6.84 (m, 4H), 6.58 (d, 2H), 5.79 (sbr, 1H), 4.26 (d, 1H), 3.81 (sbr, 2H), 3.46 (t, 1H), 2.39 (m, 2H), 2.31 (m, 2H), 1.98 (m, 2H) ppm; and 4-[2-[4-[[4-[4-(2-oxazolyl)phenoxy]phenyl]amino]-1-piperidinyl]ethyl]benzoic acid; ¹H NMR (400 MHz, DMSO-d₆, 120° C.) δ 7.92 (m, 5H), 7.39 (d, 2H), 7.22 (s, 1H), 7.04 (d, 2H), 6.93 (m, 4H), 3.61 (m, 3H), 3.39 (m, 2H), 3.24 (m, 2H), 3.14 (m, 2H), 2.18 (dbr, 2H), 1.84 (qbr, 2H) ppm;

4-[[[1-[(4-phenoxyphenyl)methyl]piperidin-4-yl]amino]methyl]benzoic acid; ¹H NMR (300 MHz, CD₃OD) δ 7.96 (d, 2H), 7.45 (d, 2H), 7.35 (dd, 2H), 7.33 (d, 2H), 7.12 (dd, 1H), 6.98 (d, 2H), 6.96 (d, 2H), 4.16 (s, 2H), 3.62 (s, 2H), 3.08 (m, 1H), 3.06 (d, 2H), 2.21 (dd, 2H), 2.15 (d, 2H), 1.70 (dddd, 2H) ppm;

4-[[methyl[[(R)-1-[(4-phenoxyphenyl)methyl]-3-pyrrolidinyl]methyl]amino]methyl]benzoic acid;

4-[[methyl[[(S)-1-[(4-phenoxyphenyl)methyl]-3-pyrrolidinyl]methyl]amino]methyl]benzoic acid; ¹H NMR (300 MHz, CD₃OD) δ 7.89 (d, 2H), 7.37 (d, 2H), 7.35 (dd, 2H), 7.28 (d, 2H), 7.12 (dd, 1H), 6.98 (d, 2H), 6.96 (d, 2H), 3.87 (s, 2H), 3.54 (d, 1H), 3.48 (d, 1H), 3.10 (m, 1H), 2.93 (m, 1H), 2.80 (m, 1H), 2.58 (m, 1H), 2.55 (m, 1H), 2.39 (m, 2H), 2.20 (s, 3H), 2.07 (m, 1H), 1.56 (m, 1H) ppm;

4-[[[1-[[4-(4-chlorophenoxy)phenyl]methyl]piperidin-4-yl]amino]methyl]benzoic acid; ¹H NMR (400 MHz, DMSO-d₆) δ 7.82 (d, 2H), 7.44 (m, 2H), 7.4 (m, 2H), 7.28 (m, 2H), 6.94 (m, 4H), 3.88 (s, 2H), 3.42 (s, 2H), 2.78 (m, 2H), 2.48 (m, 1H), 1.92 (m, 4H), 1.42 (m, 2H) ppm;

4-[[[[(RS)-1-[[4-[2-(4-fluorophenyl)ethoxy]phenyl]methyl]-2-piperidinyl]methyl]methylamino]methyl]benzoic acid; ¹H NMR (400 MHz, DMSO-d₆) δ 7.93 (d, 2H), 7.52 (d, 2H), 7.41 (d, 2H), 7.39 (dt, 2H), 7.18 (t, 2H), 7.03 (d, 2H), 4.22 (m, 3H), 3.04 (m, 3H), 2.26 (sbr, 3H), 2.03 (m, 1H), 1.65 (m, 5H) ppm;

4-[[[(3-exo)-8-[[4-(4-bromophenoxy)phenyl]methyl]-8-azabicyclo[3.2.1]oct-3-yl]methylamino]methyl]benzoic acid; ¹H NMR (400 MHz, DMSO-d₆) δ 7.92 (dbr, 2H), 7.58 (m, 4H), 7.39 (dbr, 2H), 7.12 (d, 2H), 7.00 (d, 2H), 4.15 (s, 2H), 3.76 (s, 1H), 3.59 (s, 1H), 2.42/2.20 (mbr, 8H), 2.140/2.00 (mbr, 6H) ppm;

4-[[[1-[[4-(4-bromophenoxy)phenyl]methyl]-4-methyl-4-piperidinyl]methylamino]methyl]benzoic acid; ¹H NMR (400 MHz, DMSO-d₆) δ 8.56 (d, 2H), 8.18 (d, 2H), 8.11 (q, 2H), 8.02 (d, 2H), 7.62 (d, 2H), 7.52 (d, 2H), 5.18 (dbr, 1H), 4.83 (s, 2H), 4.61 (s, 1H), 3.92 (sbr, 2H), 3.74 (sbr, 2H), 3.11 (s, 3H), 2.84 (dbr, 1H), 2.62 (sbr, 3H), 2.09 (s, 3H) ppm;

4-[[[1-[[4-(4-bromophenoxy)phenyl]methyl]-4-piperidinyl]methylamino]methyl]benzoic acid; ¹H NMR (400 MHz, DMSO-d₆) δ 7.86 (d, 2H), 7.56 (d, 2H), 7.38 (d, 2H), 7.29 (d, 2H), 6.95 (q, 4H), 3.60 (s, 2H), 3.44 (s, 2H), 2.84 (d, 2H), 2.38 (t, 1H), 1.91 (sbr, 2H), 1.72 (dbr, 2H), 1.51 (qbr, 2H) ppm;

4-[[[[(R)-1-[[4-(4-bromophenoxy)phenyl]methyl]-2-piperidinyl]methyl]methylamino]methyl]benzoic acid; ¹H NMR (400 MHz, DMSO-d₆) δ 7.84 (d, 2H), 7.50 (d, 2H), 7.36 (d, 2H), 7.25 (d, 2H), 6.95/6.88 (m, 4H), 4.07 (d, 1H), 3.47 (dd, 2H), 3.23 (d, 1H), 2.63/2.49 (m, 2H), 2.29 (dd, 2H), 2.10 (s, 3H), 2.03 (t, 1H), 1.70/1.66 (m, 1H), 1.52/1.24 (m, 6H) ppm;

4-[[methyl[[(R)-1-[[4-[4-(2-oxazolyl)phenoxy]phenyl]methyl]-2-piperidinyl]methyl]amino]methyl]-benzoic acid; ¹H NMR (400 MHz, CD₃OD) δ 8.00 (dt, 2H), 7.96 (d, 1H), 7.91 (d, 2H), 7.43 (d, 2H), 7.35 (d, 2H), 7.27 (d, 1H), 7.11/7.06 (m, 4H), 4.53 (d, 1H), 3.94 (d, 1H), 3.71 (d, 1H), 3.52 (d, 1H), 3.38/3.34 (m, 1H), 3.09 (dd, 1H), 3.03/2.98 (m, 1H), 2.87/2.82 (m, 1H), 2.39 (dd, 1H), 2.28 (s, 3H), 2.02/1.97 (m, 1H), 1.81/1.56 (m, 5H) ppm;

4-[[methyl[[(S)-1-[[4-[4-(2-oxazolyl)phenoxy]phenyl]methyl]-2-piperidinyl]methyl]amino]methyl]-benzoic acid; ¹H NMR (400 MHz, CD₃OD) δ 8.00 (dt, 2H), 7.96 (d, 1H), 7.91 (d, 2H), 7.43 (d, 2H), 7.35 (d, 2H), 7.27 (d, 1H), 7.11/7.06 (m, 4H), 4.53 (d, 1H), 3.94 (d, 1H), 3.71 (d, 1H), 3.52 (d, 1H), 3.38/3.34 (m, 1H), 3.09 (dd, 1H), 3.03/2.98 (m, 1H), 2.87/2.82 (m, 1H), 2.39 (dd, 1H), 2.28 (s, 3H), 2.02/1.97 (m, 1H), 1.81/1.56 (m, 5H) ppm;

4-[[[[(R)-1-[[4-[4-(2-oxazolyl)phenoxy]phenyl]methyl]-2-pyrrolidinyl]methyl]methylamino]methyl]-benzoic acid; ¹H NMR (400 MHz, DMSO-d₆) δ 8.16 (d, 1H), 7.94 (dt, 2H), 7.86 (d, 2H), 7.36 (d, 2H), 7.32 (d, 1H), 7.30 (d, 2H), 7.06 (dt, 2H), 7.01 (d, 2H), 4.11 (d, 1H), 3.50 (s, 2H), 2.35 (d, 1H), 2.76 (t, 1H), 2.65 (t, 1H), 2.49/2.44 (m, 1H), 2.26 (dd, 1H), 2.14 (s, 3H), 2.13/2.06 (m, 1H), 1.92/1.86 (m, 1H), 1.60/1.51 (m, 3H) ppm;

6-[[[1-[[4-(4-chlorophenoxy)phenyl]methyl]-4-piperidinyl]methyl]amino]-3-pyridinecarboxylic acid; ¹H NMR (400 MHz, DMSO-d₆) δ 8.45 (m, 1H), 7.78 (m, 1H), 7.38 (m, 5H), 6.98 (m, 4H), 6.47 (m, 1H), 3.35 (m, 2H), 3.21 (m, 2H), 2.83 (m, 2H), 1.96 (m, 2H), 1.64 (m, 2H), 1.55 (m, 1H), 1.18 (m, 2H) ppm;

1-[(4-phenoxyphenyl)methyl]-4-piperidinemethanamine;

ethyl 1,6-dihydro-6-oxo-2-[[[1-[(4-phenoxyphenyl)methyl]-4-piperidinyl]methyl]amino]-5-pyrimidinecarboxylate; ¹H NMR (400 MHz, DMSO-d₆) δ 8.21 (s, 1H), 7.58 (m, 2H), 7.42 (m, 2H), 7.16 (m, 1H), 7.08 (m, 4H), 4.22 (m, 2H), 4.12 (m, 2H), 3.33 (m, 4H), 2.82 (m, 2H), 1.82 (m, 3H), 1.55 (m, 1H), 1.23 (t, 3H) ppm; and 1,6-dihydro-6-oxo-2-[[[1-[(4-phenoxyphenyl)methyl]-4-piperidinyl]methyl]amino]-5-pyrimidinecarboxylic acid; ¹H NMR (400 MHz, DMSO-d₆) δ 8.24 (m, 1H), 7.58 (m, 2H), 7.42 (m, 2H), 7.16 (m, 1H), 7.08 (m, 4H), 4.22 (m, 2H), 3.83 (m, 2H), 3.33 (m, 2H), 2.82 (m, 2H), 1.82 (m, 3H), 1.55 (m, 1H) ppm.

Synthetic Example 16

Compounds of Formula (I)

A. 4-(2,2,3,3-Tetrafluoropropoxy)benzaldehyde (250 mg, 1.06 mmol) and methyl 4-[[(1S,4S)-2,5-diazabicyclo[2.2.1]hept-2-yl]methyl]benzoate (260.7 mg, 1.06 mmol) were dissolved in dichloromethane (5.9 mL). After 15 min, sodium triacetoxyborohydride (448.7 mg, 2.12 mmol) was added. The reaction mixture was stirred overnight at room temperature. Then, saturated sodium bicarbonate solution was added. The mixture was stirred for 30 min and then extracted with dichloromethane. The combined organic layers were washed with water, dried over sodium sulfate, and concentrated under reduced pressure. Flash chromatography gave 177 mg of methyl 4-[[(1S,4S)-5-[[4-(2,2,3,3-tetrafluoropropoxy)phenyl]methyl]-2,5-diazabicyclo[2.2.1]hept-2-yl]methyl]benzoate; $^1$H NMR (300 MHz, CDCl$_3$) δ 7.98 (d, 2H), 7.43 (d, 2H), 7.31 (d, 2H), 6.87 (d, 2H), 6.07 (tt, 1H), 4.33 (tt, 2H), 3.91 (s, 3H), 3.81 (d, 1H), 3.76 (d, 1H), 3.71 (d, 1H), 3.64 (d, 1H), 3.28 (br s, 2H), 2.84 (d, 2H), 2.65 (dd, 2H), 1.74 (s, 2H) ppm.

B. Methyl 4-[[(1S,4S)-5-[[4-(2,2,3,3-tetrafluoropropoxy)phenyl]methyl]-2,5-diazabicyclo[2.2.1]hept-2-yl]methyl]benzoate (177 mg, 0.38 mmol) was stirred with 1.9 mL aqueous sodium hydroxide solution (2 M) in 3.9 mL methanol overnight at room temperature, and then concentrated under reduced pressure. The residue was diluted with water, adjusted to pH 8 with 1 M aqueous hydrochloric acid, and extracted with butanol. The combined organic layers were concentrated under reduced pressure. Flash chromatography gave 91 mg of 4-[[(1S,4S)-5-[[4-(2,2,3,3-tetrafluoropropoxy)phenyl]methyl]-2,5-diazabicyclo[2.2.1]hept-2-yl]methyl]benzoic acid; $^1$H NMR (300 MHz, CD$_3$OD) δ 7.92 (d, 2H), 7.41 (d, 2H), 7.40 (d, 2H), 7.02 (d, 2H), 6.32 (tt, 1H), 4.45 (ft, 2H), 3.98 (d, 2H), 3.88 (d, 2H), 3.69 (br s, 1H), 3.64 (br s, 1H), 3.17 (d, 1H), 3.12 (d, 1H), 2.90 (dd, 1H), 2.85 (dd, 1H), 2.02 (s, 2H) ppm.

Synthetic Example 17

Compounds of Formula (I)

Following the general procedures described herein and exemplified in Synthetic Example 16, the following compounds, as well as other compounds encompassed within Formula (I), can be synthesized utilizing the appropriate starting materials:

4-[[(1S,4S)-5-[[4-(2,2,3,3,3-Pentafluoropropoxy)phenyl]methyl]-2,5-diazabicyclo[2.2.1]hept-2-yl]methyl]benzoic acid; $^1$H NMR (300 MHz, CD$_3$OD) δ 7.92 (d, 2H), 7.40 (d, 2H), 7.39 (d, 2H), 7.00 (d, 2H), 4.60 (t, 2H), 3.94 (d, 1H), 3.92 (d, 1H), 3.83 (d, 1H), 3.82 (d, 1H), 3.59 (br s, 1H), 3.57 (br s, 1H), 3.11 (d, 1H), 3.08 (d, 1H), 2.83 (dd, 1H), 2.80 (dd, 1H), 1.96 (s, 2H) ppm.

4-[[(1S,4S)-5-[[4-(2,2,3,3,4,4,4-Heptafluorobutoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.36 (d, 2H), 7.35 (d, 2H), 6.98 (d, 2H), 4.62 (tt, 2H), 3.81 (d, 1H), 3.74 (d, 1H), 3.73 (d, 1H), 3.67 (d, 1H), 3.35 (br s, 2H), 2.94 (d, 1H), 2.91 (d, 1H), 2.67 (dd, 2H), 1.80 (s, 2H) ppm.

4-[[(1S,4S)-5-[[4-[(7,7,8,8,8-Pentafluorooctyl)oxy]phenyl]methyl]-2,5-diazabicyclo[2.2.1]hept-2-yl]methyl]benzoic acid; $^1$H NMR (300 MHz, CD$_3$OD) δ 7.91 (d, 2H), 7.36 (d, 2H), 7.27 (d, 2H), 6.86 (d, 2H), 3.96 (t, 2H), 3.80 (d, 1H), 3.73 (d, 1H), 3.71 (d, 1H), 3.64 (d, 1H), 3.34 (br s, 2H), 2.93 (d, 1H), 2.92 (d, 1H), 2.67 (dd, 1H), 2.66 (dd, 1H), 2.12 (m, 2H), 1.79 (s, 2H), 1.78 (m, 2H), 1.69-1.41 (m, 6H) ppm.

4-[[(1S,4S)-5-[[4-(2,2,2-Trifluoroethoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.38 (d, 2H), 7.37 (d, 2H), 6.99 (d, 2H), 4.51 (q, 2H), 3.89 (d, 1H), 3.85 (d, 1H), 3.80 (d, 1H), 3.75 (d, 1H), 3.50 (br s, 1H), 3.49 (br s, 1H), 3.03 (d, 1H), 3.02 (d, 1H), 2.77 (dd, 1H), 2.75 (dd, 1H), 1.90 (s, 2H) ppm.

4-[[(1S,4S)-5-[[4-(Trifluoromethyl)phenyl]methyl]-2,5-diazabicyclo[2.2.1]hept-2-yl]methyl]benzoic acid; $^1$H NMR (300 MHz, CD$_3$OD) δ 7.92 (d, 2H), 7.62 (d, 2H), 7.58 (d, 2H), 7.39 (d, 2H), 3.89 (d, 1H), 3.80 (d, 1H), 3.45 (br s, 1H), 3.40 (br s, 1H), 3.01 (d, 1H), 2.95 (d, 1H), 2.76 (dd, 1H), 2.70 (dd, 1H), 1.87 (s, 2H) ppm.

4-[[(1S,4S)-5-[[4-(Trifluoromethoxy)phenyl]methyl]-2,5-diazabicyclo[2.2.1]hept-2-yl]methyl]benzoic acid; $^1$H NMR (300 MHz, CD$_3$OD) δ 7.92 (d, 2H), 7.49 (d, 2H), 7.40 (d, 2H), 7.23 (d, 2H), 3.94 (d, 1H), 3.86 (d, 2H), 3.77 (d, 1H), 3.54 (br s, 1H), 3.47 (br s, 1H), 3.07 (d, 1H), 3.00 (d, 1H), 2.81 (dd, 1H), 2.74 (dd, 1H), 1.92 (s, 2H) ppm.

4-[[(1S,4S)-5-[[4-(Difluoromethoxy)phenyl]methyl]-2,5-diazabicyclo[2.2.1]hept-2-yl]methyl]benzoic acid; $^1$H NMR (300 MHz, CD$_3$OD) δ 7.92 (d, 2H), 7.42 (d, 2H), 7.39 (d, 2H), 7.10 (d, 2H), 6.79 (t, 1H), 3.87 (d, 1H), 3.82 (d, 1H), 3.78 (d, 1H), 3.73 (d, 1H), 3.44 (br s, 1H), 3.42 (br s, 1H), 3.00 (d, 1H), 2.97 (d, 1H), 2.74 (dd, 1H), 2.71 (dd, 1H), 1.86 (s, 2H) ppm.

4-[[(1S,4S)-5-[[4-(1,1,2,2-Tetrafluoroethoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.45 (d, 2H), 7.37 (d, 2H), 7.19 (d, 2H), 6.29 (t, 1H), 3.82 (d, 1H), 3.80 (d, 1H), 3.75 (d, 1H), 3.73 (d, 1H), 3.37 (br s, 2H), 2.95 (d, 1H), 2.93 (d, 1H), 2.69 (dd, 1H), 2.68 (dd, 1H), 1.82 (s, 2H) ppm.

4-[[(1S,4S)-5-[[4-(2,2,3,4,4,4-Hexafluorobutoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.34 (d, 2H), 6.99 (d, 2H), 5.70 (d, 1H), 4.55-4.34 (m, 2H), 3.81 (d, 1H), 3.74 (d, 1H), 3.73 (d, 1H), 3.66 (d, 1H), 3.35 (br s, 2H), 2.94 (d, 1H), 2.91 (d, 1H), 2.67 (dd, 2H), 1.80 (s, 2H) ppm.

4-[[(1S,4S)-5-[[4-(3,3,4,4,5,5,6,6,6-Nonafluorohexyl)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.35 (d, 2H), 7.24 (d, 2H), 3.85 (d, 1H), 3.80 (d, 1H), 3.76 (d, 1H), 3.72 (d, 1H), 3.40 (br s, 2H), 2.98 (d, 1H), 2.96 (d, 1H), 2.92 (m, 2H), 2.72 (dd, 1H), 2.71 (dd, 1H), 2.45 (m, 2H), 1.84 (s, 2H) ppm.

4-[[(1S,4S)-5-[[4-(3,3,4,4,4-Pentafluorobutyl)phenyl]methyl]-2,5-diazabicyclo[2.2.1]hept-2-yl]methyl]benzoic acid; $^1$H NMR (300 MHz, CD$_3$OD) δ 7.92 (d, 2H), 7.39 (d, 2H), 7.37 (d, 2H), 7.25 (d, 2H), 3.92 (d, 1H), 3.89 (d, 1H), 3.83 (d, 1H), 3.81 (d, 1H), 3.53 (br s, 2H), 3.06 (d, 2H), 2.89 (m, 2H), 2.79 (dd, 1H), 2.78 (dd, 1H), 2.40 (m, 2H), 1.93 (s, 2H) ppm.

4-[[(1S,4S)-5-[[4-(4,4,5,5,5-Pentafluoropentyl)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.30 (d, 2H), 6.90 (d, 2H), 4.05 (t, 2H), 3.83 (d, 1H), 3.75 (d, 1H), 3.68 (d, 1H), 3.39 (br s, 1H), 3.38 (br s, 1H), 2.95 (d, 2H), 2.70 (dd, 1H), 2.68 (dd, 1H), 2.35 (m, 2H), 2.04 (m, 2H), 1.83 (s, 2H) ppm.

4-[[5-[[(1S,4S)-4-(4,4,4-Trifluorobutoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.38 (d, 2H), 7.33 (d, 2H), 6.92 (d, 2H), 4.04 (t, 2H), 3.88 (d, 1H), 3.86 (d, 1H), 3.78 (d, 2H), 3.55 (br s, 1H), 3.49 (br s, 1H), 3.06 (d, 1H), 3.01 (d, 1H), 2.81 (dd, 1H), 2.75 (dd, 1H), 2.36 (m, 2H), 2.01 (m, 2H), 1.92 (s, 2H) ppm.

4-[[(1S,4S)-5-[[4-(3,3,3-Trifluoropropoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.37 (d, 2H), 7.32 (d, 2H), 6.91 (d, 2H), 4.21 (t, 2H), 3.85 (d, 1H), 3.81 (d, 1H), 3.77 (d, 1H), 3.72 (d, 1H), 3.46 (br s, 1H), 3.43 (br s, 1H), 3.00 (d, 1H), 2.99 (d, 1H), 2.75 (dd, 1H), 2.72 (dd, 1H), 2.67 (qt, 1H), 1.87 (s, 2H) ppm.

4-[[(1S,4S)-5-[[4-(1,1,2,3,3,3-Hexafluoropropoxy)phenyl]methyl]-2,5-diazabicyclo[2.2.1]hept-2-yl]methyl]benzoic acid; $^1$H NMR (300 MHz, CD$_3$OD) δ 7.91 (d, 2H), 7.46

(d, 2H), 7.38 (d, 2H), 7.19 (d, 2H), 5.75 (dbr, 2H), 3.85 (d, 1H), 3.81 (d, 1H), 3.79 (d, 1H), 3.74 (d, 1H), 3.41 (br s, 1H), 3.39 (br s, 1H), 2.98 (d, 1H), 2.95 (d, 1H), 2.72 (dd, 1H), 2.69 (dd, 1H), 1.84 (s, 2H) ppm.

Methyl 4-[[(1S,4S)-5-[[4-(3,3,4,4,4-pentafluorobutyl)phenyl]methyl]-2,5-diazabicyclo[2.2.1]hept-2-yl]methyl]benzoate; $^1$H NMR (300 MHz, CDCl$_3$) δ 7.98 (d, 2H), 7.44 (d, 2H), 7.32 (d, 2H), 7.15 (d, 2H), 3.91 (s, 3H), 3.82 (d, 1H), 3.75 (d, 1H), 3.74 (d, 1H), 3.68 (d, 1H), 3.30 (br s, 1H), 3.29 (br s, 1H), 2.88 (d, 1H), 2.86 (d, 1H), 2.86 (m, 2H), 2.67 (dd, 1H), 2.66 (dd, 1H), 2.32 (m, 2H), 1.76 (s, 2H) ppm.

Methyl 3-methoxy-4-[[(1S,4S)-5-[[4-(2,2,3,3-tetrafluoropropoxy)phenyl]methyl]-2,5-diazabicyclo[2.2.1]hept-2-yl]methyl]benzoate; $^1$H NMR (300 MHz, CDCl$_3$) δ 7.64 (dd, 1H), 7.54 (d, 1H), 7.49 (d, 1H), 7.32 (d, 2H), 6.87 (d, 2H), 6.07 (tt, 1H), 4.33 (t, 2H), 3.91 (s, 3H), 3.88 (s, 3H), 3.84 (d, 1H), 3.74 (d, 1H), 3.71 (d, 1H), 3.66 (d, 1H), 3.34 (br s, 1H), 3.30 (br s, 1H), 2.92 (d, 1H), 2.87 (d, 1H), 2.71 (dd, 2H), 1.77 (s, 2H) ppm.

Methyl 4-[[(1S,4S)-5-[[4-(2,2,3,3,4,4,4-heptafluorobutoxy)phenyl]methyl]-2,5-diazabicyclo[2.2.1]hept-2-yl]methyl]-3-methoxybenzoate; $^1$H NMR (300 MHz, CDCl$_3$) δ 7.64 (dd, 1H), 7.54 (d, 1H), 7.50 (d, 1H), 7.32 (d, 2H), 6.90 (d, 2H), 4.44 (t, 2H), 3.91 (s, 3H), 3.88 (s, 3H), 3.83 (d, 1H), 3.74 (d, 1H), 3.72 (d, 1H), 3.67 (d, 1H), 3.32 (br s, 1H), 3.30 (br s, 1H), 2.91 (d, 1H), 2.87 (d, 1H), 2.71 (dd, 2H), 1.78 (d, 1H), 1.76 (d, 1H) ppm.

3-Methoxy-4-[[(1S,4S)-5-[[4-(2,2,3,3-tetrafluoropropoxy)phenyl]methyl]-2,5-diazabicyclo[2.2.1]hept-2-yl]methyl]benzoic acid; $^1$H NMR (300 MHz, CD$_3$OD) δ 7.60 (d, 1H), 7.56 (dd, 1H), 7.39 (d, 1H), 7.36 (d, 2H), 6.99 (d, 2H), 6.32 (tt, 1H), 4.43 (t, 2H), 4.05 (d, 1H), 3.96 (d, 1H), 3.90 (s, 3H), 3.84 (d, 1H), 3.76 (d, 1H), 3.69 (br s, 1H), 3.55 (br s, 1H), 3.25 (d, 1H), 3.05 (d, 1H), 2.94 (dd, 1H), 2.80 (dd, 1H), 1.98 (s, 2H) ppm.

4-[[(1S,4S)-5-[[4-(2,2,3,3,4,4,4-Heptafluorobutoxy)phenyl]methyl]-2,5-diazabicyclo[2.2.1]hept-2-yl]methyl]-3-methoxybenzoic acid; $^1$H NMR (300 MHz, CD$_3$OD) δ 7.60 (d, 1H), 7.56 (dd, 1H), 7.39 (d, 1H), 7.36 (d, 2H), 6.99 (d, 2H), 6.32 (tt, 1H), 4.43 (t, 2H), 4.05 (d, 1H), 3.96 (d, 1H), 3.90 (s, 3H), 3.84 (d, 1H), 3.76 (d, 1H), 3.69 (br s, 1H), 3.55 (br s, 1H), 3.25 (d, 1H), 3.05 (d, 1H), 2.94 (dd, 1H), 2.80 (dd, 1H), 1.98 (s, 2H) ppm.

3-Methoxy-4-[[(1S,4S)-5-[[4-(2,2,3,3,3-pentafluoropropoxy)phenyl]methyl]-2,5-diazabicyclo[2.2.1]hept-2-yl]methyl]benzoic acid; $^1$H NMR (300 MHz, CD$_3$OD) δ 7.60 (d, 1H), 7.56 (dd, 1H), 7.40 (d, 1H), 7.37 (d, 2H), 6.98 (d, 2H), 4.59 (tq, 2H), 4.02 (d, 1H), 3.94 (d, 1H), 3.89 (s, 3H), 3.84 (d, 1H), 3.76 (d, 1H), 3.65 (br s, 1H), 3.54 (br s, 1H), 3.24 (d, 1H), 3.06 (d, 1H), 2.92 (d, 1H), 2.79 (dd, 1H), 1.97 (s, 2H) ppm.

2-Methoxy-4-[[(1S,4S)-5-[[4-(2,2,3,3-tetrafluoropropoxy)phenyl]methyl]-2,5-diazabicyclo[2.2.1]hept-2-yl]methyl]benzoic acid; $^1$H NMR (300 MHz, CD$_3$OD) δ 7.38 (d, 1H), 7.34 (d, 2H), 7.05 (d, 1H), 6.97 (d, 2H), 6.90 (dd, 1H), 6.33 (tt, 1H), 4.43 (t, 2H), 3.83 (s, 3H), 3.77 (d, 1H), 3.74 (d, 1H), 3.69 (d, 1H), 3.66 (d, 1H), 3.35 (br s, 2H), 2.92 (d, 2H), 2.66 (dd, 1H), 2.65 (dd, 1H), 1.80 (s, 2H) ppm.

2-Methoxy-4-[[(1S,4S)-5-[[4-(2,2,3,3,3-pentafluoropropoxy)phenyl]methyl]-2,5-diazabicyclo[2.2.1]hept-2-yl]methyl]benzoic acid; $^1$H NMR (300 MHz, CD$_3$OD) δ 7.40 (d, 1H), 7.35 (d, 2H), 7.06 (d, 1H), 6.98 (d, 2H), 6.91 (dd, 1H), 4.59 (tq, 2H), 3.84 (s, 3H), 3.78 (d, 1H), 3.75 (d, 1H), 3.71 (d, 1H), 3.67 (d, 1H), 3.36 (br s, 2H), 2.93 (d, 2H), 2.67 (dd, 1H), 2.66 (dd, 1H), 1.81 (s, 2H) ppm.

4-[[(1S,4S)-5-[[4-(2,2,3,3,4,4,4-Heptafluorobutoxy)phenyl]methyl]-2,5-diazabicyclo[2.2.1]hept-2-yl]methyl]-2-methoxybenzoic acid; $^1$H NMR (300 MHz, CD$_3$OD) δ 7.39 (d, 1H), 7.35 (d, 2H), 7.05 (d, 1H), 6.98 (d, 2H), 6.90 (dd, 1H), 4.63 (tt, 2H), 3.84 (s, 3H), 3.77 (d, 1H), 3.74 (d, 1H), 3.70 (d, 1H), 3.66 (d, 1H), 3.35 (br s, 2H), 2.92 (d, 2H), 2.66 (dd, 1H), 2.65 (dd, 1H), 1.80 (s, 2H) ppm.

Synthetic Example 18

Compounds of Formula (I)

A. To a solution of methyl 4-[(hexahydro-1H-1,4-diazepin-1-yl)methyl]benzoate (0.37 g, 1.5 mmol) and 4-(2,2,3,3,3-pentafluoropropyloxy)benzaldehyde (0.46 g, 1.8 mmol) in methanol (6 mL) and 1,4-dioxane (6 mL) was added a solution of borane pyridine complex (8 M in dichloromethane, 1.5 eq, 0.28 mL). The reaction mixture was stirred at RT for 16 h. The reaction mixture was concentrated and the resulting residue was dissolved in dichloromethane, washed with water and brine, dried, and concentrated. Purification by flash chromatography using a gradient of methanol in dichloromethane afforded 0.42 g of methyl 4-[[hexahydro-4-[4-(2,2,3,3,3-pentafluoropropoxy)phenyl]methyl]-1H-1,4-diazepin-1-yl]methyl]; $^1$H NMR (400 MHz, CDCl$_3$) δ 8.00 (d, 2H), 7.40 (d, 2H), 7.30 (d, 2H), 6.90 (d, 2H), 4.40 (t, 2H), 3.90 (s, 3H), 3.70 (s, 2H), 3.60 (s, 2H), 2.70 (m, 4H), 2.65 (m, 4H), 1.80 (m, 2H) ppm.

B. A solution of methyl 4-[[hexahydro-4-[[4-(2,2,3,3,3-pentafluoropropoxy)-phenyl]methyl]-1H-1,4-diazepin-1-yl]methyl]benzoate (0.35 g, 0.72 mmol) in a 1 to 1 mixture of THF and methanol (20 mL) was stirred as an aqueous 2N sodium hydroxide solution (9.8 mL, 27 eq) was added. After 16 h, the reaction mixture was concentrated. The residue was suspended in water (5 mL) and acidified to a pH of 6 with an aqueous 2N HCl solution. The resulting solid was collected by filtration and dried to afford 0.27 g of 4-[[hexahydro-4-[[4-(2,2,3,3,3-pentafluoropropoxy)phenyl]methyl]-1H-1,4-diazepin-1-yl]methyl]benzoic acid; $^1$H NMR (400 MHz, CD$_3$OD) δ 7.92 (d, 2H), 7.40 (d, 4H), 7.05 (d, 2H), 4.60 (t, 2H), 4.02 (s, 2H), 3.92 (s, 2H), 3.20 (m, 2H), 3.05 (m, 2H), 2.98 (m, 4H), 2.0 (m, 2H) ppm.

Synthetic Example 19

Compounds of Formula (I)

A. A mixture of methyl 4-[(3-oxo-8-azabicyclo[3.2.1]oct-8-yl)methyl]benzoate (0.30 g, 1.11 mmol) and 4-(2,2,3,3,4,4,4-heptafluorobutoxy)benzenamine (0.49 g, 1.68 mmol) in dichloromethane (20 mL) and acetic acid (0.064 mL, 1.0 eq) was stirred at RT under argon. After 1 h, the reaction was treated with solid sodium triacetoxyborohydride (0.37 g, 1.76 mmol) and stirred at rt for 16 h. The reaction mixture was treated with a sat. aqueous solution of sodium bicarbonate and diluted with dichloromethane. The organic phase was washed with brine, dried, and concentrated. Purification by flash chromatography using a gradient of methanol in dichloromethane gave methyl 4-[[(3-exo)-3-[[4-(2,2,3,3,4,4,4-heptafluorobutoxy)phenyl]amino]-8-azabicyclo[3.2.1]oct-8-yl]methyl]benzoate (93 mg); $^1$H NMR (400 MHz, CDCl$_3$) δ 8.0 (d, 2H), 7.50 (m, 2H), 6.80 (d, 2H), 6.45 (d, 2H), 4.40 (t, 2H), 3.90 (s, 3H), 3.60 (m, 2H), 3.20 (s, 2H), 2.25 (m, 2H), 2.20 (m, 2H), 1.95 (m, 2H), 1.70 (m, 2H), 1.58 (m, 2H) ppm.

B. A solution of methyl 4-[[(3-exo)-3-[[4-(2,2,3,3,4,4,4-heptafluorobutoxy)phenyl]amino]-8-azabicyclo[3.2.1]oct-8-yl]methyl]benzoate (64 mg, 0.12 mmol) in a 1 to 1 mixture of THF and methanol (20 mL) was stirred as an 2N aqueous sodium hydroxide solution (25 eq, 1.46 mL) was added. The reaction mixture was stirred at RT for two days. The reaction was concentrated, diluted with water (2 mL), and acidified to a pH of 6 with 2N aqueous solution of HCl. The resulting solid was collected by filtration and dried in vacuo to afford 47 mg of 4-[[(3-exo)-3-[[4-(2,2,3,3,4,4,4-heptafluorobutoxy)phenyl]amino]-8-azabicyclo[3.2.1]oct-8-yl]methyl]benzoic acid; $^1$H NMR (400 MHz, CDCl$_3$) δ 8.10 (d, 2H), 7.60 (d, 2H), 6.80 (d, 2H), 6.55 (d, 2H), 4.38 (t, 2H), 4.05 (s, 2H), 3.80 (m, 2H), 3.65 (m, 1H), 3.05 (m, 2H), 2.85 (m, 2H), 2.36 (m, 4H), 1.90 (m, 3H) ppm.

Synthetic Example 20

Further Compounds of Formula (I)

Following the general procedures described herein and exemplified in Synthetic Example 19, the following compound, as well as other compounds encompassed within Formula (I), can be synthesized utilizing the appropriate starting materials:

4-[[(3-exo)-3-[[4-(2,2,3,3,3-pentafluoropropoxy)phenyl]amino]-8-azabicyclo[3.2.1]oct-8-yl]methyl]benzoic acid; $^1$H NMR (400 MHz, DMSO-d$_6$) δ 7.85 (d, 2H), 7.45 (d, 2H), 6.80 (d, 2H), 6.45 (d, 2H), 5.10 (m, 1H), 4.60 (t, 2H), 3.60 (m, 2H), 3.42 (m, 1H), 3.05 (s, 2H), 2.0 (m, 6H), 1.62 (d, 2H) ppm.

Synthetic Example 21

Compounds of Formula (I)

A. A solution of N-1-(4-methoxycarbonylphenyl methyl) piperid-4-one (0.58 g, 2.33 mmol) and 4-(2,2,3,3,4,4,4-heptafluorobutoxy)aniline (0.4 g, 1.37 mmol) in dichloromethane (20 mL) and acetic acid (0.24 mL, 3 eq.) was stirred at rt under argon. After 1 h, the reaction was treated with solid sodium triacetoxyborohydride (0.61 g, 2.88 mmol) and stirred at rt for 2 d. The reaction mixture was treated with a sat. aqueous solution of sodium bicarbonate and diluted with dichloromethane. The organic phase was washed with brine, dried, and concentrated. Purification by flash chromatography using a gradient of methanol in dichloromethane afforded 0.71 g of methyl 4-[[4-(2,2,3,3,4,4,4-heptafluorobut-1-oxy)phenylamino]-1-piperidinyl]methyl]benzoate; $^1$H NMR (400 MHz, CDCl$_3$) δ 8.0 (d, 2H), 7.40 (d, 2H), 6.80 (d, 2H), 6.56 (d, 2H), 4.38 (t, 2H), 3.90 (s, 3H), 3.55 (s, 2H), 3.35 (br., 1H), 3.20 (m, 1H), 2.80 (m, 2H), 2.15 (t, 2H), 2.0 (d, 2H), 1.45 (m, 2H) ppm.

B. A solution of the methyl 4-[[4-(2,2,3,3,4,4,4-heptafluorobut-1-oxy)anilino]-1-piperidinyl]methyl]benzoate (0.59 g, 1.13 mmol) in a 3 to 1 mixture of THF and water (40 mL) was added LiOH·H$_2$O (8 eq, 385 mg). The reaction mixture was heated at reflux with stirring for 10 h. The reaction was allowed to cool, concentrated, diluted with water (3 mL), and acidified to a pH of 6 with an aqueous solution of 2N HCl. The solid was collected by filtration, dried, and recrystallized from water (5 mL) to give 0.32 g of 4-[[4-(2,2,3,3,4,4,4-heptafluorobut-1-oxy)phenylamino]-1-piperidinyl]methyl]benzoic acid; $^1$H NMR (400 MHz, DMSO-d$_6$) δ 7.86 (d, 2H), 7.38 (d, 2H), 6.668 (d, 2H), 6.50 (d, 2H), 4.60 (t, 2H), 3.50 (s, 2H), 3.30 (br., 1H), 3.10 (m, 2H), 2.75 (m, 2H), 2.05 (m, 2H), 1.85 (m, 2H), 1.30 (m, 2H) ppm.

Synthetic Example 22

Further Compounds of Formula (I)

Following the general procedures described herein and exemplified in Synthetic Examples 1-21, the following compounds, as well as other compounds encompassed within Formula (I) can be synthesized utilizing the appropriate starting materials:

4-[[(1S,4S)-5-[[4-(thiazol-2-yloxy)phenyl]methyl]-2,5-diazabicyclo[2.2.1]hept-2-yl]methyl]benzoic acid.

4-[[(1S,4S)-5-[[4-(benzothiazol-2-yloxy)phenyl]methyl]-2,5-diazabicyclo[2.2.1]hept-2-yl]methyl]benzoic acid; $^1$H NMR (400 MHz, DMSO) δ 7.89 (m, 3H), 7.99 (dd, 2H), 7.52 (d, 2H), 7.22 (dd, 2H), 6.99 (d, 2H), 6.56 (m, 2H), 4.21 (s, 2H), 3.85 (d, 4H), 3.61 (t, 1H), 3.33 (s, 1H), 2.48 (dd, 2H), 2.36 (m, 4H), 2.10 (d, 2H).

4-[[(1S,4S)-5-[[4-(2-methylbenzothiazol-5-yloxy)phenyl]methyl]-2,5-diazabicyclo[2.2.1]hept-2-yl]methyl]benzoic acid.

4-[[(1S,4S)-5-[[4-(2-methylbenzothiazol-6-yloxy)phenyl]methyl]-2,5-diazabicyclo[2.2.1]hept-2-yl]methyl]benzoic acid.

Methyl 4-[[(1S,4S)-5-[[4-(thiazol-4-ylmethoxy)phenyl]methyl]-2,5-diazabicyclo[2.2.1]hept-2-yl]methyl]benzoate.

4-[[(1S,4S)-5-[[4-(thiazol-4-ylmethoxy)phenyl]methyl]-2,5-diazabicyclo[2.2.1]hept-2-yl]methyl]benzoic acid.

4-[[(1S,4S)-5-[[4-(oxazol-4-ylmethoxy)phenyl]methyl]-2,5-diazabicyclo[2.2.1]hept-2-yl]methyl]benzoic acid.

Methyl 4-[[(1S,4S)-5-[[4-(oxazol-4-ylmethoxy)phenyl]methyl]-2,5-diazabicyclo[2.2.1]hept-2-yl]methyl]benzoate.

4-[[4-[[4-(benzothiazol-2-yloxy)phenyl]amino]-1-piperidinyl]methyl]benzoic acid;

4-[[(3-exo)-3-[[4-(benzothiazol-2-yloxy)phenyl]amino]-8-azabicyclo[3.2.1]oct-8-yl]methyl]benzoic acid; $^1$H NMR (400 MHz, DMSO) δ 7.86 (m, 3H), 7.66 (d, 1H), 7.45 (t, 4H), 7.37 (m, 3H), 7.30 (td, 1H), 3.81 (dd, 2H), 3.72 (m, 2H), 3.32 (d, 3H), 2.76 (t, 2H), 2.62 (td, 2H), 2.47 (m, 1H), 1.71 (s, 2H).

4-[[(3-exo)-3-[[4-(thiazol-4-ylmethoxy)phenyl]amino]-8-azabicyclo[3.2.1]oct-8-yl]methyl]benzoic acid.

Methyl 4-[[(3-exo)-3-[[4-(thiazol-4-ylmethoxy)phenyl]amino]-8-azabicyclo[3.2.1]oct-8-yl]methyl]benzoate.

4-[[(3-exo)-3-[[4-(pyrazol-1-ylmethyl)phenyl]amino]-8-azabicyclo[3.2.1]oct-8-yl]methyl]benzoic acid; $^1$H NMR (400 MHz, CD$_3$OD) δ 7.99 (m, 2H), 7.52 (m, 4H), 7.06 (d, 2H), 6.57 (m, 2H), 6.26 (t, 1H), 5.16 (s, 2H), 4.21 (s, 2H), 3.84 (s, 2H), 3.63 (t, 1H), 2.48 (d, 2H), 2.35 (t, 3H), 2.11 (d, 2H).

4-[[(3-exo)-3-[[4-(pyridin-4-ylmethyl)phenyl]amino]-8-azabicyclo[3.2.1]oct-8-yl]methyl]benzoic acid; $^1$H NMR (400 MHz, CD$_3$OD) δ 8.35 (dd, 2H), 7.99 (dd, 2H), 7.52 (d, 2H), 7.22 dd, 2H), 6.99 (d, 2H), 6.56 (m, 2H), 4.21 (s, 2H), 3.85 (d, 4H), 3.61 (t, 1H), 3.33 (s, 1H), 2.48 (dd, 2H), 2.36 (m, 4H), 2.10 (d, 2H).

4-[[(3-exo)-3-[[4-(oxazol-2-ylmethoxy)phenyl]amino]-8-azabicyclo[3.2.1]oct-8-yl]methyl]benzoic acid.

4-[[(3-exo)-3-[[4-(1,2,4-triazol-1-ylmethyl)phenyl]amino]-8-azabicyclo[3.2.1]oct-8-yl]methyl]benzoic acid; $^1$H NMR (400 MHz, CD$_3$OD) δ 8.40 (s, 1H), 7.98 (m, 2H), 7.93 (s, 1H), 7.51 (d, 2H), 7.14 (d, 2H), 6.59 (dd, 2H), 5.24 (s, 2H), 4.20 (s, 2H), 3.83 (s, 2H), 3.63 (t, 1H), 3.29 (m, 2H), 2.46 (m, 2H), 2.36 (m, 3H), 2.10 (d, 2H).

4-[[(3-exo)-3-[N-oxazol-2-ylmethyl[4-(oxazol-2-ylmethoxy)phenyl]amino]-8-azabicyclo[3.2.1]oct-8-yl]methyl]benzoic acid.

Biological Example 1

LTA$_4$ Hydrolase Homogeneous Time Resolved Fluorescence Assay

Compounds of the invention were tested in the LTA$_4$ hydrolase homogeneous time resolved fluorescence (HTRF) assay to determine their ability to inhibit the hydrolysis of LTA$_4$ to LTB$_4$. The assay analyzes the amount of LTB$_4$ produced.

LTA$_4$ HTRF assay is a two-step assay involving enzymatic conversion of LTA$_4$ to LTB$_4$, and subsequent quantification of LTB$_4$, product with HTRF assay.

The enzymatic conversion of LTA$_4$ to LTB$_4$ was performed in 384-well plates at ambient temperature in a reaction mixture containing 50 mM HEPES (pH 7.5), 0.5% BSA (fatty acid free), 18 nM recombinant human LTA$_4$ hydrolase, 150 nM LTA$_4$, 1% DMSO in the absence or presence of a compound of the invention. Reaction was stopped after 10 minutes incubation by diluting the incubation mixture 10-fold in 50 mM phosphate, 0.1% casein buffer (pH 7.0).

LTB$_4$ formed was quantified with the HTRF assay in which free LTB$_4$ competes with LTB$_4$-XL665 conjugate (acceptor) for anti-LTB$_4$ monoclonal antibody labeled with Europium cryptate (donor), thereby inhibiting the fluorescence energy transfer.

The LTB$_4$ HTRF 384-well assay was carried out by incubating LTB$_4$ samples or standards with LTB$_4$-XL665 conjugate (7.5 ng/well) and anti-LTB$_4$ monoclonal antibody-Europium cryptate conjugate (0.5 ng/well) in 50 mM phosphate, 0.4 M KF and 0.1% casein, buffer (pH 7.0) for two hours at ambient temperature. Plates were read in a RubyStar plate reader (BmG Labtechnologies Inc., NC) simultaneously at 620 nm and 665 nm to obtain signal ratios of 665 nm/620 nm. Results of energy transfer were expressed as delta F (%) which equaled [(signal ratio of sample−signal ratio of negative control)/(signal ratio of negative control)]×100%. Negative controls were control samples without LTB$_4$ or LTB$_4$-XL665.

Sample LTB$_4$ concentrations were calculated from the LTB$_4$ standard curve using the 4-parameter fit equation. For determination IC$_{50}$ values for a particular compound of the invention, eight serially diluted compound concentrations (at 1:3.16 dilution) were used in this assay. Controls without a compound of the invention or with a reference compound were run parallel in the same assay plate.

Compounds of the invention, when tested in this assay, demonstrated the ability to inhibit LTA$_4$ hydrolase activity at IC$_{50}$ values of less than 100 µM, preferably at less than 1 µM.

Biological Example 2

Peptidase Assay

Inhibition of peptidase activity was measured for the compounds of the invention by using methods similar to those described in Kull, F. et al., *The Journal of Biological Chemistry* 1999, 274 (49): 34683-34690. In particular, the peptidase activity of the compounds was measured by inhibition of the hydrolysis of L-alanine-p-nitroanilide to L-alanine and highly colored nitro-aniline as set forth below in the following reaction:

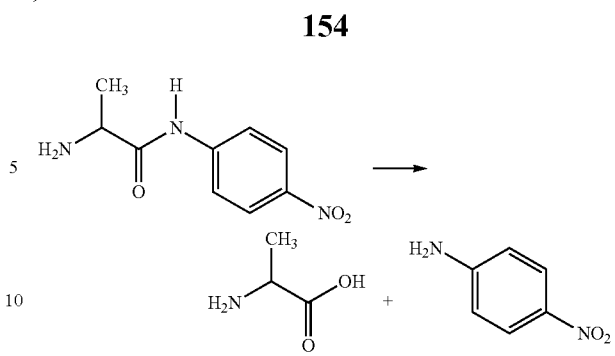

In brief, the enzyme (29 nM) was incubated with L-alanine-p-nitroanilide (1 mM) in 50 mM HEPES (pH 7.5), 100 mM KCL, 1% DMSO in the absence or presence of a compound of the invention for 1 hour at ambient temperature. Reaction was terminated by addition of acetic acid (1%). Formation of colored nitro-aniline was measured by the increase in absorbance at 405 nm in a Victor 2 plate reader (Wallac). Spontaneous hydrolysis of the substrate was corrected for by subtracting the absorbance of control incubations without enzyme. The compounds of the invention, when tested in this assay, demonstrated the ability to inhibit peptidase activity at IC50 values of less than 100 µM, preferably less than 1 µM.

Biological Example 3

Whole Blood Assay

Compounds of the invention were tested for their ability as inhibitors of LTA$_4$ hydrolase in a whole blood assay using human, mouse, rat or dog whole blood in a manner similar to that described in Penning, T. D. et al., *J. Med. Chem.* (2000), 43(4): 721-735. In this assay, compounds were tested for their ability to inhibit LTB$_4$ release upon stimulation with calcium ionophore. The LTB$_4$ levels in supernatants were measured by ELISA.

Compounds of the invention inhibited the release of LTB$_4$ upon addition of calcium ionophore in a dose-dependent manner from whole blood in all species tested.

Biological Example 4

Lewis Rat Acute Experimental Autoimmune Encephalomyelitis Assay

The compounds of the invention were tested for their efficacy in the acute Lewis Rat experimental autoimmune encephalomyelitis (EAE) assay by the following protocol:

Animals and Materials:
1. Eight-week old female Lewis Rats (Charles River).
2. Test compound vehicle (20 g Aldrich HPBCD/100 ml with saline); dose volume: 0.5 mL/injection; route: intraperitoneal; frequency: twice a day (BID) beginning on the morning of immunizations.
3. Compound of the invention; dose level: 30 mg/kg, 10 mg/kg; dose volume: 0.5 mL/injection; route: intraperitoneal; frequency: BID or once a day beginning on the morning of immunizations.
4. Prednisolone (solutions made weekly, stored at 5° C.) (Sigma Cat #P-6004); vehicle: A 1:1 solution of sterile PBS and 40% Hydroxypropyl-B-Cyclodextrin (Sigma Aldrich, St. Louis MO), prepared weekly. The prednisolone was first dissolved in the cyclodextrin vehicle by heat sonication (~30 minutes), and then the equal volume of PBS was added; dose Level: 1.5 mg/kg BID;

dose volume: 0.1 mL; route: intraperitoneal; frequency: twice a day beginning on the morning of the immunization.
5. Spinal cord homogenate preparation (from male Hartley guinea pigs, Charles River): 500-700 g guinea pigs were euthanized with $CO_2$. The spinal cords were removed and rinsed in saline, blotted once, and stored at −80° C. until the day of use. Spinal cords are then weighed and homogenized with saline at 1 g per mL of saline.
6. Antigen Emulsion: Guinea pig spinal cord homogenate was mixed 1:1 with CFA (Complete Freund's Adjuvant, Difco, Detroit, Michigan) with 1 mg/mL *Mycobacterium tuberculosis* (ground with a mortar and pestle); dose volume: 0.05 mL into each hind limb footpad for a total of 0.1 mL per rat; frequency: Single bolus injections on day 1 of immunizations.

Experiment:

On day 1, 70 female Lewis rats were immunized with a 0.05 mL subcutaneous injection into each hind footpad with the following mixture: whole guinea pig spinal cord homogenized and mixed 1 g:1 mL saline. The homogenate was then mixed 1:1 with Freund's complete adjuvant containing 1 mg/mL *Mycobacterium tuberculosis*. Rats were weighed and scored every few days up to day 10, then weighed and scored daily (once on weekends) up to day 21.

Clinical Evaluation:

| EAE Score | Symptoms |
|---|---|
| 0 | Normal |
| 1 | Limp tail |
| 2 | Incomplete paralysis of one or both hind limbs |
| 3 | Complete paralysis of one hind limb or both hind limbs can move but do not help in movement of the body |
| 4 | Complete paralysis of both hind limbs |
| 5 | Complete paralysis of hind limbs and weakness of one or both forelimbs or moribund, or death |

Rats which were borderline in scores were given a one half score, such as 3.5. Moribund mice were euthanized.

Groups (n=10):
1. Vehicle
2. Compound of the invention, 30 mg/kg BID
3. Compound of the invention, 10 mg/kg BID
4. Compound of the invention, 30 mg/kg once a day
5. 1.5 mg/kg Prednisolone Endpoint Analysis:

On day 21 of the assay, serum was collected from the groups for pharmacokinetics analysis. Spinal cords were collected from the highest scoring rats in each group for histopathologic analysis.

Results:

Compounds of the invention, when tested for their efficacy in this assay, demonstrated the ability in preventing cumulative disease burden at the doses tested.

Biological Example 5

Mouse Adoptive Experimental Autoimmune Encephalomyelitis Assay

Compounds of the invention were tested for their efficacy in the mouse adoptive experimental autoimmune encephalomyelitis (EAE) assay by the following protocol:

Animals and Materials:
1. 8 week old female SJL mice (Jackson Laboratories)
2. Myelin proteolipid protein fragment 139-151 (HCLGKWLGHPDKF)(PLP139-151), which was reconstituted to 3 mg/mL in saline and mixed 1:1 with CFA (Complete Freund's Adjuvant, Difco, Detroit, Michigan) with 4 mg/mL *Mycobacterium tuberculosis* H37Ra (ground with a mortar and pestle).
3. Test compound vehicle (20 g Aldrich HPBCD/100 mL with saline); dose volume: 0.2 mL/injection; route: intraperitoneal; frequency: BID beginning on the morning of immunizations.
4. Compound of the invention: Dose level: 30 mg/kg, 10 mg/kg; dose volume: 0.2 mL/injection; route: intraperitoneal (IP); frequency: BID or once a day beginning on the morning of immunizations
6. Prednisolone (Sigma Cat #P-6004); vehicle: a 1:1 solution of sterile PBS and 40% Hydroxypropyl-B-Cyclodextrin (Sigma Aldrich, St. Louis MO), prepared weekly. The prednisolone was first dissolved in the cyclodextrin vehicle by heat sonication (~30 minutes), and then an equal volume of PBS was added; dose level: 2.5 mg/kg BID; dose volume: 0.1 mL; route: intraperitoneal; frequency: BID daily, beginning on the morning of the immunizations.
7. Rosswell Park Memorial Institute (RPMI) 1640, with L-glu & 25 mM HEPES, 1×, 0.1 micron filtered (Life Technologies, Cat #22400-089).
8. FBS, defined (Hyclone, Cat #SH30070.01), heat inactivated.
9. MEM Non-essential amino acids solution, 10 mM, 100× (Life Technologies, Cat #11140-050).
10. 2-mercaptoethanol, 1000×, $5.5 \times 10^{-2}$ M in D-PBS (Life Technologies, Cat #21985-023).
11. Penicillin/Streptomycin (Pen/Strep), 10000 U/ug per ml (Bio*Whittaker, Cat #17-602E).
12. Hank's Balanced Salt Solution (HBSS), 1×, 0.1 micron filtered (Life Technologies, Cat #24020-117).

Experiment:
1. Forty 8-week-old female SJL mice were immunized with 0.1 mL subcutaneous (divided between base of tail & upper back) injection containing 150 μg PLP in CFA w/200 μg *Mycobacterium tuberculosis* $H37R_a$ (ground).
2. Axial, brachial and inguinal lymph node cells were collected 11 days later. The cells were placed in sterile petri dishes with HBSS. A single cell suspension of lymph node cells was obtained by pressing lymph nodes through a metal sieve and flushing with the following media:
   To 450 m: RPMI 1640 (w/L-glu and HEPES) was added:
   a) 50 mL heat inactivated FBS (Hyclone defined).
   b) 0.455 mL 2-mercaptoethanol @ $5.5 \times 10^{-2}$ M
   c) 5.0 mL Pen/Strep @ 10000 U/mL
   d) 5.0 mL Non-essential amino acids @ 10 mM
3. The cells were cultured at $6 \times 10^6$ cells/mL.
4. PLP was added to the remaining cells to obtain a final concentration of 50 μg/mL.
5. The cell cultures were incubated for 72 hours at 37° C., 7% $CO_2$.
6. The cells were harvested and washed twice in HBSS.
7. Lymph node cell viability was checked by trypan blue exclusion.
8. The concentration was adjusted to $3.6 \times 10^7$ lymph node cells per mL. $1.6 \times 10^7$ lymph node cells were injected per mouse into naive 8 week old female SJL mice; dose volume=0.5 mL/mouse, IP.
9. Mice were weighed and scored.

Clinical Evaluation:

| EAE Score | Symptoms |
|---|---|
| 0 | Normal |
| 1 | Limp tail |
| 2 | Difficulty righting/severe abnormal gait |
| 3 | Incomplete paralysis of hind limb(s) |
| 4 | Complete paralysis of both hind limbs |
| 5 | Immobile, moribund, or death |

Rats which were borderline in scores were given a one half score, such as 3.5. Moribund mice were euthanized.

Groups (n=10):
1. Vehicle
2. Compound of the invention, 30 mg/kg BID
3. Compound of the invention, 10 mg/kg BID
4. Compound of the invention, 30 mg/kg once a day
5. 1.5 mg/kg Prednisolone Results:

Compounds of the invention, when tested in this assay, demonstrated the ability to prevent cumulative disease burden in the assay at the doses tested.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disease or disorder ameliorated by the inhibition of LTA$_4$-h activity in a mammal, wherein the disease or disorder is selected from the group consisting of neurodegeneration in stroke, Alzheimer's disease, Parkinson's disease, encephalitis, HIV dementia, neuropathic pain, multiple sclerosis, and migraine, and wherein the method comprises administering to a mammal in need thereof a therapeutically effective amount of compound having Formula (I):

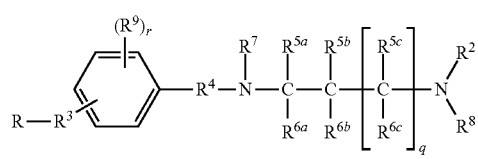

wherein:
R is the group

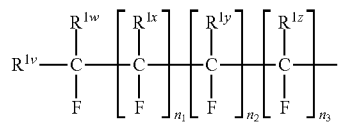

$n_1$, $n_2$, and $n_3$ are each independently 0 to 2;
r is 0 to 4;
q is 0 to 2;

$R^{1v}$, $R^{1w}$, $R^{1x}$, $R^{1y}$ and $R^{1z}$ are each independently hydrogen or fluoro;

$R^2$ and $R^7$, together with the nitrogens to which they are attached, form an optionally substituted 5- to 7-membered N-heterocyclyl;

or $R^2$ and $R^7$, together with the nitrogens to which they are attached and one of $R^{5a}$, $R^{5b}$ and $R^{5c}$, form an optionally substituted 6- to 10-membered bridged N-heterocyclyl;

or $R^2$ and $R^{5a}$, together with the nitrogen and carbon to which they are attached, form an optionally substituted 5- to 7-membered N-heterocyclyl or an optionally substituted 6- to 10-membered bridged N-heterocyclyl;

or $R^2$ and $R^{5b}$, together with the nitrogen and carbon to which they are attached, form an optionally substituted 5- to 7-membered N-heterocyclyl;

$R^3$ is —O—, —$R^{12}$—O—, or —O—$R^{12}$—;

$R^4$ is a direct bond, or an optionally substituted straight or branched alkylene chain;

each $R^{5a}$, $R^{5b}$, $R^{5c}$, $R^{6a}$, $R^{6b}$ and $R^{6c}$ are each independently hydrogen, alkyl, haloalkyl or hydroxyalkyl;

or any one of $R^{5a}$ and $R^{6a}$ together, $R^{5b}$ and $R^{6b}$ together, and $R^{5c}$ and $R^{6c}$ together can be an oxo group;

$R^7$ is hydrogen, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—N($R^{10}$)C(=O)N($R^{10}$)$R^{11}$, alkyl, haloalkyl, optionally substituted cycloalkyl, optionally substituted cycloalkylalkyl, optionally substituted aryl, optionally substituted aralkyl, optionally substituted heteroarylalkyl, or optionally substituted heterocyclylalkyl;

$R^8$ is aralkyl optionally substituted with one or more substituents selected from the group consisting of halo, nitro, cyano, optionally substituted heteroaryl, hydroxyiminoalkyl, —$R^{13}$—$OR^{10}$, —$R^{13}$—C(=O)$R^{10}$, —$R^{13}$—C(=O)$OR^{10}$, —$R^{13}$—C(=O)—$R^{13}$—N($R^{10}$)$R^{11}$, —$R^{13}$—C(=O)N($R^{10}$)—$R^{14}$—N($R^{10}$)$R^{11}$, —$R^{13}$—S(=O)$_t$N($R^{10}$)$R^{11}$ (where t is 1 or 2), —$R^{13}$—N($R^{10}$)$R^{11}$, —$R^{13}$—N($R^{10}$)C(=O)$R^{10}$, —$R^{13}$—N($R^{10}$)C(=O)—$R^{13}$—N($R^{10}$)$R^{11}$, —$R^{13}$—N($R^{10}$)—$R^{13}$—C(=O)$OR^{10}$, —$R^{13}$—N($R^{10}$)C(=O)—$R^{14}$—S(=O)$_t$N($R^{10}$)$R^{11}$ (where t is 1 or 2), —$R^{13}$—N($R^{10}$)C(=O)—$R^{13}$—N($R^{10}$)C(=O)$R^{10}$, —$R^{13}$—N($R^{10}$)C(=O)—$R^{13}$—N($R^{10}$)—$R^{14}$—N($R^{10}$)$R^{11}$, —$R^{13}$—N($R^{10}$)S(=O)$_t$N($R^{10}$)$R^{11}$ (where t is 1 or 2), and —$R^{13}$—O—$R^{14}$—C(=O)$OR^{10}$;

each $R^9$ is independently —O—$R^{10}$, alkyl, hydroxyalkyl, halo, haloalkyl, aryl or aralkyl;

each $R^{10}$ and $R^{11}$ is independently hydrogen, alkyl, haloalkyl, hydroxyalkyl, optionally substituted aryl, optionally substituted aralkyl, optionally substituted heteroaryl, optionally substituted heteroarylalkyl, optionally substituted heterocyclyl, or optionally substituted heterocyclylalkyl;

or $R^{10}$ and $R^{11}$, together with the nitrogen to which they are attached, form an optionally substituted N-heterocyclyl or an optionally substituted N-heteroaryl;

$R^{12}$ is an optionally substituted straight or branched alkylene chain, an optionally substituted straight or branched alkenylene chain, or an optionally substituted straight or branched alkynylene chain;

each $R^{13}$ is independently a direct bond, an optionally substituted straight or branched alkylene chain, an optionally substituted straight or branched alkenylene chain, or an optionally substituted straight or branched alkynylene chain; and each $R^{14}$ is independently an optionally substituted straight or branched alkylene chain, an optionally substituted straight or branched alkenylene chain, or an optionally substituted straight or branched alkynylene chain;

as a single stereoisomer or as a mixture of stereoisomers; or a pharmaceutically acceptable thereof.

2. The method of claim 1, wherein:
$R^2$ and $R^7$, together with the nitrogens to which they are attached and one of $R^{5a}$, $R^{5b}$ and $R^{5c}$, form an optionally substituted 6- to 10-membered bridged N-heterocyclyl.

3. The method according to claim 2 having the following formula (I-1):

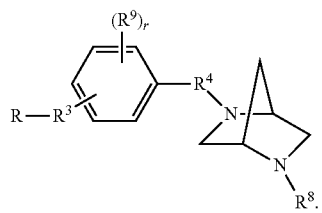

(I-1)

4. The method according to claim 3 wherein:
$R^4$ is an optionally substituted straight or branched alkylene chain;
$R^8$ is aralkyl optionally substituted with one or more substituents selected from the group consisting of —$R^{13}$—$OR^{10}$, —$R^{13}$—C(=O)$R^{10}$, —$R^{13}$—C(=O)$OR^{10}$ and —$R^{13}$—C(=O)N($R^{10}$)$R^{11}$;
each $R^9$ is independently alkyl, halo or —O—$R^{10}$;
$R^{12}$ is an optionally substituted straight or branched alkylene chain;
each $R^{13}$ is a direct bond or an optionally substituted straight or branched alkylene chain.

5. The method according to claim 4 wherein:
r is 0;
$R^4$ is an optionally substituted straight or branched alkylene chain;
$R^8$ is benzyl substituted with one or more substituents selected from —$R^{13}$—$OR^{10}$ and —$R^{13}$—C(=O)$OR^{10}$;
$R^{10}$ is hydrogen, alkyl or optionally substituted aryl; and
$R^{12}$ is $C_{1-6}$ alkylene.

6. The method of claim 1, wherein:
$R^2$ and $R^7$, together with the nitrogens to which they are attached, form an optionally substituted 5- to 7-membered N-heterocyclyl.

7. A compound according to claim 6 having the following formula (I-2):

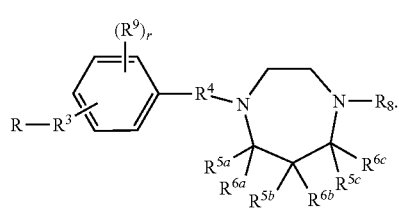

(I-2)

8. The method according to claim 6 having the following formula (I-3):

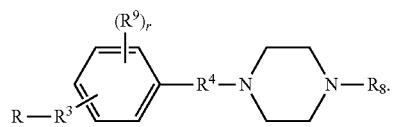

(I-3)

9. The method of claim 1, wherein:
$R^2$ and $R^{5a}$, together with the nitrogen and carbon to which they are attached, form an optionally substituted 5- to 7-membered N-heterocyclyl or an optionally substituted 6- to 10-membered bridged N-heterocyclyl;
or $R^2$ and $R^{5b}$, together with the nitrogen and carbon to which they are attached, form an optionally substituted 5- to 7-membered N-heterocyclyl.

10. The method according to claim 9 which is of formula (I-4) or formula (I-5):

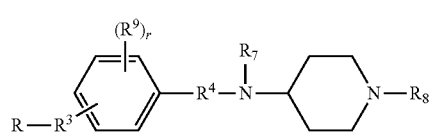

(I-4)

(I-5)

11. The method of claim 1, wherein the disease or disorder is selected from the group consisting of neurodegeneration in stroke, Alzheimer's disease, Parkinson's disease, encephalitis, and HIV dementia.

12. The method of claim 1, wherein the disease or disorder is neuropathic pain or migraine.

13. The method of claim 1, wherein $R^3$ is —$R^{12}$—O— or —O—$R^{12}$—, and $R^4$ is an optionally substituted straight or branched $C_1$-$C_6$ alkylene chain.

14. The method of claim 3, wherein $R^3$ is —$R^{12}$—O— or —O—$R^{12}$—, and $R^4$ is an optionally substituted straight or branched $C_1$-$C_6$ alkylene chain.

15. The method of claim 6, wherein $R^3$ is —$R^{12}$—O— or —O—$R^{12}$—, and $R^4$ is an optionally substituted straight or branched $C_1$-$C_6$ alkylene chain.

16. The method of claim 9, wherein $R^3$ is —$R^{12}$—O— or —O—$R^{12}$, and $R^4$ is an optionally substituted straight or branched $C_1$-$C_6$ alkylene chain.

17. The method of claim 1, wherein $n_1$, $n_2$, and $n_3$ are each independently 0 to 1.

18. The method of claim 3, wherein $n_1$, $n_2$, and $n_3$ are each independently 0 to 1.

19. The method of claim 6, wherein $n_1$, $n_2$, and $n_3$ are each independently 0 to 1.

20. The method of claim 9, wherein $n_1$, $n_2$, and $n_3$ are each independently 0 to 1.

21. A method of treating a disease or disorder ameliorated by the inhibition of $LTA_4$-h activity in a mammal, wherein the disease or disorder is selected from the group consisting of neurodegeneration in stroke, Alzheimer's disease, Parkinson's disease, encephalitis, HIV dementia, neuropathic pain, multiple sclerosis, and migraine, and
wherein the method comprises administering to a mammal in need thereof a therapeutically effective amount of compound selected from the following:
- 4-[[(1S,4S)-5-[[4-(2,2,3,3,3-pentafluoropropoxy)phenyl]methyl]-2,5-diazabicyclo[2.2.1]hept-2-yl]methyl]benzoic acid;
- 4-[(1S,4S)-5-[[4-(2-fluoroethoxy)phenyl]methyl]-2,5-diazabicyclo[2.2.1]hept-2-yl]methyl]benzoic acid;
- 4-[[(1S,4S)-5-[[4-(2,2,3,3-tetrafluoropropoxy)phenyl]methyl]-2,5-diazabicyclo[2.2.1]hept-2-yl]methyl]benzoic acid;
- 4-[[(1S,4S)-5-[[4-(2,2,3,3,4,4,4-heptafluorobutoxy)phenyl]methyl]-2,5-diazabicyclo[2.2.1]hept-2-yl]methyl]benzoic acid;
- 4-[[(1S,4S)-5-[[4-[(7,7,8,8,8-pentafluorooctyl)oxy]phenyl]methyl]-2,5-diazabicyclo[2.2.1]hept-2-yl]methyl]benzoic acid;
- 4-[(1S,4S)-5-[[4-(2,2,2-trifluoroethoxy)phenyl]methyl]-2,5-diazabicyclo[2.2.1]hept-2-yl]methyl]benzoic acid;
- 4-[[(1S,4S)-5-[[4-(trifluoromethyl)phenyl]methyl]-2,5-diazabicyclo[2.2.1]hept-2-yl]methyl]benzoic acid;
- 4-[[(1S,4S)-5-[[4-(trifluoromethoxy)phenyl]methyl]-2,5-diazabicyclo[2.2.1]hept-2-yl]methyl]benzoic acid;
- 4-[[(1S,4S)-5-[[4-(difluoromethoxy)phenyl]methyl]-2,5-diazabicyclo[2.2.1]hept-2-yl]methyl]benzoic acid;
- 4-[[(1S,4S)-5-[[4-(1,1,2,2-tetrafluoroethoxy)phenyl]methyl]-2,5-diazabicyclo[2.2.1]hept-2-yl]methyl]benzoic acid;
- 4-[[(1S,4S)-5-[[4-(2,2,3,4,4,4-hexafluorobutoxy)phenyl]methyl]-2,5-diazabicyclo[2.2.1]hept-2-yl]methyl]benzoic acid;
- 4-[[(1S,4S)-5-[[4-(3,3,4,4,5,5,6,6,6-nonafluorohexyl)phenyl]methyl]-2,5-diazabicyclo[2.2.1]hept-2-yl]methyl]benzoic acid;
- 4-[[(1S,4S)-5-[[4-(3,3,4,4,4-pentafluorobutyl)phenyl]methyl]-2,5-diazabicyclo[2.2.1]hept-2-yl]methyl]benzoic acid;
- 4-[[(1S,4S)-5-[[4-(4,4,5,5,5-pentafluoropentyl)phenyl]methyl]-2,5-diazabicyclo[2.2.1]hept-2-yl]methyl]benzoic acid;
- 4-[[(1S,4S)-5-[[4-(4,4,4-trifluorobutoxy)phenyl]methyl]-2,5-diazabicyclo[2.2.1]hept-2-yl]methyl]benzoic acid;
- 4-[(1S,4S)-5-[[4-(3,3,3-trifluoropropoxy)phenyl]methyl]-2,5-diazabicyclo[2.2.1]hept-2-yl]methyl]benzoic acid;
- 4-[[(1S,4S)-5-[[4-(1,1,2,3,3,3-hexafluoropropoxy)phenyl]methyl]-2,5-diazabicyclo[2.2.1]hept-2-yl]methyl]benzoic acid;
- methyl 4-[[(1S,4S)-5-[[4-(3,3,4,4,4-pentafluorobutyl)phenyl]methyl]-2,5-diazabicyclo[2.2.1]hept-2-yl]methyl]benzoate;
- methyl 2-methoxy-4-[[(1S,4S)-5-[[4-(2,2,3,3-tetrafluoropropoxy)phenyl]methyl]-2,5-diazabicyclo[2.2.1]hept-2-yl]methyl]benzoate;
- methyl 2-methoxy-4-[[(1S,4S)-5-[[4-(2,2,3,3,4,4,4-heptafluorobutoxy)phenyl]methyl]-2,5-diazabicyclo[2.2.1]hept-2-yl]methyl]benzoate;
- 3-methoxy-4-[[(1S,4S)-5-[[4-(2,2,3,3-tetrafluoropropoxy)phenyl]methyl]-2,5-diazabicyclo[2.2.1]hept-2-yl]methyl]benzoic acid;
- 4-[[(1S,4S)-5-[[4-(2,2,3,3,4,4,4-heptafluorobutoxy)phenyl]methyl]-2,5-diazabicyclo[2.2.1]hept-2-yl]methyl]-3-methoxybenzoic acid;
- 3-methoxy-4-[[(1S,4S)-5-[[4-(2,2,3,3,3-pentafluoropropoxy)phenyl]methyl]-2,5-diazabicyclo[2.2.1]hept-2-yl]methyl]benzoic acid;
- 2-methoxy-4-[[(1S,4S)-5-[[4-(2,2,3,3-tetrafluoropropoxy)phenyl]methyl]-2,5-diazabicyclo[2.2.1]hept-2-yl]methyl]benzoic acid;
- 2-methoxy-4-[[(1S,4S)-5-[[4-(2,2,3,3,3-pentafluoropropoxy)phenyl]methyl]-2,5-diazabicyclo[2.2.1]hept-2-yl]methyl]benzoic acid; and
- 4-[[(1S,4S)-5-[[4-(2,2,3,3,4,4,4-heptafluorobutoxy)phenyl]methyl]-2,5-diazabicyclo[2.2.1]hept-2-yl]methyl]-2-methoxybenzoic acid, as a single stereoisomer or as a mixture of stereoisomers; or a pharmaceutically acceptable salt thereof.

22. The method of claim 21, wherein the compound is 4-[[(1S,4S)-5-[[4-(4,4,4-trifluorobutoxy)phenyl]methyl]-2,5-diazabicyclo[2.2.1]hept-2-yl]methyl]benzoic acid as a single stereoisomer or as a mixture of stereoisomers; or a pharmaceutically acceptable salt thereof.

23. The method of claim 1, wherein the disease or disorder is multiple sclerosis.

* * * * *